US007674884B2

(12) United States Patent
Elson et al.

(10) Patent No.: US 7,674,884 B2
(45) Date of Patent: Mar. 9, 2010

(54) NEUTRALIZING ANTIBODIES AND METHODS OF USE THEREOF

(75) Inventors: Greg Elson, Collonges sous Saleve (FR); Olivier Leger, St. Sixt (FR)

(73) Assignee: Novimmune S.A., Geneva (CH)

( * ) Notice: Subject to any disclaimer, the term of this patent is extended or adjusted under 35 U.S.C. 154(b) by 624 days.

(21) Appl. No.: 11/151,916

(22) Filed: Jun. 14, 2005

(65) Prior Publication Data

US 2008/0050366 A1 Feb. 28, 2008

Related U.S. Application Data

(63) Continuation-in-part of application No. 11/009,939, filed on Dec. 10, 2004, now Pat. No. 7,312,320.

(60) Provisional application No. 60/528,962, filed on Dec. 10, 2003, provisional application No. 60/528,812, filed on Dec. 10, 2003, provisional application No. 60/528,811, filed on Dec. 10, 2003.

(51) Int. Cl.
*C12P 21/08* (2006.01)
*C07K 16/00* (2006.01)
*A61K 39/395* (2006.01)
*A61K 39/00* (2006.01)

(52) U.S. Cl. ............................ 530/388.22; 530/388.2; 530/388.1; 530/388.85; 530/387.1; 424/130.1; 424/133.1; 424/141.1

(58) Field of Classification Search ...................... None
See application file for complete search history.

(56) References Cited

U.S. PATENT DOCUMENTS

| | | | | |
|---|---|---|---|---|
| 5,928,893 | A * | 7/1999 | Kang et al. | 435/69.1 |
| 6,037,453 | A * | 3/2000 | Jardieu et al. | 530/387.3 |
| 6,312,693 | B1 * | 11/2001 | Aruffo et al. | 424/154.1 |
| 7,202,343 | B2 * | 4/2007 | Gudas et al. | 530/387.1 |
| 7,214,786 | B2 * | 5/2007 | Kovalic et al. | 536/23.6 |
| 7,230,083 | B2 * | 6/2007 | Jonak et al. | 530/387.1 |
| 7,241,444 | B2 * | 7/2007 | Goetsch et al. | 424/130.1 |
| 7,265,278 | B2 * | 9/2007 | Demmer et al. | 800/320 |
| 7,271,248 | B2 * | 9/2007 | Hardiman et al. | 530/387.1 |

FOREIGN PATENT DOCUMENTS

| | | | |
|---|---|---|---|
| WO | WO 200001817 | * | 1/2000 |
| WO | WO 03/013440 | | 2/2003 |
| WO | WO 2005/047330 | | 5/2005 |

OTHER PUBLICATIONS

Akashi et al., "Cutting edge: Cell surface expression and lipopolysaccharide signaling via the Toll-like receptor 4-MD-2 complex on mouse peritoneal macrophages," J. Immunol., vol. 164(7): 3471-3475 (2000).

Akashi et al., "Lipopolysaccharide interaction with cell surface Toll-like receptor 4-MD-2: Higher affinity than that with MD-2 or CD14," J. Exp. Med., vol. 198(7): 1035-1042 (2003).

Backhed et al, "TLR4-dependent recognition of lipopolysaccharide by epithelial cells requires sCD14," Cellular Microbiology, vol. 4(8): 493-501 (2002).

Buell et al., "Blockade of human P2X7 receptor function with a monoclonal antibody." Blood 92: 3521-3528 (1998).

Devaney et al., "Neutrophil elastase up-regulates interleukin via toll-like receptor 4," FEBS Letters, vol. 544 (1-3): 129-132 (2003).

GenBank Accession No. AAH20690.1 "Lymphocyte antigen 96 [*Homo sapiens*]", download Jul. 31, 2009.

GenBank Accession No. BAA78717.1 "MD-2 [*Homo sapiens*]", download Jul. 31, 2009.

GenBank Accession No. CAH72619.1 "toll-like receptor 4 [*Homo sapiens*]", download Jul. 31, 2009.

GenBank Accession No. CAH72620 "toll-like receptor 4 [*Homo sapiens*]", download Jul. 31, 2009.

GenBank Accession No. NP_056179, "MD-2 protein [*Homo sapiens*]", download Jul. 31, 2009.

GenBank Accession No. Q9Y6Y9, "RecName: Full=Lymphocyte antigen 96; AltName: Full=Protein MD-2; AltName: Full=ESPO-1; Flags: Precursor".

Ishida et al., "Hypoxia diminishes Toll-like Receptor 4 expression through reactive oxygen species generated by mitochondria in endothelial cells," J. Immunol., vol. 169(4): 2069-2075 (2002).

Johnson et al., "Activation of mammalian Toll-like receptors by endogenous agonists" Crit. Rev. Immunol., 23(1-2):15-44 (2003).

Jones and Bendig, "Rapid PCR-cloning of full-length mouse immunoglobulin variable regions." Biotechnology (N.Y.), 9: 88-89 (1991).

Kammann et al., "Rapid insertional mutagenesis of DNA by polymerase chain reaction (PCR)," Nucleic Acids Res.. vol. 17: 5404 (1989).

Kawasaki et al., "Identification of mouse MD-2 residues important for forming the cell surface TLR4-MD-2 complex recognized by anti-TLR4-MD2 antibodies, and for conferring LPS and taxol responsiveness on mouse TLR4 by alanine-scanning mutagenesis," J. Immunol., vol. 170(1): 413-420 (2003).

Kirkland et al., "Analysis of Lipopolysaccharide Binding by CD14," J. Biol. Chem., vol. 268(33): 24818-24823 (1993).

Kolbinger et al., "Humanization of a mouse anti-human IgE antibody: a potential therapeutic for IgE-mediated allergies" Protein Eng. 6, 971-980, 1993).

(Continued)

*Primary Examiner*—Manjunath N Rao
*Assistant Examiner*—Shulamith H Shafer
(74) *Attorney, Agent, or Firm*—Mintz, Levin, Cohn, Ferris, Glovsky and Popeo, P.C.; Ivor R. Elrifi

(57) ABSTRACT

This invention provides monoclonal antibodies that recognize the Toll-like Receptor 4/MD-2 receptor complex, and monoclonal antibodies that recognize the TLR4/MD2 complex as well as TLR4 when not complexed with MD-2. The invention further provides methods of using the humanized monoclonal antibodies as therapeutics. This invention also provides soluble chimeric proteins, methods of expressing and purifying soluble chimeric proteins, and methods of using soluble chimeric proteins as therapeutics, in screening assays and in the production of antibodies.

3 Claims, 37 Drawing Sheets

OTHER PUBLICATIONS

Lakhani et al., "Toll-like receptor signaling in sepsis" Curr. Opin. Pediatr. 15: 278-282 (2003).
Lenhardt et al., "Activation of innate immunity in the CNS triggers neurodegeneration through a Toll like receptor 4-dependent pathway," PNAS, vol. 100(14): 8514-8519 (2003).
Miyake, "Endotoxin recognition molecules MD-2 and Toll-like Receptor 4 as potential targets for therapeutic intervention of endotoxin shock," Current Drug Targets: Inflammation and Allergy, vol. 3(3): 291-297 (2004).
Miyake, "Innate recognition of lipopolysaccharide by CD14 and toll-like receptor 4-MD-2: unique roles for MD-2," International Immunopharmacology, vol. 3(1): 1199-128 (2003).
Nijhuis et al, "Endothelial cells are main producers of Interleukin 8 through Toll-like receptor 2 and 4 signaling during bacterial infection in leukopenic cancer patients," Clinical aid Diagnostic Laboratory Immunology, vol. 10(4): 558-563 (20030.
O'Neill, "Therapeutic targeting of Toll-like receptors for inflammatory and infectious diseases" Curr. Opin. Pharmacol. 3: 396-403 (2003).
Ohashi et al., "Cutting Edge: Heat Shock Protein 60 is a Putative Endogenous Ligand of the Toll-Like Receptor-4 Complex," J. Immunol., vol. 164: 558-561 (2000).
Okamura et al., "The Extra Domain A of Fibronectin Activates Toll-like Receptor 4," J. Biol. Chem. vol. 276(13): 10229-10233 (2001).
Pasterkamp et al., "Role of Toll-like Receptor 4 in the initiation and progression of atherosclerotic disease," Eur. J. Clin. Invest., vol. 34(5): 328-334 (2004).
Pivarcsi et al., "Expression and Function of Toll-like Receptors 2 and 4 in Human Keratinocytes," International Immunology, vol. 15(6): 721-730 (2003).
Pugin et al., "Soluble MD-2 activity in plasma from patients with severe sepsis and septic shock," Blood, vol. 104(13): 4071-4079 (2004).
Sato et al., "Reshaping a human antibody to inhibit the interleukin 6-dependent tumor cell growth," Cancer Res. vol. 53: 851-856 (1993).
Shimazu et al., "MD-2, a molecule that confers lipopolysaccharide responsiveness on Toll-like receptor 4," J. Exp. Med., vol. 189(11): 1777-1782 (1999).
Takeda et al., "Toll-like receptors" Annu. Rev. Immunol., 21: 335-76 (2003).
Yang et al., "Cellular events mediated by lipopolysaccharide-stimulated Toll-like receptor 4," J. Biol. Chem., vol. 275(27): 20861-20866 (2000).

* cited by examiner

18H10

Figure 5B
Panel 1:
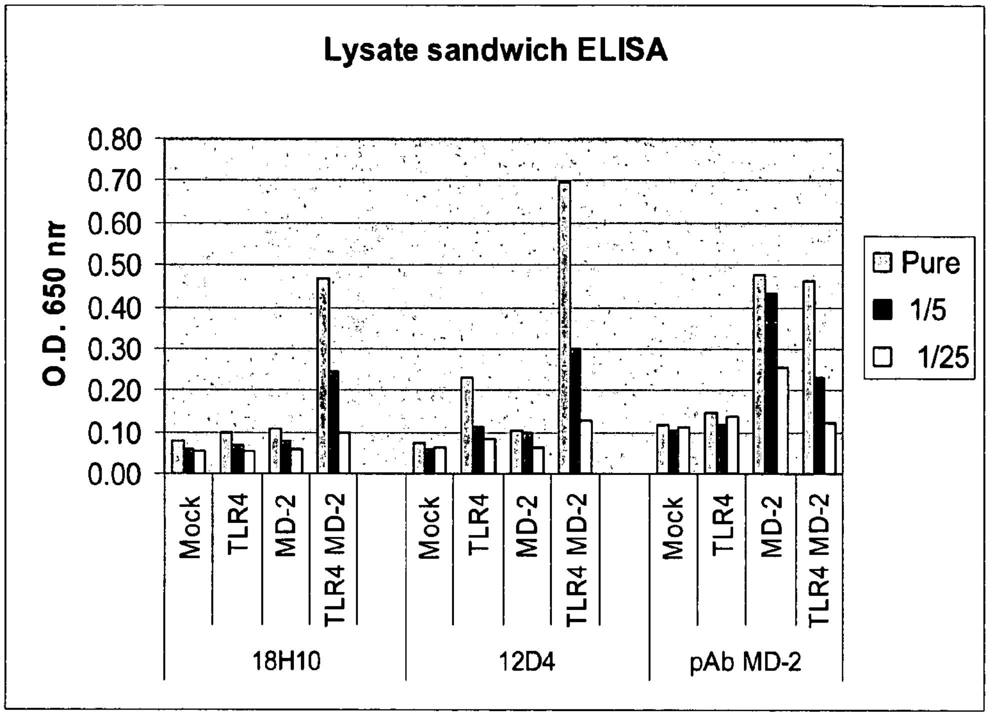
Panel 2:
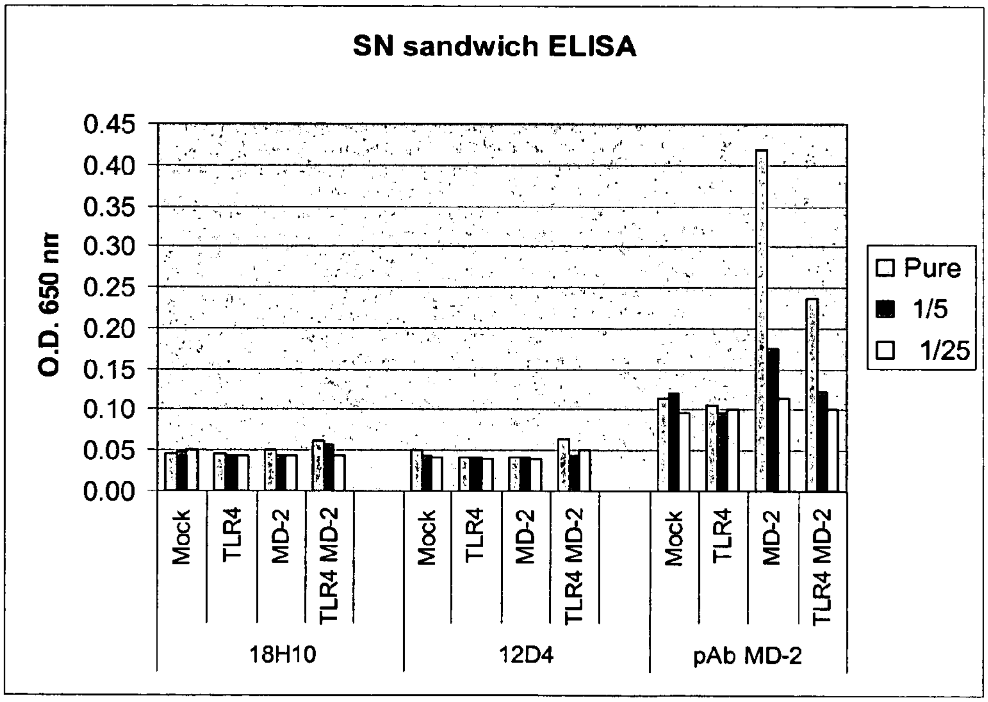

Figure 6A: 18H10 VH nucleotide sequence

```
  1 caggtgcaac tgcagcagtc tggggctgat cttgtgaggc caggggcctt
      q  v  q   l  q  q  s   g  a  d   l  v  r   p  g  a
 51 agtcaagttg tcctgcacag cttctggctt caacattaaa gactcctata
    l  v  k  l   s  c  t   a  s  g  f   n  i  k   d  s  y
101 tacactgggt gaagaagagg cctgaatggg gcctggagtg gattggatgg
      i  h  w  v   k  k  r   p  e  w   g  l  e  w   i  g  w
151 actgatcctg agaatgttaa ttctatatat gacccgaggt ttcagggcaa
      t  d  p   e  n  v  n   s  i  y   d  p  r   f  q  g
201 ggccagtata acagcagaca catcctccaa cacagccttc cttcagctca
    k  a  s  i   t  a  d   t  s  s   n  t  a  f   l  q  l
251 ccagcctgac atctgaggac actgccgtct attactgtgc taggggttat
      t  s  l   t  s  e  d   t  a  v   y  y  c   a  r  g  y
301 aacggtgttt actatgctat ggactactgg ggccaaggga cctcagtcac
      n  g  v   y  y  a   m  d  y  w   g  q  g   t  s  v
351 cgtctcctca (SEQ ID NO:1)
    t  v  s  s (SEQ ID NO:2)
```

Figure 6B: 18H10 VH protein sequence 1 qvqlqqsgad lvrpgalvkl sctasgfnik *dsyih*wvkkr pewglewig*w*
51 *tdpenvnsiy dprfqg*kasi tadtssntaf lqltsltsed tavyycar*gy*
101 *ngvyyamdy*w gqgttvtvss (SEQ ID NO:2)

Figure 6C: 18H10 VH CDR protein sequences dsyih (SEQ ID NO:3)
wtdpenvnsiydprfqg (SEQ ID NO:4)
gyngvyyamdy (SEQ ID NO:5)

Figure 6D: 18H10 VL nucleotide sequence

```
  1 caaattgttc tcacccagtc tccatcaatc atgtctgcgt ctctagggga
      q  i  v   l  t  q   s  p  s  i   m  s  a   s  l  g
 51 ggagatcacc ctaacctgca gtgccagctc gagtgtaatt tacatgcact
    e  e  i  t   l  t  c   s  a  s   s  s  v  i   y  m  h
101 ggtaccagca gaagtcaggc acttctccca aactcttgat ttataggaca
      w  y  q   q  k  s  g   t  s  p   k  l  l   i  y  r  t
151 tacaacctgg cttctggagt cccttctcgc ttcagtggca gtgggtctgg
      y  n  l   a  s  g   v  p  s  r   f  s  g   s  g  s
201 gacctttat tctctcacaa tcagcagtgt ggaggctgaa gatgctgccg
    g  t  f  y   s  l  t   i  s  s   v  e  a  e   d  a  a
251 attattactg ccatcagtgg agtagttttc cgtacacgtt cggagggggg
      d  y  y   c  h  q  w   s  s  f   p  y  t   f  g  g  g
301 accaagctgg aaatcaaacg g (SEQ ID NO:6)
      t  k  l   e  i  k   r (SEQ ID NO:7)
```

Figure 6E: 18H10 VL protein sequence 1 qivltqspsi msaslgeeit ltc*sasssvi ymh*wyqqksg tspklliy*rt*
51 *ynlas*gvpsr fsgsgsgtfy sltissveae daadyyc*hqw ssfpyt*fggg
101 tkleikr (SEQ ID NO:7)

Figure 6F: 18H10 VL CDR protein sequences sasssviymh (SEQ ID NO:8)
rtynlas (SEQ ID NO:9)
hqwssfpyt (SEQ ID NO:10)

16G7

Figure 13A: 16G7 VH nucleotide sequence

```
1    aggtgaaact gcaggagtct ggagctgagc tgatgaagcc tggggcctca
       v  k  l   q  e  s   g  a  e   l  m  k   p  g  a  s
51   gtgaagatat cctgcaaggc tactggctac aaattcagtg actactggat
       v  k  i   s  c  k   a  t  g  y  k  f  s   d  y  w
101  agagtggata aaacagaggc ctggacatgg ccttgagtgg attggagaga
     i  e  w  i   k  q  r   p  g  h   g  l  e  w   i  g  e
151  ttttgcctgg aagtggtagt actaactaca atgaggactt caaggacaag
      i  l  p   g  s  g  s   t  n  y   n  e  d   f  k  d  k
201  gccacattca cttcagatac atcctccaac acagcctaca tgcaactcag
       a  t  f   t  s  d   t  s  s  n   t  a  y   m  q  l
251  cagcctgaca tctgaagact ctgccgtcta ttactgtgca aaagaggaga
     s  s  l  t   s  e  d   s  a  v   y  y  c  a   k  e  e
301  gggcgtacta ctttggctat tggggccaag ggaccacggt caccgtctcc
      r  a  y   y  f  g  y   w  g  q   g  t  t   v  t  v  s
351  tca (SEQ ID NO:11)
       s (SEQ ID NO:12)
```

Figure 13B: 16G7 VH protein sequence

1 qvklqesgaelmkpgasvkisckatgykfs*dywie*wikqrpghglewig*e*
51 *ilpgsgstnynedfkd*katftsdtssntaymqlssltsedsavyycak*ee*
101 *rayyfgy*wgqgttvtvss (SEQ ID NO:12)

Figure 13C: 16G7 VH CDR protein sequences dywie (SEQ ID NO:13)
eilpgsgstnynedfkd (SEQ ID NO:14)
eerayyfgy (SEQ ID NO:15)

Figure 13D: 16G7 VL nucleotide sequence

```
1    gatgttttga tgacccaaac tccactctcc ctgcctgtca gtcttggaga
       d  v  l   m  t  q   t  p  l  s   l  p  v   s  l  g
51   tcaagcctcc atctcttgca ggtctagtca gagccttgaa aacagtaatg
     d  q  a  s   i  s  c   r  s  s   q  s  l  e   n  s  n
101  gaaacaccta tttgaactgg tacctccaga aaccaggcca gtctccacag
      g  n  t   y  l  n  w   y  l  q   k  p  g   q  s  p  q
151  ctcctgatct acagggtttc caaccgattt tctggggtcc tagacaggtt
       l  l  i   y  r  v   s  n  r  f   s  g  v   l  d  r
201  cagtggtagt ggatcaggga cagatttcac actgaaaatc agcagagtgg
     f  s  g  s   g  s  g   t  d  f   t  l  k  i   s  r  v
251  aggctgagga tttgggagtt tatttctgcc tccaagttac acatgtccct
      e  a  e   d  l  g  v   y  f  c   l  q  v   t  h  v  p
301  cccacgttcg gtgctgggac caagctggaa ctgaaacgg (SEQ ID NO:16)
       p  t  f   g  a  g   t  k  l  e   l  k  r (SEQ ID NO:17)
```

Figure 13E: 16G7 VL protein sequence

1 dvlmtqtplslpvslgdqasisc*rssqslensngntyln*wylqkpgqspq
51 lliy*rvsnrfs*gvldrfsgsgsgtdftlkisrveaedlgvyyfc*lqvthvp*
101 *pt*fgagtklelkr (SEQ ID NO:17)

Figure 13F: 16G7 VL CDR protein sequences rssqslensngntyln (SEQ ID NO:18)
rvsnrfs (SEQ ID NO:19)
lqvthvppt (SEQ ID NO:20)

15C1

Figure 18A: 15C1 VH nucleotide sequence

```
1    gatgtgcagc ttcaggagtc aggacctgac ctaatacaac cttctcagtc actttcactc acctgcactg
       d  v  q   l  q  e   s  g  p  d   l  i  q   p  s  q   s  l  s  l   t  c  t
71   tcactggcta ctccatcacc ggtggttata gctggcactg gatccggcag tttccaggaa acaaactgga
      v  t  g   y  s  i  t   g  g  y   s  w  h   w  i  r  q   f  p  g   n  k  l
141  atggatgggc tacatccact acagtggtta cactgacttc aacccctctc tcaaaactcg aatctctatc
      e  w  m  g   y  i  h   y  s  g   y  t  d  f   n  p  s   l  k  t   r  i  s  i
211  actcgagaca catccaagaa ccagttcttc ctgcagttga attctgtgac tactgaagac acagccacat
       t  r  d   t  s  k   n  q  f  f   l  q  l   n  s  v   t  t  e  d   t  a  t
281  attactgtgc aagaaaagat ccgtccgacg gatttcctta ctggggccaa gggactctgg tcactgtctc
      y  y  c   a  r  k  d   p  s  d   g  f  p   y  w  g  q   g  t  l   v  t  v
351  tgca (SEQ ID NO:21)
     s  a (SEQ ID NO:22)
```

Figure 18B: 15C1 VH protein sequence 1 dvqlqesgpd liqpsqslsl tctvtgysit *ggyswh*wirq fpgnklewmg
51 *yihysgytdf npslkt*risi trdtsknqff lqlnsvtted tatyycar*kd*
101 *psdgfpy*wgq gtlvtvsa (SEQ ID NO:22)

Figure 18C: 15C1 VH CDR protein sequences ggyswh (SEQ ID NO:23)
yihysgytdfnpslkt (SEQ ID NO:24)
kdpsdgfpy (SEQ ID NO:25)

Figure 18D: 15C1 VL nucleotide sequence

```
1    gacattgtga tgacccagtc tccagccacc ctgtctgtga ctccaggtga tagagtctct
       d  i  v   m  t  q   s  p  a  t   l  s  v   t  p  g   d  r  v  s
61   ctttcctgca gggccagcca gagtatcagc gaccacttac actggtatca acaaaaatca
       l  s  c   r  a  s   q  s  i  s   d  h  l   h  w  y   q  q  k  s
121  catgagtctc cacggcttct catcaaatat gcttcccatg ccatttctgg gatcccctcc
       h  e  s   p  r  l   l  i  k  y   a  s  h   a  i  s   g  i  p  s
181  aggttcagtg gcagtggatc agggacagat ttcactctca gcatcaaaag tgtggaacct
       r  f  s   g  s  g   s  g  t  d   f  t  l   s  i  k   s  v  e  p
241  gaagatattg gggtgtatta ctgtcaaaat ggtcacagtt ttccgctcac gttcggtgct
       e  d  i   g  v  y   y  c  q  n   g  h  s   f  p  l   t  f  g  a
301  gggaccaagc tggagctgaa a (SEQ ID NO:26)
       g  t  k   l  e  l   k (SEQ ID NO:27)
```

Figure 18E: 15C1 VL protein sequence 1 divmtqspat lsvtpgdrvs lsc*rasqsis dhlh*wyqqks hesprllik*y*
51 *ashais*gips rfsgsgsgtd ftlsiksvep edigvyyc*qn ghsfplt*fga
101 gtklelkr (SEQ ID NO:27)

Figure 18F: 15C1 VL CDR protein sequences rasqsisdhlh (SEQ ID NO:28)
yashais (SEQ ID NO:29)
qnghsfplt (SEQ ID NO:30)

Figure 25A: 7E3 VH nucleotide sequence

```
1   caggttactc tgaaagagtc tggccctggg atattgcagc cctcccagac cctcagtctg acttgttctt
      q  v  t   l  k  e   s  g  p  g   i  l  q   p  s  q   t  l  s  l   t  c  s
71  tctctgggtt ttcactgacc acttataata taggagtagg ctggattcgt cagccttcag ggaagggtct
      f  s  g   f  s  l  t   t  y  n   i  g  v   g  w  i  r   q  p  s   g  k  g
141 ggagtggctg gcacacattt ggtggaatga taatatttac tataatacag tccttaagag ccgactcaca
    l  e  w  l   a  h  i   w  w  n   d  n  i  y   y  n  t   v  l  k   s  r  l  t
211 ttctccaagg atacctccaa caaccaggtt ttcctcaaga tcgccagtgt ggacattgca gatactgcca
      f  s  k   d  t  s   n  n  q  v   f  l  k   i  a  s   v  d  i  a   d  t  a
281 catattactg tattcgaatg gctgagggaa ggtacgacgc tatggactac tggggtcaag gaacctcagt
      t  y  y   c  i  r  m   a  e  g   r  y  d   a  m  d  y   w  g  q   g  t  s
351 caccgtctcc tca (SEQ ID NO:31)
    v  t  v  s   s (SEQ ID NO:32)
```

Figure 25B: 7E3 VH protein sequence

```
1   qvtlkesgpg ilqpsqtlsl tcsfsgfslt tynigvgwir qpsgkglewl
51  ahiwwndniy yntvlksrlt fskdtsnnqv flkiasvdia dtatyycirm
101 aegrydamdy wgqgtsvtvs s (SEQ ID NO:32)
```

Figure 25C: 7E3 VH CDR protein sequences tynigvg (SEQ ID NO:33)
hiwwndniyyntvlks (SEQ ID NO:34)
maegrydamdy (SEQ ID NO:35)

Figure 25D: 7E3 VL nucleotide sequence

```
1   gctatccaga tgacacagag tacatcctcc ctgtctgcct ctctgggaga cagagtcacc atcaattgca
      a  i  q   m  t  q   s  t  s  s   l  s  a   s  l  g   d  r  v  t   i  n  c
71  gggcaagtca ggacatcacc aattatttaa attggtatca gcagaaacca gatggaactg tcagactcct
      r  a  s   q  d  i  t   n  y  l   n  w  y   q  q  k  p   d  g  t   v  r  l
141 gatctattat acatcaaaat tacactcagg agccccatca aggttcagtg gccgtgggtc tggaacagat
    l  i  y  y   t  s  k   l  h  s   g  a  p  s   r  f  s   g  r  g   s  g  t  d
211 tattctctca ccattagtaa cctggagcaa gaggatattg ccacttactt ttgccaacag ggtaatacgt
      y  s  l   t  i  s   n  l  e  q   e  d  i   a  t  y   f  c  q  q   g  n  t
281 ttccgtggac gttcggtgga ggcaccaaac tggaaatcaa acgt (SEQ ID NO: 36)
      f  p  w   t  f  g  g   g  t  k   l  e  i   k  r (SEQ ID NO:37)
```

Figure 25E: 7E3 VL protein sequence

```
1   aiqmtqstss lsaslgdrvt incrasqdit nylnwyqqkp dgtvrlliyy
51  tsklhsgaps rfsgrgsgtd ysltisnleq ediatyfcqq gntfpwtfgg
101 gtkleikr (SEQ ID NO:37)
```

Figure 25F: 7E3 VL CDR protein sequences rasqditnyln (SEQ ID NO:38)
ytsklhs (SEQ ID NO:39)
qqgntfpwt (SEQ ID NO:40)

MD-1 nucleic acid sequence:

```
1   ggcacgagcg gcacgagccc accatgaagg gtttcacagc cactctcttc ctctggactc
61  tgatttttcc cagctgcagt ggaggcggcg gtgggaaagc ctggcccaca cacgtggtct
121 gtagcgacag cggcttggaa gtgctctacc agagttgcga tccattacaa gattttggct
181 tttctgttga aaagtgttcc aagcaattaa aatcaaatat caacattaga tttggaatta
241 ttctgagaga ggacatcaaa gagctttttc ttgacctagc tctcatgtct caaggctcat
301 ctgttttgaa tttctcctat cccatctgtg aggcggctct gcccaagttt tctttctgtg
361 gaagaaggaa aggagagcag atttactatg ctgggcctgt caataatcct gaatttacta
421 ttcctcaggg agaataccag gttttgctgg aactgtacac tgaaaaacgg tccaccgtgg
481 cctgtgccaa tgctactatc atgtgctcct gactgtggcc tgtagcaaaa atcacagcca
541 gctgcatctc gtgggacctc caagctcctc tgactgaacc tacgtgggag gagaagcagt
601 ctgatgacag agagaggctc tacaaagaag cgcccccaaa gagtgcagct gctaatttta
661 gtcccaggac cagacatccc cagactccac agatgtaatg aagtccccga atgtatctgt
721 ttctaaggag cctcttggca gtccttaagc agtcttgagg gtccatcctt tttctctaat
781 tggtcgcctc ccaccagact cacctgcttt tcaacttttt aggagtgctt cctcacagtt
841 accaagaata aagaaagctg gccacc (SEQ ID NO:41)
```

Figure 32B

MD-1 amino acid sequence:

```
1   mkgftatlfl wtlifpscsg ggggkawpth vvcsdsglev lyqscdplqd fgfsvekcsk
61  qlksninirf giilredike lfldlalmsq gssvlnfsyp iceaalpkfs fcgrrkgeqi
121 yyagpvnnpe ftipqgeyqv llelytekrs tvacanatim cs (SEQ ID NO:42)
```

Figure 33A

MD-2 nucleic acid sequence:

```
1   ggcgggccgc tcccacttcg gcacgagggg cacgaggtaa atcttttctg cttactgaaa
61  aggaagagtc tgatgattag ttactgatcc tctttgcatt tgtaaagctt tggagatatt
121 gaatcatgtt accatttctg tttttttcca ccctgttttc ttccatattt actgaagctc
181 agaagcagta ttgggtctgc aactcatccg atgcaagtat ttcatacacc tactgtgata
241 aaatgcaata cccaatttca attaatgtta acccctgtat agaattgaaa ggatccaaag
301 gattattgca cattttctac attccaagga gagatttaaa gcaattatat ttcaatctct
361 atataactgt caacaccatg aatcttccaa agcgcaaaga agttatttgc cgaggatctg
421 atgacgatta ctctttttgc agagctctga agggagagac tgtgaataca acaatatcat
481 tctccttcaa gggaataaaa ttttctaagg gaaaatacaa atgtgttgtt gaagctattt
541 ctgggagccc agaagaaatg ctcttttgct tggagtttgt catcctacac caacctaatt
601 caaattagaa taaattgagt attt (SEQ ID NO:43)
```

Figure 33B

MD-2 amino acid sequence:

```
1   MLPFLFFSTL FSSIFTEAQK QYWVCNSSDA SISYTYCDKM QYPISINVNP CIELKGSKGL
61  LHIFYIPRRD LKQLYFNLYI TVNTMNLPKR KEVICRGSDD DYSFCRALKG ETVNTTISFS
121 FKGIKFSKGK YKCVVEAISG SPEEMLFCLE FVILHQPNSN (SEQ ID NO:44)
```

| | Myc (TLR4) | FLAG (MD-2) | 15C1 | 7E3 | HTA 125 |
|---|---|---|---|---|---|
| WT | ++ | ++ | ++ | ++ | ++ |
| MHHH | ++ | ++ | ++ | ++ | - |
| MMHH | ++ | ++ | - | - | - |
| MHMH | +/- | - | - | - | - |
| HHHM | + | + | + | + | + |

A
| Myc (TLR4) | FLAG (MD-2) | 15C1 | 7E3 |
|---|---|---|---|
| ++ | ++ | + | - |
| ++ | ++ | - | + |
TLR4
MMHH a
MMHH b
B
Myc (TLR4)
FLAG (MD-2)
15C1
7E3
MMHH a
MMHH b
ge031204.003
ge031204.004
ge031204.021
ge031204.022
ge031204.009
ge031204.010
ge031204.015
ge031204.016
Counts
FL4-H

A

```
                                                                                        (SEQ ID NO: 80)
                 1 2         3    4       5    6   7   8   9 10   11   12 13  14        15  16    17   18 19 20
Human 289 RLAYLDYYLDDIIDLFNCLTNVSSFSLVSVTIERVKDFSYNFGWQHLELVNCKFGQFPTLKLKSLKRLTFTSNKGGNAFSEVDLPSL 375
          RL Y + + DDI+  F+CL NVS+ SL  V+I+ ++D   +F WQ L ++ C+  QFPTL L  LK LT T NKG  +F +V LPSL
Mouse 288 RLTYTNDFSDDIVK-FHCLANVSAMSLAGVSIKYLEDVPKHFKWQSLSIIRCQLKQFPTLDLPFLKSLTLTMNKGSISFKKVALPSL 373
                                                                                        (SEQ ID NO: 81)
```

B

A

```
                 1  2 3         4     5     6789      101112   13 14
Human      19 QKQYWVCNSSDASISYTYCDKMCYPISINVNPCIELKGS 57 (SEQ ID NO: 82)
              +KQ W CNSSDA ISY+YCD +++PISI+  PCI L+G+
Mouse      19 EKQQWFCNSSDAIISYSYCDHLKFPISISSEPCIRLRGT 57 (SEQ ID NO: 83)
```

```
  1 mmsasrlagt lipamaflsc vrpeswepcv evvpnityqc melnfykipd nlpfstknld
 61 lsfnplrhlg sysffsfpel qvldlsrcei qtiedgayqs lshlstlilt gnpiqslalg
121 afsglsslqk lvavetnlas lenfpighlk tlkelnvahn liqsfklpey fsnltnlehl
181 dlssnkiqsi yctdlrvlhq mpllnlsldl slnpmnfiqp gafkeirlhk ltlrnnfdsl
241 nvmktciqgl aglevhrlvl gefrnegnle kfdksalegl cnltieefrl ayldyylddi
301 idlfncltnv ssfslvsvti ervkdfsynf gwqhlelvnc kfgqfptlkl kslkrltfts
361 nkggnafsev dlpslefldl srnglsfkgc csqsdfgtts lkyldlsfng vitmssnflg
421 leqlehldfq hsnlkqmsef svflslrnli yldishthtr vafngifngl sslevlkmag
481 nsfqenflpd iftelrnltf ldlsqcqleq lsptafnsls slqvlnmshn nffsldtfpy
541 kclnslqvld yslnhimtsk kqelqhfpss laflnltqnd factcehqsf lqwikdqrql
601 lvevermeca tpsdkqgmpv lslnitcqmn ktiigvsvls vlvvsvvavl vykfyfhlml
661 lagcikygrg eniydafviy ssqdedwvrn elvknleegv ppfqlclhyr dfipgvaiaa
721 niihegfhks rkvivvvsqh fiqsrwcife yeiaqtwqfl ssragiifiv lqkvektllr
781 qqvelyrlls rntyleweds vlgrhifwrr lrkalldgks wnpegtvgtg cnwqeatsi
```

(SEQ ID NO:54)

NEUTRALIZING ANTIBODIES AND METHODS OF USE THEREOF

RELATED APPLICATION

This application is a continuation-in-part of U.S. patent application Ser. No. 11/009,939, filed Dec. 10, 2004, now issued as U.S. Pat. No. 7,312,320, which claims the benefit of U.S. Provisional Application No. 60/528,812, filed Dec. 10, 2003; of U.S. Provisional Application No. 60/528,811, filed Dec. 10, 2003; and of U.S. Provisional Application No. 60/528,962, filed Dec. 10, 2003; each of which is incorporated herein by reference in its entirety.

FIELD OF THE INVENTION

This invention relates generally to the generation of neutralizing monoclonal antibodies, e.g., humanized monoclonal antibodies, that recognize the Toll-like Receptor 4/MD-2 receptor complex, to monoclonal antibodies, e.g., humanized monoclonal antibodies, that recognize both the Toll-like Receptor 4/MD-2 receptor complex and Toll-like Receptor 4 when not complexed with MD-2, and to methods of using the monoclonal antibodies as therapeutics.

BACKGROUND OF THE INVENTION

Toll receptors, first discovered in *Drosophila*, are type I transmembrane protein having leucine-rich repeats (LRRs) in the extracellular portion of the protein, and one or two cysteine-rich domains. The mammalian homologs of the *Drosophila* Toll receptors are known as "Toll-like receptors" (TLRs). TLRs play a role in innate immunity by recognizing microbial particles and activating immune cells against the source of these microbial particles.

Currently, ten types of Toll-like receptors have been identified in humans, TLRs 1-10. These TLRs are characterized by the homology of their intracellular domains to that of the IL-1 receptor, and by the presence of extracellular leucine-rich repeats. The different types of TLRs are activated by different types of microbial particles. For example, TLR4 is primarily activated by lipopolysaccharide (LPS), while TLR2 is activated by lipoteichoic (LTA), lipoarabinomannan (LAM); lipoprotein (BLP), and peptideglycans (PGN). Toll receptor homologs, such as RP105, have also been identified.

Myeloid differentiation protein-2 (MD-2), a TLR4 accessory protein, has been identified and characterized. This protein has been found to interact directly with TLR4, and MD-2 has the ability to enable post-translational modifications of TLR4, as well as facilitate its transport to the cell surface. TLR4 and MD-2 form a complex on the cell surface.

Lipopolysaccharide (LPS), a component of gram-negative bacteria, is a microbial particle capable of strongly activating the innate immune system. LPS delivers signals to immune cells via its multi-chain receptor, comprising the TLR4/MD-2 complex as the principle signaling component.

Accordingly, there exists a need for methods and compositions that modulate signaling that is mediated by the TLR4/MD-2 complex.

SUMMARY OF THE INVENTION

The invention provides monoclonal antibodies recognizing the TLR4/MD-2 receptor expressed on the cell surface. The antibodies are capable of blocking, e.g., neutralizing, LPS-induced pro-inflammatory cytokine production. The monoclonal antibody is, e.g., a humanized antibody. Antibodies of the invention include antibodies that bind the human TLR4/MD-2 receptor complex and also bind TLR4 independently of the presence of MD-2. Antibodies of the invention also include antibodies that bind the TLR4 portion of the human TLR4/MD-2 receptor complex, but binding is entirely dependent on the presence of MD-2. In addition, antibodies of the invention include antibodies that bind the human TLR4/MD-2 receptor complex and also bind MD-2 but only in the presence of TLR4.

Exemplary antibodies of the invention include, for example, the 18H10 antibody, the 16G7 antibody, the 15C1 antibody and the 7E3 antibody. These antibodies show specificity for the human TLR4/MD-2 receptor complex, and they have been shown to inhibit receptor activation and subsequent intracellular signaling via LPS. These antibodies have distinct specificities. For example, 15C1 binds TLR4 independently of the presence of MD-2, 7E3 binds to TLR4, but binding is dependent on the presence of MD-2, and 18H10 binds to MD-2, but requires the presence of TLR4, as the MAb does not bind soluble forms of MD-2.

As used herein, the terms "16G7", "mu16G7", "7E3", "mu7E3", "15C1", "mu15C1", "18H10" or "mu18H10" refer to the murine monoclonal antibody, and the terms "hu7E3", "hu15C1", or "hu18H10" refer to the humanized monoclonal antibody.

The murine monoclonal antibodies of the invention contain a heavy chain variable region having the amino acid sequence of SEQ ID NOS: 2, 12, 22 or 32 and a light chain variable region having the amino acid sequence of SEQ ID NOS: 7, 17, 27 or 37. The three heavy chain CDRs include an amino acid sequence at least 90%, 92%, 95%, 97% 98%, 99% or more identical a sequence selected from the group consisting of DSYIH (SEQ ID NO:3); WTDPENVNSIYDPRFQG (SEQ ID NO:4), GYNGVYYAMDY (SEQ ID NO:5); DYWIE (SEQ ID NO:13); EILPGSGSTNYNEDFKD (SEQ ID NO:14); EERAYYFGY (SEQ ID NO:15); GGYSWH (SEQ ID NO:23); YIHYSGYTDFNPSLKT (SEQ ID NO:24); KDPSDGFPY (SEQ ID NO:25); TYNIGVG (SEQ ID NO:33); HIWWNDNIYYNTVLKS (SEQ ID NO:34); and MAEGRYDAMDY (SEQ ID NO:35) and a light chain with three CDR that include an amino acid sequence at least 90%, 92%, 95%, 97% 98%, 99% or more identical to a sequence selected from the group consisting of the amino acid sequence of SASSSVIYMH (SEQ ID NO:8); RTYNLAS (SEQ ID NO:9); HQWSSFPYT (SEQ ID NO:10); RSSQSLENSNGNTYLN (SEQ ID NO:18); RVSNRFS (SEQ ID NO:19); LQVTHVPPT (SEQ ID NO:20); RASQSISDHLH (SEQ ID NO:28); YASHAIS (SEQ ID NO:29); QNGHSFPLT (SEQ ID NO:30); RASQDITNYLN (SEQ ID NO:38); YTSKLHS (SEQ ID NO:39); and QQGNTFPWT (SEQ ID NO:40). The antibody binds to the TLR4/MD-2 complex, to TLR4 when not complexed with MD-2, or to both.

The humanized antibodies of the invention contain a heavy chain variable region having the amino acid sequence of SEQ ID NOS: 45, 46, 49, 51 and 52. The humanized antibodies of the invention contain a light chain variable region having the amino acid sequence of SEQ ID NOS: 47, 48 50, and 53. The three heavy chain CDRs include an amino acid sequence at least 90%, 92%, 95%, 97% 98%, 99% or more identical a sequence selected from the group consisting of GGYSWH (SEQ ID NO:23); YIHYSGYTDFNPSLKT (SEQ ID NO:24); KDPSDGFPY (SEQ ID NO:25); DSYIH (SEQ ID NO:3); WTDPENVNSIYDPRFQG (SEQ ID NO:4), GYNGVYYAMDY (SEQ ID NO:5); TYNIGVG (SEQ ID NO:33); HIWWNDNIYYNTVLKS (SEQ ID NO:34); and MAEGRYDAMDY (SEQ ID NO:35). The three light chain CDRs include an amino acid sequence at least 90%, 92%, 95%, 97% 98%, 99% or more identical to a sequence selected from the group consisting of the amino acid sequence of RASQSISDHLH (SEQ ID NO:28); YASHAIS (SEQ ID NO:29); QNGHSFPLT (SEQ ID NO:30); SASSSVIYMH (SEQ ID NO:8); RTYNLAS (SEQ ID NO:9); HQWSSFPYT (SEQ ID NO:10); RASQDITNYLN (SEQ ID NO:38); YTSKLHS (SEQ ID NO:39); and QQGNTFPWT (SEQ ID NO:40). The antibody binds to the TLR4/MD-2 complex, to TLR4 when not complexed with MD-2, or to both.

Antibodies of the invention immunospecifically bind a TLR4/MD-2 complex, wherein the antibody binds to an epitope that includes one or more amino acid residues on human TLR4 between residues 289 and 375 of SEQ ID NO:54. For example, the antibody specifically binds to an epitope that includes residues selected from the group consisting of at least residues 293 through 295 of SEQ ID NO:54; at least residues 296 and 297 of SEQ ID NO:54; at least residues 319 through 321 of SEQ ID NO:54; at least residues 328 and 329 of SEQ ID NO:54; at least residues 349 through 351 of SEQ ID NO:54; and at least residues 369 through 371 of SEQ ID NO:54. For example, the antibody specifically binds to an epitope that contains at least residues 328, 329, 349 through 351 and 369 through 371 of SEQ ID NO:54. In another example, the antibody specifically binds to an epitope that includes at least residues 293 through 295, 296, 297 and 319 through 321 of SEQ ID NO:54.

Antibodies of the invention bind the TLR4/MD2 complex, wherein the antibody binds to an epitope on human MD-2 between residues 19 and 57 of SEQ ID NO:44. For example, the antibody specifically binds to an epitope that contains at least residues 53 of SEQ ID NO:44.

Antibodies of the invention also include humanized antibodies that immunospecifically bind a TLR4/MD-2 complex, wherein the antibody exhibits greater than 50% inhibition of lipopolysaccharide (LPS)-induced pro-inflammatory cytokine production in human TLR4/MD-2 transfected HEK293 cells at a concentration of 1 μg/ml. For example, antibodies of the invention exhibit greater than 55%, 60%, 65%, 70%, 75%, 80%, 85%, 90%, 92%, 95%, 97%, 98%, or 99% inhibition of LPS-induced pro-inflammatory cytokine production in human TLR4/MD-2 transfected HEK293 cells at a concentration of 1 μg/ml. As used herein, the term "pro-inflammatory cytokine" refers to those immunoregulatory cytokines that promote inflammation and/or are associated with inflammation. Pro-inflammatory cytokines, include, for example, IL-6, IL-8, TNF-alpha, IL1-alpha, IL1-beta, IFN-alpha, IFN-beta, IFN-gamma, IL-10, IL12, IL-23, IL17, and IL18.

Antibodies of the invention, for example, inhibit LPS-induced pro-inflammatory cytokine production at least two-fold, five-fold, 10-fold, 20-fold, 50-fold, 75-fold, or 100-fold more than the commercially available, anti-TLR4 non-blocking monoclonal antibody HTA125.

The present invention also provides methods of treating or preventing pathologies associated with aberrant TLR4/MD-2 activation and/or aberrant LPS activity (e.g., aberrant pro-inflammatory cytokine production such as aberrant IL-8 production), or alleviating a symptom associated with such pathologies, by administering a monoclonal antibody of the invention (e.g., a murine monoclonal or humanized monoclonal antibody) to a subject in which such treatment or prevention is desired. The subject to be treated is, e.g., human. The monoclonal antibody is administered in an amount sufficient to treat, prevent or alleviate a symptom associated with the pathology. The amount of monoclonal antibody sufficient to treat or prevent the pathology in the subject is, for example, an amount that is sufficient to reduce LPS-induced production of one or more pro-inflammatory cytokines (e.g., IL-8). As used herein, the term "reduced" refers to a decreased production of a pro-inflammatory cytokine in the presence of a monoclonal antibody of the invention, wherein the production is, for example, local pro-inflammatory cytokine production (e.g., at a site of inflamed tissue) or systemic pro-inflammatory cytokine production. LPS-induced production of a pro-inflammatory cytokine such as IL-8 is decreased when the level of pro-inflammatory cytokine (e.g., IL-8) production in the presence of a monoclonal antibody of the invention is greater than or equal to 5%, 10%, 20%, 25%, 30%, 40%, 50%, 60%, 70%, 75%, 80%, 90%, 95%, 99%, or 100% lower than a control level of pro-inflammatory cytokine production (i.e., the level of pro-inflammatory cytokine production in the absence of the monoclonal antibody). Level of pro-inflammatory cytokine production (e.g., IL-8 or IL-6) is measured, e.g., using the human whole blood or huTLR4/MD2 transfected HEK293 cellular assays described herein. Those skilled in the art will appreciate that the level of pro-inflammatory cytokine production can be measured using a variety of assays, including, for example, commercially available ELISA kits.

Pathologies treated and/or prevented using the monoclonal antibodies of the invention (e.g., a murine monoclonal or humanized monoclonal antibody) include, for example, sepsis induced by microbial products, acute inflammation, chronic inflammation (e.g., chronic inflammation associated with allergic conditions and asthma), autoimmune diseases (e.g., IBD and atherosclerosis) and diseases in which mechanical stress induces the expression of endogenous soluble stress factors (e.g., Hsp60, fibronectin, heparan sulphate, hyaluronan, gp96, β-Defensin-2 and surfactant protein A). Pathologies in which mechanical stress induces the expression of endogenous soluble stress factors include, for example, osteoarthritis and rheumatoid arthritis. Pathologies associated with mechanical stress can also occur in subjects and patients placed on respirators, ventilators and other respiratory-assist devices. Such pathologies include, for example, ventilator-induced lung injury ("VILI"), also referred to as ventilation-associated lung injury ("VALI").

Pharmaceutical compositions according to the invention can include an antibody of the invention and a carrier. These pharmaceutical compositions can be included in kits, such as, for example, diagnostic kits.

The present invention also provides soluble chimeric toll receptor proteins (also referred to herein as toll-like receptor proteins), methods for expressing toll receptor proteins, and methods for purifying such proteins in a soluble form.

The present invention provides chimeric polypeptides in which a toll-like receptor polypeptide, or a biologically active derivative thereof, is operably linked to an MD accessory polypeptide, or a biologically active derivative thereof. The toll-like receptor polypeptide is a polypeptide selected from the group consisting of TLRs 1-10 and RP105.

The MD accessory polypeptide is, for example, MD-1 or MD-2. The toll-like receptor polypeptide is, in some instances, operably linked to the MD accessory polypeptide using a flexible glycine-serine linker, which renders the toll receptor both stable during expression and soluble during purification. For example, a chimeric polypeptide of the invention includes the extracellular portion of a toll receptor fused at its C terminus to the N terminus of a mature MD protein (i.e., MD-1 or MD-2) via a flexible glycine/serine linker.

The present invention also provides methods for producing soluble chimeric fusion proteins by coupling a toll-like receptor polypeptide, or a biologically active derivative thereof, to an MD accessory polypeptide, or a biologically active derivative thereof. The present invention also provides methods for producing soluble chimeric fusion proteins by constructing a vector that includes a nucleic acid sequence encoding a toll-like receptor polypeptide (or a biologically active derivative thereof) coupled to a nucleic acid sequence encoding an MD accessory polypeptide (or a biologically active derivative thereof); transfecting a cell with this vector; culturing the cell under conditions that permit production of a fusion protein having a toll-like receptor polypeptide coupled to an MD accessory polypeptide; and isolating that fusion protein. The MD accessory polypeptide is, for example, MD-1 or MD-2, and the toll-like receptor polypeptide can be a polypeptide selected from the group consisting of TLRs 1-10 and RP105. The toll-like receptor polypeptide is operably linked to the MD accessory polypeptide by a flexible glycine-serine linker, which renders the toll receptor both stable during expression and soluble during purification.

The present invention also provides methods of treating or preventing pathologies associated with aberrant toll-like receptor function, or alleviating a symptom associated with these pathologies, by administering a soluble chimeric polypeptide of the invention to a subject in which such treatment or prevention or alleviation is desired in an amount sufficient to treat or prevent or alleviate the pathology, or a symptom thereof, in the subject. The subject to be treated is, e.g., human. The amount of soluble chimeric polypeptide sufficient to treat or prevent the pathology in the subject is an amount that is sufficient to modulate (e.g., reduce or prevent) the activation of a toll-like receptor in the subject to be treated. Activation of a toll-receptor is reduced or decreased when the level of toll-receptor activation in the presence of a chimeric protein of the invention is greater than or equal to 5%, 10%, 20%, 25%, 30%, 40%, 50%, 60%, 70%, 75%, 80%, 90%, 95%, 99%, or 100% lower than a control level of toll-like receptor activation (i.e., the level of activation the absence of the chimeric protein). The level of toll-receptor activation is measured using any of a variety of techniques known in the art. For example, the level of TLR4 activation can be measured by detecting the level of LPS-induced IL-8 production. Those skilled in the art will appreciate that the level of toll-receptor activation can also be measured, for example, by detecting activation, if any, of NF-kappa B or JNK (c-jun terminal kinase), which initiate the transcription of genes encoding pro-inflammatory cytokines (e.g., IL1-alpha, IL1-beta, IL6, and TNF-alpha). Activation of JNK and/or NF-kappa B can be detected by measuring the levels of one or more pro-inflammatory cytokines.

In some embodiments, the pathology to be treated is sepsis, acute inflammation, chronic inflammation or an autoimmune disease. For example, the pathology is any one of a variety of types of arthritis.

The present invention also includes antibodies that immunospecifically bind to the soluble chimeric polypeptides of the invention, such as, for example, monoclonal antibodies or humanized antibodies.

Pharmaceutical compositions according to the invention can include a soluble chimeric polypeptide of the invention and a carrier, and/or an antibody of the invention and a carrier. These pharmaceutical compositions can be included in kits, such as, for example, diagnostic kits.

The invention also provides methods of screening for a ligand that binds a toll-like receptor and modulates toll-like receptor activity. According to these methods of the invention, these ligands are identified by providing a chimeric polypeptide of the invention that has a property or function that is ascribable to that polypeptide; contacting the chimeric polypeptide with a candidate compound; and determining whether the candidate compound alters the property or function ascribable to the polypeptide, wherein an alteration in the property or function ascribable to the polypeptide in the presence of the candidate compound indicates that the candidate compound is a ligand that modulates toll-like receptor activity.

One skilled in the art will appreciate that the chimeric polypeptides and antibodies of the invention have a variety of uses. For example, the chimeric proteins of the invention are used as therapeutic agents to prevent the activation of TLRs in disorders such as, for example, sepsis, acute inflammation, chronic inflammation, autoimmune diseases and various forms of arthritis. The chimeric proteins of the invention are also used as immunogens in more efficient methods of generating binding and blocking anti-TLR antibodies, and/or these chimeric polypeptides can be used as reagents in assays that screen for small molecular weight binders and blockers of TLRs activity. The chimeric proteins and/or antibodies of the invention are also used as reagents in diagnostic kits or as diagnostic tools, or these chimeric proteins and/or antibodies can be used in competition assays to generate therapeutic reagents.

μg/ml) followed by purified MAb at the indicated concentration and anti-mouse IgG (H+L) HRP.

FIG. 5B is a graph demonstrating that MD-2 must be associated with TLR4 for the mu18H10 antibody to recognize it. Lysates (Panel 1, i.e., upper panel) or supernatants (Panel 2, i.e., lower panel) from HEK 293 cells, transiently transfected as indicated, were incubated in wells coated with anti-FLAG M2. Binding of a biotinylated form of mu18H10 was detected using streptavidin-HRP. Biotinylated 12D4 (an anti-TLR4 MAb) with streptavidin-HRP or a polyclonal rabbit Ab raised against soluble MD-2 with an anti rabbit IgG-HRP controlled the presence of TLR4 and MD-2 respectively. In this experiment, TLR4 had a FLAG tag at the N-terminus and was expressed using the vector pCNDA3.1(−)hygro (Invitrogen). MD-2 had FLAG and 6× Histidine tags at the C terminus and was expressed using the vector pCDNA3 (Invitrogen). Mock cells were transfected with empty plasmid.

FIGS. 6A-6F are a series of illustrations depicting the VH nucleotide sequence (SEQ ID NO:1) (FIG. 6A), the VH amino acid sequence (SEQ ID NO:2) (FIG. 6B), the VL nucleotide sequence (SEQ ID NO:6) (FIG. 6D), and the VL amino acid sequence (SEQ ID NO:7) for mu18H10 (FIG. 6E). The VH complementarity determining regions (CDRs) (SEQ ID NOs:3, 4 and 5) (FIG. 6C) and the VL CDRs (SEQ ID NOs: 8, 9 and 10) (FIG. 6F) are highlighted in the underlined, italic text in FIGS. 6B and 6E.

Figure 7:
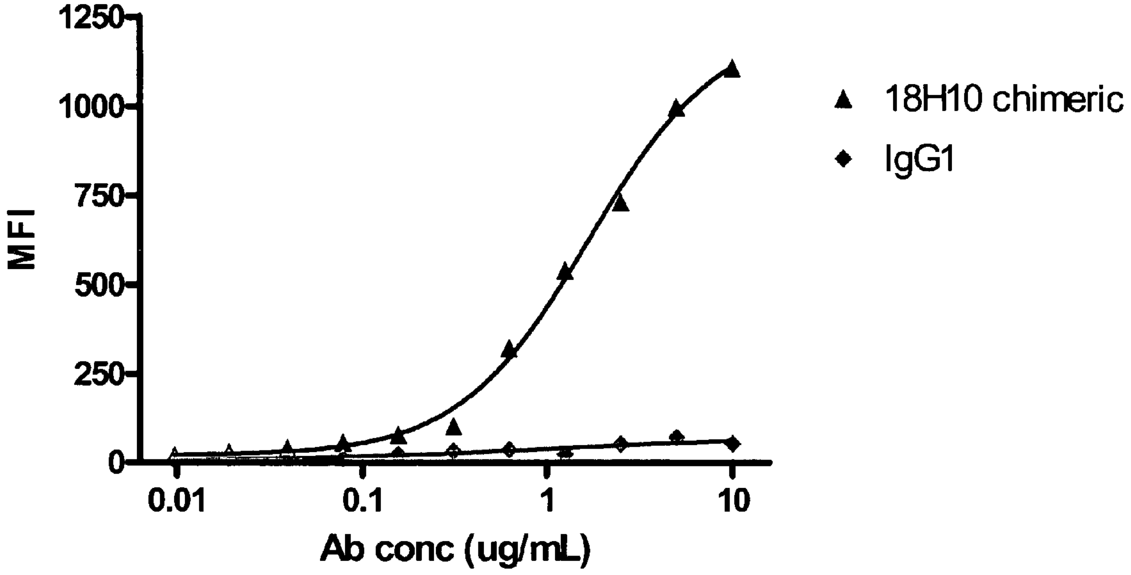

FIG. 7 is a graph depicting that the VH and VL nucleotide sequence of mu18H10 expressed as a chimeric MAb ("chimeric 18H10") is capable of binding specifically to the human TLR4/MD-2 complex on the surface of transfected CHO cells. MAb binding to the TLR4/MD-2 transfected CHO cells is shown by flow cytometry using chimeric 18H10 or an isotype matched control MAb at the concentrations indicated.

Figure 8:
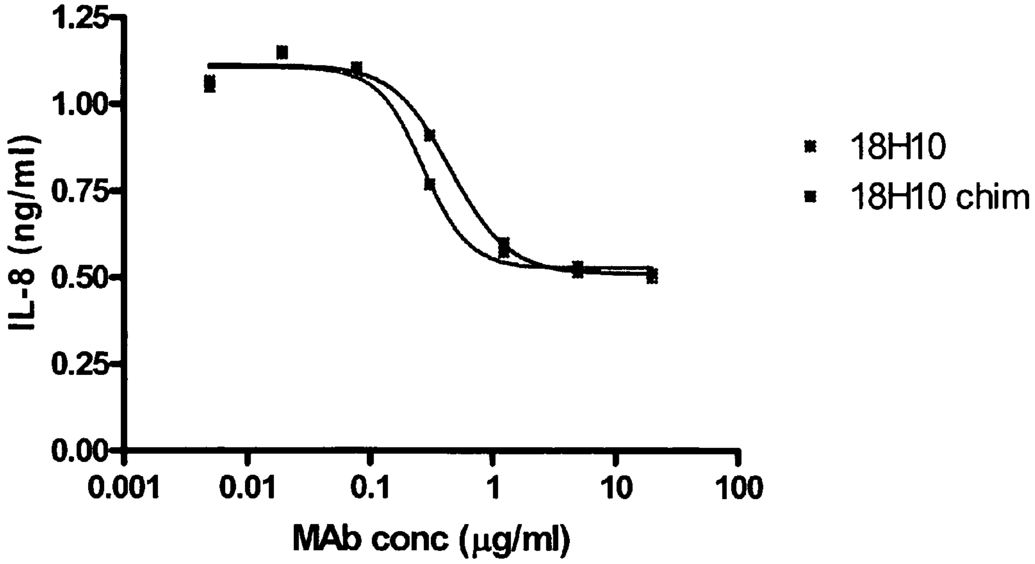

FIG. 8 is a graph depicting inhibition of lipopolysaccharide (LPS)-induced IL-8 production in TLR4/MD-2 transfected HEK 293 cells by the chimeric 18H10 MAb. Cells were incubated with mu18H10, or chimeric 18H10 at the indicated concentrations and subsequently incubated with LPS (15 ng/ml). IL-8 levels were assessed 16 hours post LPS-treatment. Inhibition of LPS-induced IL-8 production by the chimeric 18H10 was similar to the inhibition by the 18H10 mouse MAb of the invention.

Figure 9:
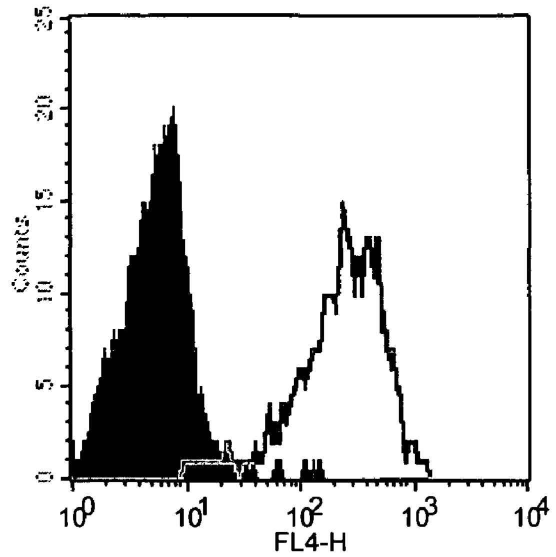

FIG. 9 is a graph depicting the binding of a murine monoclonal antibody, referred to herein as "16G7", to the TLR4/MD-2 complex. Specificity of binding is shown by flow cytometry using mock-transfected or TLR4/MD-2 transfected cells. The results using mock transfected cells are shown in the filled graph (left), while the results using TLR4/MD-2 transfected cells are shown as in the outline graph (right).

Figure 10:
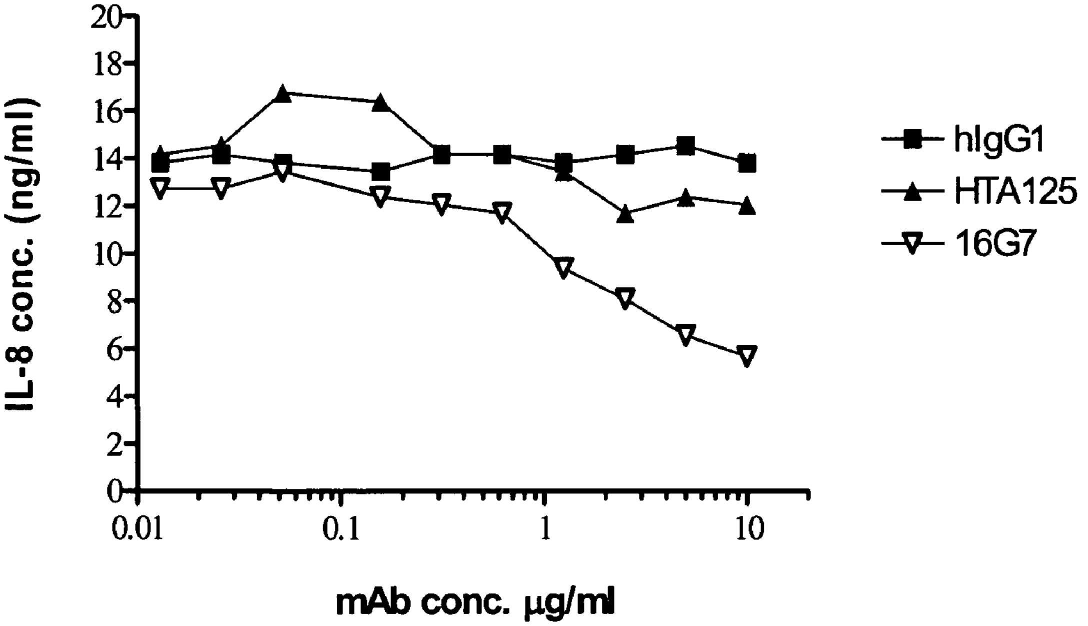

FIG. 10 is a graph depicting inhibition of lipopolysaccharide (LPS)-induced IL-8 production in TLR4/MD-2 transfected HEK 293 cells by the monoclonal antibody mu16G7. The cells were incubated with the mu16G7 monoclonal antibody, the HTA 125 anti-TLR4 MAb or an antibody control at the indicated concentrations and subsequently incubated with LPS (15 ng/ml). IL-8 levels were assessed 16 hours post LPS treatment.

Figure 11:
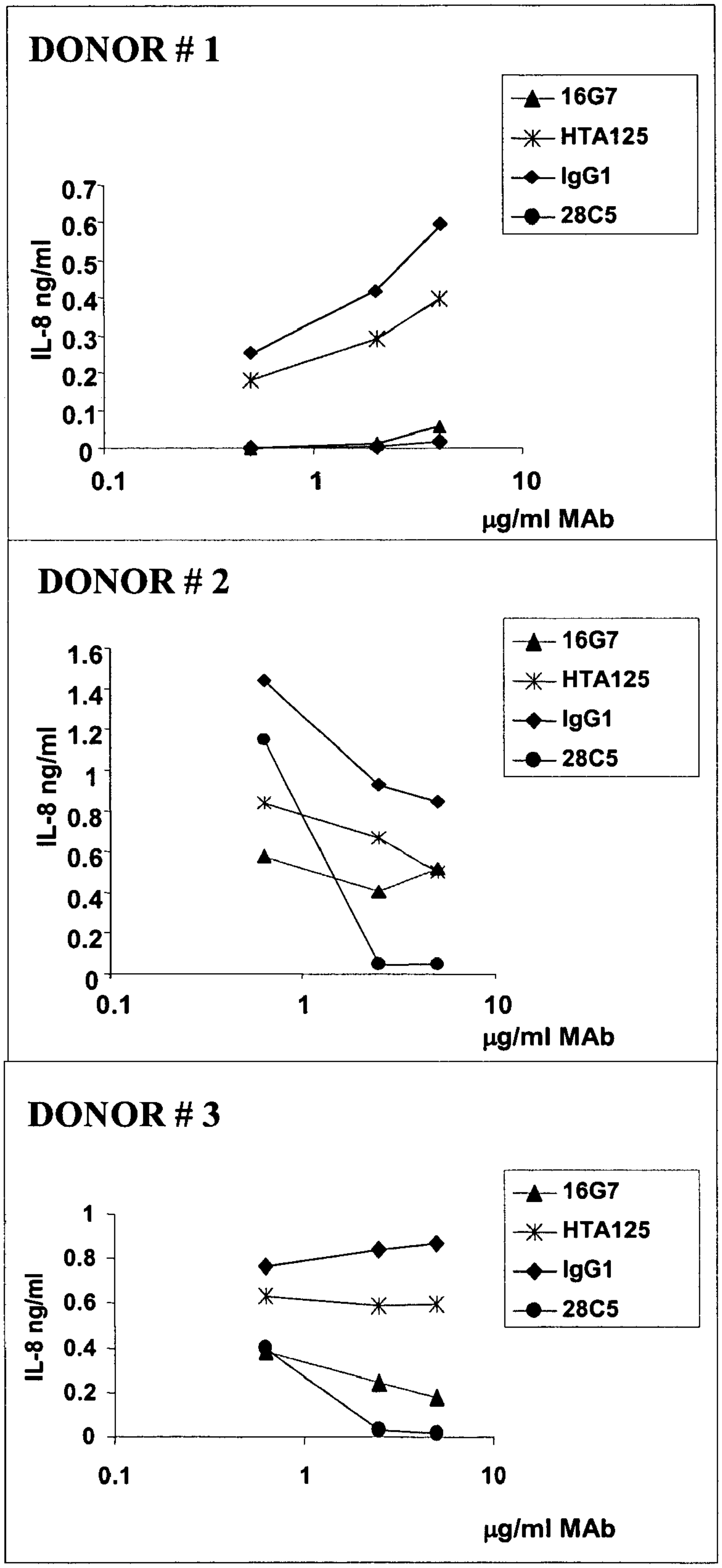

FIG. 11 is a series of graphs depicting inhibition of LPS-induced IL-8 production in human whole blood by the monoclonal antibody mu16G7. Whole blood was drawn from 3 healthy volunteers, treated with heparin and diluted 1:4 in RPMI medium. The following antibodies were added at the concentrations indicated: Isotype matched control; HTA125 (anti-human TLR4 non-blocking monoclonal antibody); mu16G7 and 28C5 (anti-human CD14 blocking monoclonal antibody). LPS was subsequently added for a final concentration of 10 ng/ml.

Figure 12:
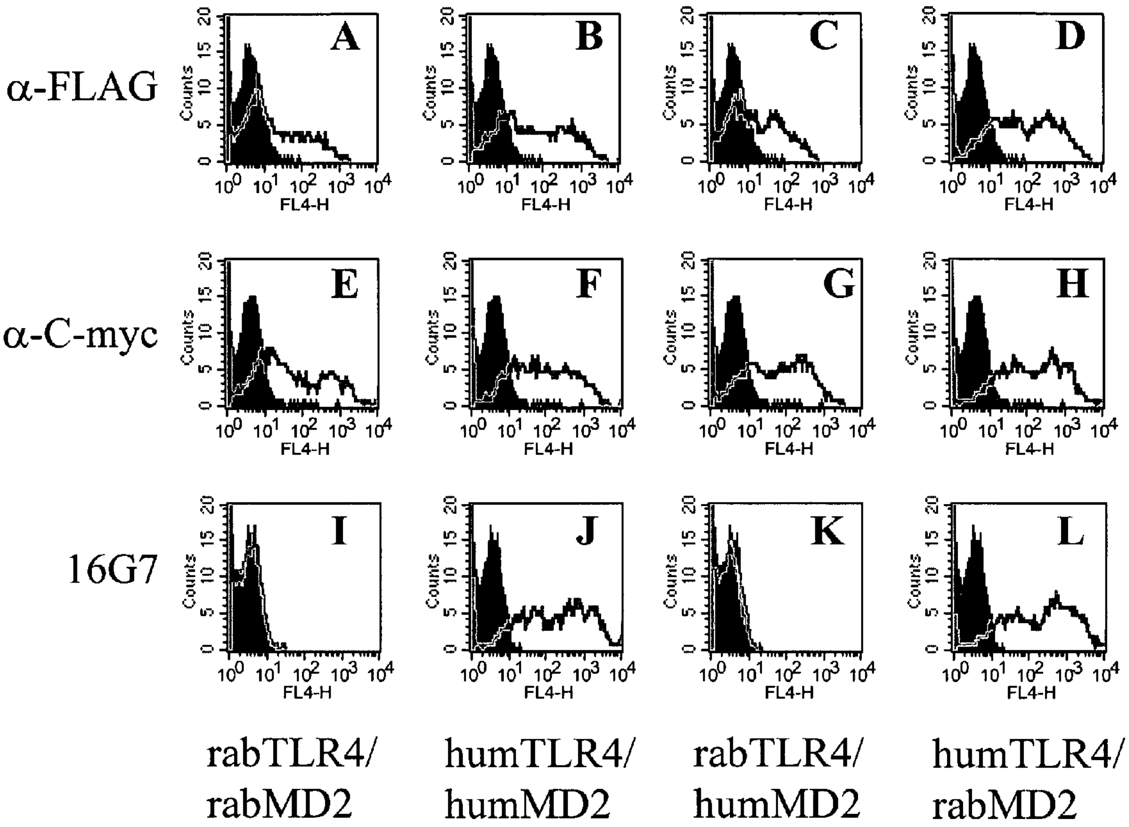

FIG. 12 is a series of graphs depicting the specificity of the mu16G7 monoclonal antibody for TLR4. The specificity of the mu16G7 antibody is shown by flow cytometry analysis of HEK 293 cells transiently transfected with either rabbit TLR4 and rabbit MD-2 (Panels A, E and I); human TLR4 and human MD-2 (Panels B, F and J); rabbit TLR4 and human MD-2 (Panels C, G and K); or human TLR4 and rabbit MD-2 (Panels D, H and L). Cells were incubated with either α-FLAG™ antibody (to detect TLR4 expression); α-C-myc antibody (to detect MD-2 expression) or the mu16G7 monoclonal antibody, followed by an APC-coupled α-mouse (H+L) antibody.

FIGS. 13A-13F are a series of illustrations depicting the VH nucleotide sequence (SEQ ID NO:11) (FIG. 13A), the VH amino acid sequence (SEQ ID NO:12) (FIG. 13B), the VL nucleotide sequence (SEQ ID NO:16) (FIG. 13D), and the VL amino acid sequence (SEQ ID NO:17) (FIG. 13E) for mu16G7. The VH complementarity determining regions (CDRs) (SEQ ID NOs: 13, 14 and 15) (FIG. 13C) and the VL CDRs (SEQ ID NOs: 18, 19 and 20) (FIG. 13F) are highlighted in the underlined, italic text in FIGS. 13B and 13E.

Figure 14:
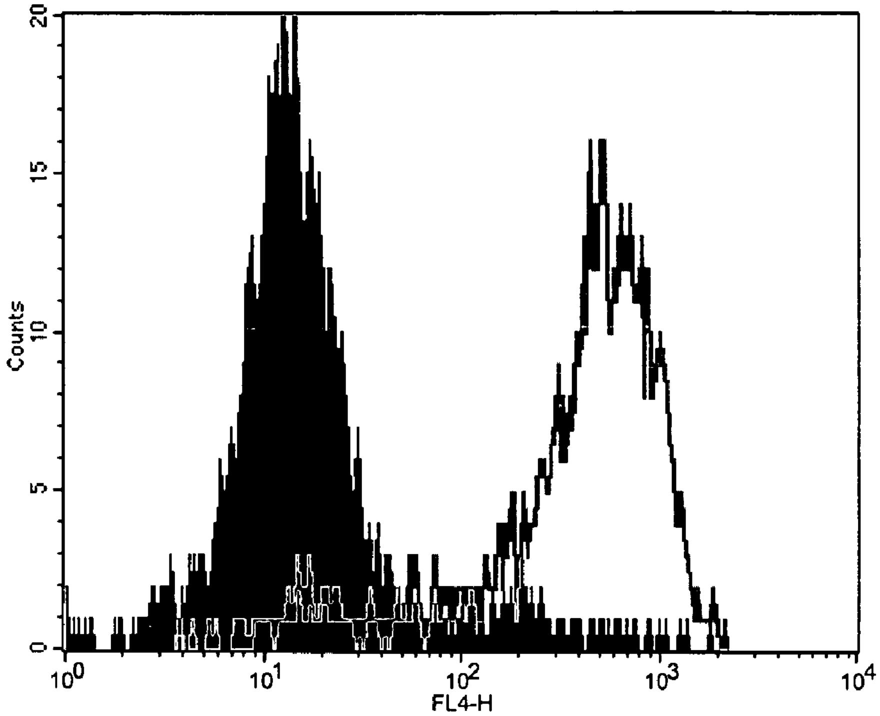

FIG. 14 is a graph depicting the binding of a murine monoclonal antibody, referred to herein as "15C1", to the TLR4/MD-2 complex. Specificity of binding is shown by flow cytometry using mock transfected or TLR4/MD-2 transfected cells. The results using mock-transfected cells are shown in the filled graph (left), while the results using TLR4/MD-2 transfected cells are shown as in the outline graph (right).

Figure 15:
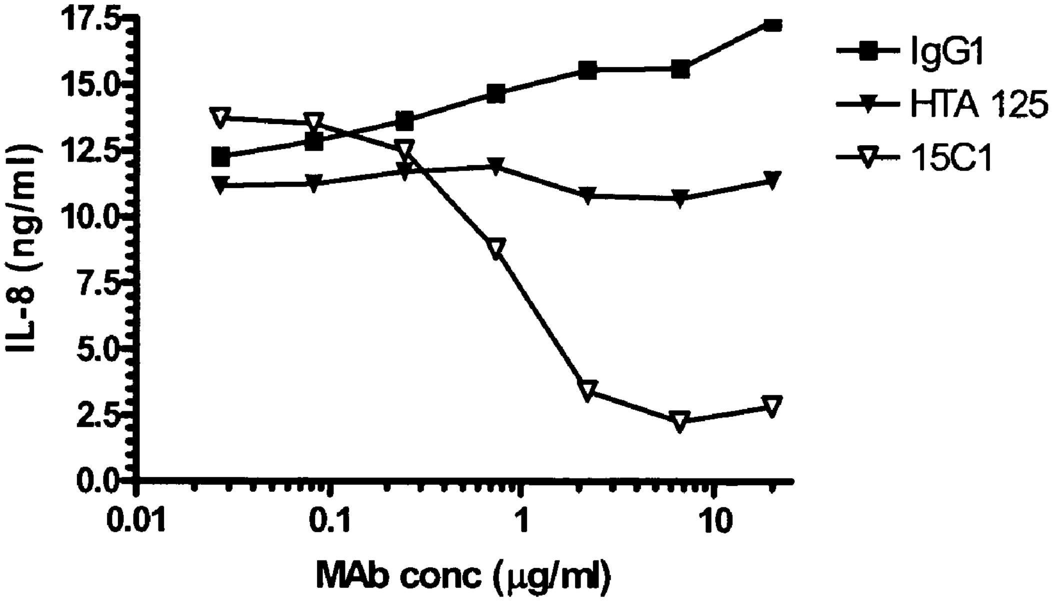

FIG. 15 is a graph depicting inhibition of lipopolysaccharide (LPS)-induced IL-8 production in TLR4/MD-2 transfected HEK 293 cells by the monoclonal antibody mu15C1. The cells were incubated with the mu15C1 monoclonal antibody, HTA 125 (anti-human TLR4 non-blocking monoclonal antibody) and an isotype-matched control (IgG1) at the indicated concentrations and subsequently incubated with LPS (15 ng/ml). IL-8 levels were assessed 16 hours post LPS treatment.

Figure 16:
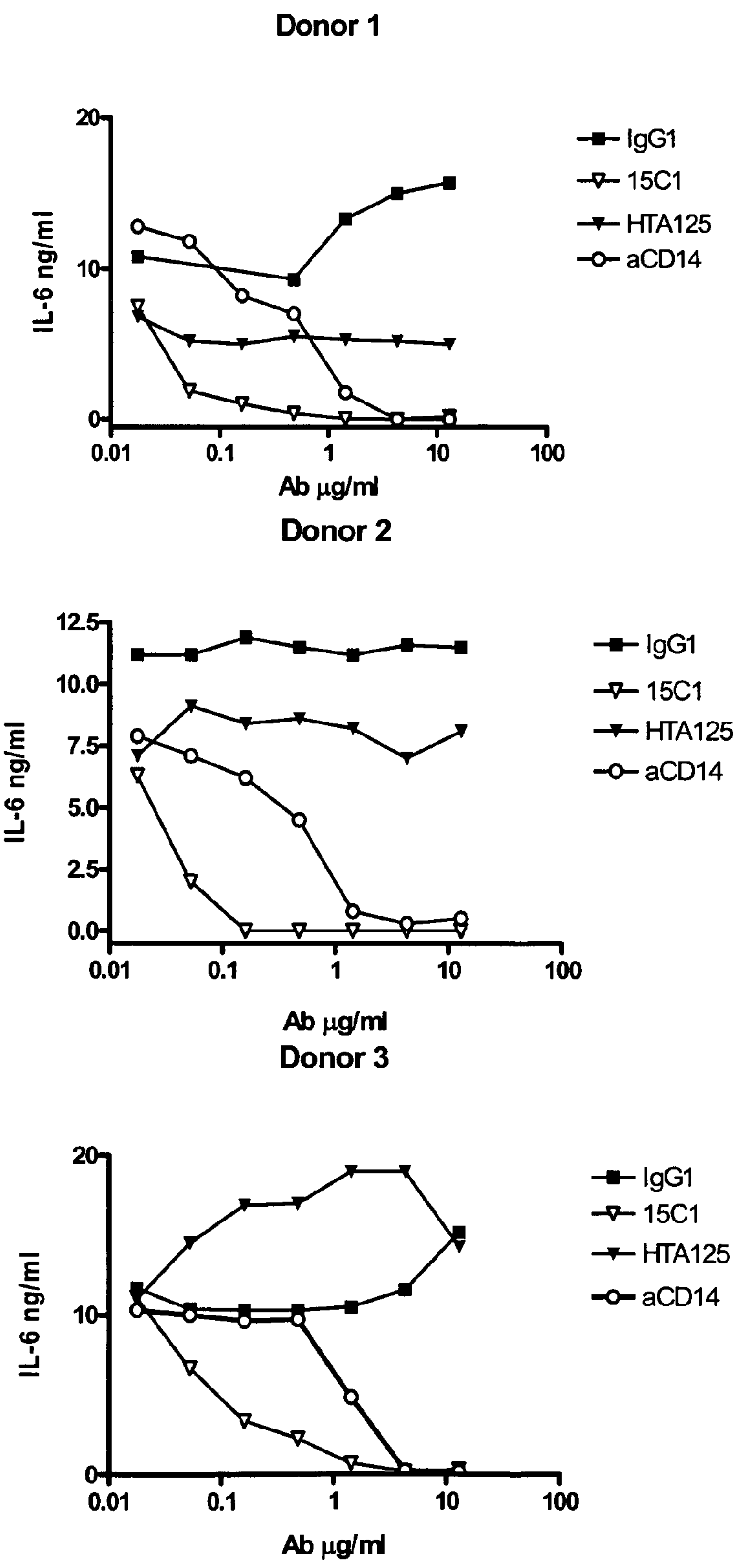

FIG. 16 is a series of graphs depicting inhibition of LPS-induced IL-6 production in human whole blood by the monoclonal antibody mu15C1. Whole blood was drawn from 3 healthy volunteers, treated with heparin and diluted 1:4 in RPMI medium. The following antibodies were added at the concentrations indicated: Isotype matched control (IgG1); HTA125 (anti-human TLR4 non-blocking monoclonal antibody); mu15C1 and 28C5 (anti-human CD14 blocking monoclonal antibody). LPS was subsequently added for a final concentration of 10 ng/ml.

Figure 17:
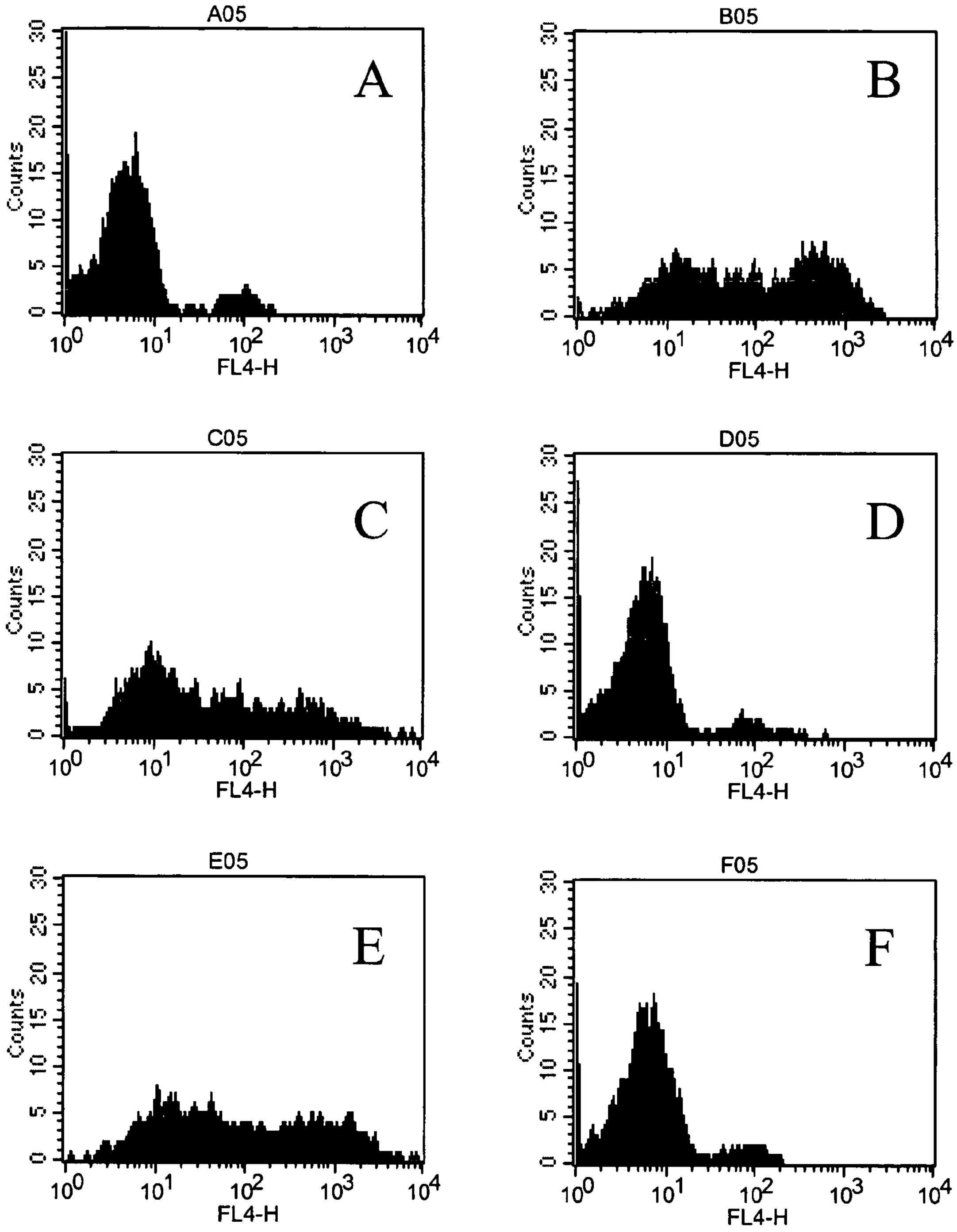

FIG. 17 is a series of graphs depicting the specificity of the mu15C1 monoclonal antibody for TLR4. The specificity of the mu15C1 antibody is shown by flow cytometry analysis of HEK 293 cells transiently transfected with either mock vector, i.e., empty vector (Panel A), human TLR4 (Panel B), human TLR4 and human MD-2 (Panel C), rabbit TLR4 and rabbit MD-2 (Panel D), human TLR4 and rabbit MD-2 (Panel E), or rabbit TLR4 and human MD-2 (Panel F). Cells were incubated with the mu15C1 monoclonal antibody (10 μg/ml), followed by an APC-coupled α-mouse (H+L) antibody.

FIGS. 18A-18F are a series of illustrations depicting the VH nucleotide sequence (SEQ ID NO:21) (FIG. 18A), the VH amino acid sequence (SEQ ID NO:22) (FIG. 18B), the VL nucleotide sequence (SEQ ID NO:26) (FIG. 18D), and the VL amino acid sequence (SEQ ID NO:27) (FIG. 18E) for mu15C1. The VH complementarity determining regions (CDRs) (SEQ ID NOs: 23, 24 and 25) (FIG. 18C) and the VL CDRs (SEQ ID NOs: 28, 29 and 30) (FIG. 18F) are highlighted in the underlined, italic text in FIGS. 18B and 18E.

Figure 19:
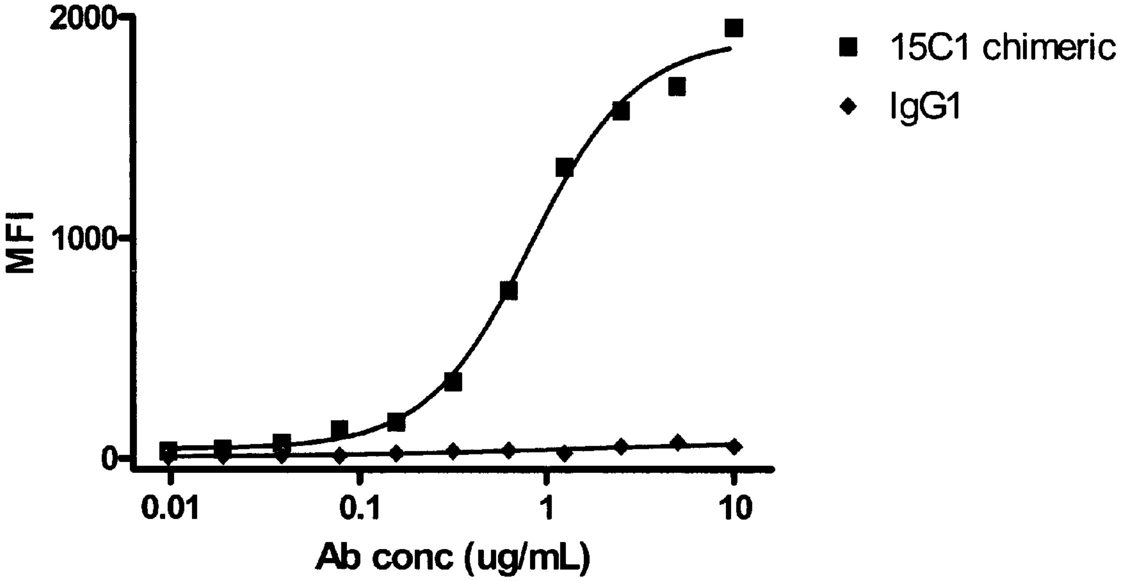

FIG. 19 is a graph depicting that the VH and VL nucleotide sequence of mu15C1 expressed as a chimeric MAb ("chimeric 15C1") is capable of binding specifically to the human TLR4/MD-2 complex on the surface of transfected CHO cells. MAb binding to the TLR4/MD-2 complex is shown by flow cytometry using chimeric 15C1 or an isotype matched control monoclonal antibody at the indicated concentration.

Figure 20:
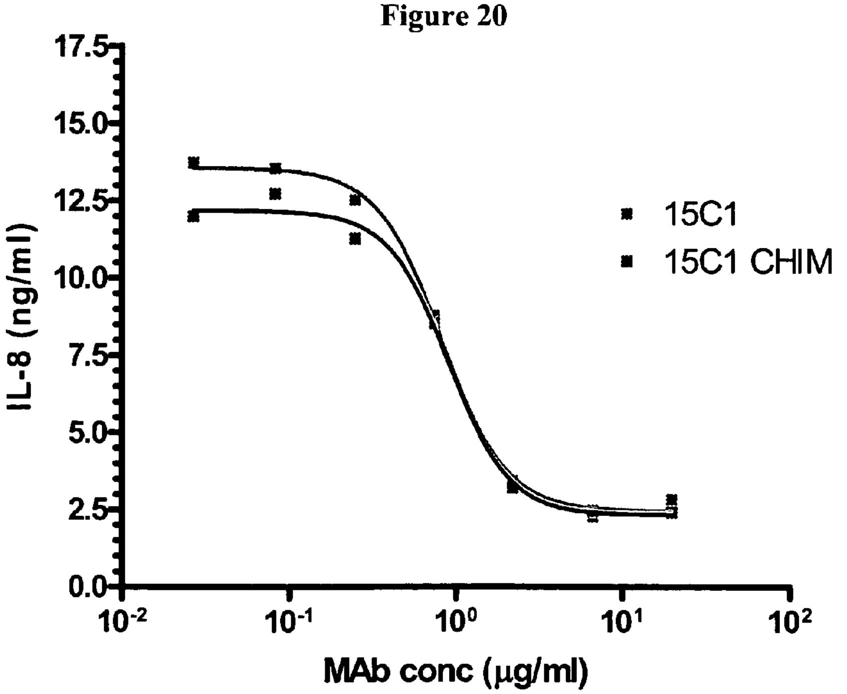

FIG. 20 is a graph depicting inhibition of lipopolysaccharide (LPS)-induced IL-8 production in TLR4/MD-2 transfected HEK 293 cells by the chimeric 15C1 MAb. Cells were incubated with mu15C1 or chimerical 15C1 at the concentrations indicated and subsequently incubated with LPS (15 ng/ml). IL-8 levels were assessed 16 hours post LPS treatment. Inhibition of LPS-induced IL-8 production by the chimeric 15C1 was similar to the inhibition by the mu15C1 mouse MAb of the invention.

Figure 21:
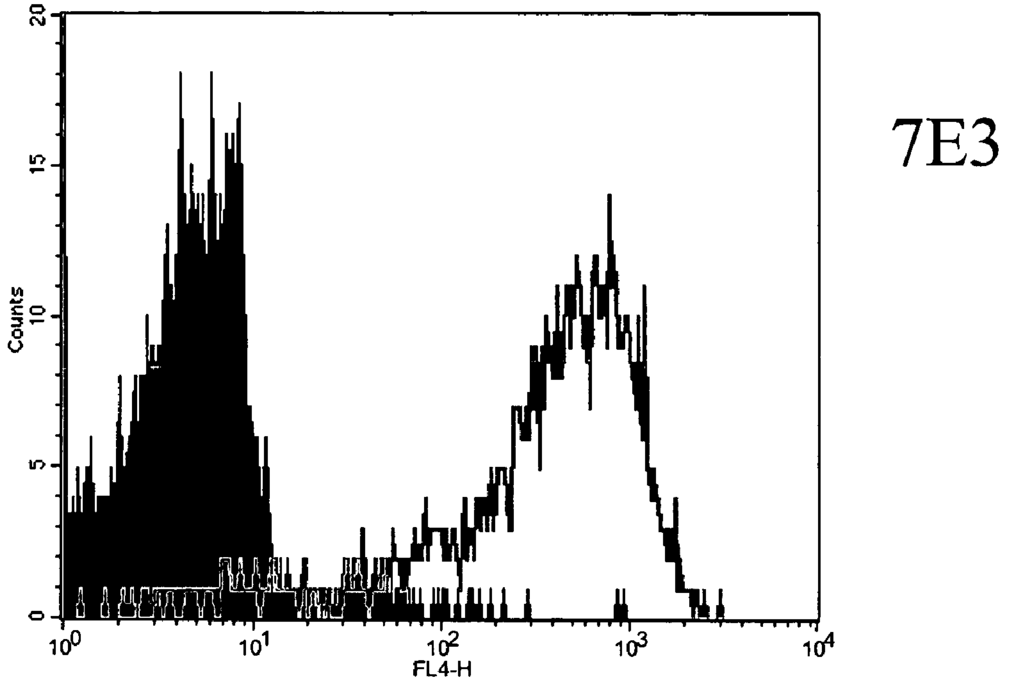

FIG. 21 is a graph depicting the binding of a murine monoclonal antibody, referred to here in as "7E3", to the TLR4/MD-2 complex. Specificity of binding is shown by flow cytometry using mock transfected or TLR4/MD-2 transfected cells. The results using mock-transfected cells are shown in the filled graph (left), while the results using TLR4/MD-2 transfected cells are shown as in the outline graph (right).

Figure 22:
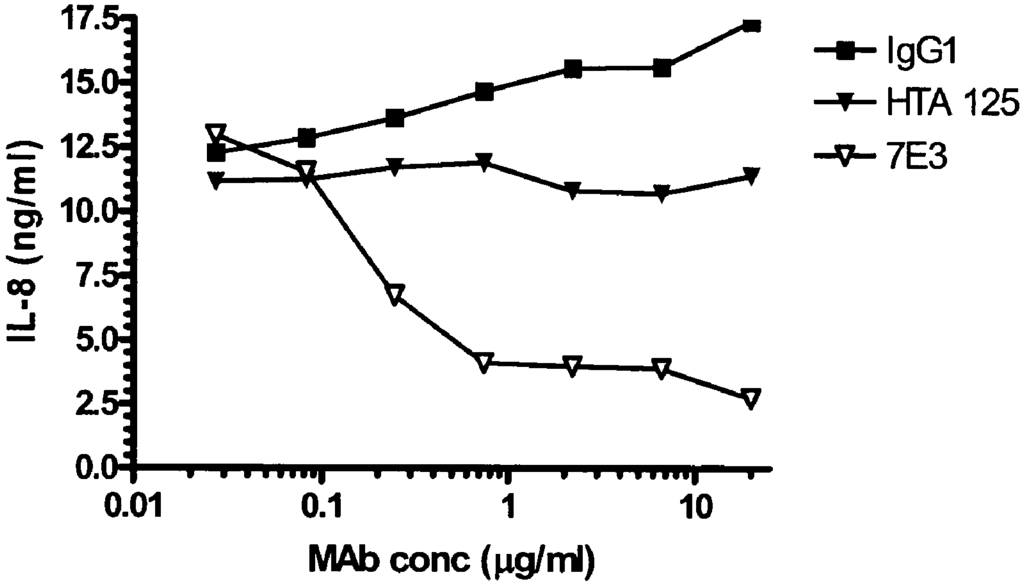

FIG. 22 is a graph depicting inhibition of lipopolysaccharide (LPS)-induced IL-8 production in TLR4/MD-2 transfected HEK 293 cells by the monoclonal antibody mu7E3. The cells were incubated with the mu7E3 monoclonal antibody, HTA 125 (anti-human TLR4 non-blocking monoclonal antibody) and an isotype-matched control (IgG1) at the indicated concentrations and subsequently incubated with LPS (15 ng/ml). IL-8 levels were assessed 16 hours post LPS treatment.

Figure 23:
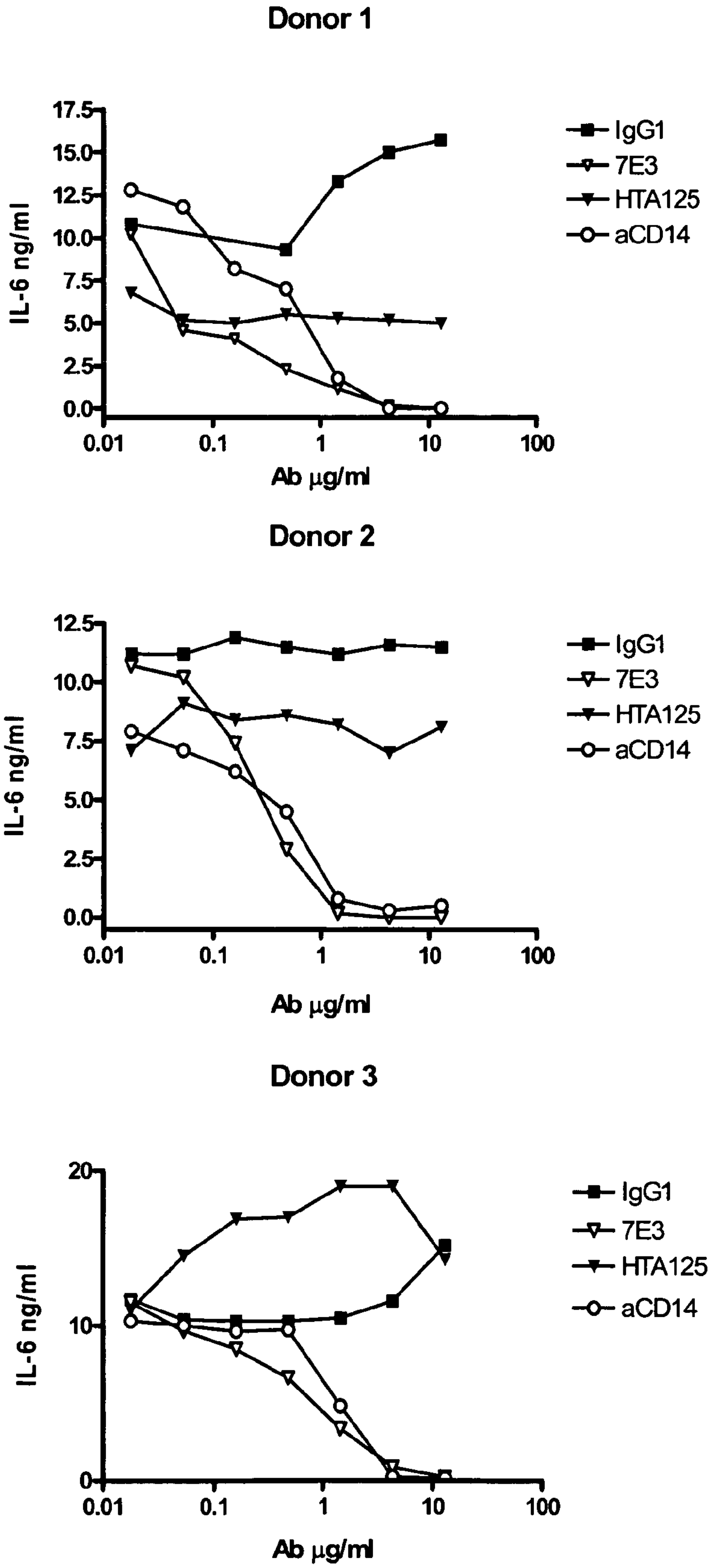

FIG. 23 is a series of graphs depicting inhibition of LPS-induced IL-6 production in human whole blood by the monoclonal antibody mu7E3. Whole blood was drawn from 3 healthy volunteers, treated with heparin and diluted 1:4 in RPMI medium. The following antibodies were added at the concentrations indicated: Isotype matched control (IgG1); HTA125 (anti-human TLR4 non-blocking monoclonal antibody); mu7E3 and 28C5 (anti-human CD14 blocking monoclonal antibody). LPS was subsequently added for a final concentration of 10 ng/ml.

Figure 24:
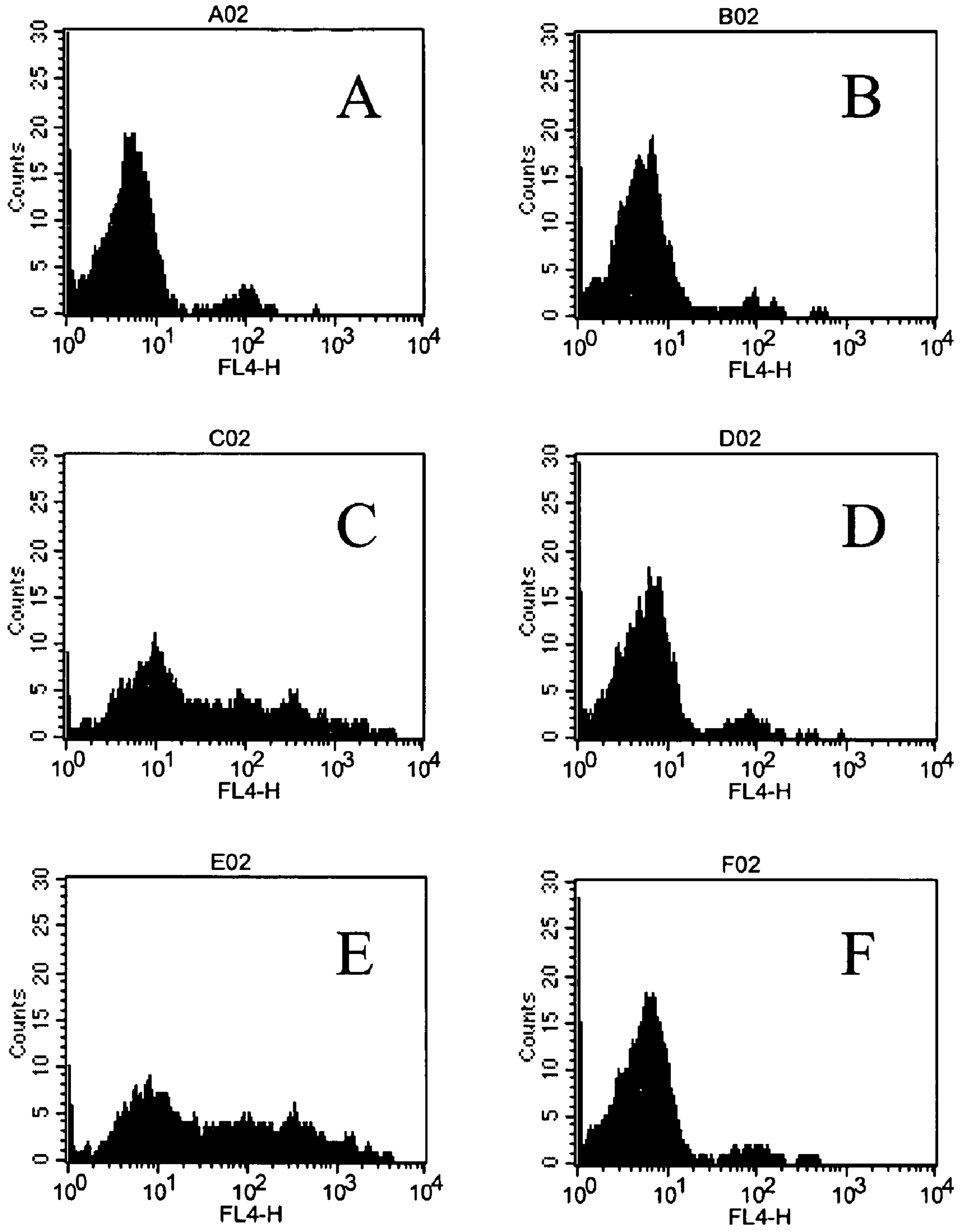

FIG. 24 is a series of graphs depicting the specificity of the mu7E3 monoclonal antibody for the TLR4/MD-2 complex. The specificity of the mu7E3 antibody is shown by flow cytometry analysis of HEK 293 cells transiently transfected with either mock vector (Panel A), human TLR4 (Panel B), human TLR4 and human MD-2 (Panel C), rabbit TLR4 and rabbit MD-2 (Panel D), human TLR4 and rabbit MD-2 (Panel E), or rabbit TLR4 and human MD-2 (Panel F). Cells were incubated with the mu7E3 monoclonal antibody (10 μg/ml), followed by an APC-coupled α-mouse (H+L) antibody.

FIGS. 25A-25F are a series of illustrations depicting the VH nucleotide sequence (SEQ ID NO:31) (FIG. 25A), the VH amino acid sequence (SEQ ID NO:32) (FIG. 25B), the VL nucleotide sequence (SEQ ID NO:36) (FIG. 25D), and the VL amino acid sequence (SEQ ID NO:37) (FIG. 25E) for mu7E3. The VH complementarity determining regions (CDRs) (SEQ ID NOs: 33, 34 and 35) (FIG. 25C) and the VL CDRs (SEQ ID NOs: 38, 39 and 40) (FIG. 25F) are highlighted in the underlined italic text in FIGS. 25B and 25E.

Figure 26:
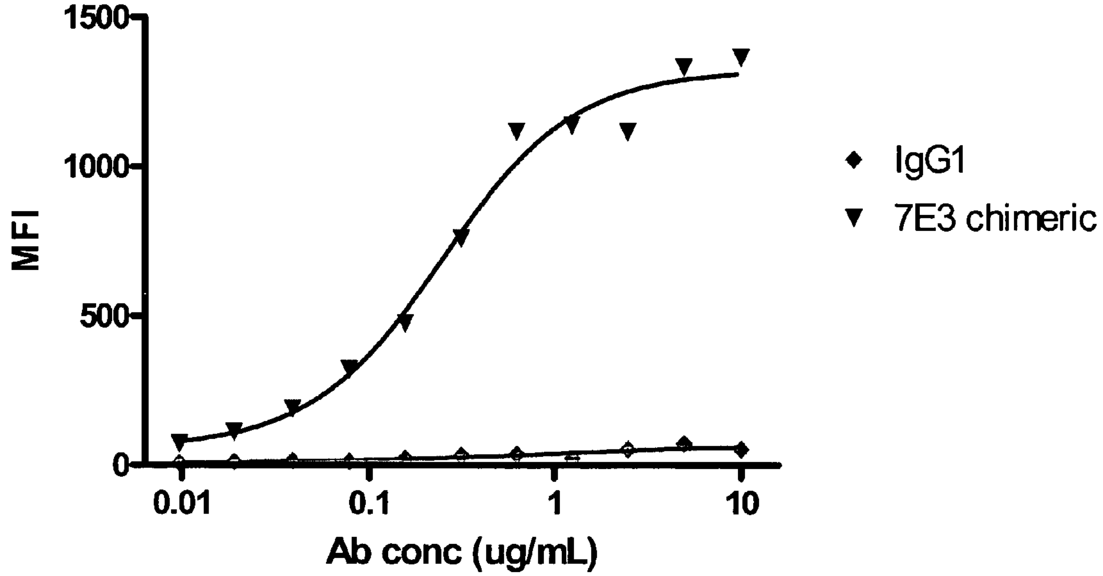

FIG. 26 is a graph illustrating that the VH and VL nucleotide sequence of mu7E3 expressed as a chimeric MAb ("chimeric 7E3") is capable of binding specifically to the human TLR4/MD-2 complex on the surface of transfected CHO cells. Monoclonal antibody binding to TLR4/MD-2 transfected CHO cells is shown by flow cytometry using chimeric 7E3 or an isotype matched control MAb at the indicated concentrations.

Figure 27:
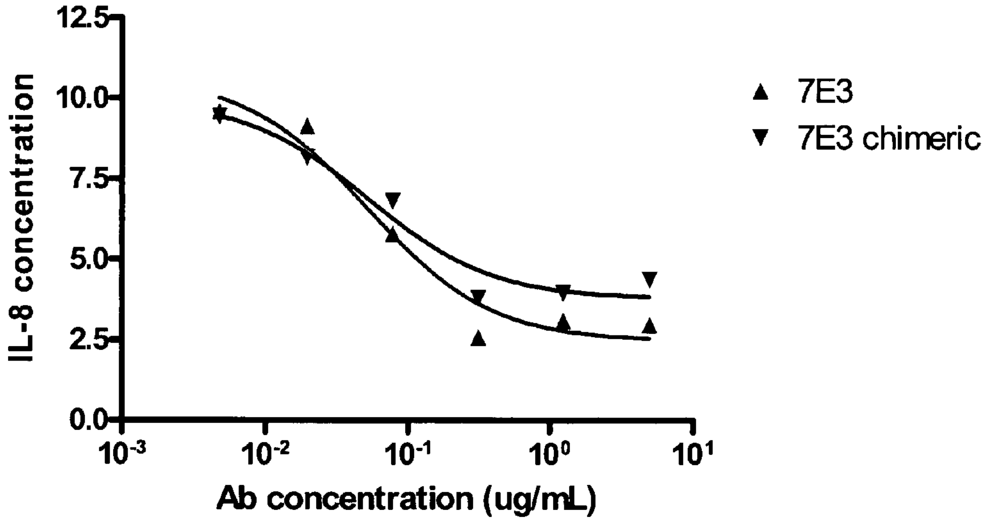

FIG. 27 is a graph depicting inhibition of lipopolysaccharide (LPS)-induced IL-8 production in TLR4/MD-2 transfected HEK 293 cells by the chimeric 7E3 MAb. Cells were incubated with chimeric 7E3 or an isotype matched MAb control at the indicated concentrations and subsequently incubated with LPS (15 ng/ml). IL-8 levels were assessed 16 hours post LPS-treatment.

Figure 28:
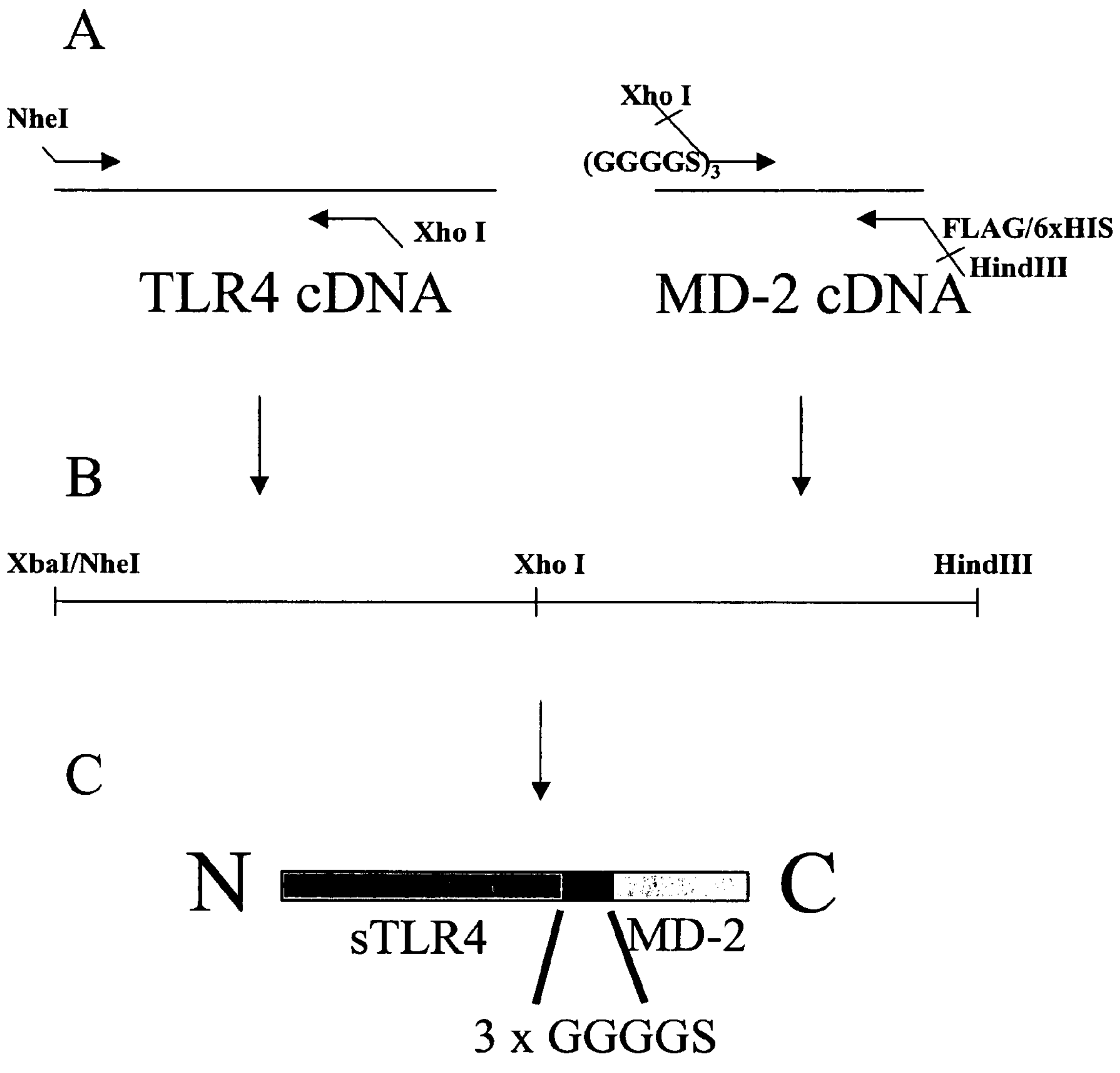

FIG. 28 is an illustration depicting the construction of a TLR4/MD-2 fusion protein cDNA according to the present invention.

Figure 29:
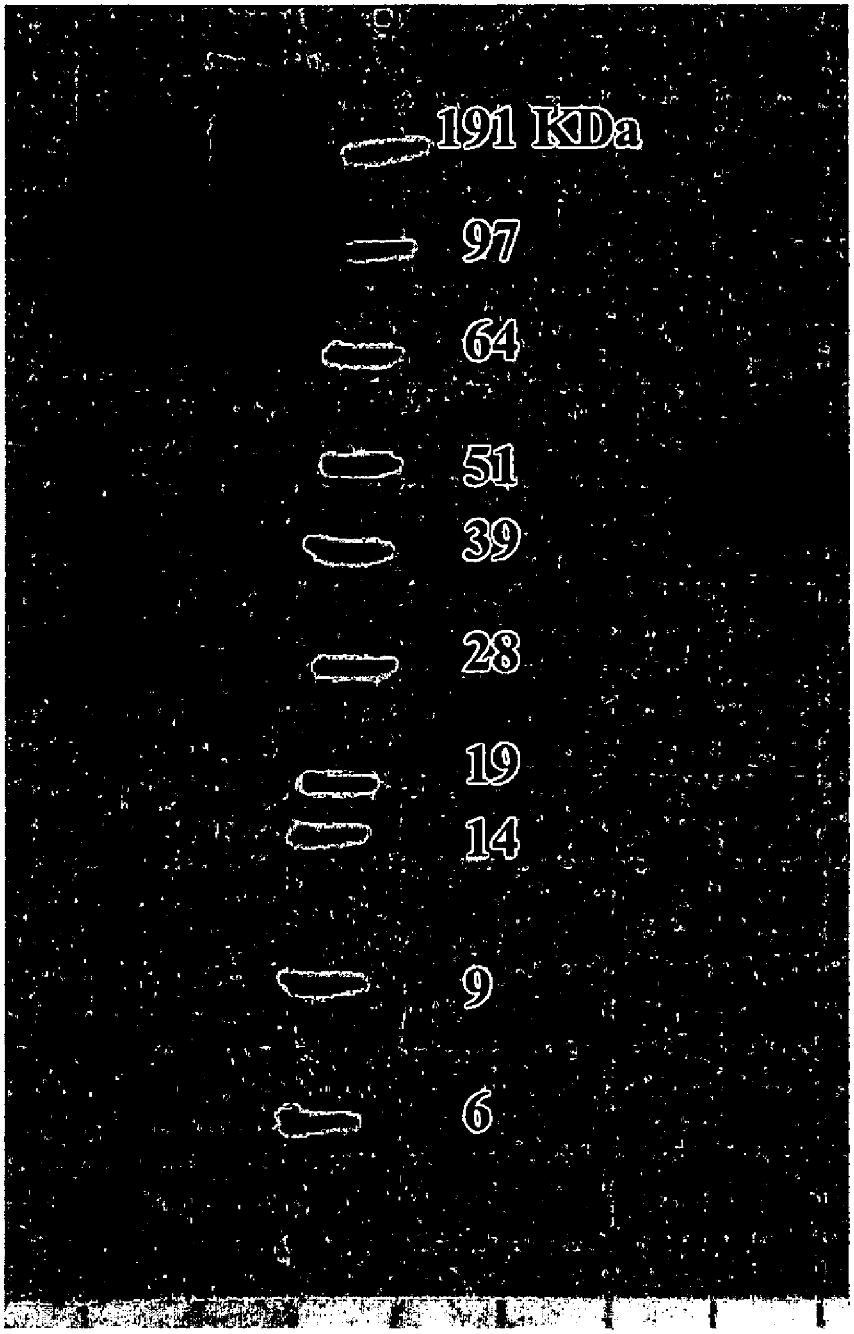

FIG. 29 is an illustration depicting the expression of a TLR4/MD-2 chimeric protein of the invention in Sf9 cell lysates and supernatant.

Figure 30:
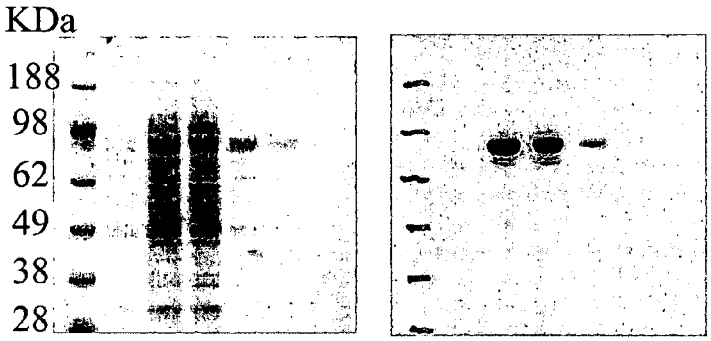

FIG. 30 is an illustration depicting the purification of a TLR4/MD-2 chimeric protein according to the invention from infected Sf9 cell lysates.

Figure 31:
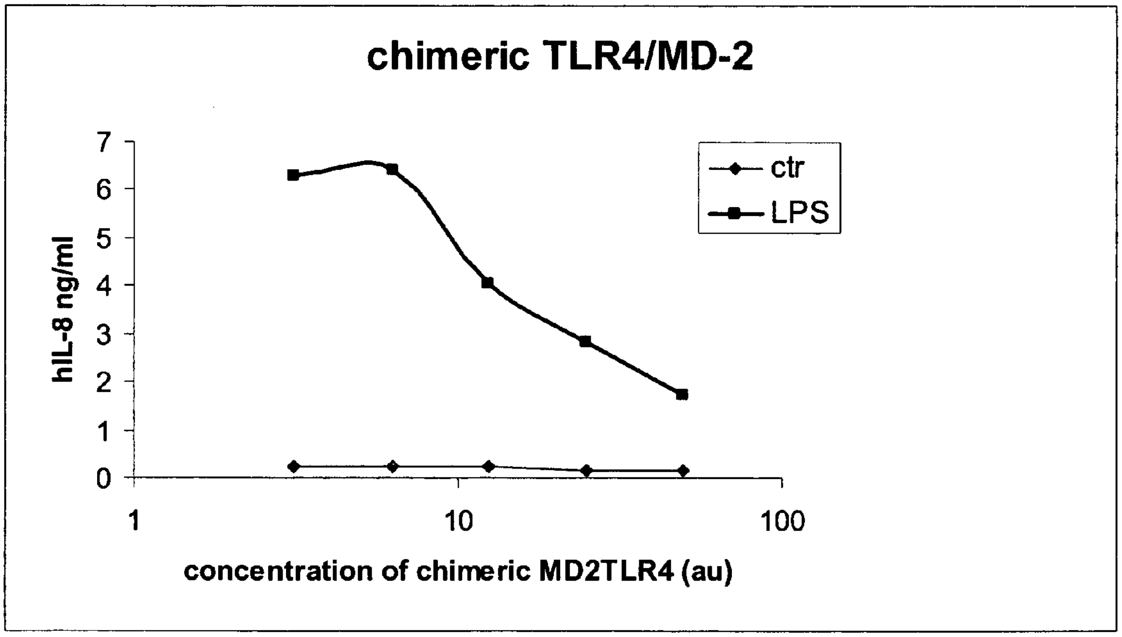

FIG. 31 is a graph depicting the inhibition of lipopolysaccharide-(LPS) induced IL-8 production using a soluble chimeric TLR4/MD-2 protein according to the present invention.

FIG. 32A illustrates a nucleic acid sequence encoding the accessory protein MD-1 (SEQ ID NO:41).

FIG. 32B depicts an amino acid sequence of a mature MD-1 accessory protein in a preferred embodiment of the invention (SEQ ID NO:42).

FIG. 33A illustrates a nucleic acid sequence encoding the accessory protein MD-2 (SEQ ID NO:43).

FIG. 33B depicts an amino acid sequence of a mature MD-2 accessory protein (SEQ ID NO:44).

FIGS. 34A, 34B and 34C are a schematic representation and a series of graphs depicting the binding of hu15C1 and hu7E3 to human-mouse hybrid versions of TLR4. FIG. 34A is a schematic representation and summary table of the mouse-human TLR4 hybrid mutants and antibody binding to these mutants. Red regions in the schematic representation depict mouse-derived sequence and the blue regions represent human-derived sequence. In the summary table of antibody binding, (++) represents strong binding, (+) represents intermediate binding and (−) indicates weak or no binding. FIG. 34B is a series of flow cytometry histograms depicting monoclonal antibody binding to transfected cells expressing the human-mouse hybrids. The HEK 293 cells were transfected with wild-type TLR4 (row 1); mouse-human-human-human (MHHH) TLR4 (row 2); mouse-mouse-human-human (row 3); mouse-human-mouse-human (MHMH) TLR4 (row 4) or human-human-human-mouse (HHHM) TLR4 (row 5). Cells were incubated with either α-FLAG™ antibody (to detect TLR4 expression); α-C-myc antibody (to detect MD-2 expression) or the hu15C1 or hu7E3 monoclonal antibody, followed by an APC-conjugated antibody. FIG. 34C is a series of flow cytometry histograms depicting monoclonal antibody binding to transfected cells expressing the human-mouse hybrids.

Figure 35:
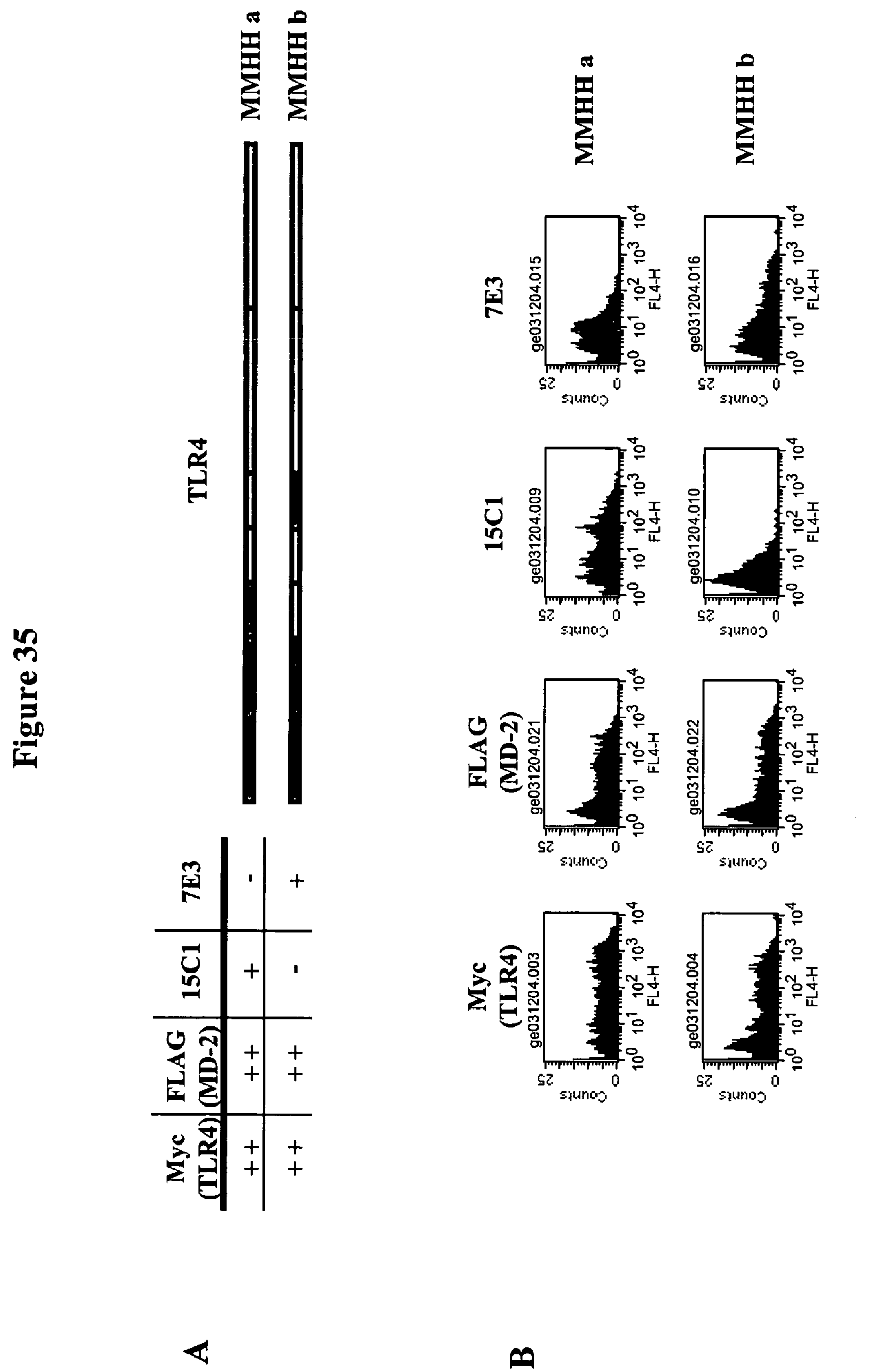

FIGS. 35A and 35B are a schematic representation and a series of graphs depicting binding of hu15C1 and hu7E3 to "fine-resolution" human-mouse hybrid versions of TLR4. FIG. 35A is a schematic representation and summary table of the "fine resolution" mouse-human TLR4 hybrid mutants and antibody binding to these mutants. Red regions represent mouse-derived sequence and blue regions represent human-derived sequence. In the summary table of antibody binding, (++) represents strong binding, (+) represents intermediate binding and (−) indicates weak or no binding. FIG. 35B is a series of flow cytometry histograms depicting MAb binding to transfected cells expressing the human-mouse hybrids.

Figure 36:
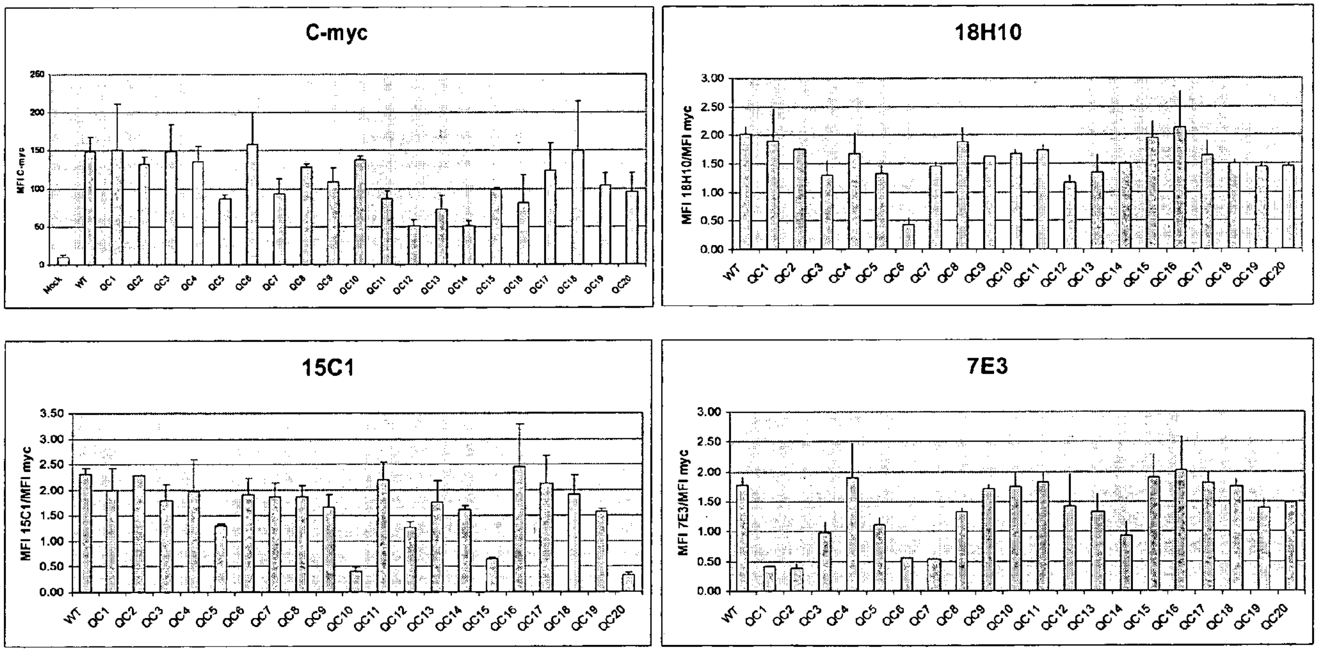

FIGS. 36A and 36B are a schematic representation and a series of graphs depicting binding of hu15C1 and hu7E3 to alanine-scanning mutants of TLR4. FIG. 36A is a schematic representation of the alanine scanning mutants (QC1-QC20; boxed from 1 to 20 on the human sequence) selected after alignment of the human and mouse TLR4 amino acid sequences from amino acids 289-375 and amino acids 288-373, respectively. Mutants were designed so that any amino acid differences between human and mouse sequences within the boxes were converted to an alanine in the human sequence (e.g., QC2 is modified from YL to AA). FIG. 36B is a series of bar graphs representing MAb binding to transfected cells expressing the TLR4 alanine-scan mutants. For C-myc, the actual MFI obtained following flow cytometric analysis is shown. For hu18H10, hu15C1 and hu7E3, values represent "normalized" antibody binding by dividing the MFI obtained for the given MAb by that obtained for the C-myc.

Figure 37:
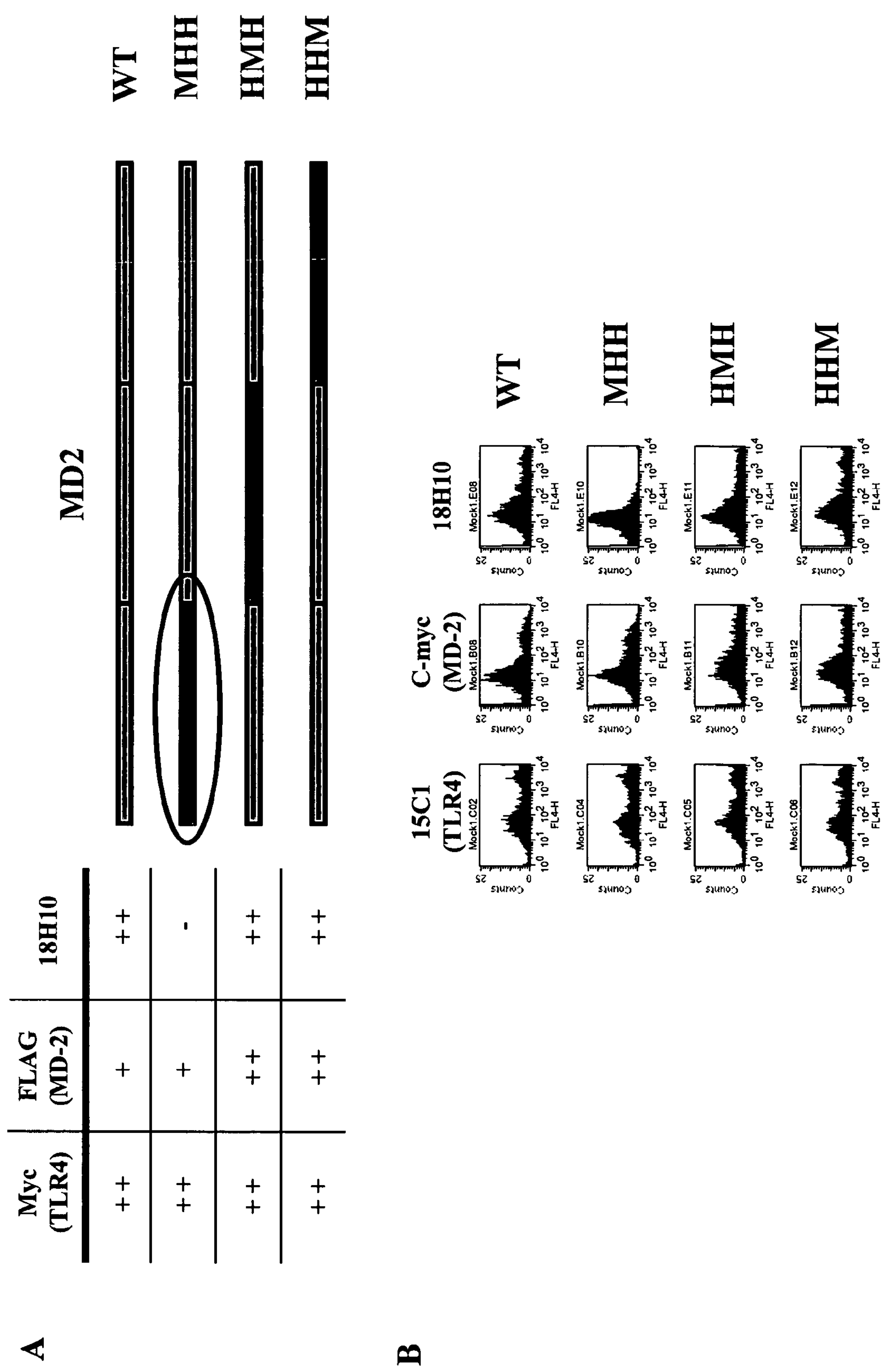

FIGS. 37A and 37B are a schematic representation and a series of graphs depicting binding of hu18H10 to human-mouse hybrid versions of MD-2. FIG. 37A is a schematic representation and summary table of the mouse-human MD-2 hybrid mutants and antibody binding to these mutants. Red regions represent mouse-derived sequence and blue regions represent human-derived sequence. In the summary table of antibody binding, (++) represents strong binding, (+) represents intermediate binding and (−) indicates weak or no binding. FIG. 37B is a series of flow cytometry histograms depicting MAb binding to transfected cells expressing the human-mouse hybrids.

Figure 38:
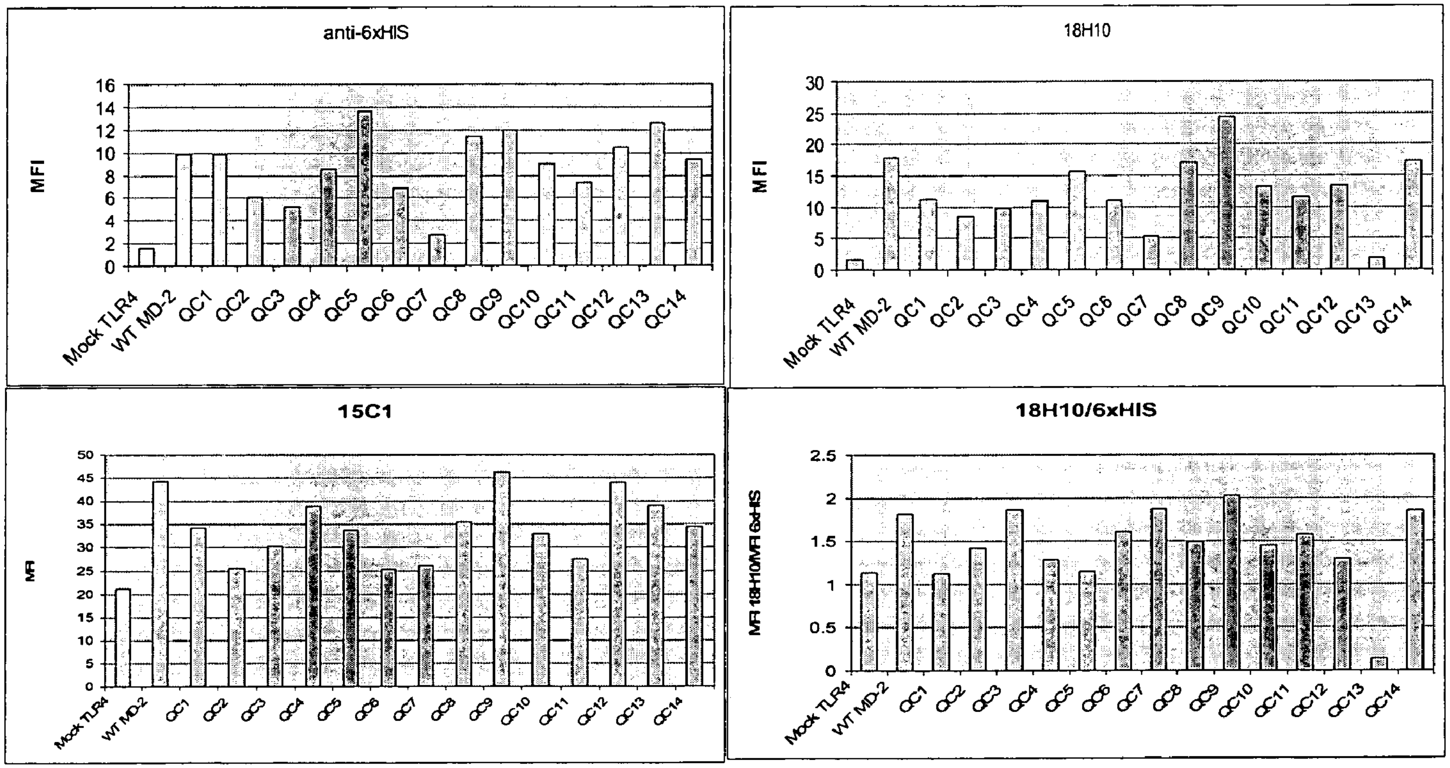

FIGS. 38A and 38B are a schematic representation and a series of graphs depicting binding of hu18H10 to alanine-scanning mutants of MD-2. FIG. 38A is a schematic representation of the alanine scanning mutants (QC1-QC14; boxed from 1 to 14 on the human sequence) selected after alignment of the human and mouse MD-2 amino acid sequences from amino acids 19-57. Mutants were designed so that any amino acid differences between human and mouse sequences were converted to an alanine in the human sequence (e.g., QC1 is modified from Q to A). FIG. 38B is a series of bar graphs representing MAb binding to transfected cells co-expressing wt TLR4 along with the MD-2 mutants. For the anti-6×HIS and hu15C1 MAbs, the actual MFI obtained following flow cytometric analysis is shown. For hu18H10, both actual MFIs and values represent "normalized" antibody binding (by dividing the MFI obtained for the MAb by that obtained for anti-6×HIS) are shown.

Figure 39:
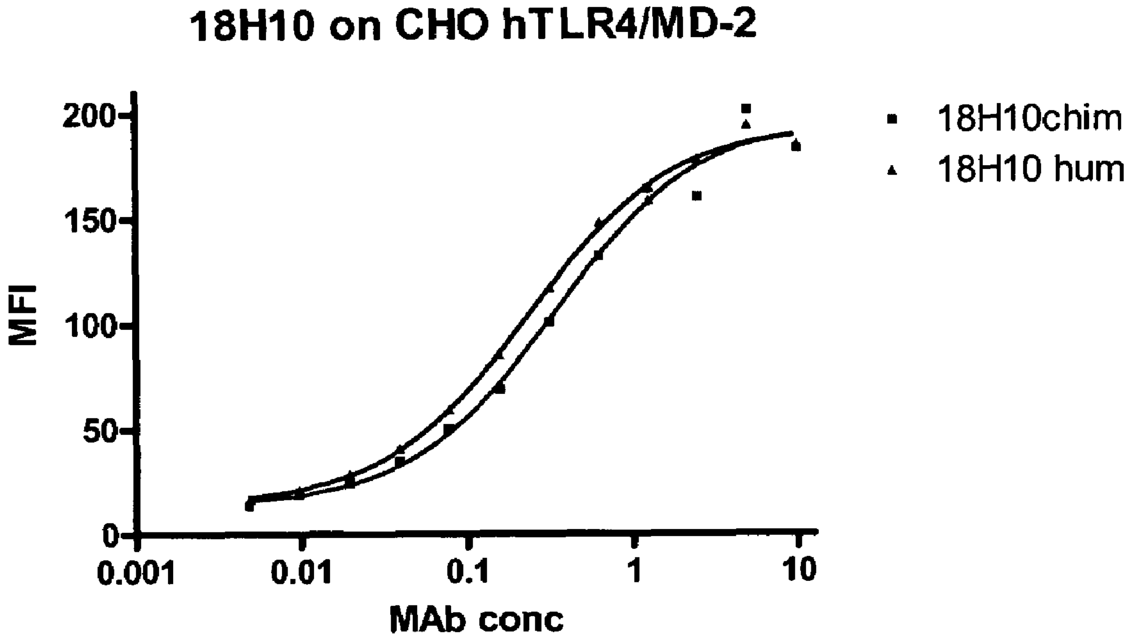

FIG. 39 is a graph depicting that the hu18H10 humanized monoclonal antibody ("18H10 hum") is capable of binding specifically to the human TLR4/MD-2 complex on the surface of transfected CHO cells. MAb binding to the TLR4/MD-2 transfected CHO cells is shown by flow cytometry using the hu18H10 antibody or the chimeric 18H10 ("18H10chim") (described above) at the concentrations indicated. Binding is measured as a cellular Mean Fluorescence Intensity (MFI) value.

Figure 40:
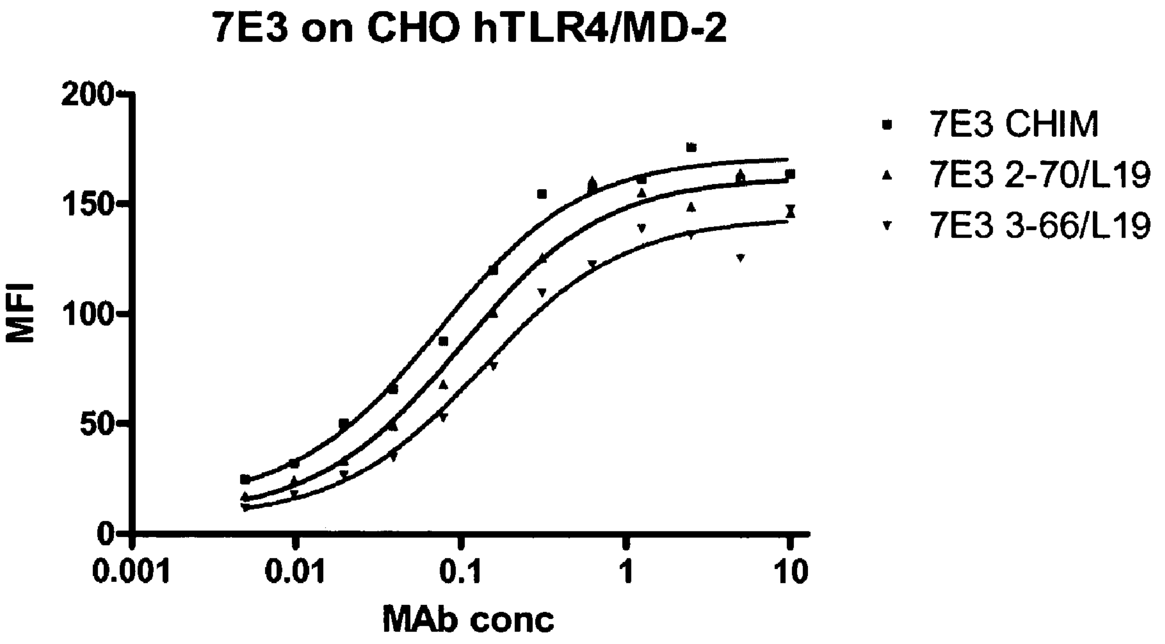

FIG. 40 is a graph depicting that the hu7E3 humanized monoclonal antibody that includes $V_H$2-70 shown in SEQ ID NO:51 ("7E3 2-70/L-19") and the hu7E3 humanized monoclonal antibody that includes $V_H$3-66 (SEQ ID NO:52) ("7E3 3-66/L19") are capable of binding specifically to the human TLR4/MD-2 complex on the surface of transfected CHO cells. MAb binding to the TLR4/MD-2 transfected CHO cells is shown by flow cytometry using the hu7E3 antibodies or the chimeric 7E3 ("7E3 CHIM") (described above) at the concentrations indicated. Binding is measured as a cellular Mean Fluorescence Intensity (MFI) value.

Figure 41:
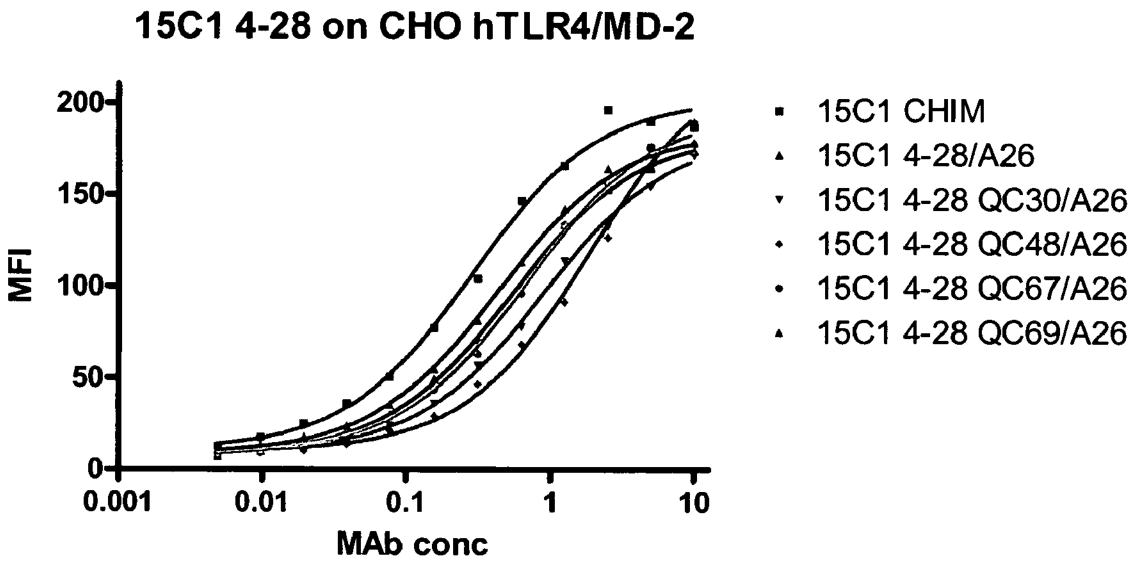

FIG. 41 is a graph depicting that the hu15C1 humanized antibody that includes $V_H$ 4-28 shown in SEQ ID NO:45 ("15C14-28/A26") and variants thereof in which residues at chosen positions have been replaced by the corresponding amino acid in the given human germline("15C1 4-28 QC 30/A26"; "15C1 4-28 QC 48/A26"; "15C1 4-28 QC 67/A26" and "15C1 4-28 QC 69/A26", see TABLE 1) are capable of binding specifically to the human TLR4/MD-2 complex on the surface of transfected CHO cells. MAb binding to the TLR4/MD-2 transfected CHO cells is shown by flow cytometry using the hu15C1 antibodies or the chimeric 15C1 ("15C1 CHIM") (described above) at the concentrations indicated. Binding is measured as a cellular Mean Fluorescence Intensity (MFI) value.

Figure 42:
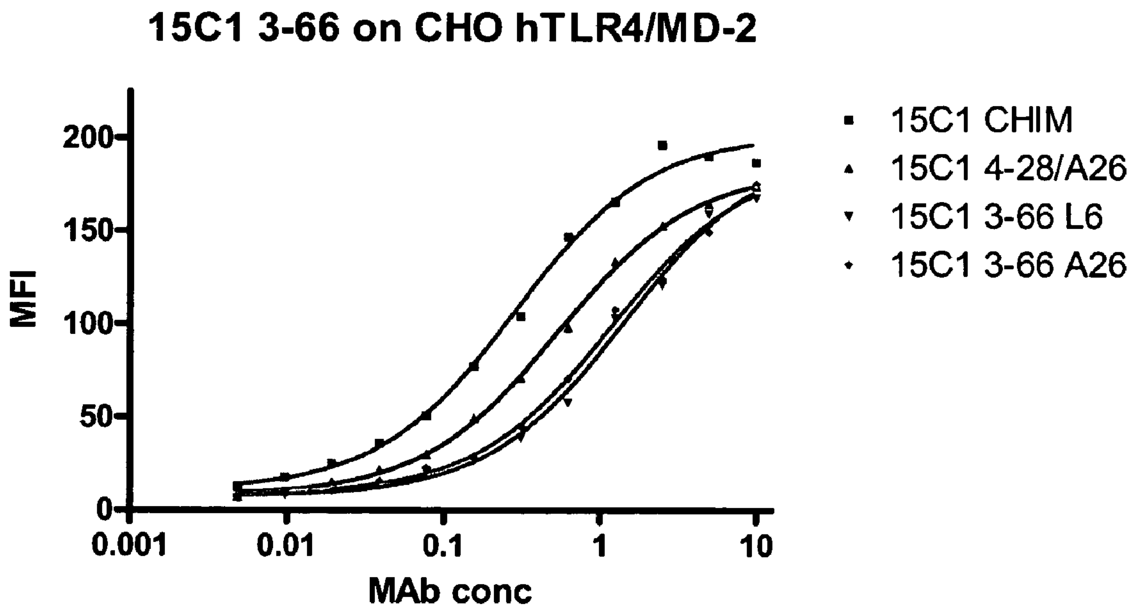

FIG. 42 is a graph depicting that the hu15C1 humanized antibody that includes $V_H$ 3-66 shown in SEQ ID NO:46 and $V_L$ L6 shown in SEQ ID NO:47 (15C1 3-66 L6) and the hu15C1 humanized antibody that includes $V_H$ 3-66 shown in SEQ ID NO:46 and $V_L$ A26 shown in SEQ ID NO:48 (15C1 3-66 A26) are capable of binding specifically to the human TLR4/MD-2 complex on the surface of transfected CHO cells. MAb binding to the TLR4/MD-2 transfected CHO cells is shown by flow cytometry using the hu15C1 3-66 L6 and hu15C1 3-66 A26 hu15C1 antibodies, the hu15C1 4-28 A26 antibody or the chimeric 15C1 ("15C1 CHIM") (described above) at the concentrations indicated. Binding is measured as a cellular Mean Fluorescence Intensity (MFI) value.

FIG. 43 depicts the amino acid sequence of human toll-like receptor 4 (TLR4).

Figure 44:
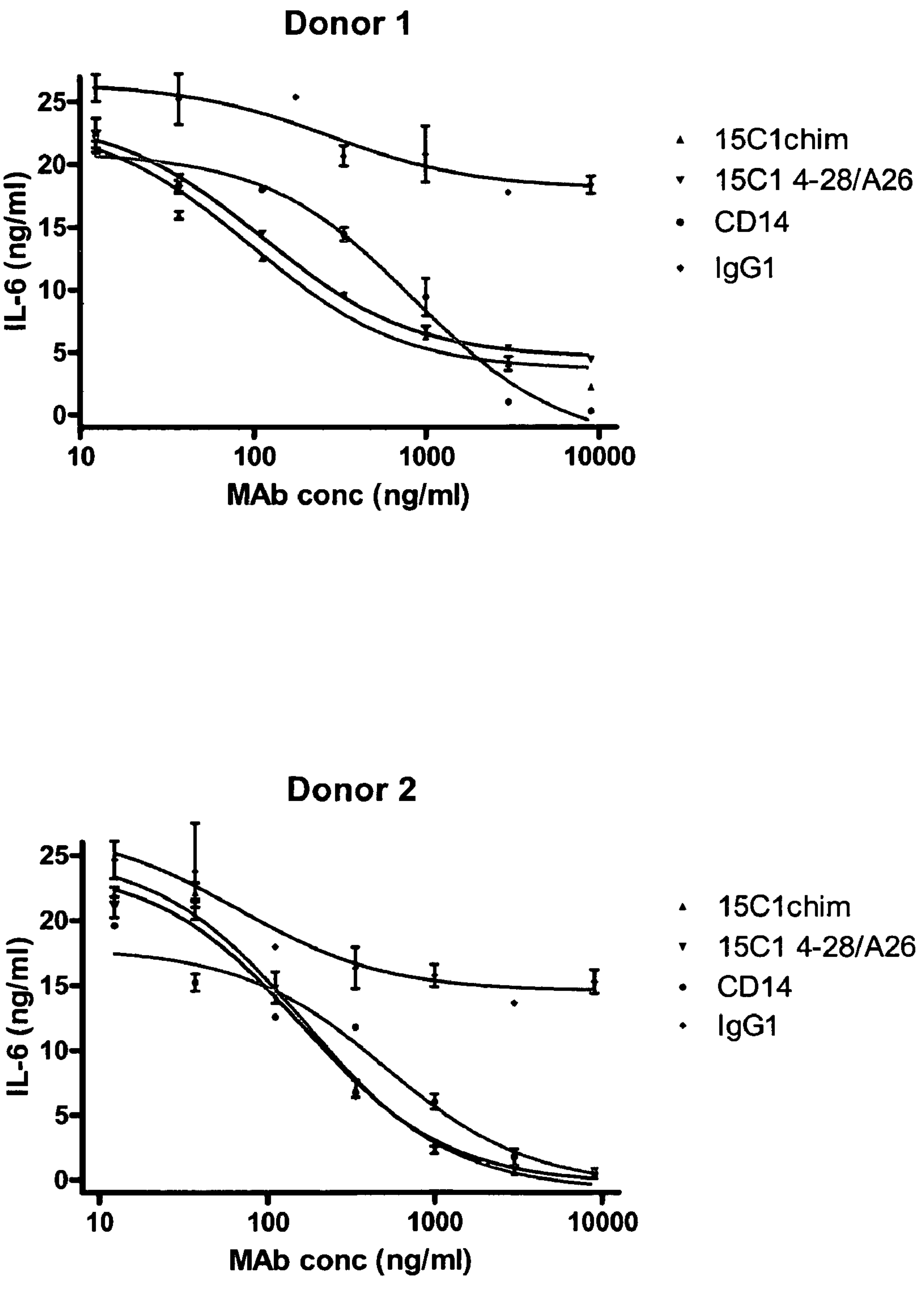

FIG. 44 is a series of graphs depicting inhibition of LPS-induced IL-6 production in human whole blood by the monoclonal antibody hu15C1 having the heavy chain variable region 4-28 and the light chain variable region A26 ("4-28/A26"). The hu15C1 4-28/A26 was compared to an isotype matched control (IgG1) and the 15C1 chimeric antibody described herein.

DETAILED DESCRIPTION OF THE INVENTION

The present invention provides monoclonal antibodies (MAbs) that specifically bind the human TLR4/MD-2 receptor complex. This receptor complex is activated by lipopolysaccharide (LPS), the major component of the outer membrane of gram-negative bacteria. The monoclonal antibodies of the invention inhibit receptor activation and subsequent intracellular signaling via LPS. Thus, the monoclonal antibodies neutralize the activation of the TLR4/MD-2 receptor complex. In particular, the invention provides monoclonal antibodies that recognize the TLR4/MD-2 receptor complex expressed on the cell surface. These monoclonal antibodies block LPS-induced IL-8 production. In addition, some monoclonal antibodies of the invention also recognize TLR4 when not complexed with MD-2. The monoclonal antibody is, e.g., a humanized antibody.

Antibodies of the invention include antibodies that bind the human TLR4/MD-2 receptor complex and also bind TLR4 independently of the presence of MD-2. Antibodies of the invention also include antibodies that bind the TLR4 portion of the human TLR4/MD-2 receptor complex but binding is dependent on the presence of MD-2, but binding is greatly enhanced by the presence of MD-2, which suggests that the presence of the MD-2 causes a conformational change in TLR4, thereby exposing an epitope bound by the antibody. In addition, antibodies of the invention include antibodies that bind the human TLR4/MD-2 receptor complex and also bind MD-2 in the presence of TLR4.

Antibodies of the invention immunospecifically bind a TLR4/MD-2 complex, wherein the antibody binds to an epitope that includes one or more amino acid residues on human TLR4 between residues 289 and 375 of SEQ ID NO:54. Antibodies of the invention immunospecifically bind the TLR4/MD2 complex, wherein the antibody binds to an epitope on human MD-2 between residues 19 and 57 of SEQ ID NO:44.

Exemplary antibodies of the invention include, for example, the 18H10 antibody, the 16G7 antibody, the 15C1 antibody and the 7E3 antibody. These antibodies show specificity for the human TLR4/MD-2 receptor complex, and they have been shown to inhibit receptor activation and subsequent intracellular signaling via LPS. These antibodies have distinct specificities. For example, 16G7 and 15C1 bind TLR4 independently of the presence of MD-2, 7E3 binds to TLR4, but binding is dependent on the presence of MD-2, and 18H10 binds to MD-2, but requires the presence of TLR4, as the MAb does not bind soluble forms of MD-2.

As used herein, the terms “16G7”, “mu16G7”, “7E3”, “mu7E3”, “15C1”, “mu15C1”, “18H10” or “mu18H10” refer to the murine monoclonal antibody, and the terms “hu7E3”, “hu15C1”, or “hu18H10” refer to the humanized monoclonal antibody.

The present invention also provides soluble chimeric toll receptor proteins (also referred to herein as toll-like receptor proteins), methods for expressing toll receptor proteins, and methods for purifying such proteins in a soluble form. The chimeric proteins are useful, e.g., in generating antibodies.

TLRs recognize microbial particles and activate immune cells against the source of these microbial particles. (See Takeda et al., Annu. Rev. Immunol., 21: 335-76 (2003), hereby incorporated by reference in its entirety). TLR4 and MD-2 have been shown to form a complex on the cell surface, and the presence of MD-2 appears essential for the responsiveness of TLR4 to various ligands, including LPS. LPS is a gram-negative bacterial outer membrane glycolipid that is capable of strongly activating the innate immune system. LPS has been implicated as one of the major factors activating the immune system during the severe generalized inflammation resulting from gram-negative infection. (Lakhani et al., Curr. Opin. Pediatr. 15: 278-282 (2003), hereby incorporated by reference in its entirety).

LPS delivers signals to immune cells via its multi-chain receptor in which the TLR4/MD-2 complex is the principle signaling component. LPS has been shown to exert its effects on the immune system via signaling through TLR4. LPS rapidly binds to the lipopolysaccharide-binding protein (LBP) in the bloodstream, and in this form, LPS interacts with the GPI-anchored cell surface protein CD14. LPS is then transferred to TLR4, which transduces an intracellular activation signal. Another protein, MD-2, has been found to be necessary for signal transduction via TLR4 to occur. MD-2 interacts directly with TLR4 and plays an important role in its post-translational modification and intracellular trafficking. In addition, MD-2 has been shown to directly bind LPS, which demonstrates the importance of this accessory protein in the LPS receptor complex. (See Miyake K., Int. Immunopharmacol. 3:119-128 (2003), hereby incorporated by reference in its entirety).

Accordingly, neutralization of LPS signaling mediated by the TLR4/MD-2 complex is a potential therapeutic strategy in the treatment of disorders such as, for example, acute systemic inflammation and sepsis induced by gram-negative bacterial infection.

DEFINITIONS

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer’s specifications or as commonly accomplished in the art or as described herein. The foregoing techniques and procedures are generally performed according to conventional methods well known in the art and as described in various general and more specific references that are cited and discussed throughout the present specification See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term “antibody” refers to immunoglobulin molecules and immunologically active portions of immunoglobulin (Ig) molecules, i.e., molecules that contain an antigen binding site that specifically binds (immunoreacts with) an antigen. By “specifically bind” or “immunoreacts with” or “immunospecifically bind” is meant that the antibody reacts with one or more antigenic determinants of the desired antigen and does not react with other polypeptides or binds at much lower affinity ($K_d>10^{-6}$). Antibodies include, but are not limited to, polyclonal, monoclonal, chimeric, dAb (domain antibody), single chain, $F_{ab}$, $F_{ab'}$ and $F_{(ab')2}$ fragments, scFvs, and an $F_{ab}$ expression library.

The basic antibody structural unit is known to comprise a tetramer. Each tetramer is composed of two identical pairs of polypeptide chains, each pair having one “light” (about 25 kDa) and one “heavy” chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term “monoclonal antibody” (MAb) or “monoclonal antibody composition”, as used herein, refers to a population of antibody molecules that contain only one molecular species of antibody molecule consisting of a unique light chain gene product and a unique heavy chain gene product. In particular, the complementarity determining regions (CDRs)

of the monoclonal antibody are identical in all the molecules of the population. MAbs contain an antigen binding site capable of immunoreacting with a particular epitope of the antigen characterized by a unique binding affinity for it.

The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin, an scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics; For example, antibodies may be raised against N-terminal or C-terminal peptides of a polypeptide. An antibody is said to specifically bind an antigen when the dissociation constant is ≦1 μM; preferably ≦100 nM and most preferably ≦10 nM.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to the Toll-like Receptor 4 (TLR4)/MD-2 complex or to TLR4 when not complexed to MD-2, when the equilibrium binding constant ($K_d$) is ≦1 μM, preferably ≦100 nM, more preferably ≦10 nM, and most preferably ≦100 pM to about 1 pM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence. Polynucleotides in accordance with the invention include the nucleic acid molecules encoding the heavy chain immunoglobulin molecules presented in SEQ ID NOS: 2, 12, 22, 32, 45, 46, 49, 51 and 52, and nucleic acid molecules encoding the light chain immunoglobulin molecules represented in SEQ ID NOS: 7, 17, 27, 37, 47, 48, 50 and 53.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of marine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the invention comprise the heavy chain immunoglobulin molecules represented in SEQ ID NOS: 2, 12, 22, 32, 45, 46, 49, 51 and 52, and the light chain immunoglobulin molecules represented in SEQ ID NOS: 7, 17, 27, 37, 47, 48, 50 and 53, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means a polymeric boron of nucleotides of at least 10 bases in length, either ribonucleotides or deoxynucleotides or a modified form of either type of nucleotide. The term includes single and double stranded forms of DNA.

The term oligonucleotide referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the invention are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes Oligonucleotides linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest will be at least 80%, and more typically with preferably increasing homologies of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman Adv. Appl. Math. 2:482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See Immunology—A Synthesis (2nd Edition, E. S. Golub and D. R. Gren, Eds., Sinauer Associates, Sunderland7 Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and which are 5' to the 5' end of the RNA transcript are referred to as "upstream sequences", sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity.

Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "polypeptide fragment" as used herein refers to a polypeptide that has an amino terminal and/or carboxy-terminal deletion, but where the remaining amino acid sequence is identical to the corresponding positions in the naturally-occurring sequence deduced, for example, from a full length cDNA sequence. Fragments typically are at least 5, 6, 8 or 10 amino acids long, preferably at least 14 amino acids long' more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has specific binding to TLR4/MD2 complex or TLR4 alone, under suitable binding conditions. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, J. Adv. Drug Res. 15:29 (1986), Veber and Freidinger TINS p. 392 (1985); and Evans et al. J. Med. Chem. 30:1229 (1987). Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: $—CH_2NH—$, $—CH_2S—$, $—CH_2—CH_2—$, $—CH{=}CH$-(cis and trans), $—COCH_2—$, $CH(OH)CH_2—$, and $—CH_2SO—$, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992)); for example, by adding internal cysteine residues capable of forming intramolecular disulfide bridges which cyclize the peptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

The term "antineoplastic agent" is used herein to refer to agents that have the functional property of inhibiting a development or progression of a neoplasm in a human, particularly a malignant (cancerous) lesion, such as a carcinoma, sarcoma, lymphoma, or leukemia. Inhibition of metastasis is frequently a property of antineoplastic agents.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present.

Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term patient includes human and veterinary subjects.

Antibodies

Monoclonal antibodies of the invention (e.g., murine monoclonal or humanized antibodies) have the ability to inhibit LPS-induced proinflammatory cytokine production. Inhibition is determined, for example, in the human whole blood and huTLR4/MD2 transfected HEK 293 cellular assays described herein. Exemplary monoclonal antibodies include, for example, the antibodies referred to herein as "mu18H10", "hu18H10", "mu16G7", "mu15C1", "hu15C1", "mu7E3" and "hu7E3". The mu18H10 and hu18H10 antibodies recognize the TLR4/MD-2 complex, but do not recognize an MD-2 protein when not complexed with TLR4. The mu16G7, mu15C1, hu15C1, mu7E3 and hu7E3 monoclonal antibodies recognize the TLR4/MD-2 complex. mu15C1, hu15C1 and 16G7 also recognize TLR4 when not complexed with MD-2.

Also included in the invention are antibodies that bind to the same epitope as the antibodies described herein. For example, antibodies of the invention immunospecifically bind a TLR4/MD-2 complex, wherein the antibody binds to an epitope that includes one or more amino acid residues on human TLR4 between residues 289 and 375 of SEQ ID NO:54. Antibodies of the invention immunospecifically bind the TLR4/MD2 complex, wherein the antibody binds to an epitope on human MD-2 between residues 19 and 57 of SEQ ID NO:44. Those skilled in the art will recognize that it is possible to determine, without undue experimentation, if a monoclonal antibody (e.g., a murine monoclonal or humanized antibody) has the same specificity as a monoclonal antibody of the invention (e.g., mu18H10, hu18H10, mu16G7, mu15C1, hu15C1, mu7E3 and/or hu7E3) by ascertaining whether the former prevents the latter from binding to the TLR4/MD-2 complex or to TLR4 when not complexed to MD-2. If the monoclonal antibody being tested competes with the monoclonal antibody of the invention, as shown by a decrease in binding by the monoclonal antibody of the invention, then the two monoclonal antibodies bind to the same, or a closely related, epitope. An alternative method for determining whether a monoclonal antibody has the specificity of monoclonal antibody of the invention is to pre-incubate the monoclonal antibody of the invention with the TLR4/MD-2 complex or a soluble TLR4 protein (with which it is normally reactive), and then add the monoclonal antibody being tested to determine if the monoclonal antibody being tested is inhibited in its ability to bind the TLR4/MD-2 complex or to bind TLR4 and TLR4 complexed with MD-2. If the monoclonal antibody being tested is inhibited then, in all likelihood, it has the same, or functionally equivalent, epitopic specificity as the monoclonal antibody of the invention. Screening of monoclonal antibodies of the invention, can be also carried out by measuring LPS-induced IL-8 production and determining whether the test monoclonal antibody is able to neutralize LPS-induced IL-8 production.

Various procedures known within the art may be used for the production of polyclonal or monoclonal antibodies directed against the TLR4/MD-2 complex, or to TLR4 when not complexed to MD-2, or against derivatives, fragments, analogs homologs or orthologs thereof. (See, for example, Antibodies: A Laboratory Manual, Harlow E, and Lane D, 1988, Cold Spring Harbor Laboratory Press, Cold Spring Harbor, N.Y., incorporated herein by reference).

Antibodies are purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

The antibodies of the invention (e.g., hu18H10, 16G7, hu15C1 and hu7E3) are monoclonal antibodies. Monoclonal antibodies that neutralize LPS-signaling that is mediated by the TLR4/MD-2 complex are generated, e.g., by immunizing BALB/c mice with combinations of cell transfectants expressing high levels of TLR4 and MD-2 on their surface and a recombinant soluble chimeric protein comprising both TLR4 and MD-2 tethered by a flexible linker sequence. Hybridomas resulting from myeloma/B cell fusions are then screened for reactivity to this TLR4/MD-2 complex.

Monoclonal antibodies are prepared, for example, using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA.

Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Monoclonal antibodies of the invention include humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', $F(ab')_2$ or other antigen-binding subsequences of antibodies) that are principally comprised of the sequence of a human immunoglobulin, and contain minimal sequence derived from a non-human immunoglobulin. Humanization is performed, e.g., by following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. (See also U.S. Pat. No. 5,225,539.) In some instances, Fv framework residues of the human immunoglobulin are replaced by corresponding non-human residues. Humanized antibodies also comprise, .e.g., residues which are found neither in the recipient antibody nor in the imported CDR or framework sequences. In general, the humanized antibody includes substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also includes at least a portion of an immunoglobulin constant region (Fc), typically that of a human immunoglobulin (Jones et al., 1986; Riechmann et al., 1988; and Presta, Curr. Op. Struct. Biol., 2:593-596 (1992)).

Fully human antibodies are antibody molecules in which the entire sequence of both the light chain and the heavy chain, including the CDRs, arise from human genes. Such antibodies are termed "human antibodies", or "fully human antibodies" herein. Monoclonal antibodies can be prepared by using trioma technique; the human B-cell hybridoma technique (see Kozbor, et al., 1983 Immunol Today 4: 72); and the EBV hybridoma technique to produce monoclonal antibodies (see Cole, et al., 1985 In: MONOCLONAL ANTIBODIES AND CANCER THERAPY, Alan R. Liss, Inc., pp. 77-96). Monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries. (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., Bio/Technology 10, 779-783 (1992); Lonberg et al., Nature 368 856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. An example of such a nonhuman animal is a mouse termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv (scFv) molecules.

An example of a method of producing a nonhuman host, exemplified as a mouse, lacking expression of an endogenous immunoglobulin heavy chain is disclosed in U.S. Pat. No. 5,939,598. It can be obtained by a method, which includes deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

One method for producing an antibody of interest, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

The antibody can be expressed by a vector containing a DNA segment encoding the single chain antibody described above.

These can include vectors, liposomes, naked DNA, adjuvant-assisted DNA. gene gun, catheters, etc. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G., et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. adenovirus, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266: 292-305 (1994)). Other methods that can be used include catheters, intravenous, parenteral, intraperitoneal and subcutaneous injection, and oral or other known routes of administration.

These vectors can be used to express large quantities of antibodies that can be used in a variety of ways. For example, to detect the presence of the TLR4/MD-2 complex and/or TLR4 in a sample. The antibody can also be used to try to bind to and disrupt TLR4/MD-2 complex-related signaling.

Techniques can be adapted for the production of single-chain antibodies specific to an antigenic protein of the invention (see e.g., U.S. Pat. No. 4,946,778). In addition, methods can be adapted for the construction of Fab expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

The invention also includes $F_v$, $F_{ab}$, $F_{ab'}$ and $F_{(ab')2}$ anti-TLR4/MD2 complex fragments or anti-TLR4 fragments, single chain anti-TLR4/MD2 or anti-TLR4 antibodies, bispecific anti-TLR4/MD2 or anti-TLR4 antibodies and heteroconjugate anti-TLR4/MD2 or anti-TLR4 antibodies.

Bispecific antibodies are antibodies that have binding specificities for at least two different antigens. In the present case, one of the binding specificities is for the TLR4/MD2 complex and/or TLR4 when not complexed with MD-2. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. $F(ab')_2$ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from *E. coli* and chemically coupled to form bispecific antibodies. Shalaby et al., J. Exp. Med. 175:217-225 (1992) describe the production of a fully humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the invention with respect to effector function, so as to enhance, e.g., the effectiveness of the antibody in treating diseases and disorders associated with aberrant LPS signaling. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol)propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238: 1098 (1987).

Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl)carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio)propionamido]hexanoate (Pierce Chem. Co., Cat #21651G); (iv) Sulfo-LC-SPDP (sulfosuccinimidyl 6 [3-(2-pyridyldithio)-propianamide]hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Use of Antibodies Against the TLR4/MD2 Complex and Antibodies Against TLR4

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration See also Baldrick P. "Pharmaceutical excipient development: the need for preclinical guidance." Regul. Toxicol Pharmacol. 32(2): 210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the invention, which include a monoclonal antibody of the invention (e.g., a murine monoclonal or humanized monoclonal antibody), are used to treat or alleviate a symptom associated with an immune-related disorder. The present invention also provides methods of treating or alleviating a symptom associated with an immune-related disorder. A therapeutic regimen is carried out by identifying a subject, e.g., a human patient suffering from (or at risk of developing) an immune-related disorder, using standard methods.

Antibodies of the invention, which are capable of inhibiting LPS-induced proinflammatory cytokine production, are useful therapeutic tools in the treatment of disorders, such as, for example, acute inflammation and sepsis induced by microbial products (e.g., LPS) and exacerbations arising from this acute inflammation, such as, for example, chronic obstructive pulmonary disease and asthma (see O'Neill, Curr. Opin. Pharmacol. 3: 396-403 (2003), hereby incorporated by reference in its entirety). Such antibodies are also useful in treating neurodegenerative autoimmune diseases. (Lehnardt et al., Proc. Natl. Acad. Sci. USA 100: 8514-8519(2003), hereby incorporated by reference in its entirety).

In addition, the antibodies of the invention are also useful as therapeutic reagents in the treatment of diseases, such as, for example, osteoarthritis, which are caused by mechanical stress, which, in turn, induces endogenous soluble "stress" factors that trigger TLR4. Endogenous soluble stress factor include e.g., Hsp60 (see Ohashi et al., J. Immunol. 164: 558-561 (2000)) and fibronectin (see Okamura et al., J. Biol. Chem. 276: 10229-10233 (2001) and heparan sulphate, hyaluronan, gp96, β-Defensin-2 or surfactant protein A (see e.g., Johnson et al., Crit. Rev. Immunol., 23(1-2):15-44 (2003), each of which is hereby incorporated by reference in its entirety). The antibodies of the invention are also useful in the treatment of a variety of disorders associated with mechanical stress, such as for example, mechanical stress that is associated with subjects and patients placed on respirators, ventilators and other respiratory-assist devices. For example, the antibodies of the invention are useful in the treatment of ventilator-induced lung injury ("VILI"), also referred to as ventilation-associated lung injury ("VALI").

Other disease areas in which inhibiting TLR4 function could be beneficial include, for example, chronic inflammation (e.g., chronic inflammation associated with allergic conditions and asthma), autoimmune diseases (e.g., inflammatory bowel disorder) and atherosclerosis (see O'Neill, Curr. Opin. Pharmacol. 3: 396-403 (2003), hereby incorporated by reference in its entirety).

Symptoms associated with these immune-related disorders include, for example, inflammation, fever, general malaise, fever, pain, often localized to the inflamed area, rapid pulse rate, joint pain or aches (arthralgia), rapid breathing or other abnormal breathing patterns, chills, confusion, disorientation, agitation, dizziness, cough, dyspnea, pulmonary infections, cardiac failure, respiratory failure, edema, weight gain, mucopurulent relapses, cachexia, wheezing, headache, and abdominal symptoms such as, for example, abdominal pain, diarrhea or constipation.

Efficaciousness of treatment is determined in association with any known method for diagnosing or treating the particular immune-related disorder. Alleviation of one or more symptoms of the immune-related disorder indicates that the antibody confers a clinical benefit.

Methods for the screening of antibodies that possess the desired specificity include, but are not limited to, enzyme linked immunosorbent assay (ELISA) and other immunologically mediated techniques known within the art.

Antibodies directed against the TLR4/MD-2 complex or to TLR4 when not complexed to MD-2 (or a fragment thereof) may be used in methods known within the art relating to the localization and/or quantitation of the TLR4/MD-2 complex or TLR4 (e.g., for use in measuring levels of the TLR4/MD-2 complex or TLR4 within appropriate physiological samples, for use in diagnostic methods, for use in imaging the protein, and the like). In a given embodiment, antibodies specific to the TLR4/MD-2 complex, or TLR4, or derivative, fragment, analog or homolog thereof, that contain the antibody derived antigen binding domain, are utilized as pharmacologically active compounds (referred to hereinafter as "Therapeutics").

An antibody specific for the TLR4/MD-2 complex or TLR4 can be used to isolate the TLR4/MD-2 complex or a TLR4 polypeptide by standard techniques, such as immunoaffinity, chromatography or immunoprecipitation. Antibodies directed against the TLR4/MD-2 complex or a TLR4 protein (or a fragment thereof) can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibodies of the invention, including polyclonal, monoclonal, humanized and fully human antibodies, may be used as therapeutic agents. Such agents will generally be employed to treat or prevent a disease or pathology associated with aberrant TLR4 signaling in a subject. An antibody preparation, preferably one having high specificity and high affinity for its target antigen, is administered to the subject and will generally have an effect due to its binding with the target. Administration of the antibody may abrogate or inhibit or interfere with the signaling function of the target (e.g., the TLR4/MD-2 complex). Administration of the antibody may abrogate or inhibit or interfere with the binding of the target (e.g., TLR4) with an endogenous ligand (e.g., TLR4 or the MD-2 accessory protein) to which it naturally binds. For example, the antibody binds to the target and neutralizes LPS-induced proinflammatory cytokine production.

A therapeutically effective amount of an antibody of the invention relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Antibodies specifically binding the TLR4/MD-2 complex or a TLR4 protein or a fragment thereof of the invention can be administered for the treatment of disorders associated with aberrant LPS signaling in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate)microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

An antibody according to the invention can be used as an agent for detecting the presence of the TLR4/MD-2 complex or a TLR4 protein (or a protein fragment thereof) in a sample. In some embodiments, the antibody contains a detectable label. Antibodies are polyclonal, or more preferably, monoclonal. An intact antibody, or a fragment thereof (e.g., $F_{ab}$, scFv, or $F_{(ab)2}$) is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Chimeric Polypeptides

The chimeric peptides of the invention include a first and second domain operably linked together. The first domain includes at least a portion of a toll-like receptor polypeptide, while the second domain includes at least a portion of an MD accessory protein. The first and second domains can occur in any order in the peptide, and the peptide can include one or more of each domain. The chimeric protein comprises at least one biologically active portion of a toll-like receptor polypeptide or MD accessory protein. The chimeric peptide is soluble. By soluble is meant the ability to dissolve in a fluid.

A "toll-like receptor polypeptide" refers to a polypeptide having an amino acid sequence corresponding to at least a portion of a toll-like receptor polypeptide. A toll-like receptor polypeptide includes, for example, TLRs 1-10 and RP105. The toll-like receptor polypeptide, and/or nucleic acids encoding the toll-like receptor polypeptide, can be constructed using toll-like receptor polypeptide encoding sequences that are known in the art and are described in, e.g. GenBank Accession Nos. (CAH72620; CAH72619; NP_003254; NP_003255; NP_003259; NP_006059; NP_057646; NP_003256; AAH33651; CAD99157; AAM23001; BAB43955; AAF05316; AAK26744; AAF78037; AAF78036; AAF78035; BAB19259; AAF64061; AAF60188; AAF89753; AAF07823; BAA78631; AAC34135; AAC34134; AAC34133; AAC34137) and are incorporated herein by reference in their entirety. Within the chimeric protein the toll-like receptor polypeptide can correspond to all or a portion of a toll-like receptor polypeptide. Preferably the toll-like receptor polypeptide includes the extracellular portion of the polypeptide.

An "MD accessory protein" refers to a polypeptide having an amino acid sequence corresponding to at least a portion of a MD accessory protein. The MD protein is, e.g., MD-1 or MD-2. The MD accessory protein, and/or nucleic acids encoding the MD accessory protein, can be constructed using MD accessory protein encoding sequences that are known in the art and are described in, e.g. GenBank Accession Nos. GenBank Accession Nos. O95711 (MD-1); AAC98152 (MD-1); Q9Y6Y9 (MD-2); NP_056179 (MD-2); AAH20690 (MD-2); and BAA78717 (MD-2). Exemplary MD accessory protein and nucleic acid sequences are is shown in FIGS. 32A, 32B, 33A and 33B. Within the chimeric protein the MD accessory protein can correspond to all or a portion of a MD accessory protein.

The chimeric protein may be linked to one or more additional moieties. For example, the chimeric protein may additionally be linked to a GST fusion protein in which the glycoprotein Ibα fusion protein sequences are fused to the C-terminus of the GST (i.e., glutathione S-transferase) sequences. Such fusion proteins can facilitate the purification of chimeric protein.

In another embodiment, the chimeric protein is includes a heterologous signal sequence (i.e., a polypeptide sequence that is not present in a polypeptide encoded by a toll-like receptor polypeptide or MD accessory protein nucleic acid) at its N-terminus. For example, the native toll-like receptor polypeptide signal sequence can be removed and replaced with a signal sequence from another protein. In certain host cells (e.g., mammalian host cells), expression and/or secretion of chimeric protein can be increased through use of a heterologous signal sequence.

An chimeric protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) Current Protocols in Molecular Biology, John Wiley & Sons, 1992). Moreover, many expression vectors are commercially available that encode a fusion moiety (e.g., an Fc region of an immunoglobulin heavy chain). A glycoprotein Ibα encoding nucleic acid can be cloned into such an expression vector such that the fusion moiety is linked in-frame to the immunoglobulin protein.

Within the chimeric protein, the term "operatively linked" is intended to indicate that the first and second polypeptides are chemically linked (most typically via a covalent bond such as a peptide bond) in a manner that allows for at least one function associated with the toll-like receptor polypeptide and MD accessory protein. When used to refer to nucleic acids encoding the chimeric protein the term operatively linked means that a nucleic acid encoding the toll-like receptor polypeptide or MD accessory protein are fused in-frame to each other. The MD accessory protein can be fused to the N-terminus or C-terminus of the toll-like receptor polypeptide. Optionally, the toll-like receptor polypeptide and MD accessory protein are linked via a spacer arm. Spacer arms provide intramolecular flexibility or adjust intramolecular distances between conjugated moieties and thereby may help preserve biological activity. A spacer arm may be in the form of a polypeptide moiety that includes spacer amino acids, e.g. proline, serine or glycine. Preferably the toll-like receptor polypeptide and MD accessory protein are linked via a flexible glycine/serine linker. Alternatively, a spacer arm may be part of the cross-linking reagent, such as in "long-chain SPDP" (Pierce Chem. Co., Rockford, Ill., cat. No. 21651 H).

In other embodiments, the toll-like receptor polypeptide and the MD accessory protein are linked by chemical coupling in any suitable manner known in the art. Many known chemical cross-linking methods are non-specific, i e.; they do not direct the point of coupling to any particular site on the toll-like polypeptide or MD accessory protein. As a result, use of non-specific cross-linking agents may attack functional sites or sterically block active sites, rendering the conjugated proteins biologically inactive.

One way to increasing coupling specificity is to directly chemical coupling to a functional group found only once or a few times in one or both of the polypeptides to be cross-linked. For example, in many proteins, cysteine, which is the only protein amino acid containing a thiol group, occurs only a few times. Also, for example, if a polypeptide contains no lysine residues, a cross-linking reagent specific for primary amines will be selective for the amino terminus of that polypeptide. Successful utilization of this approach to increase coupling specificity requires that the polypeptide have the suitably rare and reactive residues in areas of the molecule that may be altered without loss of the molecule's biological activity.

Cysteine residues may be replaced when they occur in parts of a polypeptide sequence where their participation in a cross-linking reaction would otherwise likely interfere with biological activity. When a cysteine residue is replaced, it is typically desirable to minimize resulting changes in polypeptide folding. Changes in polypeptide folding are minimized when the replacement is chemically and sterically similar to cysteine. For these reasons, serine is preferred as a replacement for cysteine. As demonstrated in the examples below, a cysteine residue may be introduced into a polypeptide's amino acid sequence for cross-linking purposes. When a cysteine residue is introduced, introduction at or near the amino or carboxy terminus is preferred. Conventional methods are available for such amino acid sequence modifications, whether the polypeptide of interest is produced by chemical synthesis or expression of recombinant DNA.

Coupling of the two constituents can be accomplished via a coupling or conjugating agent. There are several intermolecular cross-linking reagents which can be utilized, See for example, Means and Feeney, Chemical Modification of Proteins, Holden-Day, 1974, pp. 39-43. Among these reagents are, for example, J-succinimidyl 3-(2-pyridyldithio)propionate (SPDP) or N,N'-(1,3-phenylene)bismaleimide (both of which are highly specific for sulfhydryl groups and form irreversible linkages); N,N'-ethylene-bis-(iodoacetamide) or other such reagent having 6 to 11 carbon methylene bridges (which relatively specific for sulfhydryl groups); and 1,5-difluoro-2,4-dinitrobenzene (which forms irreversible linkages with amino and tyrosine groups). Other cross-linking reagents useful for this purpose include: p,p'-difluoro-m,m'-dinitrodiphenylsulfone (which forms irreversible cross-linkages with amino and phenolic groups); dimethyl adipimidate (which is specific for amino groups); phenol-1,4-disulfonylchloride (which reacts principally with amino groups); hexamethylenediisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine).

Cross-linking reagents may be homobifunctional, i.e., having two functional groups that undergo the same reaction. A preferred homobifunctional cross-linking reagent is bismaleimidohexane ("BMH"). BMH contains two maleimide functional groups, which react specifically with sulfhydryl-containing compounds under mild conditions (pH 6.5-7.7). The two maleimide groups are connected by a hydrocarbon chain. Therefore, BMH is useful for irreversible cross-linking of polypeptides that contain cysteine residues.

Cross-linking reagents may also be heterobifunctional. Heterobifunctional cross-linking agents have two different functional groups, for example an amine-reactive group and a thiol-reactive group, that will cross-link two proteins having free amines and thiols, respectively. Examples of heterobifunctional cross-linking agents are succinimidyl 4-(N-maleimidomethyl)cyclohexane-1-carboxylate ("SMCC"), m-maleimidobenzoyl-N-hydroxysuccinimide ester ("MBS"), and succinimide 4-(p-maleimidophenyl)butyrate ("SMPB"), an extended chain analog of MBS. The succinimidyl group of these cross-linkers reacts with a primary amine, and the thiol-reactive maleimide forms a covalent bond with the thiol of a cysteine residue.

Cross-linking reagents often have low solubility in water. A hydrophilic moiety, such as a sulfonate group, may be added to the cross-linking reagent to improve its water solubility. Sulfo-MBS and sulfo-SMCC are examples of cross-linking reagents modified for water solubility.

Many cross-linking reagents yield a conjugate that is essentially non-cleavable under cellular conditions. However, some cross-linking reagents contain a covalent bond, such as a disulfide, that is cleavable under cellular conditions. For example, Traut's reagent, dithiobis(succinimidylpropionate) ("DSP"), and N-succinimidyl 3-(2-pyridyldithio)propionate ("SPDP") are well-known cleavable cross-linkers. The use of a cleavable cross-linking reagent permits the cargo moiety to separate from the transport polypeptide after delivery into the target cell. Direct disulfide linkage may also be useful.

Numerous cross-linking reagents, including the ones discussed above, are commercially available. Detailed instructions for their use are readily available from the commercial suppliers. A general reference on protein cross-linking and conjugate preparation is: Wong, Chemistry Of Protein Conjugation And Cross-Linking, CRC Press (1991).

Also included in the invention are derivatives, fragments, homologs, analogs and variants of the chimeric peptides and nucleic acids encoding these peptides. For nucleic acids, derivatives, fragments, and analogs provided herein are defined as sequences of at least 6 (contiguous) nucleic acids, and which have a length sufficient to allow for specific hybridization. For amino acids, derivatives, fragments, and analogs provided herein are defined as sequences of at least 4 (contiguous) amino acids, a length sufficient to allow for specific recognition of an epitope.

The length of the fragments are less than the length of the corresponding full-length nucleic acid or polypeptide from which the chimeric peptide, or nucleic acid encoding same, is derived. Derivatives and analogs may be full length or other than full length, if the derivative or analog contains a modified nucleic acid or amino acid. Derivatives or analogs of the chimeric peptides include, e.g., molecules including regions that are substantially homologous to the peptides, in various embodiments, by at least about 30%, 50%, 70%, 80%, or 95%, 98%, or even 99%, identity over an amino acid sequence of identical size or when compared to an aligned sequence in which the alignment is done by a computer homology program known in the art. For example sequence identity can be measured using sequence analysis software (Sequence Analysis Software Package of the Genetics Computer Group, University of Wisconsin Biotechnology Center, 1710 University Avenue, Madison, Wis. 53705), with the default parameters therein.

Where a particular polypeptide is said to have a specific percent identity to a reference polypeptide of a defined length, the percent identity is relative to the reference peptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide, which is 50% identical to the reference polypeptide over its entire length. Of course, other polypeptides will meet the same criteria.

Pharmaceutical Compositions

The antibodies or soluble chimeric polypeptides of the invention (also referred to herein as "active compounds"), and derivatives, fragments, analogs and homologs thereof, can be incorporated into pharmaceutical compositions suitable for administration. Such compositions typically comprise the antibody or soluble chimeric polypeptide and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™. (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Screening Methods

The invention provides methods (also referred to herein as "screening assays") for identifying modulators, i.e., candidate or test compounds or agents (e.g., peptides, peptidomimetics, small molecules or other drugs) that modulate or otherwise interfere with the binding of TLR4 to the MD-2 accessory protein, or candidate or test compounds or agents that modulate or otherwise interfere with the signaling function of TLR4 and/or the TLR4/MD-2 complex. Also provided are methods of identifying compounds useful to treat disorders associated with aberrant LPS-signaling. The invention also includes compounds identified in the screening assays described herein.

In one embodiment, the invention provides assays for screening candidate or test compounds which modulate the signaling function of the TLR4/MD-2 complex and/or the interaction between TLR4 and MD-2. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. (See, e.g., Lam, 1997. Anticancer Drug Design 12: 145).

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. Proc. Natl. Acad. Sci. U.S.A. 90: 6909; Erb, et al., 1994. Proc. Natl. Acad. Sci. U.S.A. 91: 11422; Zuckermann, et al., 1994. J. Med. Chem. 37: 2678; Cho, et al., 1993. Science 261: 1303; Carrell, et al., 1994. Angew. Chem. Int. Ed. Engl. 33: 2059; Carell, et al., 1994. Angew. Chem. Int. Ed. Engl. 33: 2061; and Gallop, et al., 1994. J. Med. Chem. 37:1233.

Libraries of compounds may be presented in solution (see e.g., Houghten, 1992. Biotechniques 13: 412-421), or on beads (see Lam, 1991. Nature 354: 82-84), on chips (see Fodor, 1993. Nature 364: 555-556), bacteria (see U.S. Pat. No. 5,223,409), spores (see U.S. Pat. No. 5,233,409), plasmids (see Cull, et al., 1992. Proc. Natl. Acad. Sci. USA 89: 1865-1869) or on phage (see Scott and Smith, 1990. Science 249: 386-390; Devlin, 1990. Science 249: 404-406; Cwirla, et al., 1990. Proc. Natl. Acad. Sci. U.S.A. 87: 6378-6382; Felici, 1991. J. Mol. Biol. 222: 301-310; and U.S. Pat. No. 5,233,409.).

In one embodiment, a candidate compound is introduced to an antibody-antigen complex and determining whether the candidate compound disrupts the antibody-antigen complex, wherein a disruption of this complex indicates that the candidate compound modulates the signaling function of the TLR4/MD-2 complex and/or the interaction between TLR4 and MD-2. For example, the antibody is monoclonal antibody mu18H10, hu18H10 and the antigen is the TLR4/MD-2 complex. Alternatively, the monoclonal antibody is 16G7, mu15C1, hu15C1, mu7E3 or hu7E3 and the antigen is the TLR4/MD-2 complex or TLR4.

In another embodiment, a TLR4/MD-2 complex is provided and exposed to at least one neutralizing monoclonal antibody. Formation of an antibody-antigen complex is detected, and one or more candidate compounds are introduced to the complex. If the antibody-antigen complex is disrupted following introduction of the one or more candidate compounds, the candidate compounds is useful to treat disorders associated with aberrant LPS-signaling.

In another embodiment, a soluble chimeric protein of the invention is provided and exposed to at least one neutralizing monoclonal antibody. Formation of an antibody-antigen complex is detected, and one or more candidate compounds are introduced to the complex. If the antibody-antigen complex is disrupted following introduction of the one or more candidate compounds, the candidate compounds is useful to treat disorders associated with aberrant LPS-signaling.

Determining the ability of the test compound to interfere with or disrupt the antibody-antigen complex can be accomplished, for example, by coupling the test compound with a radioisotope or enzymatic label such that binding of the test compound to the antigen or biologically-active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product.

In one embodiment, the assay comprises contacting an antibody-antigen complex with a test compound, and determining the ability of the test compound to interact with the antigen or otherwise disrupt the existing antibody-antigen complex. In this embodiment, determining the ability of the test compound to interact with the antigen and/or disrupt the antibody-antigen complex comprises determining the ability of the test compound to preferentially bind to the antigen or a biologically-active portion thereof, as compared to the antibody.

In another embodiment, the assay comprises contacting an antibody-antigen complex with a test compound and determining the ability of the test compound to modulate the antibody-antigen complex. Determining the ability of the test compound to modulate the antibody-antigen complex can be accomplished, for example, by determining the ability of the antigen to bind to or interact with the antibody, in the presence of the test compound.

Those skilled in the art will recognize that, in any of the screening methods disclosed herein, the antibody may be a neutralizing antibody, such as monoclonal antibody hu18H10, hu15C1 and/or hu7E3, each of which modulates or otherwise interferes with LPS-induced proinflammatory cytokine production.

The screening methods disclosed herein may be performed as a cell-based assay or as a cell-free assay. The cell-free assays of the invention are amenable to use of either the soluble form or the membrane-bound form of the TLR4 and/or TLR4 when complexed with MD-2, and fragments thereof. In the case of cell-free assays comprising the membrane-bound forms of TLR4 and/or the TLR4/MD-2 complex, it may be desirable to utilize a solubilizing agent such that the membrane-bound form of the proteins are maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, N-dodecyl-N,N-dimethyl-3-ammonio-1-propane sulfonate, 3-(3-cholamidopropyl)dimethylamminiol-1-propane sulfonate (CHAPS), or 3-(3-cholamidopropyl)dimethylamminiol-2-hydroxy-1-propane sulfonate (CHAPSO).

In more than one embodiment, it may be desirable to immobilize either the antibody or the antigen to facilitate separation of complexed from uncomplexed forms of one or both following introduction of the candidate compound, as well as to accommodate automation of the assay. Observation of the antibody-antigen complex in the presence and absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, GST-antibody fusion proteins or GST-antigen fusion proteins can be adsorbed onto glutathione sepharose beads (Sigma Chemical, St. Louis, Mo.) or glutathione derivatized microtiter plates, that are then combined with the test compound, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly. Alternatively, the complexes can be dissociated from the matrix, and the level of antibody-antigen complex formation can be determined using standard techniques.

Other techniques for immobilizing proteins on matrices can also be used in the screening assays of the invention. For example, either the antibody (e.g. hu18H10, hu15C1, and/or hu7E3) or the antigen (e.g. the TLR4/MD-2 complex and/or a TLR4 protein) can be immobilized utilizing conjugation of biotin and streptavidin. Biotinylated antibody or antigen molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, other antibodies reactive with the antibody or antigen of interest, but which do not interfere with the formation of the antibody-antigen complex of interest, can be derivatized to the wells of the plate, and unbound antibody or antigen trapped in the wells by antibody conjugation. Methods for detecting such complexes, in addition to those described above for the GST-immobilized complexes, include immunodetection of complexes using such other antibodies reactive with the antibody or antigen.

The invention further pertains to novel agents identified by any of the aforementioned screening assays and uses thereof for treatments as described herein.

Diagnostic Assays

Antibodies of the present invention can be detected by appropriate assays, e.g., conventional types of immunoassays. For example, a sandwich assay can be performed in which the TLR4/MD-2 complex or a TLR4 protein or fragment thereof is affixed to a solid phase. Incubation is maintained for a sufficient period of time to allow the antibody in the sample to bind to the immobilized polypeptide on the solid phase. After this first incubation, the solid phase is separated from the sample. The solid phase is washed to remove unbound materials and interfering substances such as non-specific proteins which may also be present in the sample. The solid phase containing the antibody of interest (e.g. monoclonal antibody hu18H10, hu15C1 and/or hu7E3) bound to the immobilized polypeptide is subsequently incubated with a second, labeled antibody or antibody bound to a coupling agent such as biotin or avidin. This second antibody may be another anti-TLR4/MD-2 complex antibody, another anti-TLR4 antibody or another antibody. Labels for antibodies are well-known in the art and include radionuclides, enzymes (e.g. maleate dehydrogenase, horseradish peroxidase, glucose oxidase, catalase), fluors (fluorescein isothiocyanate, rhodamine, phycocyanin, fluorescarmine), biotin, and the like. The labeled antibodies are incubated with the solid and the label bound to the solid phase is measured. These and other immunoassays can be easily performed by those of ordinary skill in the art.

An exemplary method for detecting the presence or absence of the TLR4/MD-2 complex or a TLR4 protein in a biological sample involves obtaining a biological sample from a test subject and contacting the biological sample with a labeled monoclonal antibody according to the invention such that the presence of TLR4/MD-2 complex or TLR4 is detected in the biological sample.

As used herein, the term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. That is, the detection method of the invention can be used to detect TLR4/MD-2 complex or TLR4 in a biological sample in vitro as well as in vivo. For example, in vitro techniques for detection of TLR4/MD-2 complex or TLR4 include enzyme linked immunosorbent assays (ELISAs), Western blots, immunoprecipitations, and immunofluorescence. Furthermore, in vivo techniques for detection of TLR4/MD-2 complex or TLR4 include introducing into a subject a labeled anti-TLR4/MD-2 complex or anti-TLR4 antibody. For example, the antibody can be labeled with a radioactive marker whose presence and location in a subject can be detected by standard imaging techniques.

In one embodiment, the biological sample contains protein molecules from the test subject. One preferred biological sample is a peripheral blood leukocyte sample isolated by conventional means from a subject.

The invention also encompasses kits for detecting the presence of TLR4/MD-2 complex or TLR4 in a biological sample. For example, the kit can comprise: a labeled compound or agent capable of detecting TLR4/MD-2 complex or TLR4, when not complexed with MD-2, (e.g., an anti-TLR4/MD-2 complex monoclonal antibody or an anti-TLR4 monoclonal antibody) in a biological sample; means for determining the amount of TLR4/MD-2 complex or TLR4 in the sample; and means for comparing the amount of TLR4/MD-2 complex or TLR4 in the sample with a standard. The compound or agent can be packaged in a suitable container. The kit can further comprise instructions for using the kit to detect TLR4/MD-2 complex or TLR4 in a sample.

The invention will be further described in the following examples, which do not limit the scope of the invention described in the claims.

EXAMPLES

Example 1

Materials and Methods for the Generation of Murine 18H10 Monoclonal Antibody A. Generation of Stable TLR4/MD-2 Transfectants Stable TLR4/MD-2 transfectants were generated in CHO-K1 and HEK 293 cells. For CHO-K1 cells, human TLR4 cDNA encoding an N-terminal c-myc epitope tag was cloned into pCDNA3.1(−)hygro (Invitrogen), and human MD-2 cDNA encoding C-terminal c-Myc and Protein C epitope tags was cloned into pCDNA3 (Invitrogen). Both constructs were co-transfected into CHO cells using Fugene 6™ reagent (Roche), according to the manufacturer's guidelines. Antibiotic resistant cells were selected in culture medium containing 500 μg/ml G418 and 250 μg/ml hygromycin B (both from Invitrogen).

To select for cells expressing the TLR4/MD-2 complex, $1\times10^7$ cells/ml were incubated in 1×PBS supplemented with 1% BSA and 10 μg/ml anti-protein C monoclonal antibody (Roche). Cells were washed once and then incubated in the same buffer with PE-conjugated goat anti-mouse IgG (H+L) antibody (1:200 dilution; Anwara). Cells were subsequently incubated with anti-PE microbeads (Miltenyi Biotec) and passed through a Midi MACS LS column. Cells retained on the column were eluted and placed back in culture with antibiotic selection. Rounds of sorting were continued until a uniformly positive population of cells expressing the TLR4/MD-2 complex was obtained.

B. Generation of Recombinant MD-2 and Chimeric TLR4/MD-2 Protein

To generate recombinant soluble MD-2, cDNA encoding the protein with C terminal FLAG and 6×HIS tags for detection and purification purposes was cloned into pFASTBAC1 and subsequently inserted into bacmid DNA by homologous recombination. Following generation of a viral stock, Sf9 cells were superinfected. 48 hours later, the recombinant protein was purified from infected cell supernatants using a NiNTA affinity matrix (Qiagen).

To generate the recombinant TLR4/MD-2 chimeric protein, cDNA encoding the extracellular portion of human TLR4 linked to MD-2 via a glycine serine ($GGGGS_3$) linker was assembled using PCR. FLAG and 6×HIS tags were included at the C-terminus of MD-2 for detection and purification purposes. The cDNA cassette was cloned into the baculovirus expression vector pFASTBAC1 (Invitrogen) and subsequently inserted into bacmid DNA by homologous recombination. Following generation of a viral stock, Sf9 cells were superinfected. 48 hours later, the recombinant fusion protein was purified from cell lysates using an anti-FLAG™ M2 MAb affinity matrix (Sigma).

C. Immunization of Mice 8 week old female BALB/c mice (IFFA CREDO) were immunized with a subcutaneous injection (s.c.) of $10^6$ CHO cells/ml in RIBI adjuvant (Sigma) at days 0, 7 and 28 as previously described in Buell et al., Blood 92: 3521-3528 (1998), hereby incorporated by reference in its entirety.

D. Specific Serum Titrations

The mice were bled at days 0 and 14. TLR4/MD-2 specific antibody titers were assessed in the sera by FACS analysis on TLR4/MD-2 transfected 293 cells. Cells were incubated with mice sera at 1:250, 1:2500 and 1:25000 dilutions, washed, incubated with APC-conjugated goat anti-mouse IgG (H+L) antibody (Molecular Probes) and analyzed on a FACScalibur (Becton Dickenson) in the FL-4 channel.

E. B Cell/Myeloma Fusions

Mice having specific TLR4/MD-2 serum antibodies were "hyperboosted" subcutaneously (s.c.) with the chimeric TLR4/MD-2 fusion protein either 3 or 4 days prior to fusion. Draining lymph nodes were obtained as a source of B cells for fusion with the mouse myeloma cell line P3-X63-Ag8.653. B cell extraction and cellular fusions were performed as previously described in Buell et al., Blood 92: 3521-3528 (1998), hereby incorporated by reference in its entirety. Cells were plated at an approximate concentration of $10^4$ myeloma cells/well and grown for 10-14 days in culture medium supplemented with HAT (Sigma).

F. Hybridoma Screening

Supernatants from wells containing viable hybridoma cells were screened on mock transfected cells vs. TLR4/MD-2 transfected myeloma cells for TLR4/MD-2 specificity by FACS analysis. Cells were then incubated with supernatant and goat-anti mouse IgG (H+L) antibody (Molecular Probes). Cells were analyzed on a FACScalibur in the FL-4 channel.

G. Monoclonal Antibody Specificity by FACS

Figure 4:
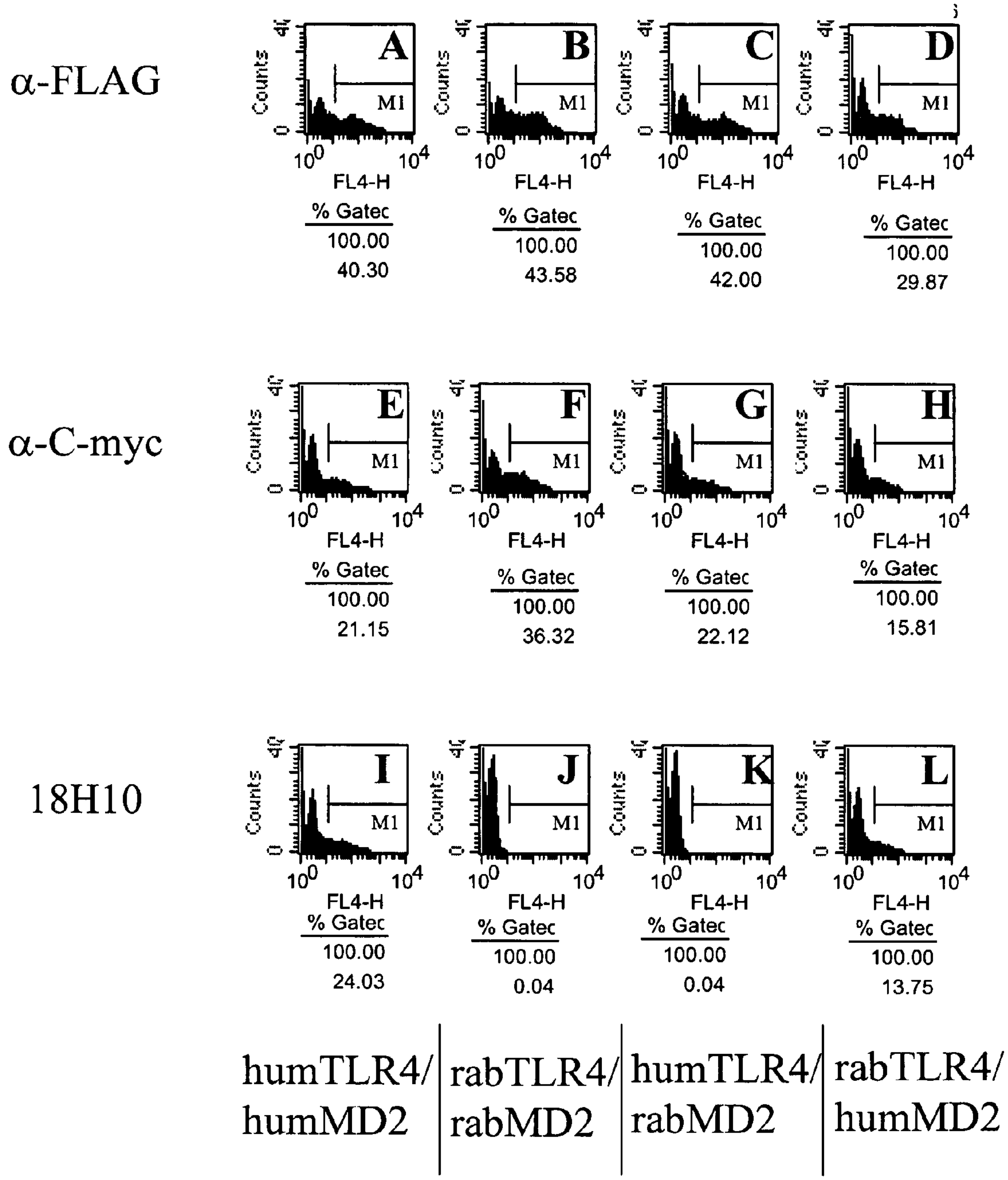
FIG. 4 is a series of graphs depicting the specificity of the mu18H 10 monoclonal antibody for MD-2. The specificity of the mu18H10 antibody is shown by flow cytometry analysis of HEK 293 cells transiently transfected with either human TLR4 and human MD-2 (Panels A, E and I); rabbit TLR4 and rabbit MD-2 (Panels B, F and J); human TLR4 and rabbit MD-2 (Panels C, G and K); or rabbit TLR4 and human MD-2 (Panels D, H and L). Cells were incubated with either α-FLAG™ antibody (to detect TLR4 expression); α-C-myc antibody (to detect MD-2 expression) or the mu18H10 monoclonal antibody, followed by an APC-coupled α-mouse (H+L) antibody.

HEK 293 cells were plated in 6 well plates at a density of $2.5\times10^5$ cells/well in 2 ml culture medium containing 10% FBS. 16 hours post-plating, cells were transfected with 0.75 μg of the appropriate vector(s) using Fugene™ reagent (Roche) according to the manufacturer's guidelines. 48 hours post-transfection, cells were stained with the appropriate monoclonal antibody (as indicated in FIG. 4) and an APC-coupled goat anti-mouse IgG (H+L) antibody (Molecular Probes) and analyzed using the FACScalibur in the FL-4 channel.

H. Monoclonal Antibody Specificity by Direct ELISA

Recombinant soluble MD-2 with C terminal FLAG and histidine epitope tags was coated at a concentration of 5 μg/ml in 50 μl PBS on ELISA plates (Nunc Maxisorp). Wells were blocked with 200 μl PBS 2% BSA and subsequently incubated with the appropriate MAb at the indicated concentration in PBS 1% BSA. Following 3 wash steps with PBS 0.05% Tween 20, 50 μl HRP conjugated goat anti-mouse IgG (H+L) at a 1:5000 dilution was added to the wells. Following a further wash step, binding was revealed using TMB substrate. Plates were read at a wavelength of 650 nm.

I. Monoclonal Antibody Specificity by Sandwich ELISA

For sample preparation, HEK 293 cells were transfected with the appropriate plasmid constructs using the Fugene 6™ transfection reagent as described in paragraph G above. 48 hours post-transfection, cells were collected and cleared by centrifugation. Cells were subsequently incubated with biotinylated mu18H10 (10 μg/ml) and lysed in 20 mM Tris pH 7.4, 150 mM NaCl, 1% NP40 containing COMPLETE™ protease inhibitors (Roche).

To perform the sandwich ELISA, Nunc maxisorp plate wells were coated with 50 μl of the anti-FLAG™ M2 MAb (Sigma) at a concentration of 5 μg/ml in PBS. Wells were blocked with 200 μl PBS 2% BSA and subsequently incubated with 50 μl of the appropriate samples at the indicated dilution. Wells were washed three times with 200 μl PBS 0.05% Tween 20 and incubated with 50 μl of the appropriate antibody (10 μg/ml for biotinylated mu18H10 and 12D4, 1 μg/ml for the polyclonal anti-MD-2 MAb). Following a wash step as above, wells were incubated with 50 μl of the appropriate detection antibody (HRP conjugated streptavidin at a dilution of 1:1500 for the biotinylated MAbs and HRP conjugated anti-rabbit IgG (H+L) at a dilution of 1:5000 for the polyclonal rabbit Ab). Following a further wash step, binding was revealed using TMB substrate. Plates were read at a wavelength of 650 nm.

J. Cellular Assay 1

Monoclonal antibody was first purified from hybridoma cell supernatant using protein G affinity chromatography.

TLR4/MD-2 transfected HEK 293 cells were plated in culture medium containing 10% FBS at $5\times10^5$ cells/ml in 96 well plates and left to adhere overnight. The culture medium was subsequently removed and replaced with 100 μl culture medium containing 2% FBS and the appropriate monoclonal antibody at twice the desired final concentration for 30 minutes at 37° C. LPS (K12LD25, Sigma) was then added to the cells at a concentration of 30 ng/ml in 100 μl culture medium containing 2% FBS. Cells were incubated at 37° C. for 16 hours and supernatants harvested. IL-8 content was measured by sandwich ELISA using the monoclonal antibody pair 801E and M802B (Endogen).

K. Cellular Assay 2

Human whole blood was diluted 1:4 in RPMI (Sigma) and plated at 100 μl/well in 96 well plates with the appropriate monoclonal antibody at twice the desired final concentration for 30 minutes at 37° C. LPS (K12LD25, Sigma), dosed at twice the desired final concentration, was subsequently added in 100 μl RPMI containing 5 mg/ml HSA and incubated for 6 hours at 37° C. Plates were then centrifuged at 2000 rpm for 5 minutes and the supernatant from each well was retained. IL-8 concentrations were determined by sandwich ELISA using the monoclonal antibody pair 801E and M802B (Endogen), as described above.

L. 18H10 VH and VL Sequences $10^7$ hybridoma cells were harvested and washed once with PBS before being resuspended in 1 ml Trizol™ reagent (Invitrogen). Total RNA was subsequently extracted according to the manufacturer's guidelines. cDNA encoding the VH and VL from three independent subclones of the mu18H10 hybridoma was generated by RT-PCR using oligonucleotide primers specific for mouse leader sequences and constant domains (Jones and Bendig, Biotechnology, 9: 88-89 (1991)). Amplified products were cloned into the pGEM-T easy vector (Promega Corp.) and sequenced using the T7 and SP6 primers.

The VH and VL cDNAs were subsequently cloned in mammalian expression vectors containing the human IgG1 and human kappa constant regions respectively in order to express 7E3 as a chimeric MAb ("chimeric 7E3"). To produce recombinant chimeric MAb, HEK 293 cells were plated in 6 well plates at a density of $2.5\times10^5$ cells/well in 2 ml culture medium containing 10% FBS. 16 hours post-plating, cells were transfected with 0.75 μg of the appropriate vector(s) using Fugene™ reagent (Roche) according to the manufacturer's guidelines. 48 hours post-transfection, supernatant was harvested and antibody was purified using protein G affinity chromatography.

Example 2

Generation of mu18H10 MAbs Directed Against the Human TLR4/MD-2 Complex

Figure 1:
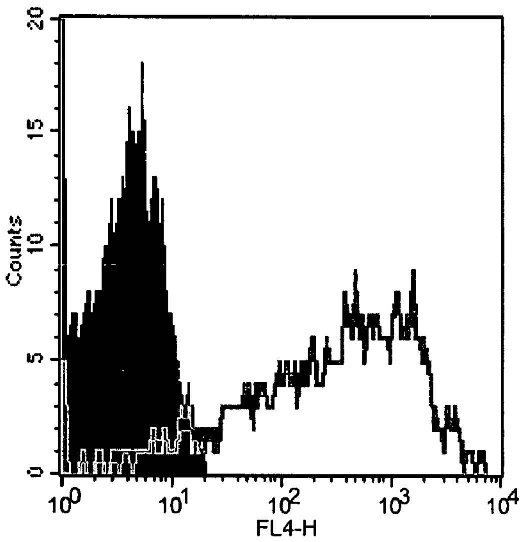
FIG. 1 is a graph depicting the binding of a murine monoclonal antibody, referred to herein as "18H10", to the TLR4/MD-2 complex. Specificity of binding is shown by flow cytometry using mock transfected or TLR4/MD-2 transfected cells. The results using mock-transfected cells are shown in the filled graph (left), while the results using TLR4/MD-2 transfected cells are shown as in the outline graph (right).

Mice immunized with CHO cells expressing surface TLR4/MD-2 were monitored for specific serum titers. Those showing a response to TLR4/MD-2 were "hyperboosted" with recombinant TLR4/MD-2 chimeric protein. This strategy was chosen in order to ensure that the immune system was initially exposed to a conformational TLR4/MD-2 complex and minimize the response to non-specific CHO cellular antigens and simultaneously maximizing the TLR4/MD-2-specific response upon hyperboosting. Screening by FACS of supernatants from hybridomas resulting from B cell/myeloma fusions was performed on mock transfected vs. TLR4/MD-2 transfected CHO cells. Monoclonal antibody from one particular clone, referred to herein as mu18H10, demonstrated specific binding to TLR4/MD-2 transfected CHO cells (FIG. 1). This antibody was found to have the IgG2b κ isotype, as determined by FACS using the mouse Ig isotyping CBA kit (Beckton Dickenson).

Figure 2:
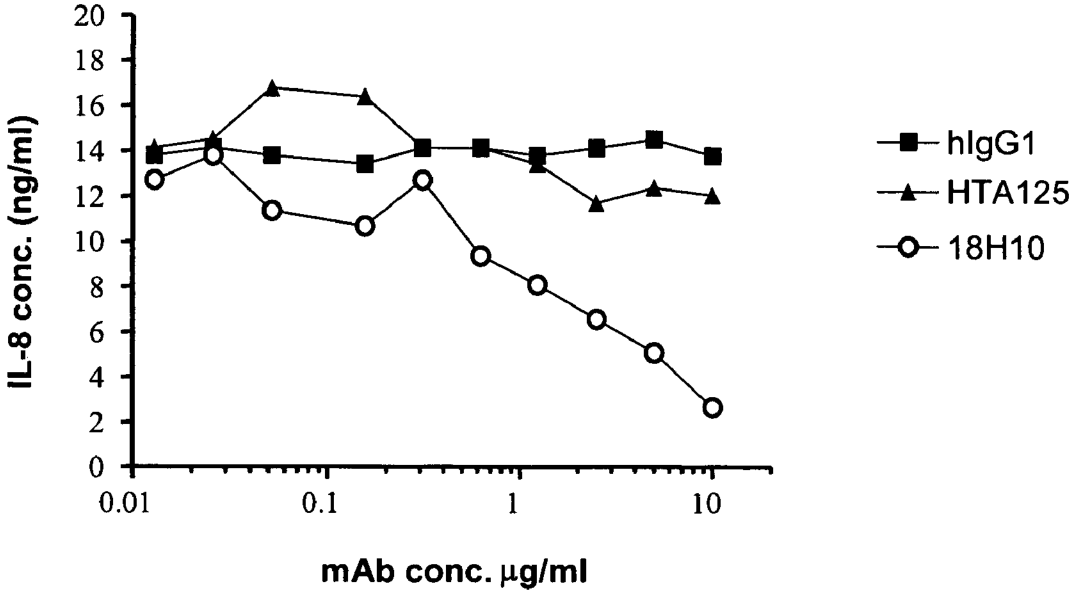
FIG. 2 is a graph depicting inhibition of lipopolysaccharide (LPS)-induced IL-8 production in TLR4/MD-2 transfected HEK 293 cells by the monoclonal antibody mu18H10. The cells were incubated with either mu18H10, HTA 125 (a commercially available anti-human TLR4 non-blocking MAb) or an antibody control at the indicated concentrations and subsequently incubated with LPS (15 ng/ml). IL-8 levels were assessed 16 hours post LPS treatment.

Example 3 mu18H10 MAb Neutralization of LPS Activity on TLR4/MD-2 Transfected HEK 293 Cells LPS is known to have the ability to induce IL-8 production in HEK 293 cells transfected with the TLR4/MD-2 complex. The ability of mu18H10 to inhibit this IL-8 induction was analyzed by pre-incubating cells with the antibody for 30 minutes prior to LPS administration. FIG. 2 shows that mu18H10 inhibited the effects of LPS on HEK 293 cells, even at concentrations below 1 μg/ml.

Example 4 mu18H10 MAb Neutralization of LPS Activity on Human Whole Blood

Figure 3:
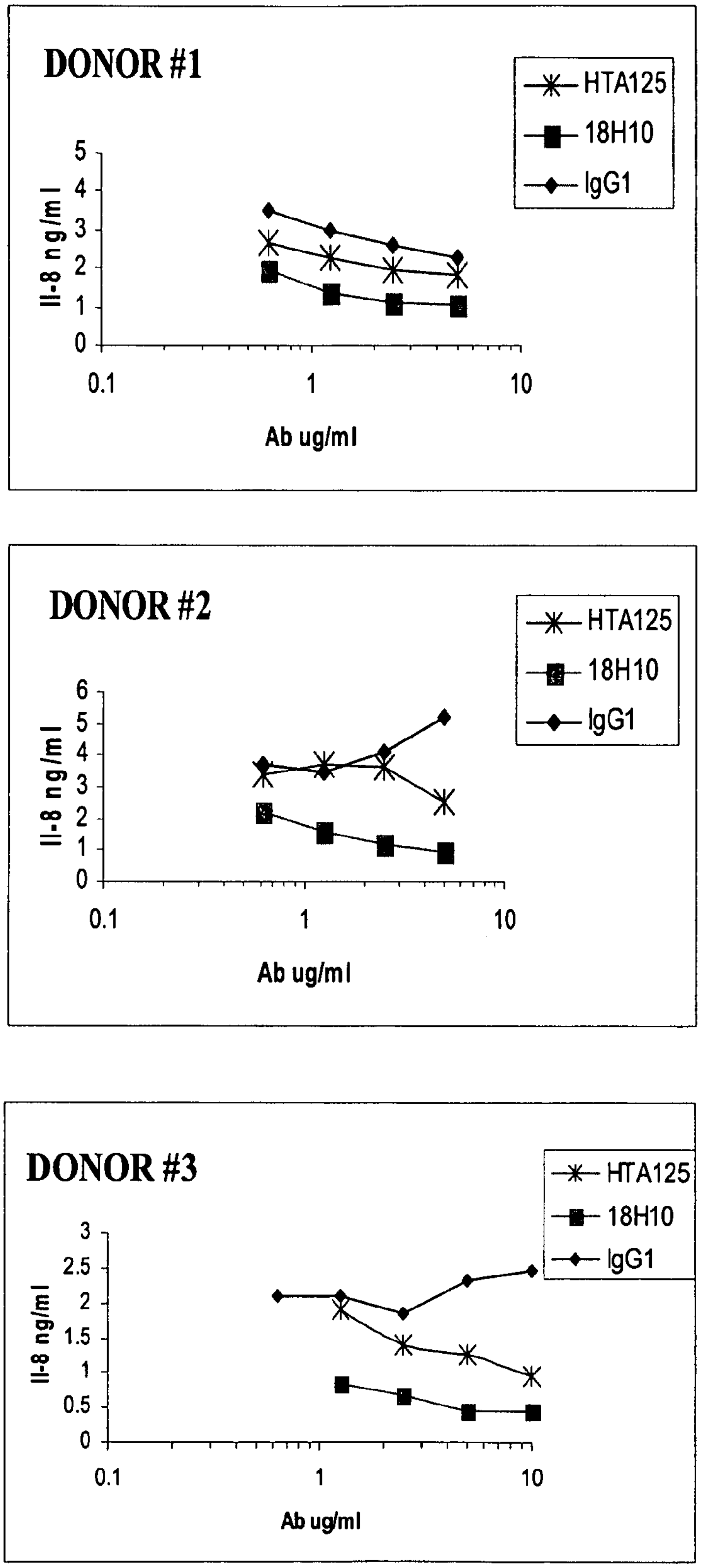
FIG. 3 is a series of graphs depicting inhibition of LPS-induced IL-8 production in human whole blood by the monoclonal antibody mu18H10. Whole blood was drawn from 3 healthy volunteers, treated with heparin and diluted 1:4 in RPMI medium. The following antibodies were added at the concentrations indicated: control monoclonal antibody; HTA125 and mu18H10. LPS was subsequently added for a final concentration of 10 ng/ml, and IL-8 levels were measured 6 hours post LPS treatment.

The ability of mu18H10 to inhibit LPS-induced IL-8 production in human whole blood was tested. mu18H10 neutralizing activity was tested in blood from 3 different donors using a range of monoclonal antibody concentrations from 0.5 to 10 μg/ml. FIG. 3 demonstrates that mu18H10 significantly reduced the level of IL-8 induced by LPS in all 3 donors, as compared to an isotype matched control. mu18H10 was found to be more potent than a previously described α-TLR4 blocking monoclonal antibody (purchased from e-biosciences). These results indicate that the neutralizing epitope recognized by mu18H10 on transfected HEK 293 cells is also exposed on the surface on cells in whole blood, and that mu18H10 is potent enough to inhibit the activity of LPS in whole blood, even at concentrations below 1 μg/ml.

Example 5 mu18H10 Specificity

In order to determine the specificity of the mu18H10 monoclonal antibody, the fact that mu18H10 does not recognize the rabbit ortholog of the TLR4/MD-2 complex (previously cloned) was exploited. cDNAs for either human or rabbit TLR4 with N-terminal FLAG™ epitope tag and either human or rabbit MD-2 with C-terminal c-Myc and protein C epitope tags were transfected in HEK 293 cells in the following combinations: (1) human TLR4 and human MD-2; (2) rabbit TLR4 and rabbit MD-2; (3) human TLR4 and rabbit MD-2; (4) rabbit TLR4 and human MD-2. FIG. 4 shows FACS analysis of these cells following antibody staining, which revealed that mu18H10 recognized cells expressing the human TLR4/MD-2 complex and a combination of human TLR4 and rabbit MD-2, but not the rabbit TLR4/MD-2 complex nor a combination of rabbit TLR4 and human MD-2. These results indicate that the epitope recognized by mu18H10 is situated on human MD-2 (FIG. 4).

Figure 5A:
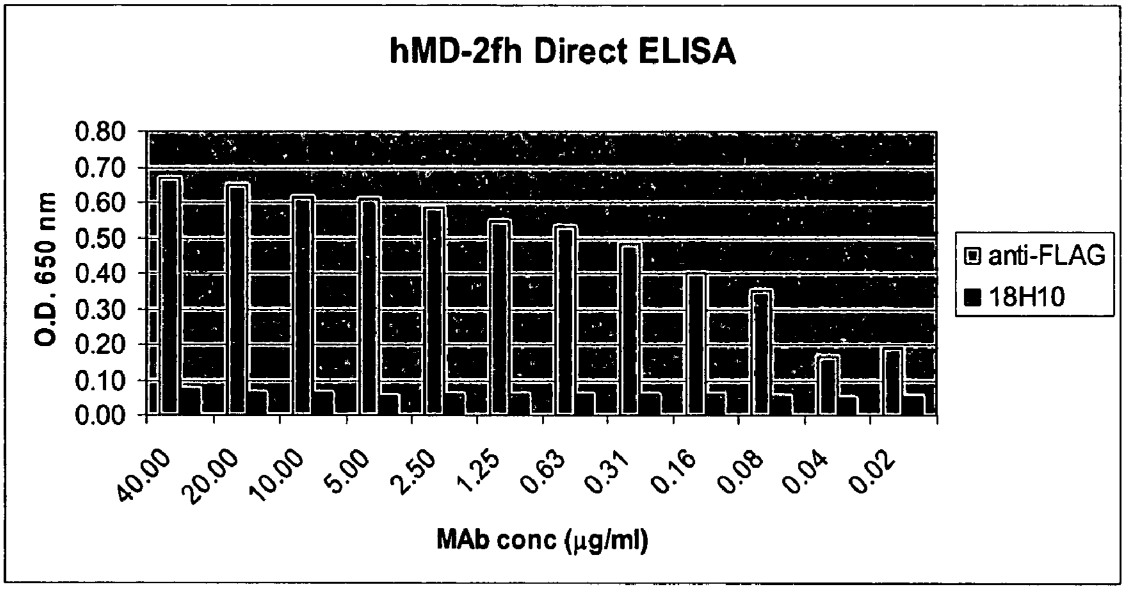
FIG. 5A is a graph demonstrating the lack of specificity of mu18H10 for recombinant soluble MD-2 purified from baculovirus-infected insect cell supernatants as determined by ELISA. Protein was coated directly on 96-well plates (5

Although mu18H10 shows specificity for MD-2, it was determined that mu18H10 only recognizes MD-2 in the context of its interaction with TLR4. Using direct ELISA, no binding of mu18H10 to recombinant soluble MD-2 generated with the baculovirus expression system was detected (FIG. 5*a*). In addition, FIG. 5*b* reveals that mu18H10 only bound to a complex of TLR4 and MD-2 as shown from co-transfected cell lysates, and did not recognize either MD-2 alone in transfected cell lysates/supernatants or TLR4 alone in transfected cell lysates. These data indicate that mu18H10 is specific for the TLR4/MD-2 complex and does not recognize either component of the complex separately.

Example 6 mu18H10 VH and VL Sequences

VH and VL sequences from the mu18H10 hybridoma clone were amplified from total RNA by RT-PCR. Sequence analysis is shown in FIGS. 6A-6F.

The mu18H10 antibody includes a heavy chain variable region (SEQ ID NO:2, FIG. 6B) encoded by the nucleic acid sequence of SEQ ID NO:1 shown in FIG. 6A, and a light chain variable region (SEQ ID NO:7, FIG. 6E) encoded by the nucleic acid sequence of SEQ ID NO:6 shown in FIG. 6D. The amino acids encompassing the complementarity determining regions (CDR) as defined by Chothia et al. 1989, E. A. Kabat et al., 1991 are highlighted in underlined and italicized text in FIGS. 6B and 6E and shown in FIGS. 6C and 6F. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the mu18H10 antibody have the following sequences: DSYIH (SEQ ID NO:3); WTDPENVNSIYDPRFQG (SEQ ID NO:4), and GYNGVYYAMDY (SEQ ID NO:5). The light chain CDRs of the mu18H10 antibody have the following sequences: SASSSVIYMH (SEQ ID NO:8); RTYNLAS (SEQ ID NO:9); and HQWSSFPYT (SEQ ID NO:10).

Example 7

Chimeric 18H10 Binds to hTLR4 hMD2 Transfected CHO Cells

In order to demonstrate the specificity of the cloned 18H10 VH and VL for the hTLR4/MD-2 complex, FACS analysis was performed on hTLR4/MD-2 transfected CHO cells using the chimeric 18H10 MAb (FIG. 6). Specific binding of MAb at the indicated concentration was detected using an APC-labeled goat-anti-human IgG (H+L) secondary antibody. An irrelevant isotype-matched human IgG1 MAb was used as a control.

Example 8

Chimeric 18H10 Inhibits LPS-Induced IL-8 Production in hTLR4 hMD2 Transfected HEK 293 Cells In order to demonstrate the neutralizing capacity of the cloned 18H10 VH and VL for LPS, the ability of 18H10 to inhibit LPS dependent IL-8 induction of hTLR4/MD-2 transfected HEK 293 cells was tested (as described above). FIG. 7 shows that chimeric 18H10 inhibited the effects of LPS on HEK 293 cells in a manner very similar to that of the original 18H10 mouse MAb.

Example 9

Materials and Methods for the Generation of mu16G7 Monoclonal Antibody

A. Generation of Stable TLR4/MD-2 Transfectants

Stable TLR4/MD-2 transfectants were generated in CHO-K1 and HEK 293 cells. For CHO-K1 cells, human TLR4 cDNA encoding an N-terminal c-myc epitope tag was cloned into pCDNA3.1(−)hygro (Invitrogen), and human MD-2 cDNA encoding C-terminal c-Myc and Protein C epitope tags was cloned into pCDNA3 (Invitrogen). Both constructs were co-transfected into CHO cells using Fugene 6™ reagent (Roche), according to the manufacturer's guidelines. Antibiotic resistant cells were selected in culture medium containing 500 μg/ml G418 and 250 μg/ml hygromycin B (both from Invitrogen).

For HEK 293 cells, human TLR4 cDNA encoding an N-terminal FLAG™ epitope tag was cloned into pCDNA3.1 (−)hygro (Invitrogen), and human MD-2 cDNA encoding C-terminal FLAG™ and 6×Histidine epitope tags was cloned into pCDNA3 (Invitrogen). Both constructs were transfected into HEK 293 cells, and antibiotic resistant cells were selected in culture medium containing 500 μg/ml G418 and 250 μg/ml hygromycin B (both from Invitrogen), as described above.

To select for cells expressing the TLR4/MD-2 complex, $1\times10^7$ cells/ml were incubated in 1×PBS supplemented with 1% BSA and either 10 μg/ml anti-protein C monoclonal antibody (for CHO cells; Roche) or anti-FLAG monoclonal antibody (for 293 cells; Sigma). Cells were washed once and then incubated in the same buffer with PE-conjugated goat anti-mouse IgG (H+L) antibody (1:200 dilution; Anwara). Cells were subsequently incubated with anti-PE microbeads (Miltenyi Biotec) and passed through a Midi MACS LS column. Cells retained on the column were eluted and placed back in culture with antibiotic selection. Rounds of sorting were continued until a uniformly positive population of cells expressing the TLR4/MD-2 complex was obtained.

B. Immunization of Mice 8 week old female BALB/c mice (IFFA CREDO) were immunized as described above in Example 1, subsection C.

C. Specific Serum Titrations

Mice sera titrations were performed as described above in Example 1, subsection D.

D. B Cell/Myeloma Fusions

Mice having specific TLR4/MD-2 serum antibodies were "hyperboosted" subcutaneously (s.c.) with TLR4/MD-2 transfected HEK 293 either 3 or 4 days prior to fusion. Draining lymph nodes were obtained as a source of B cells for fusion with the mouse myeloma cell line P3-X63-Ag8.653. B cell extraction and cellular fusions were performed as previously described in Buell et al., Blood 92: 3521-3528 (1998), hereby incorporated by reference in its entirety. Cells were plated at an approximate concentration of $10^4$ myeloma cells/well and grown for 10-14 days in culture medium supplemented with HAT (Sigma).

E. Hybridoma Screening

Hybridomas were screened as described above in Example 1, subsection F.

F. Monoclonal Antibody Specificity

The specificity of the mu16G7 monoclonal antibody was determined as described above in Example 1, subsection G.

G. Cellular Assay 1

Cellular Assay I was performed as described above in Example 1, subsection J.

H. Cellular Assay 2

Cellular Assay II was performed as described above in Example 1, subsection K.

I. 16G7 VH and VL Sequences $10^7$ hybridoma cells were harvested and washed once with PBS before being resuspended in 1 ml Trizol™ reagent (Invitrogen). Total RNA was subsequently extracted according to the manufacturer's guidelines. cDNA encoding the VH and VL from the mu16G7 clone was generated by RT-PCR with the mouse ScFv module (Amersham Biosciences) according to the manufacturer's guidelines. Amplified products were cloned into the pGEM-T easy vector (Promega Corp.) and sequenced using the T7 and SP6 primers.

Example 10

Generation of mu16G7 MAbs Directed Against the Human TLR4/MD-2 Complex

Mice immunized with CHO cells expressing surface TLR4/MD-2 were monitored for specific serum titers. Those showing a response to TLR4/MD-2 were "hyperboosted" with HEK 293 TLR4/MD-2 transfectants. This strategy was chosen in order to minimize the response to non-specific CHO cellular antigens, while simultaneously maximizing the TLR4/MD-2-specific response. Screening by FACS of supernatants from hybridomas resulting from B cell/myeloma fusions was performed on mock transfected vs. TLR4/MD-2 transfected CHO cells. Monoclonal antibody from a specific clone, referred to herein as mu16G7, demonstrated specific binding to TLR4/MD-2 transfected CHO cells (FIG. 9). mu16G7 was found to have the IgG1 κ isotype, as determined by FACS using the mouse Ig isotyping CBA kit (Beckton Dickenson).

Example 11 mu16G7 Neutralization of LPS Activity on TLR4/MD-2 Transfected HEK 293 Cells

LPS is known to have ability to induce IL-8 production in HEK 293 cells transfected with the TLR4/MD-2 complex. The ability of mu16G7 to inhibit this IL-8 induction was analyzed by pre-incubating cells with each antibody for 30 minutes prior to LPS administration. FIG. 10 shows that mu16G7 inhibited the effects of LPS on HEK 293 cells, even at sub-microgram/ml concentrations.

Example 12 mu16G7 Neutralization of LPS Activity on Human Whole Blood

The ability of mu16G7 to inhibit LPS-induced IL-8 production in human whole blood was tested. mu16G7 neutralizing activity was tested in blood from 3 different donors using a range of monoclonal antibody concentrations from 0.5 to 5 μg/ml. FIG. 11 demonstrates that mu16G7 significantly reduced the level of IL-8 induced by LPS in all 3 donors, as compared to an isotype matched control. mu16G7 was found to be more potent than a previously described α-TLR4 blocking monoclonal antibody (from e-biosciences). (See Shimazu et al. J. Exp. Med. 189: 1777-1782 (1999)). In some cases, mu16G7 was found to be as potent as an α-CD14 blocking monoclonal antibody that was also included in the study. (See Kirkland et al. J. Biol. Chem. 268: 24818-24823(1993)). These results indicate that the neutralizing epitope recognized by mu16G7 on transfected HEK 293 cells is also exposed on the surface on cells in whole blood, and that mu16G7 is potent enough to inhibit the activity of LPS in whole blood, even at concentrations below 1 μg/ml.

Example 13 mu16G7 Specificity

In order to determine the specificity of the mu16G7 monoclonal antibody, the fact that mu16G7 does not recognize the rabbit ortholog of the TLR4/MD-2 complex (previously cloned) was exploited. cDNAs for either rabbit or human TLR4 with N-terminal FLAG™ epitope tag and MD-2 with C-terminal c-Myc and protein C epitope tags were transfected in HEK 293 cells in the following combinations: (1) rabbit TLR4 and rabbit MD-2; (2) human TLR4 and human MD-2; (3) rabbit TLR4 and human MD-2; (4) human TLR4 and rabbit MD-2. FIG. 12 shows FACS analysis of these cells following antibody staining, which revealed that mu16G7 recognized cells expressing the human TLR4/MD-2 complex and a combination of human TLR4 and rabbit MD-2, but not the rabbit TLR4/MD-2 complex nor a combination of rabbit TLR4 and human MD-2. These results indicate that the epitope recognized by mu16G7 is situated on human TLR4 (FIG. 12).

Example 14 mu16G7 VH and VL Sequences

VH and VL sequences from the mu16G7 hybridoma clone were amplified from total RNA by RT-PCR. Sequence analysis is shown in FIGS. 13A-13F. Alignment of the mu16G7 VH and VL nucleotide sequences with known mouse VH and VL sequences (using the International Immunogenetics Information System; which can be found at http://imgt.cines.fr) reveals that the mu16G7 VH sequence most closely resembles the IgHV1 subfamily, while the mu16G7 VL belongs to the IgKV1 subfamily.

The mu16G7 antibody includes a heavy chain variable region (SEQ ID NO:12, FIG. 13B) encoded by the nucleic acid sequence of SEQ ID NO:11 shown in FIG. 13A, and a light chain variable region (SEQ ID NO:17, FIG. 13E) encoded by the nucleic acid sequence of SEQ ID NO:16 shown in FIG. 13D. The amino acids encompassing the CDR as defined by Chothia et al. 1989, E. A. Kabat et al., 1991 are highlighted in underlined and italicized text in FIGS. 13B and 13E and shown in FIGS. 13C and 13F. The heavy chain CDRs of the mu16G7 antibody have the following sequences: DYWIE (SEQ ID NO:13); EILPGSGSTNYNEDFKD (SEQ ID NO:14); and EERAYYFGY (SEQ ID NO:15). The light chain CDRs of the mu16G7 antibody have the following sequences: RSSQSLENSNGNTYLN (SEQ ID NO:18); RVSNRFS (SEQ ID NO:19); and LQVTHVPPT (SEQ ID NO:20).

Example 15

Materials and Methods for the Generation of mu15C1 Monoclonal Antibody

A. Generation of Stable TLR4/MD-2 Transfectants

Stable TLR4/MD-2 transfectants were generated in CHO-K1 and HEK 293 cells as described above in Example 9, subsection A.

B. Generation of Recombinant MD-2 and Chimeric TLR4/MD-2 Protein

To generate recombinant soluble MD-2, cDNA encoding the protein with C terminal FLAG and 6×HIS tags for detection and purification purposes was cloned into pFASTBAC1 and subsequently inserted into bacmid DNA by homologous recombination. Following generation of a viral stock, Sf9 cells were superinfected. 48 hours later, the recombinant protein was purified from infected cell supernatants using a NiNTA affinity matrix (Qiagen).

To generate the recombinant TLR4/MD-2 chimeric protein, cDNA encoding the extracellular portion of human TLR4 linked to MD-2 via a glycine serine ($GGGGS_3$) linker was assembled using PCR. FLAG and 6×HIS tags were included at the C-terminus of MD-2 for detection and purification purposes. The cDNA cassette was cloned into the baculovirus expression vector pFASTBAC1 (Invitrogen) and subsequently inserted into bacmid DNA by homologous recombination. Following generation of a viral stock, Sf9 cells were superinfected. 48 hours later, the recombinant fusion protein was purified from cell lysates using an anti-FLAG™ M2 MAb affinity matrix (Sigma).

C. Immunization of Mice 8 week old female BALB/c mice (IFFA CREDO) were immunized as described above in Example 1, subsection C.

D. Specific Serum Titrations

Mice serum titrations were performed as described above in Example 1, subsection D.

E. B Cell/Myeloma Fusions

B cell extraction and cellular fusion were performed and analyzed as described above in Example 9, subsection D.

F. Hybridoma Screening

Hybridoma screening was performed as described above in Example 1, subsection F.

G. Monoclonal Antibody Specificity

The specificity of the mu15C1 monoclonal antibody was determined as described above in Example 1, subsection G.

H. Cellular Assay 1

Cellular Assay I was performed as described above in Example 1, subsection J.

I. Cellular Assay 2

Cellular Assay II was performed as described above in Example 1, subsection K.

J. 15C1 VH and VL Sequences $10^7$ hybridoma cells were harvested and washed once with PBS before being resuspended in 1 ml Trizol™ reagent (Invitrogen). Total RNA was subsequently extracted according to the manufacturer's guidelines. cDNA encoding the VH and VL from the mu15C1 clone was generated by RT-PCR with the mouse ScFv module (Amersham Biosciences) according to the manufacturer's guidelines. Amplified products were cloned into the pGEM-T easy vector (Promega Corp.) and sequenced using the T7 and SP6 primers.

The VH and VL cDNAs were subsequently cloned in mammalian expression vectors containing the human IgG1 and human kappa constant regions respectively in order to express mu15C1 as a chimeric MAb ("chimeric 15C1"). To produce recombinant chimeric MAb, HEK 293 cells were plated in 6 well plates at a density of $2.5\times10^5$ cells/well in 2 ml culture medium containing 10% FBS. 16 hours post-plating, cells were transfected with 0.75 μg of the appropriate vector (s) using Fugene™ reagent (Roche) according to the manufacturer's guidelines. 48 hours post-transfection, supernatant was harvested and antibody was purified using protein G affinity chromatography.

Example 16

Generation of MAbs Directed Against the Human TLR4/MD-2 Complex

Mice immunized with CHO cells expressing surface TLR4/MD-2 were monitored for specific serum titers. Those showing a response to TLR4/MD-2 were "hyperboosted" with HEK 293 TLR4/MD-2 transfectants. This strategy was chosen in order to minimize the response to non-specific CHO cellular antigens, while simultaneously maximizing the TLR4/MD-2-specific response. Screening by FACS of supernatants from hybridomas resulting from B cell/myeloma fusions was performed on mock-transfected vs. TLR4/MD-2-transfected CHO cells. Monoclonal antibody from a specific clone, referred to herein as mu15C1, demonstrated specific binding to TLR4/MD-2 transfected CHO cells (FIG. 14). mu15C1 was found to have the IgG1 κ isotype, as determined by FACS using the mouse Ig isotyping CBA kit (Beckton Dickenson).

Example 17

Neutralization of LPS Activity on TLR4/MD-2 Transfected HEK 293 Cells

LPS is known to have ability to induce IL-8 production in HEK 293 cells transfected with the TLR4/MD-2 complex. The ability of mu15C1 to inhibit this IL-8 induction was analyzed by pre-incubating cells with each antibody for 30 minutes prior to LPS administration. FIG. 15 shows that mu15C1 inhibited the effects of LPS on HEK 293 cells, even at sub-microgram/ml concentrations.

Example 18

Neutralization of LPS Activity on Human Whole Blood

The ability of mu15C1 to inhibit LPS-induced IL-8 production in human whole blood was tested. mu15C1 neutralizing activity was tested in blood from 3 different donors using a range of monoclonal antibody concentrations from 0.5 to 5 μg/ml. FIG. 16 demonstrates that mu15C1 significantly reduced the level of IL-8 induced by LPS in all 3 donors, as compared to an isotype matched control. mu15C1 was found to be more potent than a previously described α-TLR4 blocking monoclonal antibody (from e-biosciences). (See Shimazu et al. J. Exp. Med. 189: 1777-1782 (1999)). In some cases, mu15C1 was found to be as potent as an α-CD14 blocking monoclonal antibody that was also included in the study. (See Kirkland et al. J. Biol. Chem. 268: 24818-24823(1993)). These results indicate that the neutralizing epitope recognized by mu15C1 on transfected HEK 293 cells is also exposed on the surface on cells in whole blood, and that mu15C1 is potent enough to inhibit the activity of LPS in whole blood, even at concentrations below 1 μg/ml.

Example 19 mu15C1 Specificity

In order to determine the specificity of the mu15C1 monoclonal antibody, the fact that mu15C1 does not recognize the rabbit ortholog of the TLR4/MD-2 complex (previously cloned) was exploited. cDNAs for either rabbit or human TLR4 with N-terminal FLAG™ epitope tag and MD-2 with C-terminal c-Myc and protein C epitope tags were transfected in HEK 293 cells in the following combinations: (1) mock vector (2) human TLR4 alone (3) human TLR4 and human MD-2 (4) rabbit TLR4 and rabbit MD-2; (5) human TLR4 and rabbit MD-2; (6) rabbit TLR4 and human MD-2. FIG. 17 shows FACS analysis of these cells following antibody staining, which revealed that mu15C1 recognized cells expressing human TLR4 alone, the human TLR4/MD-2 complex and a combination of human TLR4 and rabbit MD-2, but not the rabbit TLR4/MD-2 complex nor a combination of rabbit TLR4 and human MD-2. These results indicate that the epitope recognized by mu15C1 is situated on human TLR4 (FIG. 17).

Example 20 mu15C1 VH and VL Sequences

VH and VL sequences from the mu15C1 hybridoma clone were amplified from total RNA by RT-PCR using oligonucleotide primers specific for mouse leader sequences and constant domains (Jones and Bendig, Biotechnology, 9: 88-89 (1991)). Sequence analysis is shown in FIGS. 18A-18F.

The mu15C1 antibody includes a heavy chain variable region (SEQ ID NO:22, FIG. 18B) encoded by the nucleic acid sequence of SEQ ID NO:21 shown in FIG. 18A, and a light chain variable region (SEQ ID NO:27, FIG. 18E) encoded by the nucleic acid sequence of SEQ ID NO:26 shown in FIG. 18D. The amino acids encompassing the CDR as defined by Chothia et al. 1989, E. A. Kabat et al., 1991 are highlighted in underlined and italicized text in FIGS. 18B and 18E and shown in FIGS. 18C and 18F. The heavy chain CDRs of the mu15C1 antibody have the following sequences: GGYSWH (SEQ ID NO:23); YIHYSGYTDFNPSLKT (SEQ ID NO:24); and KDPSDGFPY (SEQ ID NO:25). The light chain CDRs of the mu15C1 antibody have the following sequences: RASQSISDHLH (SEQ ID NO:28); YASHAIS (SEQ ID NO:29); and QNGHSFPLT (SEQ ID NO:30).

Example 21

Chimeric 15C1 Binds to hTLR4 hMD2 Transfected CHO Cells

In order to demonstrate the specificity of the cloned 15C1 VH and VL for the hTLR4/MD-2 complex, FACS analysis on hTLR4/MD-2 transfected CHO cells using the chimeric 15C1 MAb was performed (FIG. 19). Specific binding of MAb at the indicated concentration was detected using an APC-labeled goat-anti-human IgG (H+L) secondary antibody. An irrelevant isotype-matched human IgG1 MAb was used as a control.

Example 22

Chimeric 15C1 Inhibits LPS-Induced IL-8 Production in hTLR4 hMD2 Transfected HEK 293 Cells In order to demonstrate the neutralizing capacity of the cloned 15C1 VH and VL for LPS, the ability of 15C1 to inhibit LPS dependent IL-8 induction of hTLR4/MD-2 transfected HEK 293 cells was tested (as described above). FIG. 20 shows that chimeric 15C1 inhibited the effects of LPS on HEK 293 cells in a manner very similar to that of the 15C1 MAb.

Example 23

Materials and Methods for the Generation of mu7E3 Monoclonal Antibody

A. Generation of Stable TLR4/MD-2 Transfectants

Stable TLR4/MD-2 transfectants were generated in CHO-K1 and HEK 293 cells as described above in Example 9, subsection A.

B. Generation of Recombinant MD-2 and Chimeric TLR4/MD-2 Protein

Recombinant soluble MD-2 was generated as described above in Example 15, subsection B.

To generate the recombinant TLR4/MD-2 chimeric protein, cDNA encoding the extracellular portion of human TLR4 linked to MD-2 via a glycine serine ($GGGGS_3$) linker was assembled using PCR. FLAG and 6×HIS tags were included at the C-terminus of MD-2 for detection and purification purposes. The cDNA cassette was cloned into the baculovirus expression vector pFASTBAC1 (Invitrogen) and subsequently inserted into bacmid DNA by homologous recombination. Following generation of a viral stock, Sf9 cells were superinfected. 48 hours later, the recombinant fusion protein was purified from cell lysates using an anti-FLAG™ M2 MAb affinity matrix (Sigma).

C. Immunization of Mice 8 week old female BALB/c mice (IFFA CREDO) were immunized as described above in Example 1, subsection C.

D. Specific Serum Titrations

Mice serum titrations were performed as described above in Example 1, subsection D.

E. B Cell/Myeloma Fusions

B cell extraction and cellular fusion were performed and analyzed as described above in Example 9, subsection D.

F. Hybridoma Screening

Hybridoma screening was performed as described above in Example 1, subsection F.

G. Monoclonal Antibody Specificity

The specificity of the mu7E3 monoclonal antibody was determined as described above in Example 1, subsection G.

H. Cellular Assay 1

Monoclonal antibody was first purified from hybridoma cell supernatant using protein G affinity chromatography.

Cellular Assay I was performed as described above in Example 1, subsection J.

I. Cellular Assay 2

Cellular Assay II was performed as described above in Example 1, subsection K.

J. 7E3 VH and VL Sequences $10^7$ hybridoma cells were harvested and washed once with PBS before being resuspended in 1 ml Trizol™ reagent (Invitrogen). Total RNA was subsequently extracted according to the manufacturer's guidelines. cDNA encoding the VH and VL from the mu7E3 clone was generated by RT-PCR using oligonucleotide primers specific for mouse leader sequences and constant domains (Jones and Bendig, Biotechnology, 9: 88-89 (1991)). Amplified products were cloned into the pGEM-T easy vector (Promega Corp.) and sequenced using the T7 and SP6 primers.

The VH and VL cDNAs were subsequently cloned in mammalian expression vectors containing the human IgG1 and human kappa constant regions respectively in order to express mu7E3 as a chimeric MAb ("chimeric 7E3"). To produce recombinant chimeric MAb, HEK 293 cells were plated in 6 well plates at a density of $2.5\times10^5$ cells/well in 2 ml culture medium containing 10% FBS. 16 hours post-plating, cells were transfected with 0.75 μg of the appropriate vector(s) using Fugene™ reagent (Roche) according to the manufacturer's guidelines. 48 hours post-transfection, supernatant was harvested and antibody was purified using protein G affinity chromatography.

Example 24

Generation of MAbs Directed Against the Human TLR4/MD-2 Complex

Mice immunized with CHO cells expressing surface TLR4/MD-2 were monitored for specific serum titers. Those showing a response to TLR4/MD-2 were "hyperboosted" with HEK 293 TLR4/MD-2 transfectants. This strategy was chosen in order to minimize the response to non-specific CHO cellular antigens, while simultaneously maximizing the TLR4/MD-2-specific response. Screening by FACS of supernatants from hybridomas resulting from B cell/myeloma fusions was performed on mock transfected vs. TLR4/MD-2 transfected CHO cells. Monoclonal antibody from a specific clone, referred to herein as mu7E3, demonstrated specific binding to TLR4/MD-2 transfected CHO cells (FIG. 21). mu7E3 was found to have the IgG1 κ isotype, as determined by FACS using the mouse Ig isotyping CBA kit (Beckton Dickenson).

Example 25

Neutralization of LPS Activity on TLR4/MD-2 Transfected HEK 293 Cells

LPS is known to have ability to induce IL-8 production in HEK 293 cells transfected with the TLR4/MD-2 complex. The ability of mu7E3 to inhibit this IL-8 induction was analyzed by pre-incubating cells with each antibody for 30 minutes prior to LPS administration. FIG. 22 shows that mu7E3 inhibited the effects of LPS on HEK 293 cells, even at sub-microgram/ml concentrations.

Example 26

Neutralization of LPS Activity on Human Whole Blood

The ability of mu7E3 to inhibit LPS-induced IL-8 production in human whole blood was tested. mu7E3 neutralizing activity was tested in blood from 3 different donors using a range of monoclonal antibody concentrations from 0.5 to 5 μg/ml. FIG. 23 demonstrates that mu7E3 significantly reduced the level of IL-8 induced by LPS in all 3 donors, as compared to an isotype matched control. mu7E3 was found to be more potent than a previously described α-TLR4 blocking monoclonal antibody (purchased from e-biosciences). (See Shimazu et al. J. Exp. Med. 189: 1777-1782 (1999)). In some cases, mu7E3 was found to be as potent as an α-CD14 blocking monoclonal antibody that was also included in the study. (See Kirkland et al. J. Biol. Chem. 268: 24818-24823(1993)). These results indicate that the neutralizing epitope recognized by mu7E3 on transfected HEK 293 cells is also exposed on the surface on cells in whole blood, and that mu7E3 is potent enough to inhibit the activity of LPS in whole blood, even at concentrations below 1 μg/ml.

Example 27 mu7E3 Specificity

In order to determine the specificity of the mu7E3 monoclonal antibody, the fact that mu7E3 does not recognize the rabbit ortholog of the TLR4/MD-2 complex (previously cloned) was exploited. cDNAs for either rabbit or human TLR4 with N-terminal FLAG™ epitope tag and MD-2 with C-terminal c-Myc and protein C epitope tags were transfected in HEK 293 cells in the following combinations: (1) mock vector (2) human TLR4 alone (3) human TLR4 and human MD-2 (4) rabbit TLR4 and rabbit MD-2; (5) human TLR4 and rabbit MD-2; (6) rabbit TLR4 and human MD-2. FIG. 24 shows FACS analysis of these cells following antibody staining, which revealed that mu7E3 recognized cells expressing the human TLR4/MD-2 complex and a combination of human TLR4 and rabbit MD-2, but not the rabbit TLR4/MD-2 complex nor a combination of rabbit TLR4 and human MD-2. These results indicate that the epitope recognized by mu7E3 is situated human TLR4 but the presence of MD-2 is essential for MAb binding (FIG. 24).

Example 28 mu7E3 VH and VL Sequences

VH and VL sequences from the mu7E3 hybridoma clone were amplified from total RNA by RT-PCR. Sequence analysis is shown in FIGS. 25A-25F.

The mu7E3 antibody includes a heavy chain variable region (SEQ ID NO:32, FIG. 25B) encoded by the nucleic acid sequence of SEQ ID NO:31 shown in FIG. 25A, and a light chain variable region (SEQ ID NO:37, FIG. 25E) encoded by the nucleic acid sequence of SEQ ID NO:36 shown in FIG. 25D. The amino acids encompassing the CDR as defined by Chothia et al. 1989, E. A. Kabat et al., 1991 are highlighted in underlined and italicized text in FIGS. 25B and 25E and shown in FIGS. 25C and 25F. The heavy chain CDRs of the mu7E3 antibody have the following sequences: TYNIGVG (SEQ ID NO:33); HIWWNDNIYYNTVLKS (SEQ ID NO:34); and MAEGRYDAMDY (SEQ ID NO:35). The light chain CDRs of the mu7E3 antibody have the following sequences: RASQDITNYLN (SEQ ID NO:38); YTSKLHS (SEQ ID NO:39); and QQGNTFPWT (SEQ ID NO:40).

Example 29

Chimeric 7E3 Binds to hTLR4 hMD2 Transfected CHO Cells

In order to demonstrate the specificity of the cloned 7E3 VH and VL for the hTLR4/MD-2 complex, FACS analysis on hTLR4/MD-2 transfected CHO cells using the chimeric 7E3 MAb was performed (FIG. 26). Specific binding of MAb at the indicated concentration was detected using an APC-labeled goat-anti-human IgG (H+L) secondary antibody. An irrelevant isotype-matched human IgG1 MAb was used as a control.

Example 30

Chimeric 7E3 Inhibits LPS-Induced IL-8 Production in hTLR4 hMD2 Transfected HEK 293 Cells In order to demonstrate the neutralizing capacity of the cloned 7E3 VH and VL for LPS, the ability of 7E3 to inhibit LPS dependent IL-8 induction of hTLR4/MD-2 transfected HEK 293 cells was tested as described above. FIG. 27 shows that chimeric 7E3 inhibited the effects of LPS on HEK 293 cells.

Example 31

Construction of TLR4/MD-2 Fusion Protein cDNA and Cloning into pFASTBAC1

The extracellular portion of TLR4 linked to MD-2 via a glycine serine ($GGGGS_3$) linker was assembled using PCR. FLAG and 6×HIS tags were included at the C-terminus of MD-2 for detection and purification purposes. (FIG. 28).

FIGS. 28A-C illustrate the construction of this TLR4/MD-2 fusion protein cDNA according to the present invention. cDNA encoding the extracellular portion of human TLR4 (sTLR4) was amplified by PCR, and unique NheI/XhoI restriction sites were introduced into 5' non-annealing primer extensions. The $(GGGGS)_3$ coding sequence and unique XhoI site was introduced into the 5' non-annealing extension of the sense primer, and a unique HindIII site was introduced into the 5' non-annealing extension of the antisense primer. (Panel A). Panel B depicts the sequential cloning of the amplified sTLR4 and $(GGGGS)_3$/MD-2 cDNAs into pFASTBAC1 between the unique XbaI and HindIII restriction site. Panel C depicts a proposed protein product following expression of the sTLR4/MD-2 cDNA in Sf9 cells.

Example 32

Expression of the TLR4/MD-2 Chimeric Protein in SF9 Cell Lysates and Supernatants The cDNA cassette of Example 1 was cloned into the baculovirus expression vector pFASTBAC1 (Invitrogen) and subsequently inserted into bacmid DNA by homologous recombination. Following generation of a viral stock, Sf9 cells were superinfected and expression of the TLR4/MD-2 fusion protein was analyzed in the cell lysate at 48 and 72 hours post infection by Western blotting. (FIG. 29).

FIG. 29 demonstrates the expression of a TLR4/MD-2 chimeric protein of the invention in Sf9 cell lysates and supernatants. Protein expression in the Sf9 cell lysates and supernatants was detected by Western blotting using the anti-FLAG M2 antibody: Lane 1 depicts cleared lysate at 48 hours post infection; lane 2 depicts cleared lysate at 72 hours post infection; lane 3 depicts cleared supernatant at 48 hours post infection; lane 4 depicts cleared supernatant at 72 hours post infection; and lane 5 contains a reference protein (FLAG tagged). The molecular weight marker sizes in FIG. 29 are shown in KDa. The predicted molecular weight of TLR4/

MD-2 chimeric protein is approximately 90 KDa, and the appearance of probable degradation product occurs at approximately 28 KDa.

Example 33

Purification of the TLR4/MD-2 Chimeric Protein from Infected SF9 Cell Lysates

To purify the fusion protein, Sf9 cells were harvested 48 hours post superinfection and lysed in 20 mM Tris pH7.4, 150 mM NaCl, 1% NP40 with COMPLETE™ protease inhibitors (Roche) at a concentration of 5 volumes/gram cells. Following a fifteen hour (15') incubation at 4° C., lysates were cleared by centrifugation (4000 rpm) and filtration (0.22 μm) and passed through an anti-FLAG M2 MAb affinity matrix (Sigma). Unbound protein was removed from the matrix by successive washing with 20 mM Tris (pH 7.4), 150 mM NaCl, 1% NP40 and 20 mM Tris (pH 7.4), 150 mM NaCl. Bound protein was eluted from the column with 100 mM glycine (pH 2.75) and collected in 0.5 ml fractions. Fractions were rapidly brought to neutral pH through the addition of 50 μl of 1M Tris (pH 9). Protein content was analyzed by western blotting (with peroxidase conjugated anti-FLAG M2) and Coomassie brilliant blue staining. (FIG. 30).

FIG. 30 demonstrates the presence of purified TLR4/MD-2 chimeric protein in infected Sf9 cell lysates. Protein in the cell lysates was detected by Coomassie brilliant blue staining (FIG. 30, left panel) or Western blotting (FIG. 30, right panel) using the anti-FLAG M2 antibody. Lanes 1-5 depict 0.5 ml eluted fractions from the anti-FLAG M2 affinity column.

Example 34

Inhibition of LPS Induced IL-8 Production using Chimeric Soluble TLR4/MD-2

Lipopolysaccharide (LPS) (15 ng/ml) was preincubated with a purified chimeric TLR4/MD-2 according to the present invention at varying concentrations and subsequently incubated with TLR4/MD-2 transfected HEK 293 cells. FIG. 31 is a graph depicting IL-8 production in the cell culture medium 24 hours post treatment.

As seen in FIG. 31, purified chimeric TLR4/MD-2 was shown to have an inhibitory effect on the LPS-induced IL-8 production in TLR4/MD-2 transfected HEK cells, thereby indicating that the purified TLR4/MD-2 protein of the invention was at least partially conformationally correct.

Example 35

Humanization of 18H10, 15C1, and 7E3 Antibodies

Design and Construction of the CDR-Grafted Variable Regions

Mu15C1, mu18H10 and mu7 E3 antibodies were humanized by CDR-grafting (Jones et al, Nature 321:522-525, 1986; Verhofyen et al. Science, 239: 1634-1536, 1988). "CDR-grafting" involves redesigning the variable region so that the amino acids comprising the non-human (i.e., mouse) binding site are integrated into the framework of a human antibody variable region. In order to accomplish the humanization process, the choice of the human framework and the extent of mouse variable region sequence to be transferred are determined.

The human framework for the humanization process was selected from all published sequences for human germline immunoglobulin genes which are used to create the human antibody repertoire (see The international ImMunoGeneTics database, IMGT, available online). For mu15C1, two candidates for each V gene were chosen, namely IGHV3-66 (also known as DP-86) and IGHV4-28 (also known as DP-48) for the heavy chain and IGKV3-11 (also known as L6) and IGKV6-21 (also known as A26) for the Kappa light chain. For mu7E3, two candidates for the heavy chains were chosen, namely IGHV3-66 (or DP-86) and IGHV2-70 (also known as DP-27) and one candidate for the Kappa light chain IGKV1-12 (also known as L19). For mu18H10 one candidate for each V gene was chosen: IGHV1-69 (also known as DP-10) for the heavy chain and IGKV3-11 (or L6) for the light chain.

The extent of the mouse sequences that are to be transferred is determined as follows. Firstly, the antigen binding surface is predominantly located on a series of loops, known as CDRs, three per V gene, which extend from the β-barrel framework. In all cases, the residues chosen for transfer corresponded to the broad definition of CDRs as defined by Kabat (hypervariable regions; Kabat et al, Sequences of Proteins of Immunological Interest, Fifth edition, U.S. Department of Health and Human Services, U.S. Government Printing Office)) and Chothia (structural loops; Chothia et al, Nature, 342:877-883, 1989). In addition, residues not identified in the structural loops or hypervariable regions may contribute to antigen binding directly or indirectly by affecting binding site topology, by inducing a stable packing of the individual variable domains, or by stabilizing the inter-variable domain interaction. Such residues were identified by sequence alignment analysis and noting "idiosyncratic" residues, followed by examination of their structural location and likely effects.

Once the relevant sequence choices have been made the humanized variable region DNA were generated using any of the following procedures: by gene synthesis using suitable overlapping oligonucleotides (exemplified by Kolbinger et al., Protein Eng. 6, 971-980, 1993)), or by using simultaneous or sequential site-directed PCR mutagenesis of existing DNA sequences (Kammann et al., Nucleic Acids Res. 17, 5404). For example, PCR primers coding for the new CDRs were hybridized to a DNA template that was a fully human or humanized variable region that was designed based on the same, or a very similar human variable region (exemplified by Sato et al., Cancer Res. 53, 851-856 1993). Several minor variants in the design of the humanized V genes were obtained using the QuikChange site directed mutagenesis technique originally described by Stratagene.

Following the construction and sequencing of the DNA sequences coding for the light and heavy chain leader sequences plus humanized variable regions, the leader-variable regions were converted to humanized whole IgG genes for expression in mammalian cells by sub-cloning into vectors that contain a human light or heavy expression cassette.

Humanized Versions of the 15C1 Antibody

The hu15C1 antibodies of the invention include the variable heavy chain ($V_H$) 4-28 shown below in SEQ ID NO:45 or the $V_H$ 3-66 shown below in SEQ ID NO:46. The hu15C1 antibodies of the invention include the variable light chain ($V_L$) L6 shown below in SEQ ID NO:47 or A26 shown below in SEQ ID NO:48. The amino acids encompassing the complementarity determining regions (CDR) as defined by Chothia et al. 1989, E. A. Kabat et al., 1991 are boxed in the sequences provided below. (See Chothia, C, et al., Nature 342:877-883 (1989); Kabat, E A, et al., Sequences of Protein of immunological interest, Fifth Edition, US Department of Health and Human Services, US Government Printing Office (1991)).

15C1 Hu $V_H$ version 4-28
QVQLQESGPG LVKPSDTLSL TCAVSGYSI $X_1$ GGYSWHWIRQ PPGKGLEW $X_2$G
YIHYSGYTDF NPSLKTR $X_3$T $X_4$ SRDTSKNQFS LKLSSVTAVD TAVYYCARKD
PSDGFPYWGQ GTLVTVSS(SEQ ID NO: 45)

CDR 1: GGYSWH (SEQ ID NO: 85)
CDR 2: YIHYSGYTDFNPSLKT (SEQ ID NO: 86)
CDR 3: KDPSDGFPY (SEQ ID NO: 87)

Where $X_1$ is Thr or Ser
Where $X_2$ is Ile or Met
Where $X_3$ is Val or Ile
Where $X_4$ is Met or Ile 15C1 Hu $V_H$ version 3-66
EVQLVESGGG LVQPGGSLRL SCA$X_1$SGYSIT GGYSWHWVRQ APGKGLEW$X_2$S
YIHYSGYTDF NPSLKTRFTI SRDNSKNT$X_3$Y LQMNSLRAED TAVYYCARKD
PSDGFPYWGQ GTLVTVSS (SEQ ID NO: 46)

CDR 1: GGYSWH (SEQ ID NO: 85)
CDR 2: YIHYSGYTDFNPSLKT (SEQ ID NO: 86)
CDR 3: KDPSDGFPY (SEQ ID NO: 87)

Where $X_1$ is Ala or Val
Where $X_2$ is Val or Met
Where $X_3$ is Leu or Phe

15C1 Hu VL version L6
EIVLTQSPAT LSLSPGERAT LSCRASQSIS DHLHWYQQKP GQAPRLLI$X_1$Y
ASHAISGIPA RFSGSGSGTD FTLTISSLEP EDFAVYYCQN GHSFPLTFGG GTKVEIK
(SEQ ID NO: 47)

CDR 1: RASQSISDHLH (SEQ ID NO: 88)
CDR 2: YASHAIS (SEQ ID NO: 89)
CDR 3: QNGHSFPLT (SEQ ID NO: 90)

Where $X_1$ is Lys or Tyr

15C1 Hu VL version A26
EIVLTQSPDF QSVTPKEKVT ITCRASQSIS DHLHWYQQKP DQSPKLLIKY
ASHAISGVPS RFSGSGSGTD FTLTINSLEA EDAATYYCQN GHSFPLTFGG GTKVEIK
(SEQ ID NO: 48)

CDR 1: RASQSISDHLH (SEQ ID NO: 88)
CDR 2: YASHAIS (SEQ ID NO: 89)
CDR 3: QNGHSFPLT (SEQ ID NO: 90)

Tables 1 and 2 present alignments of the amino acid sequences that were used to design humanized 15C1 $V_H$ regions:

TABLE 1

| 15C1 humanized Heavy chain 4-28 | | | | | | |
|---|---|---|---|---|---|---|
| Kabat Numbering | Chothia Numbering | IGMT Numbering | Mouse 15C1 VH | Germline IGHV-4-28 | Reshaped Version 1 15C1 VH | Comments |
| FR1-1 | 1 | FR1-1 | *D* | *Q* | Q | Vernier zone |
| 2 | 2 | 2 | **V** | **V** | V | LOOP H1 2/11A H2 V |
| 3 | 3 | 3 | **Q** | **Q** | Q | |
| 4 | 4 | 4 | **L** | **L** | L | |
| 5 | 5 | 5 | **Q** | **Q** | Q | |

TABLE 1-continued

15C1 humanized Heavy chain 4-28

| Kabat Numbering | Chothia Numbering | IGMT Numbering | Mouse 15C1 VH | Germline IGHV-4-28 | Reshaped Version 1 15C1 VH | Comments |
|---|---|---|---|---|---|---|
| 6 | 6 | 6 | E | E | E | |
| 7 | 7 | 7 | S | S | S | |
| 8 | 8 | 8 | G | G | G | |
| 9 | 9 | 9 | P | P | P | |
| 10 | 10 | 11 | D | G | G | |
| 11 | 11 | 12 | L | L | L | |
| 12 | 12 | 13 | I | V | V | |
| 13 | 13 | 14 | Q | K | K | |
| 14 | 14 | 15 | P | P | P | |
| 15 | 15 | 16 | S | S | S | |
| 16 | 16 | 17 | Q | D | D | |
| 17 | 17 | 18 | S | T | T | |
| 18 | 18 | 19 | L | L | L | |
| 19 | 19 | 20 | S | S | S | |
| 20 | 20 | 21 | L | L | L | LOOP H1 2/11A H20 L |
| 21 | 21 | 22 | T | T | T | |
| 22 | 22 | 23 | C | C | C | LOOP H1 2/11A H22 C |
| 23 | 23 | 24 | T | A | A | Surface residue |
| 24 | 24 | 25 | V* | V* | V* | canonical H1 2(6) LOOP H1 2/11A H24 V |
| 25 | 25 | FR1-26 | T | S | S | |
| 26 | 26 CDR1 Chothia | 27 IMGT CDR1 | G* | G* | G* | canonical H1 2(6) LOOP H1 2/11A H26 G |
| 27 | 27 | 28 | Y* | Y* | Y* | canonical H1 2(6) Vernier zone |
| 28 | 28 | 29 | S | S | S | Vernier zone |
| 29 | 29 | 30 | I* | I* | I* | canonical H1 2(6) LOOP H1 2/11A H29 I Vernier zone |

TABLE 1-continued

| 15C1 humanized Heavy chain 4-28 | | | | | | |
|---|---|---|---|---|---|---|
| Kabat Numbering | Chothia Numbering | IGMT Numbering | Mouse 15C1 VH | Germline IGHV-4-28 | Reshaped Version 1 15C1 VH | Comments |
| FR1-30 | **30** | **31** | **T** | *S* | T or S | Vernier zone |
| **31 CDR1 Kabat** | **31** | **32** | **G** | *S* | G | |
| **32** | **31A** | **33** | **G** | *S* | G | LOOP H1 2/11A H31A D but G in 15C1 |
| **33** | **32** | **34** | **Y** | *N* | Y | |
| **34** | **33 CDR1 Chothia** | **35 IMGT CDR1** | *S* | *W* | S | LOOP H1 2/11A H33 A but S in 15C1 |
| **35** | 34 | 39 | **W*** | **W*** | W* | canonical H1 2(6) LOOP H1 2/11A H34 W VH/VL interface |
| **35A CDR1 Kabat** | 35 | 40 | H | *G* | H | |
| FR2-36 | 36 | 41 | **W** | **W** | W | LOOP H1 2/11A H36 W |
| 37 | 37 | 42 | **I** | **I** | I | VH/VL interface |
| 38 | 38 | 43 | **R** | **R** | R | |
| 39 | 39 | 44 | **Q** | **Q** | Q | VH/VL interface |
| 40 | 40 | 45 | *F* | *P* | P | |
| 41 | 41 | 46 | **P** | **P** | P | |
| 42 | 42 | 47 | **G** | **G** | G | |
| 43 | 43 | 48 | *N* | *K* | K | |
| 44 | 44 | 49 | *K* | *G* | G | |
| 45 | 45 | 50 | **L** | **L** | L | VH/VL interface (+) |
| 46 | 46 | 51 | **E** | **E** | E | |
| 47 | 47 | 52 | **W** | **W** | W | LOOP H2 1/9A H47 WY VH/VL interface Vernier zone |
| 48 | 48 | 53 | *M* | *I* | M or I | LOOP H1 2/11A H48 M Vernier zone |
| FR2-**49** | 49 | 54 | **G** | **G** | G | Vernier zone |

TABLE 1-continued

15C1 humanized Heavy chain 4-28

| Kabat Numbering | Chothia Numbering | IGMT Numbering | Mouse 15C1 VH | Germline IGHV-4-28 | Reshaped Version 1 15C1 VH | Comments |
|---|---|---|---|---|---|---|
| 50 CDR2 Kabat | 50 | 55 | **Y** | **Y** | Y | LOOP H1 2/11A H50 Y Vernier zone |
| 51 | 51 | 56 CDR2 IMGT | **I** | **I** | I | LOOP H2 1/9A H51 IMV |
| 52 | 52 CDR2 Chothia | 57 | *H* | *Y* | H | |
| 53 | 53 | 58 | **Y** | **Y** | Y | LOOP H1 2/11A H53 Y |
| 54 | 54 | 59 | **S** | **S** | S | |
| 55 | 55 | 60 | **G*** | **G*** | G* | canonical H2 class 1 (16) GD LOOP H2 1/9A H55 G |
| 56 | 56 CDR2 Chothia | 61 | *Y* | *S* | Y | |
| 57 | 57 | 62 CDR2 IMGT | **T** | **T** | T | |
| 58 | 58 | 66 | *D* | *Y* | **D** | |
| 59 | 59 | 67 | *F* | *Y* | **F** | LOOP H2 1/9A H59 YL But F in 15C1 |
| 60 | 60 | 68 | **N** | **N** | N | |
| 61 | 61 | 69 | **P** | **P** | P | |
| 62 | 62 | 70 | **S** | **S** | S | |
| 63 | 63 | 71 | **L** | **L** | L | |
| 64 | 64 | 72 | **K** | **K** | K | |
| 65 CDR2 Kabat | 65 | 74 | *T* | *S* | **T** | |
| FR3-66 | 66 | 75 | **R** | **R** | R | |
| 67 | 67 | 76 | *I* | *V* | I or V | Vernier zone Clos to CDRs |
| 68 | 68 | 77 | *S* | *T* | T | |
| 69 | 69 | 78 | **I** | *M* | I or M | LOOP H1 2/11A H69 I LOOP H2 1/9A H69 IM Vernier zone |
| 70 | 70 | 79 | *T* | *S* | S | |

TABLE 1-continued

15C1 humanized Heavy chain 4-28

| Kabat Number-ing | Chothia Number-ing | IGMT Number-ing | Mouse 15C1 VH | Germline IGHV-4-28 | Reshaped Version 1 15C1 VH | Comments |
|---|---|---|---|---|---|---|
| 71 | 71 | 80 | **R*** | *V** | R* or [V*] | canonical H2 class 1(16) RKVI<br>LOOP H2 1/9A H71<br>Vernier zone |
| 72 | 72 | 811 | **D** | **D** | [D] | |
| 73 | 73 | 82 | **T** | **T** | [T] | Vernier zone |
| 74 | 74 | 83 | **S** | **S** | [S] | |
| 75 | 75 84 | **K** | **K** | [K] | | |
| 76 | 76 | 85 | **N** | **N** | [N] | LOOP H1 2/11A H76 N |
| 77 | 77 | 86 | **Q** | **Q** | [Q] | |
| 78 | 78 | 87 | **F** | **F** | [F] | LOOP H1 2/11A H78 F<br>Vernier zone |
| 79 | 89 | 88 | *F* | *S* | [S] | |
| 80 | 80 | 89 | **L** | **L** | [L] | LOOP H1 2/11A H80 L |
| 81 | 81 | 90 | **Q** | *K* | [K] | |
| 82 | 82 | 91 | **L** | **L** | [L] | |
| 82A | 82A | 92 **N** | *S* | [S] | | |
| 82B | 82B | 93 | **S** | **S** | [S] | |
| 82C | 82C | 94 | **V** | **V** | [V] | |
| 83 | 83 | 95 | **T** | **T** | [T] | |
| 84 | 84 | 96 | *T* | *A* | [A] | |
| 85 | 85 | 97 | **E** | *V* | [V] | |
| 86 | 86 | 98 | **D** | **D** | [D] | |
| 87 | 87 | 99 | **T** | **T** | [T] | |
| 88 | 88 | 100 | **A** | **A** | [A] | |
| 89 | 89 | 101 | *T* | *V* | [V] | |
| 90 | 90 | 102 | **Y** | **Y** | [Y] | |
| 91 | 91 | 103 | **Y** | **Y** | [Y] | VH/VL interface |

TABLE 1-continued

15C1 humanized Heavy chain 4-28

| Kabat Numbering | Chothia Numbering | IGMT Numbering | Mouse 15C1 VH | Germline IGHV-4-28 | Reshaped Version 1 15C1 VH | Comments |
|---|---|---|---|---|---|---|
| 92 | 92 | 104 | **C** | **C** | C | LOOP H1 2/11A H92 C |
| 93 | 93 | **105 CDR3 IMGT** | **A A** | A | VH/VL interface Vernier zone | |
| FR3-94 | 94 | **105 CDR3 IMGT** | **R*** | **R*** | R* | canonical H1 2(6) Vernier zone |
| **95 CDR3 Kabat** | **95 CDR3 Chothia** | | K | | K | VH/VL interface |
| **96** | **96** | | D | | D | LOOP H1 2/11A H96 W But D in 15C1 |
| **97** | **97** | | P | | P | |
| **98** | **98** | | S | | S | |
| **99** | **99** | | D | | D | |
| **100** | **100** | | G | Y | G | |
| **100A** | | | F | F | F | VH/VL interface (+) |
| **101** | **101** | | P | D | P | |
| **102 CDR3 Kabat** | **102 CDR3 Chothia** | | Y | Y IGHJ-4 | Y | |
| FR4-103 | 103 | | **W** | W | W | VH/VL interface (+) Vernier zone |
| 104 | 104 | | **G** | G | G | |
| 105 | 105 | | **Q** | Q | Q | |
| 106 | 106 | | **G** | G | G | |
| 107 | 107 | | **T** | T | T | |
| 108 | 108 | | **L** | L | L | |
| 109 | 109 | | **V** | V | V | |
| 110 | 110 | | **T** | T | T | |
| 111 | 111 | | **V** | V | V | |

TABLE 1-continued

| 15C1 humanized Heavy chain 4-28 | | | | | | |
|---|---|---|---|---|---|---|
| Kabat Numbering | Chothia Numbering | IGMT Numbering | Mouse 15C1 VH | Germline IGHV-4-28 | Reshaped Version 1 15C1 VH | Comments |
| 112 | 112 | | **S** | [S] | [S] | |
| FR4-113 | 113 | | *A* | [S] | [S] | |

Legend: The first column (Kabat numbering) gives the residue number according to Kabat et al. (1991); the second column (Chothia numbering) gives the residue number according to Chothia; the third column (IMGT numbering) gives the IMGT unique Lefranc numbering for 15C1 $V_H$; the fourth column (mouse 15C1 $V_H$) gives the amino acid sequence of the $V_H$ region of mouse 15C1 anti-TLR4 MD2 antibody used as donor sequence for CDR-grafting; the fifth column (Human Germline IGHV4-28) gives the sequence amino acid of the human germline immunoglobulin heavy variable 4-28 used as acceptor sequence for CDR-grafting; and the sixth column (Reshaped version 1 15C1 VH) gives the amino acid sequence of humanized version of 15C1 $V_H$ region. The positions of framework segments (FR1, FR2, FR3, and FR4) and the complementarity-determining segments (CDR1, CDR2, and CRD3) with are shown in column one.

As used in Tables 1, (*) indicates parts of main canonical structure for the CDR loops defined by Chothia et al. (1989). The bolded entries with no underlining represent positions in FRs and CDRs where the human and mouse amino acid residues are identical. The italicized entries represent positions in FRs where the human residue differs from the analogous mouse residue number. The underlined entries (bolded or not bolded) represent positions in FRs and CDRs where the human amino acid residue was replaced by the corresponding mouse residue. The boxed entries represent human residues conserved in the humanized version.

TABLE 2

| 15C1 humanized Heavy chain 3-66 | | | | | | |
|---|---|---|---|---|---|---|
| Kabat Numbering | Chothia Numbering | IGMT Numbering | Mouse 15C1 VH | Germline IGHV3-66 | Humanized version 3-66 | Comments |
| FR1-1 | 1 | FR1-1 | *D* | *E* | [E] | Vernier zone |
| <u>2</u> | 2 | 2 | **V** | **V** | [V] | LOOP H1 2/11A H2 V |
| 3 | 3 | 3 | **Q** | **Q** | [Q] | |
| <u>4</u> | 4 | 4 | **L** | **L** | [L] | |
| 5 | 5 | 5 | *Q* | *V* | [V] | |
| <u>6</u> | 6 | 6 | **E** | **E** | [E] | |
| 7 | 7 | 7 | **S** | **S** | [S] | |
| 8 | 8 | 8 | **G** | **G** | [G] | |
| 9 | 9 | 9 | *P* | *G* | [G] | |
| 10 | 10 | 11 | *D* | *G* | [G] | |
| 11 | 11 | 12 | **L** | **L** | [L] | |
| 12 | 12 | 13 | *I* | *V* | [V] | |

TABLE 2-continued

15C1 humanized Heavy chain 3-66

| Kabat Numbering | Chothia Numbering | IGMT Numbering | Mouse 15C1 VH | Germline IGHV3-66 | Humanized version 3-66 | Commants |
|---|---|---|---|---|---|---|
| 13 | 13 | 14 | **Q** | **Q** | Q | |
| 14 | 14 | 15 | **P** | **P** | P | |
| 15 | 15 | 16 | *S* | *G* | G | |
| 16 | 16 | 17 | *Q* | *G* | G | |
| 17 | 17 | 18 | **S** | **S** | S | |
| 18 | 18 | 19 | **L** | **L** | L | |
| 19 | 19 | 20 | *S* | *R* | R | |
| 20 | 20 | 21 | **L** | **L** | L | LOOP H1 2/11A H20 L |
| 21 | 21 | 22 | *T* | *S* | S | |
| 22 | 22 | 23 | **C** | **C** | C | LOOP H1 2/11A H22 C |
| 23 | 23 | 24 | *T* | *A* | A | Surface residue |
| 24 | 24 | 25 | *V** | *A* | V or A | canonical H1 2(6) LOOP H1 2/11A H24 V |
| 25 | 25 | FR1-26 | *T* | *S* | S | |
| 26 | **26 CDR1 Chothia** | **27 IMGT CDR1** | **G*** | **G** | G | canonical H1 2(6) LOOP H1 2/11A H26 G |
| 27 | **27** | **28** | *Y** | *F* | Y | canonical H1 2(6) Vernier zone |
| 28 | **28** | **29** | *S* | *T* | S | Vernier zone |
| 29 | **27** | **30** | *I** | *V* | I | canonical H1 2(6) LOOP H1 2/11A H29 I Vernier zone |
| FR1-30 | **30** | **31** | *T* | *S* | T | Vernier zone |
| **31 CDR1 Kabat** | **31** | **32** | *G* | *S* | G | |
| **32** | **31A** | **33** | *G* | *N* | G | LOOP H1 2/11A H31 A D but G in 15C1 |
| **33** | **32** | **34** | **Y** | **Y** | Y | |
| **34** | **33 CDR1 Chothia** | **35 IMGT CDR1** | *S* | *M* | S | LOOP H1 2/11A H33 A but S in 15C1 |

TABLE 2-continued

15C1 humanized Heavy chain 3-66

| Kabat Numbering | Chothia Numbering | IGMT Numbering | Mouse 15C1 VH | Germline IGHV3-66 | Humanized version 3-66 | Comments |
|---|---|---|---|---|---|---|
| **35** | 34 39 | *W** | | W | canonical H1 2(6) LOOP H1 2/11A H34 W VH/VL interface | |
| **35A CDR1 Kabat** | 35 | 40 | *H* | *S* | H | |
| FR2-36 | 36 | 41 | **W** | **W** | W | LOOP H1 2/11A H36 W |
| 37 | 37 | 42 | *I* | *V* | V | VH/VL interface |
| 38 | 38 | 43 | **R** | **R** | R | |
| 39 | 39 | 44 | **Q** | **Q** | Q | VH/VL interface |
| 40 | 40 | 45 | *F* | *A* | A | |
| 41 | 41 | 46 | **P** | **P** | P | |
| 42 | 42 | 47 | **G** | **G** | G | |
| 43 | 43 | 48 | *N* | *K* | K | |
| 44 | 44 | 49 | *H* | *G* | G | |
| 45 | 45 | 50 | **L** | **L** | L | VH/VL interface (+) |
| 46 | 46 | 51 | **E** | **E** | E | |
| 47 | 47 | 52 | **W** | **W** | W | LOOP H2 1/9A H47 WY VH/VL interface Vernier zone |
| 48 | 48 | 53 | *M* | *V* | M or V | LOOP H1 2/11A H49 M Vernier zone |
| FR2-49 | 49 | 54 | *G* | *S* | S | Vernier zone |
| **50 CDR2 Kabat** | 50 | 55 | *Y* | *V* | Y | LOOP H1 2/11A H50 Y Vernier zone |
| **51** | 51 | **56 CDR2 IMGT** | **I** | **I** | I | LOOP H2 1/9A H51 IMV |
| **52** | **52 CDR2 Chothia** | **57** | *H* | *Y* | H | |
| **53** | **53** | **58** | *Y* | *S* | Y | LOOP H1 2/11A H53 Y |

TABLE 2-continued

15C1 humanized Heavy chain 3-66

| Kabat Numbering | Chothia Numbering | IGMT Numbering | Mouse 15C1 VH | Germline IGHV3-66 | Humanized version 3-66 | Commants |
|---|---|---|---|---|---|---|
| **54** | **54** | **59** | *S* | *G* | S | |
| **55** | **55** | **60** | **G*** | **G** | [G] | canonical H2 class 1 (16) GD<br>LOOP H2 1/9A H55 G |
| **56** | **56 CDR2 Chothia** | **61** | *Y* | *S* | Y | |
| **57** | 57 | **62 CDR2 IMGT** | **T** | **T** | [G] | |
| **58** | 58 | 66 | *D* | *Y* | **D** | |
| **59** | 59 | 67 | *F* | *Y* | **F** | LOOP H2 1/9A H59 YL<br>But F in 15C1 |
| **60** | 60 | 68 | *N* | *A* | **N** | |
| **61** | 61 | 69 | *P* | *D* | P | |
| **62** | 62 | 70 | **S** | **S** | [S] | |
| **63** | 63 | 71 | *L* | *V* | **L** | |
| **64** | 64 | 72 | **K** | **K** | [K] | |
| **65 CDR2 Kabat** | 65 | 74 | *T* | *G* | **T** | |
| FR3-66 | 66 | 75 | **R** | **R** | [R] | |
| 67 | 67 | 76 | *I* | *F* | [F] | Vernier zone<br>Close to CDRs |
| 68 | 68 | 77 | *S* | *T* | [T] | |
| 69 69 | 78 | **I** | **I** | [I] | LOOP H1 2/11A H69 I<br>LOOP H2 1/9A H69 IM<br>Vernier zone | |
| 70 | 70 | 79 | *T* | *S* | [S] | |
| 71 | 71 | 80 | **R*** | **R** | [R] | canonical H2 class 1(16) RKVI<br>LOOP H2 1/9A H71 RKV<br>Vernier zone |
| 72 | 72 | 81 | **D** | **D** | [D] | |
| 73 | 73 | 82 | *T* | *N* | [N] | Vernier zone |

TABLE 2-continued

15C1 humanized Heavy chain 3-66

| Kabat Numbering | Chothia Numbering | IGMT Numbering | Mouse 15C1 VH | Germline IGHV3-66 | Humanized version 3-66 | Commants |
|---|---|---|---|---|---|---|
| 74 | 74 | 83 | **S** | **S** | S | |
| 75 | 75 | 84 | **K** | **K** | K | |
| 76 | 76 | 85 | **N** | **N** | N | LOOP H1 2/11A H76 N |
| 77 | 77 | 86 | *Q* | *T* | T | |
| 78 | 78 | 87 | *F* | *L* | F or L | LOOP H1 2/11A H78 F Vernier zone |
| 79 | 89 | 88 | *F* | *Y* | Y | |
| 80 | 80 | 89 | **L** | **L** | L | LOOP H1 2/11A H80 L |
| 81 | 81 90 | **Q** | **Q** | Q | | |
| 82 | 82 | 91 | *L* | *M* | M | |
| 82A | 82A | 92 | **N** | **N** | N | |
| 82B | 82B | 93 | **S** | **S** | S | |
| 82C | 82C | 94 | *V* | *L* | L | |
| 83 | 83 | 95 | *T* | *R* | R | |
| 84 | 84 | 96 | *T* | *A* | A | |
| 85 | 85 | 97 | **E** | **E** | E | |
| 86 | 86 | 98 | **D** | **D** | D | |
| 87 | 87 | 99 | **T** | **T** | T | |
| 88 | 88 | 100 | **A** | **A** | A | |
| 89 | 89 | 101 | *T* | *V* | V | |
| 90 | 90 | 102 | **Y** | **Y** | Y | |
| 91 | 91 | 103 | **Y** | **Y** | Y | VH/VL interface |
| 92 | 92 | 104 | **C** | **C** | C | LOOP H1 2/11A H92 C |
| 93 | 93 | **105 CDR3 IMGT** | **A A** | A | VH/VL interface Vernier zone | |
| FR3-94 | 94 | M or V | **R*** | **R** | R | canonical H1 2(6) Vernier zone |

TABLE 2-continued

15C1 humanized Heavy chain 3-66

| Kabat Numbering | Chothia Numbering | IGMT Numbering | Mouse 15C1 VH | Germline IGHV3-66 | Humanized version 3-66 | Commants |
|---|---|---|---|---|---|---|
| **95 CDR3 Kabat** | **95 CDR3 Chothia** | | K | | K | VH/VL interface |
| **96** | **96** | | D | | D | LOOP H1 2/11A H96 W But D in 15C1 |
| **97** | **97** | | P | | P | |
| **98** | **98** | | S | | S | |
| **99** | **99** | | D | | D | |
| **100** | **100** | | *G* | *Y* | G | |
| **100A** | | | **F** | **F** | F | VH/VL interface (+) |
| **101** | **101** | | *P* | *D* | P | |
| **102 CDR3 Kabat** | **102 CDR3 Chothia** | | **Y** | **Y** | Y | |
| FR4-103 | 103 | | **W** | **W** | W | VH/VL interface (+) Vernier zone |
| 104 | 104 | | **G** | **G** | G | |
| 105 | 105 | | **Q** | **Q** | Q | |
| 106 | 106 | | **G** | **G** | G | |
| 107 | 107 | | **T** | **T** | T | |
| 108 | 108 | | **L** | **L** | L | |
| 109 | 109 | | **V** | **V** | V | |
| 110 | 110 | | **T** | **T** | T | |
| 111 | 111 | | **V** | **V** | V | |
| 112 | 112 | | **S** | **S** | S | |
| FR4-113 | 113 | | *A* | *S* | S | |

Legend: The first column (Kabat numbering) gives the residue number according to Kabat et al (1991); the second column (Chothia numbering) gives the residue number according to Chothia; the third column (IMGT numbering) gives the IMGT unique Lefranc numbering for 15C1 VH; the fourth column (mouse 15C1 VH) gives the amino acid sequence of the $V_H$ region of mouse 15C1 anti-TLR4 MD2 antibody used as donor sequence for CDR-grafting; the fifth column (Human Germline IGHV 3-66) gives the sequence amino acid of the human germline immunoglobulin heavy variable 3-66 used as acceptor sequence for CDR-grafting; and the sixth column (Humanized version 3-66) gives the amino acid sequence of the humanized version of 15C1 $V_H$ region. The positions of framework segments (FR1, FR2, FR3, and FR4) and the complementarity-determining segments (CDR1, CDR2, and CDR3) with are shown in column one.

As used in Table 2, (*) indicates parts of main canonical structure for the CDR loops as defined by Chothia et al. (1989). The bolded entries, not underlined, represent positions in FRs and CDRs where the human and mouse amino acid residues are identical. The italicized entries represent positions in FRs where the human residue differs from the analogous mouse residue number. The underlined entries (bolded or not bolded) represent positions in FRs and CDRs where the human amino acid residue was replaced by the corresponding mouse residue. The boxed entries represent human residues conserved in the humanized version.

Tables 3 and 4 present alignments of the amino acid sequences that were used to design the humanized 15C1 $V_L$ regions:

TABLE 3

| | | | 15C1 humanized Light chain A26 | | | |
|---|---|---|---|---|---|---|
| Kabat | # | FR or CDR | Mouse 15C1 Light | Human Germline A26 IGKV6-21 | Humanized 15C1 VL A26 | Comments |
| 1 | 1 | FR1 | **D** | *E* | E | |
| 2 | 2 | \| | **I** | **I** | I | L1 class 2/11A (11) I |
| 3 | 3 | \| | **V** | **V** | V | |
| 4 | 4 | \| | **M** | *L* | L | Vernier zone |
| 5 | 5 | \| | **T** | **T** | T | |
| 6 | 6 | \| | **Q** | **Q** | Q | |
| 7 | 7 | \| | **S** | **S** | S | |
| 8 | 8 | \| | **P** | **P** | P | |
| 9 | 9 | \| | **A** | *D* | D | |
| 10 | 10 | \| | **T** | *F* | F | |
| 11 | 11 | \| | **L** | *Q* | Q | |
| 12 | 12 | \| | **S** | **S** | S | |
| 13 | 13 | \| | **V** | **V** | V | |
| 14 | 14 | \| | **T** | **T** | T | |
| 15 | 15 | \| | **P** | **P** | P | |
| 16 | 16 | \| | **G** | *K* | K | |
| 17 | 17 | \| | *D* | *E* | E | |
| 18 | 18 | \| | **R** | *K* | K | |
| 19 | 19 | \| | **V** | **V** | V | |
| 20 | 20 | \| | *S* | *T* | T | |
| 21 | 21 | \| | **L** | *I* | I | |
| 22 | 22 | \| | **S** | *T* | T | |
| 23 | 23 | FR1 | **C** | **C** | C | |
| **24** | **24** | CDR1 | **R** | **R** | R | |
| 25 | 25 | \| | **A** | **A** | A | L1 class 2/11A (11) A |
| 26 | 26 | \| | **S** | **S** | S | |
| 27 | 27 | \| | **Q** | **Q** | Q | |
| 28 | 28 | \| | **S** | **S** | S | |
| 29 | 29 | \| | **I** | **I** | I | L1 class 2/11A (11) IV |
| 30 | 30 | \| | S | *G* | S | |
| 31 | 31 | \| | D | *S* | D | |
| 32 | 32 | \| | H | *S* | H | |
| 33 | 38 | \| | **L** | **L** | L | L1 class 2/11A (11) L |
| **34** | **34** | CDR1 | **H** | **H** | H | |
| 35 | 35 | FR2 | **W** | **W** | W | L1 class 2/11A (11) W |
| 36 | 36 | \| | **Y** | **Y** | Y | VH/VL inter<br>Vernier zone |
| 37 | 37 | \| | **Q** | **Q** | Q | |
| 38 | 38 | \| | **Q** | **Q** | Q | VL/VH inter |
| 39 | 39 | \| | **K** | **K** | K | |
| 40 | 40 | \| | *S* | *P* | P | |
| 41 | 41 | \| | *H* | *D* | D | |
| 42 | 42 | \| | *E* | *Q* | Q | |
| 43 | 43 | \| | **S** | **S** | S | |
| 44 | 44 | \| | **P** | **P** | P | VL/VH inter+ |
| 45 | 45 | \| | **R** | *K* | K | |
| **46** | 46 | \| | **L** | **L** | L | VL/VH inter<br>Vernier zone |
| 47 | 47 | \| | **L** | **L** | L | Vernier zone |

TABLE 3-continued

15C1 humanized Light chain A26

| Kabat | # | FR or CDR | Mouse 15C1 Light | Human Germline A26 IGKV6-21 | Humanized 15C1 VL A26 | Comments |
|---|---|---|---|---|---|---|
| 48 | 48 | \| | I | I | I | L2 class 1/7A (7) IV |
| 49 | 49 | FR2 | K | K | K | Vernier zone |
| 50 | 50 | CDR2 | Y | Y | Y | |
| 51 | 51 | \| | A | A | A | |
| 52 | 52 | \| | S | S | S | |
| 53 | 53 | \| | H | Q | H | |
| 54 | 54 | \| | A | S | A | |
| 55 | 55 | \| | I | F | I | |
| 56 | 56 | CDR2 | S | S | S | |
| 57 | 57 | FR3 | G | G | G | |
| 58 | 58 | \| | I | V | V | |
| 59 | 59 | \| | P | P | P | |
| 60 | 60 | \| | S | S | S | |
| 61 | 61 | \| | R | R | R | |
| 62 | 62 | \| | F | F | F | |
| 63 | 63 | \| | S | S | S | |
| 64 | 64 | \| | G | G | G | L2 class 1/7A (7) G |
| 65 | 65 | \| | S | S | S | |
| 66 | 66 | \| | G | G | G | Vernier zone |
| 67 | 67 | \| | S | S | S | |
| 68 | 68 | \| | G | G | G | Vernier zone |
| 69 | 69 | \| | T | T | T | Vernier zone |
| 70 | 70 | \| | D | D | D | |
| 71 | 71 | \| | F | F | F | L1 class 2/11A (11) YF |
| 72 | 72 | \| | T | T | T | |
| 73 | 73 | \| | L | L | L | |
| 74 | 74 | \| | S | T | T | |
| 75 | 75 | \| | I | I | I | |
| 76 | 76 | \| | K | N | N | |
| 77 | 77 | \| | S | S | S | |
| 78 | 78 | \| | V | L | L | |
| 79 | 79 | \| | E | E | E | |
| 80 | 80 | \| | P | A | A | |
| 81 | 81 | \| | E | E | E | |
| 82 | 82 | \| | D | D | D | |
| 83 | 83 | \| | I | A | A | |
| 84 | 84 | \| | G | A | A | |
| 85 | 85 | \| | V | T | T | |
| 86 | 86 | \| | Y | Y | Y | |
| 87 | 87 | \| | Y | Y | Y | VL/VH inter |
| 88 | 88 | FR3 | C | C | C | |
| 89 | 89 | CDR3 | Q | H | Q | VL/VH inter |
| 90 | 90 | \| | N | Q | N | L3 class 1/9A (9) QNH |
| 91 | 91 | \| | G | S | G | VL/VH inter |
| 92 | 92 | \| | H | S | H | |
| 93 | 93 | \| | S | S | S | |
| 94 | 94 | \| | E | L | F | |
| 95 | 95 | \| | P | P | P | L3 class 1/9A (9) P |
| 96 | 96 | \| | L | L | L | VL/VH inter+ |
| 97 | 97 | CDR3 | T | T | T | |
| 98 | 98 | FR4 | F | F | F | VL/VH inter+ Vernier zone |
| 99 | 99 | \| | G | G | G | |
| 100 | 100 | \| | A | G | G | |
| 101 | 101 | \| | G | G IGKJ4 | G IGKJ4 | |
| 102 | 102 | \| | T | T | T | |
| 103 | 103 | \| | K | K | K | |
| 104 | 104 | \| | L | V | V | |
| 105 | 105 | \| | E | E | E | |
| 106 | 106 | \| | L | I | I | |
| 107 | 107 | FR4 | K | K | K | |

Legend: The first column (Kabat) gives the residue number according to Kabat et al. (1991); The second column (#) gives the residue number in regular sequence; The third column (FR or CDR) is convenient to identify the framework segments (FR1, FR2, FR3, and FR4) and the complementarity-determining segments (CDR1, CDR2, and CDR3) with the three CDRs separating the four FRs; The fourth column (mouse 15C1 Light) gives the amino acid sequence of the $V_L$ region of mouse 15C1 antibody; The fifth column (Human GermalineA26 IGKV6-21) gives the sequence amino acid of the human germline Kappa light chain A26 or IGKV6-21; The sixth column (Humanized 15C1 VL A26) gives the amino acid sequence of humanized version of 15C1 VL A26.

As used in Table 3, (*) represents part of main canonical structure for the CDR loops as defined by Chothia et al. (1989). Bolded entries, not underlined, represent positions in FRs and CDRs where the human and mouse amino acid residues are identical. Italicized entries represent positions in FRs where the human residue differs from the analogous mouse residue number. Underlined entries (bolded or not bolded) represent positions in FRs and CDRs where the human amino acid residue was replaced by the corresponding mouse residue.

TABLE 4

| | | | 15C1 Humanized Light chain L6 | | | |
|---|---|---|---|---|---|---|
| Kabat | # | FR or CDR | Mouse 15C1 Light | Human Germline L6 IGKV3-11 | Humanized 15C1 VL L6 | Comments |
| 1 | 1 | FR1 | *D* | *E* | E | |
| 2 | 2 | \| | **I** | **I** | I* | L1 class 2/11A (11) I |
| 3 | 3 | \| | **V** | **V** | V | |
| 4 | 4 | \| | *M* | *L* | L | Vernier zone |
| 5 | 5 | \| | **T** | **T** | T | |
| 6 | 6 | \| | **Q** | **Q** | Q | |
| 7 | 7 | \| | **S** | **S** | S | |
| 8 | 8 | \| | **P** | **P** | P | |
| 9 | 9 | \| | **A** | **A** | A | |
| 10 | 10 | \| | **T** | **T** | T | |
| 11 | 11 | \| | **L** | **L** | L | |
| 12 | 12 | \| | **S** | **S** | S | |
| 13 | 13 | \| | V | L | L | |
| 14 | 14 | \| | T | S | S | |
| 15 | 15 | \| | **P** | **P** | P | |
| 16 | 16 | \| | **G** | **G** | G | |
| 17 | 17 | \| | *D* | *E* | E | |
| 18 | 18 | \| | **R** | **R** | R | |
| 19 | 19 | \| | *V* | *A* | A | |
| 20 | 20 | \| | *S* | *T* | T | |
| 21 | 21 | \| | **L** | **L** | L | |
| 22 | 22 | \| | **S** | **S** | S | |
| 23 | 23 | FR1 | **C** | **C** | C | |
| **24** | **24** | CDR1 | **R** | **R** | R | |
| 25 | 25 | \| | **A** | **A** | A* | L1 class 2/11A (11) A |
| 26 | 26 | \| | **S** | **S** | S | |
| 27 | 27 | \| | **Q** | **Q** | Q | |
| 28 | 28 | \| | **S** | **S** | S | |
| 29 | 29 | \| | I | *V* | I* | L1 class 2/11A (11) IV |
| 30 | 30 | \| | **S** | **S** | S | |
| 31 | 31 | \| | D | *S* | D | |
| 32 | 32 | \| | H | *Y* | H | |
| 33 | 33 | \| | **L** | **L** | L* | L1 class 2/11A (11) L |
| **34** | **34** | CDR1 | H | *A* | H | |
| 35 | 35 | FR2 | **W** | **W** | W* | L1 class 2/11A (11) W |
| 36 | 36 | \| | **Y** | **Y** | Y | VH/VL inter Vernier zone |
| 37 | 37 | \| | **Q** | **Q** | Q | |
| 38 | 38 | \| | **Q** | **Q** | Q | VL/VH inter |
| 39 | 39 | \| | **K** | **K** | K | |
| 40 | 40 | \| | *S* | *P* | P | |
| 41 | 41 | \| | *H* | *G* | G | |
| 42 | 42 | \| | *E* | *Q* | Q | |
| 43 | 43 | \| | *S* | *A* | A | |
| 44 | 44 | \| | **P** | **P** | P | VL/VH inter+ |
| 45 | 45 | \| | **R** | **R** | R | |
| **46** | 46 | \| | **L** | **L** | L | VL/VH inter Vernier zone |
| 47 | 47 | \| | **L** | **L** | L | Vernier zone |
| **48** | 48 | \| | **I** | **I** | I* | L2 class 1/7A (7) IV |
| 49 | 49 | FR2 | *K* | *Y* | K OR Y | Vernier zone |
| **50** | **50** | CDR2 | Y | *D* | Y | |
| 51 | 51 | \| | **A** | **A** | A | |
| 52 | 52 | \| | **S** | **S** | S | |
| 53 | 53 | \| | H | *N* | H | |
| 54 | 54 | \| | A | *R* | A | |
| 55 | 55 | \| | I | *A* | I | |
| **56** | **56** | CDR2 | S | *T* | S | |
| 57 | 57 | FR3 | **G** | **G** | G | |
| **58** | 58 | \| | **I** | **I** | I | |
| 59 | 59 | \| | **P** | **P** | P | |

TABLE 4-continued

15C1 Humanized Light chain L6

| Kabat | # | FR or CDR | Mouse 15C1 Light | Human Germline L6 IGKV3-11 | Humanize d 15C1 VL L6 | Comments |
|---|---|---|---|---|---|---|
| 60 | 60 | \| | *S* | *A* | A | |
| 61 | 61 | \| | **R** | **R** | R | |
| 62 | 62 | \| | **F** | **F** | F | |
| 63 | 63 | \| | **S** | **S** | S | |
| 64 | 64 | \| | **G** | **G** | G* | L2 class 1/7A (7) G |
| 65 | 65 | \| | **S** | **S** | S | |
| 66 | 66 | \| | **G** | **G** | G | Vernier zone |
| 67 | 67 | \| | **S** | **S** | S | |
| 68 | 68 | \| | **G** | **G** | G | Vernier zone |
| 69 | 69 | \| | **T** | **T** | T | Vernier zone |
| 70 | 70 | \| | **D** | **D** | D | |
| **71** | 71 | \| | **F** | **F** | F* | L1 class 2/11A (11) YF |
| 72 | 72 | \| | **T** | **T** | T | |
| 73 | 73 | \| | **L** | **L** | L | |
| 74 | 74 | \| | *S* | *T* | T | |
| 75 | 75 | \| | **I** | **I** | I | |
| 76 | 76 | \| | *K* | *S* | S | |
| 77 | 77 | \| | **S** | **S** | S | |
| 78 | 78 | \| | *V* | *L* | L | |
| 79 | 79 | \| | **E** | **E** | E | |
| 80 | 80 | \| | **P** | **P** | P | |
| 81 | 81 | \| | **E** | **E** | E | |
| 82 | 82 | \| | **D** | **D** | D | |
| 83 | 83 | \| | *I* | *F* | F | |
| 84 | 84 | \| | *G* | *A* | A | |
| 85 | 85 | \| | **V** | **V** | V | |
| 86 | 86 | \| | **Y** | **Y** | Y | |
| 87 | 87 | \| | **Y** | **Y** | Y | VL/VH inter |
| 88 | 88 | FR3 | **C** | **C** | C | |
| **89** | **89** | CDR3 | **Q** | **Q** | Q | VL/VH inter |
| 90 | 90 | \| | N | *Q* | N* | L3 class 1/9A (9) QNH |
| 91 | 91 | \| | G | *R* | G | VL/VH inter |
| 92 | 92 | \| | H | *S* | H | |
| 93 | 93 | \| | S | *N* | S | |
| 94 | 94 | \| | F | *W* | F | |
| 95 | 95 | \| | **P** | **P** | P* | L3 class 1/9A (9) P |
| 96 | 96 | \| | **L** | L | L | VL/VH inter+ |
| **97** | **97** | CDR3 | **T** | T | T | |
| 98 | 98 | FR4 | **F** | F | F | VL/VH inter+ Vernier zone |
| 99 | 99 | \| | **G** | G | G | |
| 100 | 100 | \| | *A* | G | G | |
| 101 | 101 | \| | **G** | G IGKJ4 | G | |
| 102 | 102 | \| | **T** | T | T | |
| 103 | 103 | \| | **K** | K | K | |
| 104 | 104 | \| | *L* | V | V | |
| 105 | 105 | \| | **E** | E | E | |
| 106 | 106 | \| | *L* | I | I | |
| 107 | 107 | FR4 | **K** | K | K | |

Legend: The first column (Kabat) gives the residue number according to Kabat et al. (1991); The second column (#) gives the residue number in regular sequence; The third column (FR or CDR) is convenient to identify the framework segments (FR1, FR2, FR3, and FR4) and the complementarity-determining segments (CDR1, CDR2, and CDR3) with the three CDRs separating the four FRs; The fourth column (mouse 15C1 Light) gives the amino acid sequence of the $V_L$ region of mouse 15C1 anti-TLR4 MD2 antibody; The fifth column (Human Germline L6 or IGKV3-11) gives the sequence amino acid of the human germline Kappa light chain L6 or IGKV3. The sixth column (Humanized 15C1 VL L6) gives the amino acid sequences of humanized 15C1 light chain.

As used in Table 4, (*) represents part of main canonical structure for the CDR loops as defined by Chothia et al. (1989). Bolded entries, not underlined, represent positions in FRs and CDRs where the human and mouse amino acid residues are identical. Italicized entries represent positions in FRs where the human residue differs from the analogous mouse residue number. Underlined entries (bolded or not bolded) represent positions in FRs and CDRs where the human amino acid residue was replaced by the corresponding mouse residue.

Humanized Versions of the 18H10 Antibody

The hu18H10 antibodies of the invention include the $V_H$ 1-69 shown below in SEQ ID NO:49. The hu18H10 antibodies of the invention include the $V_L$ L6 shown below in SEQ ID NO:50. The amino acids encompassing the complementarity determining regions (CDR) as defined by Chothia et al. 1989, E. A. Kabat et al., 1991 are boxed in the sequences provided below. (See Chothia, C, et al., Nature 342:877-883 (1989); Kabat, E A, et al., Sequences of Protein of immunological interest, Fifth Edition, US Department of Health and Human Services, US Government Printing Office (1991)).

18H10 Hu VH version 1-69

QVQLQSGAE VKKPGSSVKV SCKASGFNIK DSYIHWVRQA PGQGLEW$X_1$GW TDPENVNSIY DPRFQGRVTI TAD$X_2$STSTAY $X_3$ELSSLRSED TAVYYCARGY NGVYYAMDYW GQGTTVTVSS(SEQ ID NO: 49)

CDR 1: DSYIH (SEQ ID NO: 91)
CDR 2: WTDPENVNSIYDPRFQG (SEQ ID NO: 92)
CDR 3: GYNGVYYAMDY (SEQ ID NO: 93)

Where $X_1$ is Met or Ile
Where $X_2$ is Lys or Thr
Where $X_3$ is Met or Leu

18H10 Hu VH version L6

EIVLTQSPAT LSLSPGERAT LSCSASSSVI YMHWYQQKPG QAPRLLIYRT YNLASGIPAR FSGSGSGTD$X_1$ TLTISSLEPE DFAVYYCHQW SSFPYTFGQG TKVEIK (SEQ ID NO: 50)

CDR 1: SASSSVIYMH (SEQ ID NO: 94)
CDR 2: RTYNLAS (SEQ ID NO: 95)
CDR 3: HQWSSFPYT (SEQ ID NO: 96)

Where $X_1$ is Phe or Tyr

Table 5 presents alignments of the amino acid sequences that were used to design the humanized 15C1 $V_H$ region:

TABLE 5

| | | | 18H10 Humanized Heavy chain 1-69 | | | |
|---|---|---|---|---|---|---|
| Kabat Numbering | Chothia Numbering | IGMT Numbering | Mouse 18H10 VH | Human Germline UGHV1-69 | Humanized 18H10 VH 1-69 | Comments |
| FR1-1 | 1 | FR1-1 | *E* | *Q* | Q | Vernier zone |
| 2 | 2 | 2 | **V** | **V** | V | LOOP H1 1/10A H2 VIG |
| 3 | 3 | 3 | **Q** | **Q** | Q | |
| 4 | 4 | 4 | **L** | **L** | L | LOOP H1 1/10A H4 LV |
| 5 | 5 | 5 | *Q* | *V* | V | |
| 6 | 6 | 6 | **Q** | **Q** | Q | |
| 7 | 7 | 7 | **S** | **S** | S | |
| 8 | 8 | 8 | **G** | **G** | G | |
| 9 | 9 | 9 | **A** | **A** | A | |
| 10 | 10 | 11 | *D* | *E* | E | |
| 11 | 11 | 12 | *L* | *V* | V | |
| 12 | 12 | 13 | *V* | *K* | K | |
| 13 | 13 | 14 | *R* | *K* | K | |

TABLE 5-continued

18H10 Humanized Heavy chain 1-69

| Kabat Number-ing | Chothia Number-ing | IGMT Number-ing | Mouse 18H10 VH | Human Germline UGHV1-69 | Humanized 18H10 VH 1-69 | Comments |
|---|---|---|---|---|---|---|
| 14 | 14 | 15 | **P** | **P** | P | |
| 15 | 15 | 16 | **G** | **G** | G | |
| 16 | 16 | 17 | *A* | *S* | S | |
| 17 | 17 | 18 | *L* | *S* | S | |
| 18 | 18 | 19 | **V** | **V** | V | |
| 19 | 19 | 20 | **K** | **K** | K | |
| 20 | 20 | 21 | *L* | *V* | V | LOOP H1 1/10A H20 LIMV |
| 21 | 21 | 22 | **S** | **S** | S | |
| 22 | 22 | 23 | **C** | **C** | C | LOOP H1 1/10A H22 C |
| 23 | 23 | 24 | *T* | *K* | K | Surface residue |
| 24 | 24 | 25 | **A*** | **A*** | A* | canonical H1 2(6) LOOP H1 1/10A H24 TAVGS |
| 25 | 25 | FR1-26 | **S** | **S** | S | |
| 26 | **26 CDR1 Chothia** | **27 IMGT CDR1** | **G*** | **G*** | G* | canonical H1 2(6) LOOP H1 1/10A H26 G |
| 27 | **27** | **28** | F* | G* | G* | canonical H1 2(6) Vernier zone |
| 28 | **28** | **29** | *N* | *T* | T | Vernier zone |
| 29 | **29** | **30** | I* | F* | F* | canonical H1 2(6) LOOP H1 1/10A H29 IFLS Vernier zone |
| FR1-30 | **30** | **31** | *K* | *S* | S | Vernier zone |
| **31 CDR1 Kabat** | **31** | **32** | *D* | *S* | **D** | |
| **32** | **32 CDR1 Chothia** | **33** | *S* | *Y* | S | LOOP H1 1/10A H31 A IHYFTNCED but S in 18H10 |
| **33** | 33 | **34** | *Y* | *A* | Y | LOOP H1 1/10A H33 YAWGTLV LOOP H2 2/10A H33 YWGATL |
| **34** | 34 | **35 IMGT CDR1** | **I** | **I** | I | LOOP H1 1/10A IVMW |

TABLE 5-continued

18H10 Humanized Heavy chain 1-69

| Kabat Numbering | Chothia Numbering | IGMT Numbering | Mouse 18H10 VH | Human Germline UGHV1-69 | Humanized 18H10 VH 1-69 | Comments |
|---|---|---|---|---|---|---|
| 35 | 35 | 39 | *H** | *S** | H* | canonical H1 2(6)<br>LOOP H1 1/10A H35 HENQSYT<br>VH/VL interface |
| FR2-36 | 36 | 41 | **W** | **W** | W | LOOP H1 1/10A H36 W |
| 37 | 37 | 42 | **V** | **V** | V | VH/VL interface |
| 38 | 38 | 43 | *K* | *R* | R | |
| 39 | 39 | 44 | *K* | *Q* | Q | VH/VL interface |
| 40 | 40 | 45 | *R* | *A* | A | |
| 41 | 41 | 46 | **P** | **P** | P | |
| 42 | 42 | 47 | *E* | *G* | G | |
| 43 | 43 | 48 | *W* | *Q* | Q | |
| 44 | 44 | 49 | **G** | **G** | G | |
| 45 | 45 | 50 | **L** | **L** | L | VH/VL interface (+) |
| 46 | 46 | 51 | **E** | **E** | E | |
| 47 | 47 | 52 | **W** | **W** | W | LOOP H2 2/10A H47 WY<br>VH/VL interface<br>Vernier zone |
| 48 | 48 | 53 | *I* | *M* | I or M | LOOP H1 1/10A H48 IMVL<br>Vernier zone |
| FR2-49 | 49 | 54 | **G** | **G** | G | Vernier zone |
| **50 CDR2 Kabat** | 50 | 55 | *W* | *G* | W | LOOP H2 2/10A H50 REWYGQVLNKA<br>Vernier zone |
| **51** | 51 | **56 CDR2 IMGT** | *T* | *I* | **T** | LOOP H1 1/10A H51 LIVTSN<br>LOOP H2 2/10A H51 LI but T for 18H10 |
| **52** | **52 CDR2 Chothia** | **57** | *D* | *I* | **D** | LOOP H2 2/10A H52 DLNSY |
| **52 A** | | | **P** | **P** | **P** | |
| **53** | **53** | **58** | *E* | *I* | E | LOOP H2 2/10A H53 AGYSKTN but E for 18H10 |
| **54** | **54** | **59** | *N* | *F* | N | LOOP H2 2/10A H54 NSTKDG |
| **55** | **55** | **60** | *V** | *G** | V* | |

TABLE 5-continued

18H10 Humanized Heavy chain 1-69

| Kabat Numbering | Chothia Numbering | IGMT Numbering | Mouse 18H10 VH | Human Germline UGHV1-69 | Humanized 18H10 VH 1-69 | Comments |
|---|---|---|---|---|---|---|
| **56** | **56 CDR2 Chothia** | **61** | *N* | *T* | N | LOOP H2 2/10A H56 YREDGVSA but N for 18H10 |
| **57** | 57 | **62 CDR2 IMGT** | *S* | *A* | S | |
| **58** | 58 | 66 | *I* | *N* | I | LOOP H2 2/10A H58 KNTSDRGFY but I for 18H10 |
| **59** | 59 | 67 | **Y** | **Y** | Y | LOOP H2 2/10A H59 Y |
| **60** | 60 | 68 | *D* | *A* | **D** | |
| **61** | 61 | 69 | *P* | *Q* | P | |
| **62** | 62 | 70 | *R* | *K* | R | |
| **63** | 63 | 71 | **F** | **F** | F | |
| **64** | 64 | 72 | **Q** | **Q** | Q | |
| **65 CDR2 Kabat** | 65 | 74 | **G** | **G** | G | |
| FR3-66 | 66 | 75 | *K* | *R* | R | |
| 67 | 67 | 76 | *A* | *V* | V | Vernier zone Close to CDRs |
| 68 | 68 | 77 | *S* | *T* | T | |
| 69 | 69 | 78 | **I** | **I** | I | LOOP H1 1/10A ILFMV Very unusual residue LOOP H2 2/10A H69 IFLM But F in 7E3 Vernier zone |
| 70 | 70 | 79 | **T** | **T** | T | |
| 71 | 71 | 80 | **A*** | **A*** | A* | canonical H2 class 1(16) RKVI LOOP H2 2/10A H71 VAL Vernier zone |
| 72 | 72 | 81 | **D** | **D** | D | |
| 73 | 73 | 82 | *T* | *K* | K | Vernier zone |
| 74 | 74 | 83 | **S** | **S** | S | |
| 75 | 75 | 84 | *S* | *T* | T | |
| 76 | 76 | 85 | *N* | *S* | S | |

TABLE 5-continued

| 18H10 Humanized Heavy chain 1-69 | | | | | | |
|---|---|---|---|---|---|---|
| Kabat Numbering | Chothia Numbering | IGMT Numbering | Mouse 18H10 VH | Human Germline UGHV1-69 | Humanized 18H10 VH 1-69 | Comments |
| 77 | 77 | 86 | **T** | **T** | T | |
| 78 | 78 | 87 | **A** | **A** | A | LOOP H1 1/1A H78 ALVYF<br>LOOP H2 H78 ALV<br>Vernier zone |
| 79 | 89 | 88 | *F* | *Y* | Y | |
| 80 | 80 | 89 | *L* | *M* | M | LOOP H1 1/10A H80 LM |
| 81 | 81 | 90 | *Q* | *E* | E | |
| 82 | 82 | 91 | **L** | **L** | L | |
| 82A | 82A | 92 | *T* | *S* | S | |
| 82B | 82B | 93 | **S** | **S** | S | |
| 82C | 82C | 94 | **L** | **L** | L | |
| 83 | 83 | 95 | *T* | *R* | R | |
| 84 | 84 | 96 | **S** | **S** | S | |
| 85 | 85 | 97 | **E** | **E** | E | |
| 86 | 86 | 98 | **D** | **D** | D | |
| 87 | 87 | 99 | **T** | **T** | T | |
| 88 | 88 | 100 | **A** | **A** | A | |
| 89 | 89 | 101 | **V** | **V** | V | |
| 90 | 90 | 102 | **Y** | **Y** | Y | LOOP H1 1/10A H90 YF |
| 91 | 91 | 103 | **Y** | **Y** | Y | VH/VL interface |
| 92 | 92 | 104 | **C** | **C** | C | LOOP H1 1/10A H92 C |
| 93 | 93 | **105 CDR3 IMGT** | **A** | **A** | A | VH/VL interface<br>Vernier zone |
| FR3-94 | 94 | **106 CDR3 IMGT** | **R*** | **R*** | R* | LOOP H1 1/10A J94 RKFSHN<br>canonical H1 2(6)<br>Vernier zone |
| **95 CDR3 Kabat** | **95 CDR3 Chothia** | | *G* | | G | VH/VL interface |
| **96** | **96** | | *Y* | | Y | |

TABLE 5-continued

18H10 Humanized Heavy chain 1-69

| Kabat Numbering | Chothia Numbering | IGMT Numbering | Mouse 18H10 VH | Human Germline UGHV1-69 | Humanized 18H10 VH 1-69 | Comments |
|---|---|---|---|---|---|---|
| 97 | 97 | | *N* | Y | N | |
| 98 | 98 | | *G* | Y | G | |
| 99 | 99 | | *V* | Y | V | |
| 100 | 100 | | **Y** | **Y** | Y | |
| 100A | 100A | | **Y** | **Y** | Y | VH/VL interface (+) |
| 100 B | 100 B | | A | G | A | |
| 100 C | 100 C | | **M** | **M** | M | |
| 101 | 101 | | **D** | **D** | D | |
| 102 CDR3 Kabat | 102 CDR3 Chothia | | *Y* | V IGHJ-6 | Y | LOOP H1 1/10A H102 YHVISDG |
| FR4-103 | 103 | | **W** | W | W | VH/VL interface (+) Vernier zone |
| 104 | 104 | | **G** | G | G | |
| 105 | 105 | | **Q** | Q | Q | |
| 106 | 106 | | **G** | G | G | |
| 107 | 107 | | **T** | T | T | |
| 108 | 108 | | **T** | T | T | |
| 109 | 109 | | **V** | V | V | |
| 110 | 110 | | **T** | T | T | |
| 111 | 111 | | **V** | V | V | |
| 112 | 112 | | **S** | S | S | |
| FR4-113 | 113 | | **S** | S | S | |

Legend: The first column (Kabat numbering) gives the residue number according to Kabat et al. (1991); The second column (Chothia numbering) gives the residue number according to Chothia; The third column (IMGT numbering) gives the IMGT unique Lefranc numbering for 15C1 VH. The fourth column (mouse 15C1 VH) gives the amino acid sequence of the $V_H$ region of mouse 15C1 anti-TLR4 MD2 antibody used as donor sequence for CDR-grafting; The fifth column (Human Germline IGHV1-69) gives the sequence amino acid of the human germline immunoglobulin heavy variable 1-69 (IMGT denomination) used as acceptor sequence for CDR-grafting. The sixth column (Humanized 18H10 VH 1-69) gives the amino acid sequence of the humanized version of 18H10 heavy chain. The positions of framework segments (FR1, FR2, FR3, and FR4) and the complementarity-determining segments (CDR1, CDR2, and CDR3) with are shown in column one.

As used in Table 5, (*) indicates parts of main canonical structure for the CDR loops as defined by Chothia et al. (1989). Bolded entries, not underlined, represent positions in FRs and CDRs where the human and mouse amino acid residues are identical. Italicized entries represent positions in FRs where the human residue differs from the analogous mouse residue number. Underlined entries (bolded or not bolded) represent positions in FRs and CDRs where the human amino acid residue was replaced by the corresponding mouse residue. Boxed entries represent human residues conserved in the humanized version.

Table 6 presents alignments of the amino acid sequences that were used to design the humanized 15C1 $V_L$ region:

TABLE 6

| 18H10 humanized Light chain L6 | | | | | | |
|---|---|---|---|---|---|---|
| Kabat | # | FR or CDR | Mouse 18H10 Light | Human Germline L6 IGKV3-11 | Humanized 18H10 VL L6 | Comments |
| 1 | 1 | FR1 | Q | E | E | |
| 2 | 2 | \| | **I** | **I** | I* | L1 class 1/10 I |
| 3 | 3 | \| | **V** | **V** | Q | |
| 4 | 4 | \| | **L** | **L** | L | Vernier zone |
| 5 | 5 | \| | **T** | **T** | T | |
| 6 | 6 | \| | **Q** | **Q** | V | |
| 7 | 7 | \| | **S** | **S** | S | |
| 8 | 8 | \| | **P** | **P** | P | |
| 9 | 9 | \| | S | A | A | |
| 10 | 10 | \| | I | T | T | |
| 11 | 11 | \| | M | L | L | |
| 12 | 12 | \| | **S** | **S** | S | |
| 13 | 13 | \| | A | L | L | |
| 14 | 14 | \| | **S** | **S** | S | |
| 15 | 15 | \| | L | P | P | |
| 16 | 16 | \| | **G** | **G** | G | |
| 17 | 17 | \| | **E** | **E** | E | |
| 18 | 18 | \| | E | R | R | |
| 19 | 19 | \| | I | A | A | |
| 20 | 20 | \| | **T** | **T** | T | |
| 21 | 21 | \| | **L** | **L** | L | |
| 22 | 22 | \| | T | S | S | |

TABLE 6-continued

18H10 humanized Light chain L6

| Kabat | # | FR or CDR | Mouse 18H10 Light | Human Germline L6 IGKV3-11 | Humanized 18H10 VL L6 | Comments |
|---|---|---|---|---|---|---|
| 23 | 23 | FR1 | **C** | **C** | C* | L1 class 1/10 C |
| **24** | **24** | CDR1 | S | R | S | |
| 25 | 25 | \| | **A** | **A** | A* | L1 class 1/10 A |
| 26 | 26 | \| | **S** | **S** | S | |
| 27 | 27 | \| | S | Q | S | |
| 28 | 28 | \| | **S** | **S** | S | |
| 29 | 29 | \| | | V | | |
| 30 | 30 | \| | V | S | V* | L1 class 1/10 V |
| 31 | 31 | \| | I | S | I | |
| 32 | 32 | \| | **Y** | **Y** | Y | |
| 33 | 38 | \| | M | L | M* | L1 class 1/10 LM |
| **34** | **34** | CDR1 | H | A | H | |
| 35 | 35 | FR2 | **W** | **W** | W* | L1 class 1/10 W |
| 36 | 36 | \| | **Y** | **Y** | Y | VH/VL inter Vernier zone |
| 37 | 37 | \| | **Q** | **Q** | V | |
| 38 | 38 | \| | **Q** | **Q** | V | VL/VH inter |
| 39 | 39 | \| | **K** | **K** | K | |
| 40 | 40 | \| | S | P | P | |
| 41 | 41 | \| | **G** | **G** | G | |
| 42 | 42 | \| | T | Q | V | |
| 43 | 43 | \| | S | A | A | |
| 44 | 44 | \| | **P** | **P** | P | VL/VH inter+ |
| 45 | 45 | \| | K | R | R | |
| **46** | **46** | \| | **L** | **L** | L | VL/VH inter Vernier zone |
| 47 | 47 | \| | **L** | **L** | L | Vernier zone |
| **48** | 48 | \| | **I** | **I** | I* | L2 class 1/7A (7) IV |
| 49 | 49 | FR2 | **Y** | **Y** | Y | Vernier zone |
| **50** | **50** | CDR2 | R | D | R | |

TABLE 6-continued

18H10 humanized Light chain L6

| Kabat | # | FR or CDR | Mouse 18H10 Light | Human Germline L6 IGKV3-11 | Humanized 18H10 VL L6 | Comments |
|---|---|---|---|---|---|---|
| 51 | 51 | \| | T | A | T | |
| 52 | 52 | \| | Y | S | Y | |
| 53 | 53 | \| | **N** | **N** | N | |
| 54 | 54 | \| | L | R | L | |
| 55 | 55 | \| | A | A | A | |
| **56** | **56** | CDR2 | S | T | S | |
| 57 | 57 | FR3 | **G** | **G** | G | |
| 58 | 58 | \| | V | I | I | |
| 59 | 59 | \| | **P** | **P** | P | |
| 60 | 60 | \| | S | A | A | |
| 61 | 61 | \| | **R** | **R** | R | |
| 62 | 62 | \| | **F** | **F** | F | |
| 63 | 63 | \| | **S** | **S** | S | |
| 64 | 64 | \| | **G** | **G** | G* | L2 class 1/7A (7) G |
| 65 | 65 | \| | **S** | **S** | S | |
| 66 | 66 | \| | **G** | **G** | G | Vernier zone |
| 67 | 67 | \| | **S** | **S** | S | |
| 68 | 68 | \| | **G** | **G** | G | Vernier zone |
| 69 | 69 | \| | **T** | **T** | T | Vernier zone |
| 70 | 70 | \| | F | D | D | |
| 71 | 71 | \| | Y | F | Y or F* | L1 class 1/10 Y |
| 72 | 72 | \| | S | T | T | |
| 73 | 73 | \| | **L** | **L** | L | |
| 74 | 74 | \| | **T** | **T** | T | |
| 75 | 75 | \| | **I** | **I** | I | |
| 76 | 76 | \| | **S** | **S** | S | |
| 77 | 77 | \| | **S** | **S** | S | |

TABLE 6-continued

18H10 humanized Light chain L6

| Kabat | # | FR or CDR | Mouse 18H10 Light | Human Germline L6 IGKV3-11 | Humanized 18H10 VL L6 | Comments |
|---|---|---|---|---|---|---|
| 78 | 78 | \| | V | L | L | |
| 79 | 79 | \| | **E** | **E** | E | |
| 80 | 80 | \| | A | P | P | |
| 81 | 81 | \| | **E** | **E** | E | |
| 82 | 82 | \| | **D** | **D** | D | |
| 83 | 83 | \| | A | F | F | |
| 84 | 84 | \| | **A** | **A** | A | |
| 85 | 85 | \| | D | V | Q | |
| 86 | 86 | \| | **Y** | **Y** | Y | |
| 87 | 87 | \| | **Y** | **Y** | Y | |
| 88 | 88 | FR3 | **C** | **C** | C | |
| **89** | **89** | CDR3 | H | Q | H | VL/VH inter |
| 90 | 90 | \| | **Q** | **Q** | Q* | L3 class 1/9A (9) QNH |
| 91 | 91 | \| | W | R | W | VL/VH inter |
| 92 | 92 | \| | **S** | **S** | S | |
| 93 | 93 | \| | S | N | S | |
| 94 | 94 | \| | F | W | F | |
| 95 | 95 | \| | **P** | **P** | P* | L3 class 1/9A (9) P |
| 96 | 96 | \| | **Y** | Y | Y | VL/VH inter+ |
| **97** | **97** | CDR3 | **T** | T | T | |
| 98 | 98 | FR4 | **F** | F | F | VL/VH inter+ Vernier zone |
| 99 | 99 | \| | G | G | G | |
| 100 | 100 | \| | G | V | V | |
| 101 | 101 | \| | **G** | G IGKJ2 | G | |
| 102 | 102 | \| | **T** | T | T | |
| 103 | 103 | \| | **K** | K | K | |

TABLE 6-continued

| | | | | | | |
|---|---|---|---|---|---|---|
| | | | 18H10 humanized Light chain L6 | | | |
| Kabat | # | FR or CDR | Mouse 18H10 Light | Human Germline L6 IGKV3-11 | Humanized 18H10 VL L6 | Comments |
| 104 | 104 | \| | **L** | L | Q | |
| 105 | 105 | \| | **E** | E | E | |
| 106 | 106 | \| | **I** | I | I | |
| 107 | 107 | FR4 | **K** | K | K | |

Legend: The first column (Kabat) gives the residue number according to Kabat et al. (1991); The second column (#) gives the residue number in regular sequence; The third column (FR or CDR) is convenient to identify the framework segments (FR1, FR2, FR3, and FR4) and the complementarity-determining segments (CDR1, CDR2, and CDR3) with the three CDRs separating the four FRs; The fourth column (mouse 18H10 Light) gives the amino acid sequence of the $V_L$ region of mouse 18H10 anti-TLR4 MD2 antibody; The fifth column (Human Germline L6 or IGKV3-11) gives the sequence amino acid of the human germline Kappa light chain L6 or IGKV3. The sixth column (Humanized 18H10 VL L6) gives the amino acid sequences of humanized 18H10 light chain.

As used in Table 6, (*) represents part of main canonical structure for the CDR loops as defined by Chothia et al. (1989). Bolded entries, not underlined, represent positions in FRs and CDRs where the human and mouse amino acid residues are identical. Italicized entries represent positions in FRs and CDRs where human residues differ from analogous mouse residues numbers. Underlined entries (bolded or not bolded) represent positions in FRs and CDRs where the human amino acid residue was replaced by the corresponding mouse residue. Boxed entries represent human residues conserved in the humanized version.

Humanized Versions of the 7E3 Antibody

The hu7E3 antibodies of the invention include the $V_H$ 2-70 shown below in SEQ ID NO:51 or the $V_H$ 3-66 shown below in SEQ ID NO:52. The hu7E3 antibodies of the invention include the $V_L$ L19 shown below in SEQ ID NO:53. The amino acids encompassing the complementarity determining regions (CDR) as defined by Chothia et al. 1989, E. A. Kabat et al., 1991 are boxed in the sequences provided below. (See Chothia, C, et al., Nature 342:877-883 (1989); Kabat, E A, et al., Sequences of Protein of immunological interest, Fifth Edition, US Department of Health and Human Services, US Government Printing Office (1991)).

7E3 Hu VH version 2-70
QVTLRESGPA LVKPTQTLTL TCTFSGFSLX$_1$ TYNIGVGWIR QPPGKALEWL
AHIWWNDNIY YNTVLKSRLT X$_2$SKDTSKNQV VLTMTNMDPV DTATYYCX$_3$RM
AEGRYDAMDY WGQGTLVTVS S (SEQ ID NO: 51)

CDR 1: TYNIGVG (SEQ ID NO: 97)
CDR 2: HIWWNDNIYYNTVLKS (SEQ ID NO: 98)
CDR 3: MAEGRYDAMDY (SEQ ID NO: 99)

Where $X_1$ is Ser or Thr
Where $X_2$ is Ile or Phe
Where $X_3$ is Ile or Ala

7E3 Hu VH version 3-66
EVQLVESGGG LVQPGGSLRL SCAX$_1$SGFSLT TYNIGVGWVR QAPGKGLEWX$_2$
SHIWWNDNIY YNTVLKSRLT X$_3$Sx$_4$DNSKNTX$_5$ YLQMNSLRAE DTAVYYCX$_3$RM
AEGRYDAMDY WGQGTLVTVS S (SEQ ID NO: 52)

CDR 1: TYNIGVG (SEQ ID NO: 97)
CDR 2: HIWWNDNIYYNTVLKS (SEQ ID NO: 98)
CDR 3: MAEGRYDAMDY (SEQ ID NO: 99)

Where $X_1$ is Phe or Ala
Where $X_2$ is Val or Leu
Where $X_3$ is Ile or Phe
Where $X_4$ is Lys or Arg
Where $X_5$ is Leu or Val
Where $X_6$ is Ile or Ala -continued 7E3 Hu VL version L19
DIQMTQSPSS VSASVGDRVT ITCRASQDIT NYLNWYQQKP GKAPKLLIYY
TSKLHSGVPS RFSGSGSGTD $X_1$TLTISSLQP EDFATY$X_2$CQQ GNTFPWTFGG
GTKVEIK (SEQ ID NO: 53)

CDR 1: RASQDITNYLN (SEQ ID NO: 100)
CDR 2: YTSKLHS (SEQ ID NO: 101)
CDR 3: QQGNTFPWT (SEQ ID NO: 102)

Where $X_1$ is Phe or Tyr
Where $X_2$ is Tyr or Phe

Tables 7 and 8 present alignments of the amino acid sequences that were used to design the humanized 15C1 $V_H$ regions:

TABLE 7

7E3 humanized Heavy chain 3-66

| Kabat Numbering | Chothia Numbering | IGMT Numbering | Mouse 7E3VH | Germline IGHV3-66 | Version 3-66 7E3 VH | Comments |
|---|---|---|---|---|---|---|
| FR1-1 | 1 | FR1-1 | Q | E | E | Vernier zone |
| 2 | 2 | 2 | V | V | V | |
| 3 | 3 | 3 | T | Q | Q | |
| 4 | 4 | 4 | L | L | L | |
| 5 | 5 | 5 | K | V | V | |
| 6 | 6 | 6 | E | E | E | |
| 7 | 7 | 7 | S | S | S | |
| 8 | 8 | 8 | G | G | G | |
| 9 | 9 | 9 | P | G | G | |
| 10 | 10 | 11 | G | G | G | |
| 11 | 11 | 12 | I | L | L | |
| 12 | 12 | 13 | L | V | V | |
| 13 | 13 | 14 | Q | Q | Q | |
| 14 | 14 | 15 | P | P | P | |
| 15 | 15 | 16 | S | G | G | |
| 16 | 16 | 17 | Q | G | G | |
| 17 | 17 | 18 | T | S | S | |
| 18 | 18 | 19 | L | L | L | |
| 19 | 29 | 20 | S | R | R | |
| 20 | 20 | 21 | L | L | L | LOOP H1 3/12A H20 L |
| 21 | 21 | 22 | T | S | S | |
| 22 | 22 | 23 | C | C | C | LOOP H1 3/12A H22 C |
| 23 | 23 | 24 | S | A | A | Surface residue |
| 24 | 24 | 25 | F* | A | F* or A | canonical H1 2(6)<br>LOOP H1 3/12A H24 VF |
| 25 | 25 | FR1-26 | S | S | S | |
| 26 | 26<br>CDR1<br>Chothia | 27<br>IMGT<br>CDR1 | G* | G | G* | canonical H1 2(6)<br>LOOP H1 3/12A H26 G |
| 27 | 27 | 28 | F* | F | F* | canonical H1 2(6)<br>Vernier zone |
| 28 | 28 | 29 | S | T | S | LOOP H1 3/12A H28 S<br>Vernier zone |
| 29 | 29 | 30 | L* | V | L* | canonical H1 2(6)<br>LOOP H1 2/11A H29 IL<br>Vernier zone |
| FR1-30 | 30 | 31 | T | S | T | Vernier zone |
| 31<br>CDR1<br>Kabat | 31 | 32 | T | S | T | |
| 32 | 31A | 33 | Y | N | Y | LOOP H1 2/11A H31A D<br>but G in 15C1 |
| 33 | 31B | 34 | N | Y | N | |
| 34 | 32<br>CDR1<br>Chothia | 35 | I | M | I | |
| 35 | 33 | 36<br>IMGT<br>CDR1 | G* | S | G* | canonical H1 2(6)<br>LOOP H1 2/11A H34 WV<br>VH/VL interface |
| 35A | 34 | 39 | V | | V | |
| 35B | 35 | 40 | G | | G | |

TABLE 7-continued

7E3 humanized Heavy chain 3-66

| Kabat Numbering | Chothia Numbering | IGMT Numbering | Mouse 7E3VH | Germline IGHV3-66 | Version 3-66 7E3 VH | Comments |
|---|---|---|---|---|---|---|
| **CDR1 Kabat** | | | | | | |
| FR2-36 | 36 | 41 | **W** | **W** | W | LOOP H1 2/11A H36 W |
| 37 | 37 | 42 | *I* | *V* | V | VH/VL interface |
| 38 | 38 | 43 | **R** | **R** | R | |
| 39 | 39 | 44 | **Q** | **Q** | Q | VH/VL interface |
| 40 | 40 | 45 | *P* | *A* | A | |
| 41 | 41 | 46 | *S* | *P* | P | |
| 42 | 42 | 47 | **G** | **G** | G | |
| 43 | 43 | 48 | **K** | **K** | K | |
| 44 | 44 | 49 | **G** | **G** | G | |
| 45 | 45 | 50 | **L** | **L** | L | VH/VL interface (+) |
| 46 | 46 | 51 | **E** | **E** | E | |
| 47 | 47 | 52 | **W** | **W** | W | LOOP H2 1/9A H47 WY<br>VH/VL interface<br>Vernier zone |
| 48 | 48 | 53 | *L* | *V* | L or V | LOOP H1 3/12A H48 ML<br>Vernier zone |
| FR2-49 | 49 | 54 | *A* | *S* | S | Vernier zone |
| **50** | 50 | 55 | *H* | *V* | H | Vernier zone |
| **CDR2 Kabat** | | | | | | |
| **51** | 51 | **56 CDR2 IMGT** | **I** | **I** | I | LOOP H2 1/9A H51 IMV |
| **52** | **52 CDR2 Chothia** | **57** | *W* | *Y* | W | |
| **53** | **53** | **58** | *W* | *S* | W | LOOP H1 3/12A H53 YW |
| **54** | **54** | **59** | *N* | *G* | N | |
| **55** | **55** | **60** | *D** | *G* | D* | canonical H2 class 1 (16) GD<br>LOOP H2 1/9A H55 G<br>But D in 7E3 |
| **56** | **56 CDR2 Chothia** | **61** | *N* | *S* | N | |
| **57** | 57 | **62 CDR2 IMGT** | *I* | *T* | I | |
| **58** | 58 | 66 | **Y** | **Y** | Y | |
| **59** | 59 | 67 | **Y** | **Y** | Y | LOOP H2 1/9A H59 YL |
| **60** | 60 | 68 | *N* | *A* | N | |
| **61** | 61 | 69 | *T* | *D* | T | |
| **62** | 62 | 70 | *V* | *S* | V | |
| **63** | 63 | 71 | *L* | *V* | L | |
| **64** | 64 | 72 | **K** | **K** | K | |
| **65** | 65 | 74 | *S* | *G* | S | |
| **CDR2 Kabat** | | | | | | |
| FR3- 66 | 66 | 75 | **R** | **R** | R | |
| 67 | 67 | 76 | *L* | *F* | L or F | Vernier zone<br>Close to CDRs |
| 68 | 68 | 77 | **T** | **T** | T | |
| 69 | 69 | 78 | *F* | *I* | F or I | Very unusual residue<br>LOOP H2 1/9A H69 IM<br>But F in 7E3<br>Vernier zone |
| 70 | 70 | 79 | **S** | **S** | S | |
| 71 | 71 | 80 | *K** | *R* | K* or R | canonical H2 class 1(16) RKVI<br>LOOP H2 1/9A H71 RKV<br>Vernier zone |
| 72 | 72 | 81 | **D** | **D** | D | |
| 73 | 73 | 82 | *T* | *N* | N | Vernier zone |
| 74 | 74 | 83 | S | S | S | |
| 75 | 75 | 84 | *N* | *K* | K | |
| 76 | 76 | 85 | **N** | **N** | N | |
| 77 | 77 | 86 | *Q* | *T* | T | |
| 78 | 78 | 87 | *V* | *L* | V or L | LOOP H1 3/12A H78 FV<br>Vernier zone |
| 79 | 89 | 88 | *F* | *Y* | Y | |
| 80 | 80 | 89 | **L** | **L** | L | LOOP H1 3/12A H80 IL |

TABLE 7-continued

| 7E3 humanized Heavy chain 3-66 | | | | | | |
|---|---|---|---|---|---|---|
| Kabat Numbering | Chothia Numbering | IGMT Numbering | Mouse 7E3VH | Germline IGHV3-66 | Version 3-66 7E3 VH | Comments |
| 81 | 81 | 90 | *K* | *Q* | Q | |
| 82 | 82 | 91 | *I* | *M* | M | |
| 82A | *82A* | 92 | *A* | *N* | N | |
| 82B | *82B* | 93 | **S** | **S** | S | |
| 82C | *82C* | 94 | *V* | *L* | L | |
| 83 | 83 | 95 | *D* | *R* | R | |
| 84 | 84 | 96 | *I* | *A* | A | |
| 85 | 85 | 97 | *A* | *E* | E | |
| 86 | 86 | 98 | **D** | **D** | D | |
| 87 | 87 | 99 | **T** | **T** | T | |
| 88 | 88 | 100 | **A** | **A** | A | |
| 89 | 89 | 101 | *T* | *V* | V | |
| 90 | 90 | 102 | **Y** | **Y** | Y | |
| 91 | 91 | 103 | **Y** | **Y** | Y | VH/VL interface |
| 92 | 92 | 104 | **C** | **C** | C | LOOP H1 3/12A H92 C |
| 93 | 93 | **105 CDR3 IMGT** | *I* | *A* | I or A | VH/VL interface |
| FR3- 94 | 94 | **106** | **R*** | **R** | R* | Vernier zone canonical H1 2(6) Vernier zone |
| **95 CDR3 Kabat** | 95 CDR3 Chothia | **107 CDR3 IMGT** | M | | M | VH/VL interface |
| **96** | **96** | | A | | A | |
| **97** | **97** | | E | | E | |
| **98** | **98** | | G | | G | |
| **99** | **99** | | R | | R | |
| **100** | **100** | | Y | | Y | |
| **100A** | **100 A** | | D | | D | VH/VL interface (+) |
| **100 B** | **100 B** | | A | | A | |
| **100 C** | **100 C** | | M | | M | |
| **101** | **101** | | D | D | D | |
| **102 CDR3 Kabat** | **102 CDR3 Chothia** | | Y | Y | Y | |
| FR4-103 | 103 | | **W** | W | W | VH/VL interface (+) Vernier zone |
| 104 | 104 | | **G** | G | G | |
| 105 | 105 | | **Q** | Q | Q | |
| 106 | 106 | | **G** | G | G | |
| 107 | 107 | | **T** | T | T | |
| 108 | 108 | | *S* | T | T | |
| 109 | 109 | | **V** | V | V | |
| 110 | 110 | | **T** | T | T | |
| 111 | 111 | | **V** | V | V | |
| 112 | 112 | | **S** | S | S | |
| FR4-113 | 113 | | **S** | S | S | |

Legend: The first column (Kabat numbering) gives the residue number according to Kabat et al. (1991); The second column (Chothia numbering) gives the residue number according to Chothia; The third column (IMGT numbering) gives the IMGT unique Lefranc numbering. The fourth column (mouse 7E3 VH) gives the amino acid sequence of the $V_H$ region of mouse 7E3 anti-TLR4 MD2 antibody used as donor sequence for CDR-grafting; The fifth column (Human Germline IGHV3-66) gives the sequence amino acid of the human germline immunoglobulin heavy variable 2-26.used as acceptor sequence for CDR-grafting. The sixth column (Reshaped version 3-66 7E3 VH) gives the amino acid sequence of the reshaped human 7E3 $V_H$ region. The mouse amino acid residues which are kept in the humanized version are in yellow.

The positions of framework segments (FR1, FR2, FR3, and FR4) and the complementarity—determining regions (CDR1, CDR2, and CDR3) are shown in column one. (*) indicates parts of main canonical structure for the CDR loops as defined by Chothia et al. (1989). Bolded entries, not underlined represent positions in FRs and CDRs where the human and mouse amino acid residues are identical. Italicized entries represent positions in FRs where the human residue differs from the analogous mouse residue number. Underlined entries (bolded or not bolded) represent positions in FRs and CDRs where the human amino acid residue was replaced by the corresponding mouse residue. Boxed entries represent human residues conserved in the reshaped human version.

TABLE 8

| Kabat Numbering | Chothia Numbering | IGMT Numbering | Humanized Heavy chain 2-70 Mouse 7E3 VH | Human Germline IGHV2-70 | Human Version 2-70 7E3 VH | Comments |
|---|---|---|---|---|---|---|
| FR1-1 | FR1-1 | FR1-1 | **Q** | **Q** | Q | Vernier zone |
| 2 | 2 | 2 | **V** | **V** | V | |
| 3 | 3 | 3 | **T** | **T** | T | |
| 4 | 4 | 4 | **L** | **L** | L | |
| 5 | 5 | 5 | **K** | *R* | R | |
| 6 | 6 | 6 | **E** | **E** | E | |
| 7 | 7 | 7 | **S** | **S** | S | |
| 8 | 8 | 8 | **G** | **G** | G | |
| 9 | 9 | 9 | **P** | **P** | P | |
| 10 | 10 | 11 | *G* | *A* | A | |
| 11 | 11 | 12 | *I* | *L* | L | |
| 12 | 12 | 13 | *L* | *V* | V | |
| 13 | 13 | 14 | *Q* | *K* | K | |
| 14 | 14 | 15 | **P** | **P** | P | |
| 15 | 15 | 16 | *S* | *T* | T | |
| 16 | 16 | 17 | **Q** | **Q** | Q | |
| 17 | 17 | 18 | **T** | **T** | T | |
| 18 | 18 | 19 | **L** | **L** | L | |
| 19 | 19 | 20 | *S* | *T* | T | |
| 20 | 20 | 21 | **L** | **L** | L | LOOP H1 3/12A H20 L |
| 21 | 21 | 22 | **T** | **T** | T | |
| 22 | 22 | 23 | **C** | **C** | C | LOOP H1 3/12A H22 C Conserved amino acid |
| 23 | 23 | 24 | *S* | *T* | T | Surface residue |
| 24 | 24 | 25 | **F*** | **F*** | F* | canonical H1 2(6) LOOP H1 3/12A H24 VF |
| 25 | FR1-25 | FR1-26 | **S** | **S** | S | |

TABLE 8-continued

| Kabat Numbering | Chothia Numbering | IGMT Numbering | Mouse 7E3 VH | Human Germline IGHV2-70 | Human Version 2-70 7E3 VH | Comments |
|---|---|---|---|---|---|---|
| | | | Humanized Heavy chain 2-70 | | | |
| 26 | **26 CDR1 Chothia** | **27 IMGT CDR1** | **G*** | **G*** | G* | canonical H1 2(6) LOOP H1 3/12A H26 G |
| 27 | **27** | **28** | **F*** | **F*** | F* | canonical H1 2(6) Vernier zone |
| 28 | **28** | **29** | **S** | **S** | S | LOOP H1 3/12 A H28 S Vernier zone |
| 29 | **29** | **30** | **L*** | **L*** | L* | canonical H1 2(6) LOOP H1 2/11 A H29 IL Vernier zone |
| FR1-30 | **30** | **31** | *T* | *S* | T or S | Vernier zone |
| 31 CDR1 Kabat | **31** | **32** | **T** | **T** | T | |
| 32 | **31A** | **33** | *Y* | *S* | Y | LOOP H1 2/11A H31A D but G in 15C1 |
| 33 | **31B** | **34** | *N* | *G* | N | |
| 34 | **32 CDR1 Chothia** | **35** | *I* | *M* | I | |
| 35 | 33 | **36 IMGT CDR1** | **G*** | *C** | G* | canonical H1 2(6) LOOP H1 2/11A H34 WV VH/VL interface |
| **35A** | 34 | 39 | **V** | **V** | V | |
| **35B CDR1 Kabat** | 35 | 40 | *G* | *S* | G | |
| FR2-36 | 36 | 41 | **W** | **W** | W | LOOP H1 2/11A H36 W Conserved amino acid |
| 37 | 37 | 42 | **I** | **I** | I | VH/VL interface |
| 38 | 38 | 43 | **R** | **R** | R | |
| 39 | 39 | 44 | **Q** | **Q** | Q | VH/VL interface |
| 40 | 40 | 45 | **P** | **P** | P | |
| 41 | 41 | 46 | *S* | *P* | P | |
| 42 | 42 | 47 | **G** | **G** | G | |
| 43 | 43 | 48 | **K** | **K** | K | |
| 44 | 44 | 49 | *G* | *A* | A | |
| 45 | 45 | 50 | **L** | **L** | L | VH/VL interface (+) |

TABLE 8-continued

| | | | Humanized Heavy chain 2-70 | | | |
|---|---|---|---|---|---|---|
| Kabat Numbering | Chothia Numbering | IGMT Numbering | Mouse 7E3 VH | Human Germline IGHV2-70 | Human Version 2-70 7E3 VH | Comments |
| 46 | 46 | 51 | **E** | **E** | E | |
| 47 | 47 | 52 | **W W** | W | LOOP H2 1/9A H47 WY VH/VL interface Vernier zone | |
| 48 | 48 | 53 | **L** | **L** | L | LOOP H1 3/12A H48 ML Vernier zone |
| FR2-49 | 49 | 54 | **A** | **A** | A | Vernier zone |
| **50 CDR2 Kabat** | 50 | 55 | **H** | *L* | H | Vernier zone |
| **51** | 51 | **56 CDR2 IMGT** | **I** | **I** | I | LOOP H2 1/9A H51 IMV |
| **52** | **52 CDR2 Chothia** | **57** | *W* | *D* | W | |
| **53** | **53** | **58** | **W** | **W** | W | LOOP H1 3/12A H53 YW |
| **54** | **54** | **59** | **N** | *D* | N | |
| **55** | **55** | **60** | **D*** | **D*** | D* | canonical H2 class 1 (16) GD LOOP H2 1/9A H55 G But D in 7E3 |
| **56** | **56 CDR2 Chothia** | **61** | *N* | *D* | N | |
| **57** | 57 | **62 CDR2 IMGT** | *I* | *K* | I | |
| **58** | 58 | 66 | **Y** | **Y** | Y | |
| **59** | 59 | 67 | **Y** | **Y** | Y | LOOP H2 1/9A H59 YL |
| **60** | 60 | 68 | *N* | *S* | N | |
| **61** | 61 | 69 | **T** | **T** | T | |
| **62** | 62 | 70 | *V* | *S* | V | |
| **63** | 63 | 71 | **L** | **L** | L | |
| **64** | 64 | 72 | **K** | **K** | K | |
| **65 CDR2 Kabat** | 65 | 74 | **S** | **T** | S | |

TABLE 8-continued

| Kabat Numbering | Chothia Numbering | IGMT Numbering | Humanized Heavy chain 2-70<br>Mouse 7E3 VH | Human Germline IGHV2-70 | Human Version 2-70 7E3 VH | Comments |
|---|---|---|---|---|---|---|
| FR3-66 | 66 | 75 | **R** | **R** | R | |
| 67 | 67 | 76 | **L** | **L** | L | Verbier zone<br>Close to CDRs |
| 68 | 68 | 77 | **T** | **T** | T | |
| 69 | 69 | 78 | *F* | *I* | F or I | Very unusual residue<br>LOOP H2 1/9A H69 IM<br>But F in 7E3<br>Vernier zone |
| 70 | 70 | 79 | **S** | **S** | S | |
| 71 | 71 | 80 | **K*** | **K*** | K* | canonical H2 class 1(16)<br>RKVI<br>LOOP H2 1/9A H71 RKV<br>Vernier zone |
| 72 | 722 | 81 | **D** | **D** | D | |
| 73 | 73 | 82 | **T** | **T** | T | Vernier zone |
| 74 | 74 | 83 | **S** | **S** | S | |
| 75 | 75 | 84 | *N* | *K* | K | |
| 76 | 76 | 85 | **N** | **N** | N | |
| 77 | 77 | 86 | **Q** | **Q** | Q | |
| 78 | 78 | 87 | **V** | **V** | V | LOOP H1 3/12A H78 FV<br>Vernier zone |
| 79 | 89 | 88 | *F* | *V* | V | |
| 80 | 80 | 89 | **L** | **L** | L | LOOP H1 3/12A H80 IL<br>Conserved amino acid |
| 81 | 81 | 90 | *K* | *T* | T | |
| 82 | 82 | 91 | *I* | *M* | M | |
| 82A | 82A | 92 | *A* | *T* | T | |
| 82B | 82B | 93 | *S* | *N* | N | |
| 82C | 82C | 94 | *V* | *M* | M | |
| 83 | 83 | 95 | **D** | **D** | D | |
| 84 | 84 | 96 | *I* | *P* | P | |
| 85 | 85 | 97 | *A* | *V* | V | |
| 86 | 86 | 98 | **D** | **D** | D | |

TABLE 8-continued

| | | | Humanized Heavy chain 2-70 | | | |
|---|---|---|---|---|---|---|
| Kabat Number-ing | Chothia Number-ing | IGMT Number-ing | Mouse 7E3 VH | Human Germline IGHV2-70 | Human Version 2-70 7E3 VH | Comments |
| 87 | 87 | 99 | **T** | **T** | T | |
| 88 | 88 | 100 | **A** | **A** | A | |
| 89 | 89 | 101 | **T** | **T** | T | |
| 90 | 90 | 102 | **Y** | **Y** | Y | |
| 91 | 91 | 103 | **Y** | **Y** | Y | VH/VL interface |
| 92 | 92 | 104 | **C** | **C** | C | LOOP H1 3/12A H92 C Conserved amino acid |
| 93 | 93 | **105 CDR3 IMGT** | *I* | *A* | I or A | VH/VL interface Vernier zone |
| FR3-94 | 94 | **106** | **R*** | **R*** | R* | canonical H1 2(6) Vernier zone |
| **95 CDR3 Kabat** | **95 CDR3 Chothia** | **107 CDR 3 IMG T** | M | *I* | M | VH/VL interface |
| **96** | **96** | | A | | A | |
| **97** | **97** | | E | | E | |
| **98** | **98** | | G | | G | |
| **99** | **99** | | R | | R | |
| **100** | **100** | | Y | | Y | |
| **100A** | **100A** | | **D** | | **D** | VH/VL interface (+) |
| **100 B** | **100 B** | | A | Y | A | |
| **100 C** | **100 C** | | M | F | M | |
| **101** | **101** | | **D** | D | D | |
| **102 CDR3 Kabat** | **102 CDR3 Chothia** | | Y | Y IGHJ-4 | Y | |
| FR4-103 | 103 | | **W** | W | W | VH/VL interface (+) Vernier zone |
| 104 | 104 | | **G** | G | G | |
| 105 | 105 | | **Q** | Q | Q | |

TABLE 8-continued

| | | | Humanized Heavy chain 2-70 | | | |
|---|---|---|---|---|---|---|
| Kabat Numbering | Chothia Numbering | IGMT Numbering | Mouse 7E3 VH | Human Germline IGHV2-70 | Human Version 2-70 7E3 VH | Comments |
| 106 | 106 | | **G** | G | G | |
| 107 | 107 | | **T** | T | T | |
| 108 | 108 | | *S* | L | L | |
| 109 | 109 | | **V** | V | V | |
| 110 | 110 | | **T** | T | T | |
| 111 | 111 | | **V** | V | V | |
| 112 | 112 | | **S** | S | S | |
| FR4-113 | 113 | | **S** | S | S | |

Legend: The first column (Kabat numbering) gives the residue number according to Kabat et al. (1991); the second column (Chothia numbering) gives the residue number according to Chothia; the third column (IMGT numbering) gives the IMGT unique Lefranc numbering. The fourth column (mouse 7E3 VH) gives the amino acid sequence of the $V_H$ region of mouse 7E3 anti-TLR4 MD2 antibody used as donor sequence for CDR-grafting; The fifth column (Human Germline IGHV2-70) gives the sequence amino acid of the human germline immunoglobulin heavy variable 2-70.used as acceptor sequence for CDR-grafting. The sixth column (Humanized version 2-70 7E3 VH) gives the amino acid sequence of the humanized version of 7E3 $V_H$ region. The mouse amino acid residues which are kept in the humanized version are in yellow.

The positions of framework segments (FR1, FR2, FR3, and FR4) and the complementarity-determining regions (CDR1, CDR2, and CDR3) are shown in column one. (*) indicates parts of main canonical structure for the CDR loops as defined by Chothia et al. (1989). Bolded entries, not underlined, represent positions in FRs and CDRs where the human and mouse amino acid residues are identical. Italicized entries represent positions in FRs where the human residue differs from the analogous mouse residue number. Underlined entries (bolded or not bolded) represent positions in FRs and CDRs where the human amino acid residue was replaced by the corresponding mouse residue. Boxed entries represent human residues conserved in the reshaped human version.

Table 9 presents alignments of the amino acid sequences that were used to design the humanized 15C1 $V_L$ region:

TABLE 9

| | | | | 7E3 humanized Light chain L19 | | |
|---|---|---|---|---|---|---|
| Kabat | Chothia | FR or CDR | Mouse 7E3 Light | Human Germline L19 IGKV1-12 IGKV1D-12 | Reshaped human 7E3 L19 | Comments Chothia canonical definitions |
| 1 | 1 | FR1 | *A* | *D* | D | |
| 2 | 2 | \| | **I** | **I** | I* | L1 class 2/11A (11) L2 I<br>L3 1/9A (9) L2 ILV |
| 3 | 3 | \| | **Q** | **Q** | Q | L3 1/9A (9) L3 VQLE |
| 4 | 4 | \| | **M** | **M** | M | L1 class 2/11A (11) L4 ML<br>L3 1/9A (9) L4 ML |
| 5 | 5 | \| | **T** | **T** | T | |
| 6 | 6 | \| | **Q** | **Q** | Q | |

TABLE 9-continued

7E3 humanized Light chain L19

| Kabat | Chothia | FR or CDR | Mouse 7E3 Light | Human Germline L19 IGKV1-12 IGKV1D-12 | Reshaped human 7E3 L19 | Comments Chothia canonical definitions |
|---|---|---|---|---|---|---|
| 7 | 7 | \| | **S** | **S** | S | |
| 8 | 8 | \| | *T* | *P* | P | |
| 9 | 9 | \| | **S** | **S** | S | |
| 10 | 10 | \| | **S** | **S** | S | |
| 11 | 11 | \| | *L* | *V* | V | |
| 12 | 12 | \| | **S** | **S** | S | |
| 13 | 13 | \| | **A** | **A** | A | |
| 14 | 14 | \| | **S** | **S** | S | |
| 15 | 15 | \| | *L* | *V* | V | |
| 16 | 16 | \| | **G** | **G** | G | |
| 17 | 17 | \| | **D** | **D** | D | |
| 18 | 18 | \| | **R** | **R** | R | |
| 19 | 19 | \| | **V** | **V** | V | |
| 20 | 20 | \| | **T** | **T** | T | |
| 21 | 21 | \| | **I** | **I** | I | |
| 22 | 22 | \| | *N* | *T* | T | |
| 23 | 23 | FR1 | **C** | **C** | C | L1 class 2/11A (11) L23 C |
| **24** | **24** | CDR 1 | **R** | **R** | R | |
| 25 | 25 | \| | **A** | **A** | A* | L1 class 2/11A (11) L25 A |
| 26 | 26 | \| | **S** | **S** | S | L1 class 2/11A (11) L26 S |
| 27 | 27 | \| | **Q** | **Q** | Q | |
| 28 | 28 | \| | D | *G* | D | L1 class 2/11A (11) L28 NSDE<br>L3 1/9A (9) L28 SNDTE |
| 29 | 29 | \| | I | I | I* | L1 class 2/11A (11) L29 IV |
| 30 | 30 | \| | T | *S* | T | L3 1/9A (9) L30 DLYVISNFHGT |

TABLE 9-continued

7E3 humanized Light chain L19

| Kabat | Chothia | FR or CDR | Mouse 7E3 Light | Human Germline L19 IGKV1-12 IGKV1D-12 | Reshaped human 7E3 L19 | Comments Chothia canonical definitions |
|---|---|---|---|---|---|---|
| 31 | 31 | \| | N | *S* | N | L3 1/9A (9) L31 SNTKG |
| 32 | 32 | \| | Y | *W* | Y | L3 1/9A (9) L32 FYNAHSR |
| 33 | 33 | \| | **L** | **L** | L* | L1 class 2/11A (11) L33 LV L3 1/9A (9) L33 MLVIF |
| **34** | **34** | CDR 1 | N | *A* | N | L1 class 2/11A (11) L34 AGNSHVF |
| 35 | 35 | FR2 | **W** | **W** | W* | L1 class 2/11A (11) L35 W |
| 36 | 36 | \| | **Y** | **Y** | Y | L1 class 2/11A (11) L36 YLF VL/VH interface |
| 37 | 37 | \| | **Q** | **Q** | Q | |
| 38 | 38 | \| | **Q** | **Q** | Q | VL/VH inter |
| 39 | 39 | \| | **K** | **K** | K | |
| 40 | 40 | \| | **P** | **P** | P | |
| 41 | 41 | \| | *D* | *G* | G | |
| 42 | 42 | \| | *G* | *K* | K | |
| 43 | 43 | \| | *T* | *A* | A | |
| 44 | 44 | \| | *V* | *P* | P | VL/VH interface |
| 45 | 45 | \| | *R* | *K* | K | |
| 46 | 46 | \| | **L** | **L** | L | L1 class 2/11A (11) L46 LRV VL/VH interface + |
| 47 | 47 | \| | **L** | **L** | L | Vernier zone |
| 48 | 48 | \| | **I** | **I** | I* | L2 class 1/7A (7) IV |
| 49 | 49 | FR2 | **Y** | **Y** | Y | L1 class 2/11A (11) L49 YHFK |
| **50** | **50** | CDR 2 | Y | *A* | Y | |
| 51 | 51 | \| | T | *A* | T | L1 class 2/11A (11) L51 ATGV |
| 52 | 52 | \| | **S** | **S** | S | |
| 53 | 53 | \| | K | *S* | K | |
| 54 | 54 | \| | **L** | **L** | L | |

TABLE 9-continued

7E3 humanized Light chain L19

| Kabat | Chothia | FR or CDR | Mouse 7E3 Light | Human Germline L19 IGKV1-12 IGKV1D-12 | Reshaped human 7E3 L19 | Comments Chothia canonical definitions |
|---|---|---|---|---|---|---|
| 55 | 55 | \| | H | *Q* | H | |
| **56** | **56** | CDR 2 | **S** | **S** | S | |
| 57 | 57 | FR3 | **G** | **G** | G | |
| 58 | 58 | \| | *A* | *V* | V | |
| 59 | 59 | \| | **P** | **P** | P | |
| 60 | 60 | \| | **S** | **S** | S | |
| 61 | 61 | \| | **R** | **R** | R | |
| 62 | 62 | \| | **F** | **F** | F | |
| 63 | 63 | \| | **S** | **S** | S | |
| 64 | 64 | \| | **G** | **G** | G* | L2 class 1/7A (7) G |
| 65 | 65 | \| | *R* | *S* | S | |
| 66 | 66 | \| | **G** | **G** | G | Vernier zone |
| 67 | 67 | \| | **S** | **S** | S | |
| 68 | 68 | \| | **G** | **G** | G | Vernier zone |
| 69 | 69 | \| | **T** | **T** | T | Vernier zone |
| 70 | 70 | \| | **D** | **D** | D | |
| 71 | 71 | \| | *Y* | *F* | Y OR F* | L1 class 2/11A (11) L71 YF |
| 72 | 72 | \| | *S* | *T* | T | |
| 73 | 73 | \| | **L** | **L** | L | |
| 74 | 74 | \| | **T** | **T** | T | |
| 75 | 75 | \| | **I** | **I** | I | |
| 76 | 76 | \| | **S** | **S** | S | |
| 77 | 77 | \| | *N* | *S* | S | |
| 78 | 78 | \| | **L** | **L** | L | |
| 79 | 79 | \| | *E* | *Q* | Q | |

TABLE 9-continued

7E3 humanized Light chain L19

| Kabat | Chothia | FR or CDR | Mouse 7E3 Light | Human Germline L19 IGKV1-12 IGKV1D-12 | Reshaped human 7E3 L19 | Comments Chothia canonical definitions |
|---|---|---|---|---|---|---|
| 80 | 80 | \| | *Q* | *P* | P | |
| 81 | 81 | \| | **E** | **E** | E | |
| 82 | 82 | \| | **D** | **D** | D | |
| 83 | 83 | \| | *I* | *F* | F | |
| 84 | 84 | \| | **A** | **A** | A | |
| 85 | 85 | \| | **T** | **T** | T | |
| 86 | 86 | \| | **Y** | **Y** | Y | |
| 87 | 87 | \| | *F* | *Y* | F OR Y | VL/VH interface |
| 88 | 88 | FR3 | **C** | **C** | C | L3 1/9A (9) L88 C |
| **89** | **89** | CDR 3 | **Q** | **Q** | Q | L3 1/9A (9) L89 QSGFL VL/VH inter |
| 90 | 90 | \| | **Q** | **Q** | **24** | L1 class 2/11A (11) L90 HQ L3 1/9A (9) L90 QNH |
| 91 | 91 | \| | G | *A* | G | L3 1/9A (9) L91 NFGSRDHTYV VL/VH inter |
| 92 | 92 | \| | **N** | **N** | N | L3 1/9A (9) L92 NYWTSRQHAD |
| 93 | 93 | \| | T | *S* | T | L1 class 2/11A (11) L93 GSNTREA L3 1/9A (9) L93 ENGHTSRA |
| 94 | 94 | \| | **F** | **F** | Y | L3 1/9A (9) L94 DYTVLHNIWPS BUT L94 F |
| 95 | 95 | \| | **P** | **P** | P* | L3 1/9A (9) L95 P |
| 96 | 96 | \| | **W** | L | **W** | L3 1/9A (9) L96 PLYRIWF VL/VH inter+ |
| **97** | **97** | CDR 3 | **T** | T | T | L3 1/9A (9) L97 T |
| 98 | 98 | FR4 | **F** | F | F | L3 1/9A (9) L98 F VL/VH inter+ |
| 99 | 99 | \| | **G** | G | G | |
| 100 | 100 | \| | **G** | G | G | |
| 101 | 101 | \| | **G** | G IGKJ4 | G | |
| 102 | 102 | \| | **T** | T | T | |

TABLE 9-continued

| | | | | 7E3 humanized Light chain L19 | | |
|---|---|---|---|---|---|---|
| Kabat | Chothia | FR or CDR | Mouse 7E3 Light | Human Germline L19 IGKV1-12 IGKV1D-12 | Reshaped human 7E3 L19 | Comments Chothia canonical definitions |
| 103 | 103 | \| | **K** | K | K | |
| 104 | 104 | \| | *L* | V | V | |
| 105 | 105 | \| | **E** | E | E | |
| 106 | 106 | \| | **I** | I | I | |
| 107 | 107 | FR4 | **K** | K | K | |

Legend: The first column (Kabat) gives the residue number according to Kabat et al. (1991); The second column (Chothia) gives the residue number according to Chothia; The third column (FR or CDR) is convenient to identify the framework segments (FR1, FR2, FR3, and FR4) and the complementarity-determining segments (CDR1, CDR2, and CDR3) with the three CDRs separating the four FRs; The fourth column (mouse 7E3 Light) gives the amino acid sequence of the $V_L$ region of mouse 7E3 anti-TLR4 MD2 antibody; The fifth column (Human Germline L19 IGKV1-12 IGKV1D-12) gives the sequence amino acid of the human germline Kappa light chain L19 IGKV1-12 IGKV1D-12. The sixth column (Reshaped human 7E3) gives the amino acid sequences of humanized 7E3 light chain.

As used in Table 9, (*) represents part of main canonical structure for the CDR loops as defined by Chothia et al. (1989). Bolded entries, not underlined, represent positions in FRs and CDRs where the human and mouse amino acid residues are identical. Italicized entries represent positions in FRs where the human residue differs from the analogous mouse residue number. Underlined entries (bolded or not bolded) represent positions in FRs and CDRs where the human amino acid residue was replaced by the corresponding mouse residue. Boxed entries represent human germline gene residues

Example 36 hu18H10 Binds hTLR4 hMD2 Expressed on CHO Cells

In order to demonstrate the ability of the hu18H10 humanized monoclonal antibody to bind to the human TLR4/MD-2 complex, flow cytometry experiments (as described above) were performed using chimeric 18H10 as a positive control. FIG. 39 shows that hu18H10 bound TLR4/MD-2 in a manner very similar to that of the 18H10 chimeric antibody described above.

Example 37 hu7E3 Humanized Monoclonal Antibodies Bind hTLR4 hMD2 Expressed on CHO Cells In order to demonstrate the ability of the hu7E3 humanized monoclonal antibodies to bind to the human TLR4/MD-2 complex, flow cytometry experiments (as described above) were performed using chimeric 7E3 as a positive control. The hu7E3 antibodies tested included a hu7E3 antibody that includes VH 2-70 shown in SEQ ID NO:51 and the $V_L$ L19 shown in SEQ ID NO:53 ("7E3 2-70/L19") and a hu7E3 antibody that includes $V_H$ 3-66 shown in SEQ ID NO:52 and the $V_L$ L19 shown in SEQ ID NO:53 ("7E3 3-66/L19") FIG. 40 shows that hu7E3 MAbs bound TLR4/MD-2 in a manner similar to that of the 7E3 chimeric antibody described above.

Example 38 hu15C1 Humanized Monoclonal Antibodies Bind hTLR4 hMD2 Expressed on CHO Cells In order to demonstrate the ability of the hu7E3 humanized monoclonal antibodies to bind to the human TLR4/MD-2 complex, flow cytometry experiments (as described above) were performed using chimeric 15C1 as a positive control. The hu15C1 antibodies tested included the hu15C1 antibody that includes $V_H$ 4-28 shown in SEQ ID NO:45 and the $V_L$ A26 shown in SEQ ID NO:48 ("15C1 4-28/A26") and variants thereof in which residues at certain positions (QC ##, Kabat numbering) have been replaced by the corresponding amino acids in the given human germline ("15C1 4-28 QC 30/A26"; "15C1 4-28 QC 48/A26"; "15C1 4-28 QC 67/A26" and "15C1 4-28 QC 69/A26", see Table 1). Other hu15C1 antibodies tested include a hu15C1 antibody that includes $V_H$ 3-66 shown in SEQ ID NO:46 and the $V_L$ L6 shown in SEQ ID NO:47 ("15C1 3-66/L6") and a hu15C1 antibody that includes $V_H$ 3-66 shown in SEQ ID NO:46 and the $V_L$ A26 shown in SEQ ID NO:48 ("15C1 3-66/L6"). FIGS. 41 and 42 demonstrate that the hu15C1 antibodies MAbs bound TLR4/MD-2 in a manner similar to that of the 15C1 chimeric antibody described above.

Example 39

TLR4 and MD2 Epitope Mapping Studies hu15C1, hu7E3 and hu18H10 are three monoclonal antibodies (MAbs) showing specificity for the human TLR4/MD-2 receptor complex. This receptor complex is activated by lipopolysaccharide (LPS) the major component of the outer membrane of gram-negative bacteria. All three MAbs are capable of inhibiting receptor activation and subsequent intracellular signaling via LPS, but interestingly, all three have distinct specificities. hu15C1 binds TLR4 independently of the presence of MD-2. hu7E3 binds to TLR4, but binding is greatly enhanced by the presence of MD-2, suggesting that the presence of the latter causes a conformational change in TLR4 exposing an epitope bound by hu7E3. hu18H10 binds to MD-2, but requires the presence of TLR4, as the MAb does not bind soluble forms of MD-2.

The aim of this study was to identify small regions and individual amino acids of both the TLR4 and MD-2 sequences important for the binding of hu15C1, hu7E3 and hu18H10. The amino acid sequence of human TLR4 (GenBank Accession No. O00206) is shown in FIG. 43. The amino acid sequence of Human MD2 (GenBank Accession No. Q9Y6Y9) is shown in FIG. 33B.

As none of the hu15C1, hu7E3 and hu18H10 MAbs demonstrate cross-reactivity to the mouse TLR4/MD-2 receptor complex, a strategy utilizing mouse-human hybrids, whereby segments of the human TLR4 and MD-2 proteins were replaced by the equivalent mouse segments was used to identify defined linear regions of human TLR4 and MD-2 essential for the binding of the MAbs. Furthermore, these regions were mutated at amino acid residues differing between the human and mouse sequences in order to identify individual amino acids essential for the binding of these MAbs.

Generation of Mouse-Human Hybrid TLR4 Mutants.

To generate the mouse-human-human-human (MHHH), human TLR4, cloned into the mammalian expression vector pCDNA3.1(−)hygro (Invitrogen) was modified by introducing a novel HpaI site and destroying an existing HpaI site by site-directed mutagenesis with the following oligonucleotides: 5' GACCATTGAAGAATTCCGGTTCTCTTGCTCTCCTCG 3' (SEQ ID NO:55); 5' CGAGGTAGTAGTCTAAGTATGTTAACCGGAATTCTTCAATGGTC 3' (SEQ ID NO:56) (introduction of novel HpaI site) and 5' GGCAACATTTAGAATTAGTCAA CTGTAAATTTGGACAG 3' (SEQ ID NO:57); 5' CTGTCCAAATTTACAGTTG ACTAATTCTAAATGTTGCC 3' (SEQ ID NO:58) (destruction of existing HpaI site). Site-directed mutagenesis was performed using the QuikChange™ kit (Stratagene) following the manufacturer's instructions. The N-terminal region of mouse TLR4 was amplified by PCR using the following oligonucleotides: 5' ATTTGTATAGTTAACCTGAACTCATC 3' (SEQ ID NO:59) and 5' GGGGCGGCCGCGGGAAGCTTG AATCCCTGCATAG 3' (SEQ ID NO:60). This mouse DNA fragment replaced the corresponding human DNA fragment in the HpaI-mutated human TLR4 vector (above) by cloning at the unique NotI and HpaI restriction sites.

To generate HHHM, the C-terminal region of mouse TLR4 was amplified by PCR using the following oligonucleotides: 5' GGGGATATCTTTGCAAACAC AACAAACTTGAC 3' (SEQ ID NO:61) and 5' GGGCTCGAGCTTGTACATATAACAG GTAG 3' (SEQ ID NO:62). This mouse DNA fragment replaced the corresponding human DNA fragment in the human TLR4 vector by cloning at the unique EcoRV and XhoI restriction sites.

To generate MMHH, the MHHH construct was modified by site-directed mutagenesis (as above) to introduce a unique AgeI restriction site into the TLR4 sequence using the following oligonucleotides: 5' GCTTTTTCAGAAGTTGATCTACCGGTCCTTG AGTTTCTAGATCTCAGT 3' (SEQ ID NO:63) and 5' ACTGAGATCTAG AAACTCAAGGACCGGTAGATCAACTTCTGAAAAAGC 3' (SEQ ID NO:64). In parallel, an internal region of mouse TLR4 was amplified by PCR using the following oligonucleotides: 5' CATTGATGAGTTCAGGTTAAC 3' (SEQ ID NO:65) and 5' ATGCACCGGTAGGGCCACTTTTTTAAAACTG 3' (SEQ ID NO:66). This mouse DNA fragment replaced the corresponding human DNA fragment in the AgeI-mutated MHHH vector (above) by cloning at the unique HpaI and AgeI restriction sites.

To generate the mouse-human-mouse-human (MHMH) hybrid, an internal region of mouse TLR4 was amplified by PCR using the following oligonucleotides: 5' ATGCACCGGTTCTCAGCTATCTAGATCTTAG 3' (SEQ ID NO:67) and 5' ATGCGATATCTGAAAGGGTGTTGTCTTTGAAAG 3' (SEQ ID NO:68). This mouse DNA fragment replaced the corresponding human DNA fragment in the AgeI-mutated MHHH vector (above) by cloning at the unique AgeI and EcoRV restriction sites.

To generate MMHHa, an internal region of human TLR4 was amplified by PCR using the following oligonucleotides: 5' CCGTTAACATATACAAATGATTTT TCAGATGATATTGTTAAGTTCCATTGCTTGGCGAATGTTTCTGCAATGTCTCTGGC AGGTGTGACTATTGAAAGGGTAAAAG 3' (SEQ ID NO:69) and 5' CCACCGG TAGATCAACTTCTGAAAAAGC 3' (SEQ ID NO:70). This DNA fragment replaced the corresponding human DNA fragment in the AgeI-mutated MHHH vector (above) by cloning at the unique HpaI and AgeI restriction sites.

To generate MMHHb, an internal region of human TLR4 was amplified by PCR using the following oligonucleotides: 5' CCGTTAACATACTTAGACTACTA C 3' (SEQ ID NO:71) and 5' GATATCTGAAAGGGTGTTGTCTTTGAAAGAATTGCCAGCC ATTTTTAATGTGTTGAGACTGGTCAAGCCAAGAAATATACCATCGAAGTCAATTT TGGTGTTAGTATGAGAAATGTCAAG 3' (SEQ ID NO:72). This DNA fragment replaced the corresponding human DNA fragment in the AgeI-mutated MHHH vector (above) by cloning at the unique HpaI and AgeI restriction sites.

Generation of Mouse-Human Hybrid MD-2 Mutants.

Firstly, human MD-2, cloned into the mammalian expression vector pCDNA3.1(−) (Invitrogen) was modified by site-directed mutagenesis (as above) to introduce a novel AflII restriction site with the following oligonucleotides: 5' CTCTTTTTGCAGAGCTCTTAAGGGAGAGACTGTGAA 3' (SEQ ID NO:73) and 5' TTCACAGTCTCTCCCTTAAGAGCTCTGCAAAAAGAG 3' (SEQ ID NO:74).

In order to generate MHH, the N-terminal region of mouse MD-2 was amplified by PCR using the following oligonucleotides: 5' GGAAGCTTAACCACCATG TTGCC 3' (SEQ ID NO:84) and 5' CCGGATCCCCTCAGTCTTATGC 3' (SEQ ID NO:75). This mouse DNA fragment replaced the corresponding human DNA fragment in the AflII-mutated human MD-2 vector (above) by cloning at the unique HindIII and BamHI restriction sites.

In order to generate HMH, an internal region of mouse MD-2 was amplified by PCR using the following oligonucleotides: 5' CCGGATCCAATGGATTTGTG CATG 3' (SEQ ID NO:76) and 5' GGCTTAAGAGCTCTGCAAAAAGAATAGTC 3' (SEQ ID NO:77). This mouse DNA fragment replaced the corresponding human DNA fragment in the AflII-mutated human MD-2 vector (above) by cloning at the unique BamHI and AflII restriction sites.

In order to generate HHM, the C-terminal region of mouse MD-2 was amplified by PCR using the following oligonucleotides: 5' GGCTTAAGGGAGAGACTG TGAATACATC 3' (SEQ ID NO:78) and 5' CCGCTAGCATTGACATCACGGC 3' (SEQ ID NO:79). This mouse DNA fragment replaced the corresponding human DNA fragment in the AflII-mutated human MD-2 vector (above) by cloning at the unique AflII and NheI restriction sites.

Generation of Human TLR4 and MD-2 Alanine Scanning Mutants.

All mutants were generated by site-directed mutagenesis using the QuikChange™ kit (Stratagene) as above. DNA oligonucleotides housing the appropriate mismatch mutations were used with either human TLR4 in pCDNA3.1(−) hygro or human MD-2 in pCDNA3.1(−) as appropriate. Introduction of the desired mutations was verified by DNA sequencing.

Transient Transfection of HEK 293 Cells.

HEK 293 cells, expressing both the large T and EBNA antigens to allow for episomal plasmid replication, were plated in 1 ml culture medium at $1\times10^5$ cells/well in 24 well culture plates. The following day, cells were transfected with 1 μg DNA/well (0.5 μg+0.5 μg of each plasmid for co-transfections) using 1.5 μl/well Fugene6™ transfection reagent (Roche), following the manufacture's guidelines. Cells were analyzed 48-72 hours post-transfection.

Flow Cytometry.

Binding of MAb to the surface of TLR4/MD-2 transfected HEK 293 cells was measured by flow cytometry. $1\times10^5$ cells were incubated in 96 well V-bottom plates with the appropriate MAb at a final concentration of 10 μg/ml in a volume of 50-100 μl in FACS buffer (1×PBS, 100 μg/ml BSA, 0.05% $NaN_3$). Following a 30 minute incubation at 4° C., cells were pelleted, washed once with 200 μl FACS buffer, repelleted and resuspended with allophycocyanin (APC) conjugated secondary antibody (Molecular Probes) at a 1:250 dilution in FACS buffer. Following a 30 minute incubation at 4° C., cells were washed once in 200 μl FACS buffer, fixed in 1% paraformaldehyde, 1×PBS and analyzed for fluorescence using a FACScalibur (Becton Dickenson) in the FL-4 channel.

hu15C1 and hu7E3 Bind to an 87 Amino Acid Internal Region of TLR4.

Four mouse-human hybrid mutants of TLR4 were generated in order to determine the precise region of TLR4 responsible for binding to hu15C1 and hu7E3. Transient transfection of HEK 293 cells allowed presentation of either wild type (wt) or mutated forms of TLR4 along with wt MD-2 on the cell surface. FACS analysis (FIGS. 34*a* and *b*) revealed that the complex was correctly expressed in three of the four cases (as shown by c-myc and FLAG staining). TLR4 mutant version MHMH was poorly expression on the cell surface and did not support interaction with MD-2, suggesting that the protein was not conformationally correct. This observation meant that results of binding with hu15C1 and hu7E3 could not be taken into account. Whilst versions MHHH and HHHM bound both hu15C1 and hu7E3 well, MMHH was negative for binding of both antibodies, suggesting that an 87 amino acid internal region of TLR4 (highlighted in FIG. 34*a*) is essential for interaction between TLR4 and either hu15C1 or hu7E3.

In order to determine in more detail the residues important for hu15C1 and hu7E3 binding, two additional mutants were generated whereby either the first 30 amino acids (MMHHa) or the last 32 amino acids (MMHHb) of this internal region were replaced by the corresponding mouse sequence (FIG. 35*a*). FACS analysis (FIGS. 35*a* and *b*) of transfected HEK 293 cells revealed that the complex was correctly expressed in both cases (as shown by c-myc and FLAG staining). hu15C1 bound well to MMHHa but showed no binding to MMHHb, suggesting that residues situated towards the C terminus of this internal region are critical for binding. Conversely, hu7E3 bound well to MMHHb but showed no binding to MMHHa, suggesting that residues situated towards the N terminus of this internal region are critical for binding.

HTA125 Recognizes an N-Terminal Region of TLR4.

Figure 34:
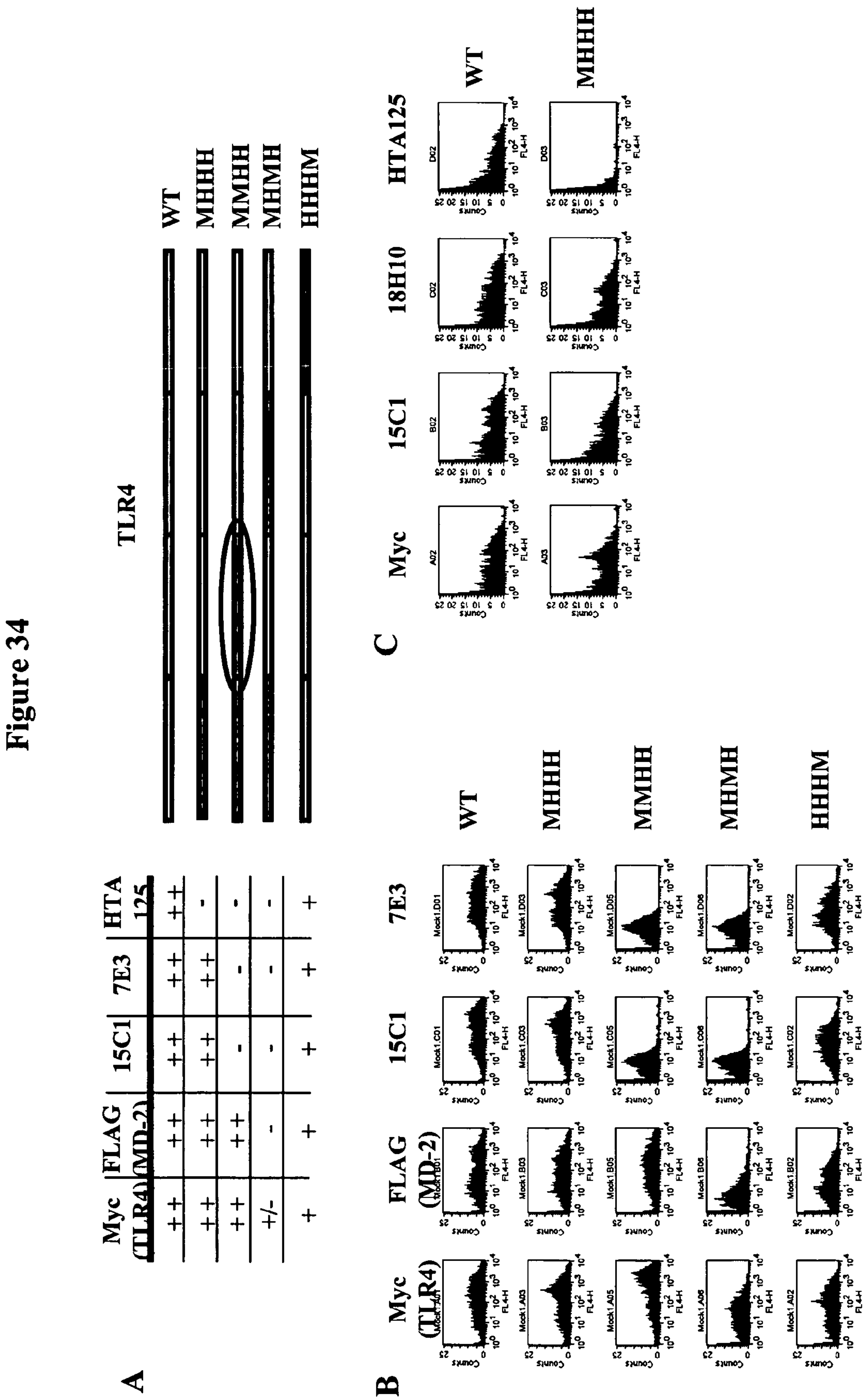

HTA125 is a commercially available non-neutralizing MAb directed against human TLR4 (E-biosciences). HTA125 was tested against the four mouse-human hybrids and found, in contrast to the neutralizing MAbs 15C1 and 7E3, an absence of binding when the N-terminal region of TLR4 was changes from human to mouse (FIG. 34 *a* and *c*).

TLR4 Amino Acid Residues Essential for hu15C1 and hu7E3 Binding.

In order to identify important residues within the 87 amino acid region of TLR4 identified above, the human sequence was aligned to the corresponding mouse TLR4 sequence within this region (alignments performed using the bl2seq program). Since hu15C1 and hu7E3 do not cross-react with mouse TLR4/MD-2, it was assumed that residues essential for MAb binding would not be conserved between the two species. All non-conserved residues in the human sequence were mutated to alanine. 20 mutant (QC 1 to QC 20) versions were constructed, each one containing two or three residues converted to alanines (FIG. 36*a*).

Following transient transfection of these mutants along with wt MD-2 in HEK 293 cells, C-myc and hu18H10 MAbs were used to detect the presence of TLR4 and MD-2 respectively on the cell surface. FACS analysis (FIG. 36*b*) showed that all TLR4 mutants were expressed at a level well above background. All mutants bound MD-2 well with the exception of QC 6. In order to determine the level of binding of hu15C1 and hu7E3 to the mutant TLR4, a "normalized" value was obtained by dividing the mean fluorescence intensity (MFI) obtained with the MAb by that obtained with C-myc. This allowed for variation in the level of expression at the cell surface between the TLR4 mutants. For hu15C1, normalized binding was seen to be greatly diminished for versions QC 10, QC 15 and QC 20. For hu7E3, QC 1, QC 2, QC 6 and QC 7 showed greatly reduced hu7E3 binding, although as hu7E3 required the presence of MD-2 for binding, lack of binding to QC 6 could simply be explained by the absence of MD-2 on the cell surface (see hu18H10 MFI for QC 6). These results confirm that residues important for hu15C1 binding are located at the C terminal end of the 87 amino acid section identified above, whereas residues important for hu15C1 binding are located towards the N terminal end.

hu18H10 Binds to a 39 Amino Acid N-Terminal Region of MD-2.

Three mouse-human hybrid mutants of MD-2 were generated in order to determine the precise region of the protein responsible for binding to hu18H10. Transient transfection of HEK 293 cells allowed presentation of either wild type (wt) or mutated forms of MD-2 along with wt TLR4 on the cell surface. FACS analysis (FIGS. 37*a* and *b*) revealed that the complex was correctly expressed in all three cases (as shown by hu15C1 and C-myc staining). Whilst versions HMH and HHM bound both hu18H10 well, MHH was negative for binding, suggesting that a 39 amino acid N-terminal region of MD-2 (highlighted in FIG. 37*a*) is essential for interaction between MD-2 and hu18H10.

MD-2 Amino Acid Residues Essential for hu18H10 Binding.

In order to identify important residues within the 39 amino acid region of MD-2 identified above, the human sequence was aligned to the corresponding mouse MD-2 sequence within this region (alignments performed using the bl2seq program). Since hu18H10 does not cross-react with mouse TLR4/MD-2, it was assumed that residues essential for MAb binding would not be conserved between the two species. Therefore, mutate all non-conserved residues in the human sequence were mutated to alanine. 14 mutant (QC 1 to QC 14) versions were constructed, each one containing a single residue converted to alanine (FIG. 38*a*).

Following transient transfection of these mutants along with wt TLR4 in HEK 293 cells, hu15C1 and anti-6×HIS MAbs were used to detect the presence of TLR4 and MD-2 respectively on the cell surface. FACS analysis (FIG. 38*b*) showed that all TLR4 mutants were expressed at a level well above background, with the exception of QC7 which appears to be poorly expressed or has lost its ability to interact with TLR4 (n.b. TLR4 was well expressed upon co-transfection with QC 7). In order to determine the level of binding of hu18H10 to the mutated versions MD-2, a "normalized" value was obtained by dividing the mean fluorescence intensity (MFI) obtained with the hu18H10 by that obtained with C-myc. This allowed for variation in the level of expression at the cell surface between the MD-2 mutants. For hu18H10, normalized binding was seen to be greatly diminished for version QC 13. These results confirm that a residue important for hu18H10 binding is located within the 37 amino acid N terminal section of MD-2 identified above.

Example 40 hu18H10 Humanized Monoclonal Antibody Inhibits LPS-Induced IL-6 Production in Human Whole Blood In order to demonstrate the neutralizing capacity of the hu18H10 humanized monoclonal antibody for LPS, the ability of hu18H10 to inhibit LPS dependent IL-6 induction of human whole blood is tested (as described above). The ability of the hu18H10 antibody to inhibit the effects of LPS on blood leucocytes is compared to that of the 18H10 chimeric antibody described above.

Example 41 hu7E3 Humanized Monoclonal Antibody Inhibits LPS-Induced IL-6 Production in Human Whole Blood To demonstrate the neutralizing capacity of hu7E3 humanized monoclonal antibodies for LPS, the ability of the hu7E3 antibody to inhibit LPS dependent IL-6 induction of human whole blood is tested (as described above). The ability of the hu7E3 antibody to inhibit the effects of LPS on blood leucocytes is compared to that of the 7E3 chimeric antibody described above.

Example 42 hu15C1 Humanized Monoclonal Antibody Inhibits LPS-Induced IL-6 Production in Human Whole Blood To demonstrate the neutralizing capacity of hu15C1 humanized monoclonal antibodies for LPS, the ability of the hu15C1 antibody to inhibit LPS dependent IL-6 induction of human whole blood was tested (as described above). The ability of the hu15C1 antibody to inhibit the effects of LPS on blood leucocytes was compared to that of the 15C1 chimeric antibody described above (FIG. 44).

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A humanized antibody that immunospecifically binds to a Toll-like receptor 4 (TLR4)/MD-2 complex, wherein the antibody comprises the heavy chain variable amino acid sequence of SEQ ID NO: 45 and wherein the antibody comprises the light chain variable amino acid sequence of SEQ ID NO: 48.

2. A pharmaceutical composition comprising the antibody of claim 1 and a carrier.

3. A kit for detecting amount of TLR4/MD-2 complex in a sample, said kit comprising the antibody of claim 1, means for determining the amount of TLR4/MD-2 complex in the sample; and means for comparing the amount of TLR4/MD-2 complex in the sample with a standard.

* * * * *

SEQUENCE LISTING

```
<160> NUMBER OF SEQ ID NOS: 102

<210> SEQ ID NO 1
<211> LENGTH: 360
<212> TYPE: DNA
<213> ORGANISM: Mus musculus

<400> SEQUENCE: 1

caggtgcaac tgcagcagtc tggggctgat cttgtgaggc caggggcctt agtcaagttg     60

tcctgcacag cttctggctt caacattaaa gactcctata tacactgggt gaagaagagg    120

cctgaatggg gcctggagtg gattggatgg actgatcctg agaatgttaa ttctatatat    180

gacccgaggt ttcagggcaa ggccagtata acagcagaca catcctccaa cacagccttc    240

cttcagctca ccagcctgac atctgaggac actgccgtct attactgtgc taggggttat    300

aacggtgttt actatgctat ggactactgg ggccaaggga cctcagtcac cgtctcctca    360


<210> SEQ ID NO 2
<211> LENGTH: 120
<212> TYPE: PRT
<213> ORGANISM: Mus musculus
```

-continued

<400> SEQUENCE: 2

```
Gln Val Gln Leu Gln Gln Ser Gly Ala Asp Leu Val Arg Pro Gly Ala
1               5                   10                  15

Leu Val Lys Leu Ser Cys Thr Ala Ser Gly Phe Asn Ile Lys Asp Ser
            20                  25                  30

Tyr Ile His Trp Val Lys Lys Arg Pro Glu Trp Gly Leu Glu Trp Ile
        35                  40                  45

Gly Trp Thr Asp Pro Glu Asn Val Asn Ser Ile Tyr Asp Pro Arg Phe
    50                  55                  60

Gln Gly Lys Ala Ser Ile Thr Ala Asp Thr Ser Ser Asn Thr Ala Phe
65                  70                  75                  80

Leu Gln Leu Thr Ser Leu Thr Ser Glu Asp Thr Ala Val Tyr Tyr Cys
                85                  90                  95

Ala Arg Gly Tyr Asn Gly Val Tyr Tyr Ala Met Asp Tyr Trp Gly Gln
            100                 105                 110

Gly Thr Thr Val Thr Val Ser Ser
        115                 120
```

<210> SEQ ID NO 3
<211> LENGTH: 5
<212> TYPE: PRT
<213> ORGANISM: Mus musculus

<400> SEQUENCE: 3

```
Asp Ser Tyr Ile His
1               5
```

<210> SEQ ID NO 4
<211> LENGTH: 17
<212> TYPE: PRT
<213> ORGANISM: Mus musculus

<400> SEQUENCE: 4

```
Trp Thr Asp Pro Glu Asn Val Asn Ser Ile Tyr Asp Pro Arg Phe Gln
1               5                   10                  15

Gly
```

<210> SEQ ID NO 5
<211> LENGTH: 11
<212> TYPE: PRT
<213> ORGANISM: Mus musculus

<400> SEQUENCE: 5

```
Gly Tyr Asn Gly Val Tyr Tyr Ala Met Asp Tyr
1               5                   10
```

<210> SEQ ID NO 6
<211> LENGTH: 321
<212> TYPE: DNA
<213> ORGANISM: Mus musculus

<400> SEQUENCE: 6

```
caaattgttc tcacccagtc tccatcaatc atgtctgcgt ctctagggga ggagatcacc      60

ctaacctgca gtgccagctc gagtgtaatt tacatgcact ggtaccagca gaagtcaggc     120

acttctccca aactcttgat ttataggaca tacaacctgg cttctggagt cccttctcgc     180

ttcagtggca gtgggtctgg gaccttttat tctctcacaa tcagcagtgt ggaggctgaa     240

gatgctgccg attattactg ccatcagtgg agtagttttc cgtacacgtt cggagggggg     300
```

-continued accaagctgg aaatcaaacg g 321

<210> SEQ ID NO 7
<211> LENGTH: 107
<212> TYPE: PRT
<213> ORGANISM: Mus musculus

<400> SEQUENCE: 7

Gln Ile Val Leu Thr Gln Ser Pro Ser Ile Met Ser Ala Ser Leu Gly
1 5 10 15

Glu Glu Ile Thr Leu Thr Cys Ser Ala Ser Ser Ser Val Ile Tyr Met
20 25 30

His Trp Tyr Gln Gln Lys Ser Gly Thr Ser Pro Lys Leu Leu Ile Tyr
35 40 45

Arg Thr Tyr Asn Leu Ala Ser Gly Val Pro Ser Arg Phe Ser Gly Ser
50 55 60

Gly Ser Gly Thr Phe Tyr Ser Leu Thr Ile Ser Ser Val Glu Ala Glu
65 70 75 80

Asp Ala Ala Asp Tyr Tyr Cys His Gln Trp Ser Ser Phe Pro Tyr Thr
85 90 95

Phe Gly Gly Gly Thr Lys Leu Glu Ile Lys Arg
100 105

<210> SEQ ID NO 8
<211> LENGTH: 10
<212> TYPE: PRT
<213> ORGANISM: Mus musculus

<400> SEQUENCE: 8

Ser Ala Ser Ser Ser Val Ile Tyr Met His
1 5 10

<210> SEQ ID NO 9
<211> LENGTH: 7
<212> TYPE: PRT
<213> ORGANISM: Mus musculus

<400> SEQUENCE: 9

Arg Thr Tyr Asn Leu Ala Ser
1 5

<210> SEQ ID NO 10
<211> LENGTH: 9
<212> TYPE: PRT
<213> ORGANISM: Mus musculus

<400> SEQUENCE: 10

His Gln Trp Ser Ser Phe Pro Tyr Thr
1 5

<210> SEQ ID NO 11
<211> LENGTH: 353
<212> TYPE: DNA
<213> ORGANISM: Mus musculus

<400> SEQUENCE: 11
aggtgaaact gcaggagtct ggagctgagc tgatgaagcc tggggcctca gtgaagatat 60
cctgcaaggc tactggctac aaattcagtg actactggat agagtggata aaacagaggc 120
ctggacatgg ccttgagtgg attggagaga ttttgcctgg aagtggtagt actaactaca 180

-continued

```
atgaggactt caaggacaag gccacattca cttcagatac atcctccaac acagcctaca    240

tgcaactcag cagcctgaca tctgaagact ctgccgtcta ttactgtgca aaagaggaga    300

gggcgtacta ctttggctat tggggccaag ggaccacggt caccgtctcc tca           353
```

<210> SEQ ID NO 12
<211> LENGTH: 118
<212> TYPE: PRT
<213> ORGANISM: Mus musculus

<400> SEQUENCE: 12

```
Gln Val Lys Leu Gln Glu Ser Gly Ala Glu Leu Met Lys Pro Gly Ala
1               5                   10                  15

Ser Val Lys Ile Ser Cys Lys Ala Thr Gly Tyr Lys Phe Ser Asp Tyr
            20                  25                  30

Trp Ile Glu Trp Ile Lys Gln Arg Pro Gly His Gly Leu Glu Trp Ile
        35                  40                  45

Gly Glu Ile Leu Pro Gly Ser Gly Ser Thr Asn Tyr Asn Glu Asp Phe
    50                  55                  60

Lys Asp Lys Ala Thr Phe Thr Ser Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Lys Glu Glu Arg Ala Tyr Tyr Phe Gly Tyr Trp Gly Gln Gly Thr
            100                 105                 110

Thr Val Thr Val Ser Ser
        115
```

<210> SEQ ID NO 13
<211> LENGTH: 5
<212> TYPE: PRT
<213> ORGANISM: Mus musculus

<400> SEQUENCE: 13

```
Asp Tyr Trp Ile Glu
1               5
```

<210> SEQ ID NO 14
<211> LENGTH: 17
<212> TYPE: PRT
<213> ORGANISM: Mus musculus

<400> SEQUENCE: 14

```
Glu Ile Leu Pro Gly Ser Gly Ser Thr Asn Tyr Asn Glu Asp Phe Lys
1               5                   10                  15

Asp
```

<210> SEQ ID NO 15
<211> LENGTH: 9
<212> TYPE: PRT
<213> ORGANISM: Mus musculus

<400> SEQUENCE: 15

```
Glu Glu Arg Ala Tyr Tyr Phe Gly Tyr
1               5
```

<210> SEQ ID NO 16
<211> LENGTH: 339
<212> TYPE: DNA
<213> ORGANISM: Mus musculus -continued

<400> SEQUENCE: 16

```
gatgttttga tgacccaaac tccactctcc ctgcctgtca gtcttggaga tcaagcctcc      60
atctcttgca ggtctagtca gagccttgaa aacagtaatg gaaacaccta tttgaactgg     120
tacctccaga aaccaggcca gtctccacag ctcctgatct acagggtttc caaccgattt     180
tctggggtcc tagacaggtt cagtggtagt ggatcaggga cagatttcac actgaaaatc     240
agcagagtgg aggctgagga tttgggagtt tatttctgcc tccaagttac acatgtccct     300
cccacgttcg gtgctgggac caagctggaa ctgaaacgg                            339
```

<210> SEQ ID NO 17
<211> LENGTH: 113
<212> TYPE: PRT
<213> ORGANISM: Mus musculus

<400> SEQUENCE: 17

```
Asp Val Glu Met Thr Gln Thr Pro Leu Ser Leu Pro Val Ser Leu Gly
1               5                   10                  15

Asp Gln Ala Ser Ile Ser Cys Arg Ser Ser Gln Ser Leu Glu Asn Ser
            20                  25                  30

Asn Gly Asn Thr Tyr Leu Asn Trp Tyr Leu Gln Lys Pro Gly Gln Ser
        35                  40                  45

Pro Gln Leu Leu Ile Tyr Arg Val Ser Asn Arg Phe Ser Gly Val Leu
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Leu Gln Val
                85                  90                  95

Thr His Val Pro Pro Thr Phe Gly Ala Gly Thr Lys Leu Glu Leu Lys
            100                 105                 110

Arg
```

<210> SEQ ID NO 18
<211> LENGTH: 16
<212> TYPE: PRT
<213> ORGANISM: Mus musculus

<400> SEQUENCE: 18

```
Arg Ser Ser Gln Ser Leu Glu Asn Ser Asn Gly Asn Thr Tyr Leu Asn
1               5                   10                  15
```

<210> SEQ ID NO 19
<211> LENGTH: 7
<212> TYPE: PRT
<213> ORGANISM: Mus musculus

<400> SEQUENCE: 19

```
Arg Val Ser Asn Arg Phe Ser
1               5
```

<210> SEQ ID NO 20
<211> LENGTH: 9
<212> TYPE: PRT
<213> ORGANISM: Mus musculus

<400> SEQUENCE: 20

```
Leu Gln Val Thr His Val Pro Pro Thr
1               5
```

-continued

<210> SEQ ID NO 21
<211> LENGTH: 354
<212> TYPE: DNA
<213> ORGANISM: Mus musculus

<400> SEQUENCE: 21
gatgtgcagc ttcaggagtc aggacctgac ctaatacaac cttctcagtc actttcactc 60
acctgcactg tcactggcta ctccatcacc ggtggttata gctggcactg gatccggcag 120
tttccaggaa acaaactgga atggatgggc tacatccact acagtggtta cactgacttc 180
aacccctctc tcaaaactcg aatctctatc actcgagaca catccaagaa ccagttcttc 240
ctgcagttga attctgtgac tactgaagac acagccacat attactgtgc aagaaaagat 300
ccgtccgacg gatttcctta ctggggccaa gggactctgg tcactgtctc tgca 354

<210> SEQ ID NO 22
<211> LENGTH: 118
<212> TYPE: PRT
<213> ORGANISM: Mus musculus

<400> SEQUENCE: 22

Asp Val Gln Leu Gln Glu Ser Gly Pro Asp Leu Ile Gln Pro Ser Gln
1 5 10 15

Ser Leu Ser Leu Thr Cys Thr Val Thr Gly Tyr Ser Ile Thr Gly Gly
20 25 30

Tyr Ser Trp His Trp Ile Arg Gln Phe Pro Gly Asn Lys Leu Glu Trp
35 40 45

Met Gly Tyr Ile His Tyr Ser Gly Tyr Thr Asp Phe Asn Pro Ser Leu
50 55 60

Lys Thr Arg Ile Ser Ile Thr Arg Asp Thr Ser Lys Asn Gln Phe Phe
65 70 75 80

Leu Gln Leu Asn Ser Val Thr Thr Glu Asp Thr Ala Thr Tyr Tyr Cys
85 90 95

Ala Arg Lys Asp Pro Ser Asp Gly Phe Pro Tyr Trp Gly Gln Gly Thr
100 105 110

Leu Val Thr Val Ser Ala
115

<210> SEQ ID NO 23
<211> LENGTH: 6
<212> TYPE: PRT
<213> ORGANISM: Mus musculus

<400> SEQUENCE: 23

Gly Gly Tyr Ser Trp His
1 5

<210> SEQ ID NO 24
<211> LENGTH: 16
<212> TYPE: PRT
<213> ORGANISM: Mus musculus

<400> SEQUENCE: 24

Tyr Ile His Tyr Ser Gly Tyr Thr Asp Phe Asn Pro Ser Leu Lys Thr
1 5 10 15

<210> SEQ ID NO 25
<211> LENGTH: 9
<212> TYPE: PRT
<213> ORGANISM: Mus musculus

```
<400> SEQUENCE: 25

Lys Asp Pro Ser Asp Gly Phe Pro Tyr
1               5

<210> SEQ ID NO 26
<211> LENGTH: 321
<212> TYPE: DNA
<213> ORGANISM: Mus musculus

<400> SEQUENCE: 26

gacattgtga tgacccagtc tccagccacc ctgtctgtga ctccaggtga tagagtctct      60

ctttcctgca gggccagcca gagtatcagc gaccacttac actggtatca acaaaaatca    120

catgagtctc cacggcttct catcaaatat gcttcccatg ccatttctgg gatcccctcc    180

aggttcagtg gcagtggatc agggacagat ttcactctca gcatcaaaag tgtggaacct    240

gaagatattg gggtgtatta ctgtcaaaat ggtcacagtt ttccgctcac gttcggtgct    300

gggaccaagc tggagctgaa a                                              321

<210> SEQ ID NO 27
<211> LENGTH: 108
<212> TYPE: PRT
<213> ORGANISM: Mus musculus

<400> SEQUENCE: 27

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp His
            20                  25                  30

Leu His Trp Tyr Gln Gln Lys Ser His Glu Ser Pro Arg Leu Leu Ile
        35                  40                  45

Lys Tyr Ala Ser His Ala Ile Ser Gly Ile Pro Ser Arg Phe Ser Gly
    50                  55                  60

Ser Gly Ser Gly Thr Asp Phe Thr Leu Ser Ile Lys Ser Val Glu Pro
65                  70                  75                  80

Glu Asp Ile Gly Val Tyr Tyr Cys Gln Asn Gly His Ser Phe Pro Leu
                85                  90                  95

Thr Phe Gly Ala Gly Thr Lys Leu Glu Leu Lys Arg
                100                 105

<210> SEQ ID NO 28
<211> LENGTH: 11
<212> TYPE: PRT
<213> ORGANISM: Mus musculus

<400> SEQUENCE: 28

Arg Ala Ser Gln Ser Ile Ser Asp His Leu His
1               5                   10

<210> SEQ ID NO 29
<211> LENGTH: 7
<212> TYPE: PRT
<213> ORGANISM: Mus musculus

<400> SEQUENCE: 29

Tyr Ala Ser His Ala Ile Ser
1               5

<210> SEQ ID NO 30
<211> LENGTH: 9
```

-continued

<212> TYPE: PRT
<213> ORGANISM: Mus musculus

<400> SEQUENCE: 30

Gln Asn Gly His Ser Phe Pro Leu Thr
1 5

<210> SEQ ID NO 31
<211> LENGTH: 363
<212> TYPE: DNA
<213> ORGANISM: Mus musculus

<400> SEQUENCE: 31
caggttactc tgaaagagtc tggccctggg atattgcagc cctcccagac cctcagtctg 60
acttgttctt tctctgggtt ttcactgacc acttataata taggagtagg ctggattcgt 120
cagccttcag ggaagggtct ggagtggctg gcacacattt ggtggaatga taatatttac 180
tataatacag tccttaagag ccgactcaca ttctccaagg atacctccaa caaccaggtt 240
ttcctcaaga tcgccagtgt ggacattgca gatactgcca catattactg tattcgaatg 300
gctgagggaa ggtacgacgc tatggactac tggggtcaag gaacctcagt caccgtctcc 360
tca 363

<210> SEQ ID NO 32
<211> LENGTH: 121
<212> TYPE: PRT
<213> ORGANISM: Mus musculus

<400> SEQUENCE: 32

Gln Val Thr Leu Lys Glu Ser Gly Pro Gly Ile Leu Gln Pro Ser Gln
1 5 10 15

Thr Leu Ser Leu Thr Cys Ser Phe Ser Gly Phe Ser Leu Thr Thr Tyr
20 25 30

Asn Ile Gly Val Gly Trp Ile Arg Gln Pro Ser Gly Lys Gly Leu Glu
35 40 45

Trp Leu Ala His Ile Trp Trp Asn Asp Asn Ile Tyr Tyr Asn Thr Val
50 55 60

Leu Lys Ser Arg Leu Thr Phe Ser Lys Asp Thr Ser Asn Asn Gln Val
65 70 75 80

Phe Leu Lys Ile Ala Ser Val Asp Ile Ala Asp Thr Ala Thr Tyr Tyr
85 90 95

Cys Ile Arg Met Ala Glu Gly Arg Tyr Asp Ala Met Asp Tyr Trp Gly
100 105 110

Gln Gly Thr Ser Val Thr Val Ser Ser
115 120

<210> SEQ ID NO 33
<211> LENGTH: 7
<212> TYPE: PRT
<213> ORGANISM: Mus musculus

<400> SEQUENCE: 33

Thr Tyr Asn Ile Gly Val Gly
1 5

<210> SEQ ID NO 34
<211> LENGTH: 16
<212> TYPE: PRT
<213> ORGANISM: Mus musculus -continued

<400> SEQUENCE: 34

His Ile Trp Trp Asn Asp Asn Ile Tyr Tyr Asn Thr Val Leu Lys Ser
1 5 10 15

<210> SEQ ID NO 35
<211> LENGTH: 11
<212> TYPE: PRT
<213> ORGANISM: Mus musculus

<400> SEQUENCE: 35

Met Ala Glu Gly Arg Tyr Asp Ala Met Asp Tyr
1 5 10

<210> SEQ ID NO 36
<211> LENGTH: 324
<212> TYPE: DNA
<213> ORGANISM: Mus musculus

<400> SEQUENCE: 36
gctatccaga tgacacagag tacatcctcc ctgtctgcct ctctgggaga cagagtcacc 60
atcaattgca gggcaagtca ggacatcacc aattatttaa attggtatca gcagaaacca 120
gatggaactg tcagactcct gatctattat acatcaaaat tacactcagg agccccatca 180
aggttcagtg gccgtgggtc tggaacagat tattctctca ccattagtaa cctggagcaa 240
gaggatattg ccacttactt ttgccaacag ggtaatacgt ttccgtggac gttcggtgga 300
ggcaccaaac tggaaatcaa acgt 324

<210> SEQ ID NO 37
<211> LENGTH: 108
<212> TYPE: PRT
<213> ORGANISM: Mus musculus

<400> SEQUENCE: 37

Ala Ile Gln Met Thr Gln Ser Thr Ser Ser Leu Ser Ala Ser Leu Gly
1 5 10 15

Asp Arg Val Thr Ile Asn Cys Arg Ala Ser Gln Asp Ile Thr Asn Tyr
20 25 30

Leu Asn Trp Tyr Gln Gln Lys Pro Asp Gly Thr Val Arg Leu Leu Ile
35 40 45

Tyr Tyr Thr Ser Lys Leu His Ser Gly Ala Pro Ser Arg Phe Ser Gly
50 55 60

Arg Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asn Thr Phe Pro Trp
85 90 95

Thr Phe Gly Gly Gly Thr Lys Leu Glu Ile Lys Arg
100 105

<210> SEQ ID NO 38
<211> LENGTH: 11
<212> TYPE: PRT
<213> ORGANISM: Mus musculus

<400> SEQUENCE: 38

Arg Ala Ser Gln Asp Ile Thr Asn Tyr Leu Asn
1 5 10

<210> SEQ ID NO 39
<211> LENGTH: 7

-continued

<212> TYPE: PRT
<213> ORGANISM: Mus musculus

<400> SEQUENCE: 39

Tyr Thr Ser Lys Leu His Ser
1 5

<210> SEQ ID NO 40
<211> LENGTH: 9
<212> TYPE: PRT
<213> ORGANISM: Mus musculus

<400> SEQUENCE: 40

Gln Gln Gly Asn Thr Phe Pro Trp Thr
1 5

<210> SEQ ID NO 41
<211> LENGTH: 866
<212> TYPE: DNA
<213> ORGANISM: Homo sapiens

<400> SEQUENCE: 41
ggcacgagcg gcacgagccc accatgaagg gtttcacagc cactctcttc ctctggactc 60
tgatttttcc cagctgcagt ggaggcggcg gtgggaaagc ctggcccaca cacgtggtct 120
gtagcgacag cggcttggaa gtgctctacc agagttgcga tccattacaa gattttggct 180
tttctgttga aaagtgttcc aagcaattaa aatcaaatat caacattaga tttggaatta 240
ttctgagaga ggacatcaaa gagctttttc ttgacctagc tctcatgtct caaggctcat 300
ctgttttgaa tttctcctat cccatctgtg aggcggctct gcccaagttt tctttctgtg 360
gaagaaggaa aggagagcag atttactatg ctgggcctgt caataatcct gaatttacta 420
ttcctcaggg agaataccag gttttgctgg aactgtacac tgaaaaacgg tccaccgtgg 480
cctgtgccaa tgctactatc atgtgctcct gactgtggcc tgtagcaaaa atcacagcca 540
gctgcatctc gtgggacctc caagctcctc tgactgaacc tacgtgggag gagaagcagt 600
ctgatgacag agagaggctc tacaaagaag cgcccccaaa gagtgcagct gctaatttta 660
gtcccaggac cagacatccc cagactccac agatgtaatg aagtccccga atgtatctgt 720
ttctaaggag cctcttggca gtccttaagc agtcttgagg gtccatcctt tttctctaat 780
tggtcgcctc ccaccagact cacctgcttt tcaacttttt aggagtgctt cctcacagtt 840
accaagaata aagaaagctg gccacc 866

<210> SEQ ID NO 42
<211> LENGTH: 162
<212> TYPE: PRT
<213> ORGANISM: Homo sapiens

<400> SEQUENCE: 42

Met Lys Gly Phe Thr Ala Thr Leu Phe Leu Trp Thr Leu Ile Phe Pro
1 5 10 15

Ser Cys Ser Gly Gly Gly Gly Gly Lys Ala Trp Pro Thr His Val Val
20 25 30

Cys Ser Asp Ser Gly Leu Glu Val Leu Tyr Gln Ser Cys Asp Pro Leu
35 40 45

Gln Asp Phe Gly Phe Ser Val Glu Lys Cys Ser Lys Gln Leu Lys Ser
50 55 60

Asn Ile Asn Ile Arg Phe Gly Ile Ile Leu Arg Glu Asp Ile Lys Glu
65 70 75 80

-continued

```
Leu Phe Leu Asp Leu Ala Leu Met Ser Gln Gly Ser Ser Val Leu Asn
                85                  90                  95

Phe Ser Tyr Pro Ile Cys Glu Ala Ala Leu Pro Lys Phe Ser Phe Cys
            100                 105                 110

Gly Arg Arg Lys Gly Glu Gln Ile Tyr Tyr Ala Gly Pro Val Asn Asn
        115                 120                 125

Pro Glu Phe Thr Ile Pro Gln Gly Glu Tyr Gln Val Leu Leu Glu Leu
    130                 135                 140

Tyr Thr Glu Lys Arg Ser Thr Val Ala Cys Ala Asn Ala Thr Ile Met
145                 150                 155                 160

Cys Ser


<210> SEQ ID NO 43
<211> LENGTH: 624
<212> TYPE: DNA
<213> ORGANISM: Homo sapiens

<400> SEQUENCE: 43

ggcgggccgc tcccacttcg gcacgagggg cacgaggtaa atcttttctg cttactgaaa      60

aggaagagtc tgatgattag ttactgatcc tctttgcatt tgtaaagctt tggagatatt     120

gaatcatgtt accatttctg ttttttttcca ccctgttttc ttccatattt actgaagctc     180

agaagcagta ttgggtctgc aactcatccg atgcaagtat ttcatacacc tactgtgata     240

aaatgcaata cccaatttca attaatgtta acccctgtat agaattgaaa ggatccaaag     300

gattattgca cattttctac attccaagga gagatttaaa gcaattatat ttcaatctct     360

atataactgt caacaccatg aatcttccaa agcgcaaaga agttatttgc cgaggatctg     420

atgacgatta ctctttttgc agagctctga agggagagac tgtgaataca acaatatcat     480

tctccttcaa gggaataaaa ttttctaagg gaaaatacaa atgtgttgtt gaagctattt     540

ctgggagccc agaagaaatg ctcttttgct tggagtttgt catcctacac caacctaatt     600

caaattagaa taaattgagt attt                                            624


<210> SEQ ID NO 44
<211> LENGTH: 160
<212> TYPE: PRT
<213> ORGANISM: Homo sapiens

<400> SEQUENCE: 44

Met Leu Pro Phe Leu Phe Phe Ser Thr Leu Phe Ser Ser Ile Phe Thr
1               5                   10                  15

Glu Ala Gln Lys Gln Tyr Trp Val Cys Asn Ser Ser Asp Ala Ser Ile
            20                  25                  30

Ser Tyr Thr Tyr Cys Asp Lys Met Gln Tyr Pro Ile Ser Ile Asn Val
        35                  40                  45

Asn Pro Cys Ile Glu Leu Lys Gly Ser Lys Gly Leu Leu His Ile Phe
    50                  55                  60

Tyr Ile Pro Arg Arg Asp Leu Lys Gln Leu Tyr Phe Asn Leu Tyr Ile
65                  70                  75                  80

Thr Val Asn Thr Met Asn Leu Pro Lys Arg Lys Glu Val Ile Cys Arg
                85                  90                  95

Gly Ser Asp Asp Asp Tyr Ser Phe Cys Arg Ala Leu Lys Gly Glu Thr
            100                 105                 110

Val Asn Thr Thr Ile Ser Phe Ser Phe Lys Gly Ile Lys Phe Ser Lys
        115                 120                 125
```

-continued

Gly Lys Tyr Lys Cys Val Val Glu Ala Ile Ser Gly Ser Pro Glu Glu
    130                 135                 140

Met Leu Phe Cys Leu Glu Phe Val Ile Leu His Gln Pro Asn Ser Asn
145                 150                 155                 160

<210> SEQ ID NO 45
<211> LENGTH: 118
<212> TYPE: PRT
<213> ORGANISM: Homo sapiens
<220> FEATURE:
<221> NAME/KEY: MISC_FEATURE
<222> LOCATION: (30)..(30)
<223> OTHER INFORMATION: Xaa is Thr or Ser
<220> FEATURE:
<221> NAME/KEY: MISC_FEATURE
<222> LOCATION: (49)..(49)
<223> OTHER INFORMATION: Xaa is Ile or Met
<220> FEATURE:
<221> NAME/KEY: MISC_FEATURE
<222> LOCATION: (68)..(68)
<223> OTHER INFORMATION: Xaa is Val or Ile
<220> FEATURE:
<221> NAME/KEY: MISC_FEATURE
<222> LOCATION: (70)..(70)
<223> OTHER INFORMATION: Xaa is Met or Ile

<400> SEQUENCE: 45

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Xaa Gly Gly
            20                  25                  30

Tyr Ser Trp His Trp Ile Arg Gln Pro Pro Gly Lys Gly Leu Glu Trp
        35                  40                  45

Xaa Gly Tyr Ile His Tyr Ser Gly Tyr Thr Asp Phe Asn Pro Ser Leu
    50                  55                  60

Lys Thr Arg Xaa Thr Xaa Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Pro Ser Asp Gly Phe Pro Tyr Trp Gly Gln Gly Thr
            100                 105                 110

Leu Val Thr Val Ser Ser
        115

<210> SEQ ID NO 46
<211> LENGTH: 118
<212> TYPE: PRT
<213> ORGANISM: Homo sapiens
<220> FEATURE:
<221> NAME/KEY: MISC_FEATURE
<222> LOCATION: (24)..(24)
<223> OTHER INFORMATION: Xaa is Ala or Val
<220> FEATURE:
<221> NAME/KEY: MISC_FEATURE
<222> LOCATION: (49)..(49)
<223> OTHER INFORMATION: Xaa is Val or Met
<220> FEATURE:
<221> NAME/KEY: MISC_FEATURE
<222> LOCATION: (79)..(79)
<223> OTHER INFORMATION: Xaa is Leu or Phe

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Xaa Ser Gly Tyr Ser Ile Thr Gly Gly

-continued

```
            20                  25                  30

Tyr Ser Trp His Trp Val Arg Gln Ala Pro Gly Lys Gly Leu Glu Trp
        35                  40                  45

Xaa Ser Tyr Ile His Tyr Ser Gly Tyr Thr Asp Phe Asn Pro Ser Leu
    50                  55                  60

Lys Thr Arg Phe Thr Ile Ser Arg Asp Asn Ser Lys Asn Thr Xaa Tyr
65                  70                  75                  80

Leu Gln Met Asn Ser Leu Arg Ala Glu Asp Thr Ala Val Tyr Tyr Cys
                85                  90                  95

Ala Arg Lys Asp Pro Ser Asp Gly Phe Pro Tyr Trp Gly Gln Gly Thr
            100                 105                 110

Leu Val Thr Val Ser Ser
        115


<210> SEQ ID NO 47
<211> LENGTH: 107
<212> TYPE: PRT
<213> ORGANISM: Homo sapiens
<220> FEATURE:
<221> NAME/KEY: MISC_FEATURE
<222> LOCATION: (49)..(49)
<223> OTHER INFORMATION: Xaa is Lys or Tyr

<400> SEQUENCE: 47

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asp His
            20                  25                  30

Leu His Trp Tyr Gln Gln Lys Pro Gly Gln Ala Pro Arg Leu Leu Ile
        35                  40                  45

Xaa Tyr Ala Ser His Ala Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Asn Gly His Ser Phe Pro Leu
                85                  90                  95

Thr Phe Gly Gly Gly Thr Lys Val Glu Ile Lys
            100                 105


<210> SEQ ID NO 48
<211> LENGTH: 107
<212> TYPE: PRT
<213> ORGANISM: Homo sapiens

<400> SEQUENCE: 48

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Asn Gly His Ser Phe Pro Leu
                85                  90                  95
```

-continued

Thr Phe Gly Gly Gly Thr Lys Val Glu Ile Lys
100 105

<210> SEQ ID NO 49
<211> LENGTH: 120
<212> TYPE: PRT
<213> ORGANISM: Homo sapiens
<220> FEATURE:
<221> NAME/KEY: MISC_FEATURE
<222> LOCATION: (48)..(48)
<223> OTHER INFORMATION: Xaa is Met or Ile
<220> FEATURE:
<221> NAME/KEY: MISC_FEATURE
<222> LOCATION: (74)..(74)
<223> OTHER INFORMATION: Xaa is Lys or Thr
<220> FEATURE:
<221> NAME/KEY: MISC_FEATURE
<222> LOCATION: (81)..(81)
<223> OTHER INFORMATION: Xaa is Met or Leu

<400> SEQUENCE: 49

Gln Val Gln Leu Val Gln Ser Gly Ala Glu Val Lys Lys Pro Gly Ser
1 5 10 15

Ser Val Lys Val Ser Cys Lys Ala Ser Gly Phe Asn Ile Lys Asp Ser
20 25 30

Tyr Ile His Trp Val Arg Gln Ala Pro Gly Gln Gly Leu Glu Trp Xaa
35 40 45

Gly Trp Thr Asp Pro Glu Asn Val Asn Ser Ile Tyr Asp Pro Arg Phe
50 55 60

Gln Gly Arg Val Thr Ile Thr Ala Asp Xaa Ser Thr Ser Thr Ala Tyr
65 70 75 80

Xaa Glu Leu Ser Ser Leu Arg Ser Glu Asp Thr Ala Val Tyr Tyr Cys
85 90 95

Ala Arg Gly Tyr Asn Gly Val Tyr Tyr Ala Met Asp Tyr Trp Gly Gln
100 105 110

Gly Thr Thr Val Thr Val Ser Ser
115 120

<210> SEQ ID NO 50
<211> LENGTH: 106
<212> TYPE: PRT
<213> ORGANISM: Homo sapiens
<220> FEATURE:
<221> NAME/KEY: MISC_FEATURE
<222> LOCATION: (70)..(70)
<223> OTHER INFORMATION: Xaa is Phe or Thr

<400> SEQUENCE: 50

Glu Ile Val Leu Thr Gln Ser Pro Ala Thr Leu Ser Leu Ser Pro Gly
1 5 10 15

Glu Arg Ala Thr Leu Ser Cys Ser Ala Ser Ser Ser Val Ile Tyr Met
20 25 30

His Trp Tyr Gln Gln Lys Pro Gly Gln Ala Pro Arg Leu Leu Ile Tyr
35 40 45

Arg Thr Tyr Asn Leu Ala Ser Gly Ile Pro Ala Arg Phe Ser Gly Ser
50 55 60

Gly Ser Gly Thr Asp Xaa Thr Leu Thr Ile Ser Ser Leu Glu Pro Glu
65 70 75 80

Asp Phe Ala Val Tyr Tyr Cys His Gln Trp Ser Ser Phe Pro Tyr Thr
85 90 95

Phe Gly Gln Gly Thr Lys Val Glu Ile Lys
100 105

-continued

<210> SEQ ID NO 51
<211> LENGTH: 121
<212> TYPE: PRT
<213> ORGANISM: Homo sapiens
<220> FEATURE:
<221> NAME/KEY: MISC_FEATURE
<222> LOCATION: (30)..(30)
<223> OTHER INFORMATION: Xaa is Ser or Thr
<220> FEATURE:
<221> NAME/KEY: MISC_FEATURE
<222> LOCATION: (71)..(71)
<223> OTHER INFORMATION: Xaa is Ile or Phe
<220> FEATURE:
<221> NAME/KEY: MISC_FEATURE
<222> LOCATION: (98)..(98)
<223> OTHER INFORMATION: Xaa is Ile or Ala

<400> SEQUENCE: 51

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Xaa Thr Tyr
            20                  25                  30

Asn Ile Gly Val Gly Trp Ile Arg Gln Pro Pro Gly Lys Ala Leu Glu
        35                  40                  45

Trp Leu Ala His Ile Trp Trp Asn Asp Asn Ile Tyr Tyr Asn Thr Val
    50                  55                  60

Leu Lys Ser Arg Leu Thr Xaa Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Xaa Arg Met Ala Glu Gly Arg Tyr Asp Ala Met Asp Tyr Trp Gly
            100                 105                 110

Gln Gly Thr Leu Val Thr Val Ser Ser
        115                 120
```

<210> SEQ ID NO 52
<211> LENGTH: 121
<212> TYPE: PRT
<213> ORGANISM: Homo sapiens
<220> FEATURE:
<221> NAME/KEY: MISC_FEATURE
<222> LOCATION: (24)..(24)
<223> OTHER INFORMATION: Xaa is Phe or Ala
<220> FEATURE:
<221> NAME/KEY: MISC_FEATURE
<222> LOCATION: (50)..(50)
<223> OTHER INFORMATION: Xaa is Val or Leu
<220> FEATURE:
<221> NAME/KEY: MISC_FEATURE
<222> LOCATION: (71)..(71)
<223> OTHER INFORMATION: Xaa is Ile or Phe
<220> FEATURE:
<221> NAME/KEY: MISC_FEATURE
<222> LOCATION: (73)..(73)
<223> OTHER INFORMATION: Xaa is Lys or Arg
<220> FEATURE:
<221> NAME/KEY: MISC_FEATURE
<222> LOCATION: (80)..(80)
<223> OTHER INFORMATION: Xaa is Leu or Val
<220> FEATURE:
<221> NAME/KEY: MISC_FEATURE
<222> LOCATION: (98)..(98)
<223> OTHER INFORMATION: Xaa is Ile or Ala

<400> SEQUENCE: 52

```
Glu Val Gln Leu Val Glu Ser Gly Gly Gly Leu Val Gln Pro Gly Gly
1               5                   10                  15
```

-continued

Ser Leu Arg Leu Ser Cys Ala Xaa Ser Gly Phe Ser Leu Thr Thr Tyr
20 25 30

Asn Ile Gly Val Gly Trp Val Arg Gln Ala Pro Gly Lys Gly Leu Glu
35 40 45

Trp Xaa Ser His Ile Trp Trp Asn Asp Asn Ile Tyr Tyr Asn Thr Val
50 55 60

Leu Lys Ser Arg Leu Thr Xaa Ser Xaa Asp Asn Ser Lys Asn Thr Xaa
65 70 75 80

Tyr Leu Gln Met Asn Ser Leu Arg Ala Glu Asp Thr Ala Val Tyr Tyr
85 90 95

Cys Xaa Arg Met Ala Glu Gly Arg Tyr Asp Ala Met Asp Tyr Trp Gly
100 105 110

Gln Gly Thr Leu Val Thr Val Ser Ser
115 120

<210> SEQ ID NO 53
<211> LENGTH: 107
<212> TYPE: PRT
<213> ORGANISM: Homo sapiens
<220> FEATURE:
<221> NAME/KEY: MISC_FEATURE
<222> LOCATION: (71)..(71)
<223> OTHER INFORMATION: Xaa is Phe or Tyr
<220> FEATURE:
<221> NAME/KEY: MISC_FEATURE
<222> LOCATION: (87)..(87)
<223> OTHER INFORMATION: Xaa is Tyr or Phe

<400> SEQUENCE: 53

Asp Ile Gln Met Thr Gln Ser Pro Ser Ser Val Ser Ala Ser Val Gly
1 5 10 15

Asp Arg Val Thr Ile Thr Cys Arg Ala Ser Gln Asp Ile Thr Asn Tyr
20 25 30

Leu Asn Trp Tyr Gln Gln Lys Pro Gly Lys Ala Pro Lys Leu Leu Ile
35 40 45

Tyr Tyr Thr Ser Lys Leu His Ser Gly Val Pro Ser Arg Phe Ser Gly
50 55 60

Ser Gly Ser Gly Thr Asp Xaa Thr Leu Thr Ile Ser Ser Leu Gln Pro
65 70 75 80

Glu Asp Phe Ala Thr Tyr Xaa Cys Gln Gln Gly Asn Thr Phe Pro Trp
85 90 95

Thr Phe Gly Gly Gly Thr Lys Val Glu Ile Lys
100 105

<210> SEQ ID NO 54
<211> LENGTH: 839
<212> TYPE: PRT
<213> ORGANISM: Homo sapiens

<400> SEQUENCE: 54

Met Met Ser Ala Ser Arg Leu Ala Gly Thr Leu Ile Pro Ala Met Ala
1 5 10 15

Phe Leu Ser Cys Val Arg Pro Glu Ser Trp Glu Pro Cys Val Glu Val
20 25 30

Val Pro Asn Ile Thr Tyr Gln Cys Met Glu Leu Asn Phe Tyr Lys Ile
35 40 45

Pro Asp Asn Leu Pro Phe Ser Thr Lys Asn Leu Asp Leu Ser Phe Asn
50 55 60

-continued

```
Pro Leu Arg His Leu Gly Ser Tyr Ser Phe Phe Ser Phe Pro Glu Leu
65                  70                  75                  80

Gln Val Leu Asp Leu Ser Arg Cys Glu Ile Gln Thr Ile Glu Asp Gly
                85                  90                  95

Ala Tyr Gln Ser Leu Ser His Leu Ser Thr Leu Ile Leu Thr Gly Asn
            100                 105                 110

Pro Ile Gln Ser Leu Ala Leu Gly Ala Phe Ser Gly Leu Ser Ser Leu
        115                 120                 125

Gln Lys Leu Val Ala Val Glu Thr Asn Leu Ala Ser Leu Glu Asn Phe
    130                 135                 140

Pro Ile Gly His Leu Lys Thr Leu Lys Glu Leu Asn Val Ala His Asn
145                 150                 155                 160

Leu Ile Gln Ser Phe Lys Leu Pro Glu Tyr Phe Ser Asn Leu Thr Asn
                165                 170                 175

Leu Glu His Leu Asp Leu Ser Ser Asn Lys Ile Gln Ser Ile Tyr Cys
            180                 185                 190

Thr Asp Leu Arg Val Leu His Gln Met Pro Leu Leu Asn Leu Ser Leu
        195                 200                 205

Asp Leu Ser Leu Asn Pro Met Asn Phe Ile Gln Pro Gly Ala Phe Lys
    210                 215                 220

Glu Ile Arg Leu His Lys Leu Thr Leu Arg Asn Asn Phe Asp Ser Leu
225                 230                 235                 240

Asn Val Met Lys Thr Cys Ile Gln Gly Leu Ala Gly Leu Glu Val His
                245                 250                 255

Arg Leu Val Leu Gly Glu Phe Arg Asn Glu Gly Asn Leu Glu Lys Phe
            260                 265                 270

Asp Lys Ser Ala Leu Glu Gly Leu Cys Asn Leu Thr Ile Glu Glu Phe
        275                 280                 285

Arg Leu Ala Tyr Leu Asp Tyr Tyr Leu Asp Asp Ile Ile Asp Leu Phe
    290                 295                 300

Asn Cys Leu Thr Asn Val Ser Ser Phe Ser Leu Val Ser Val Thr Ile
305                 310                 315                 320

Glu Arg Val Lys Asp Phe Ser Tyr Asn Phe Gly Trp Gln His Leu Glu
                325                 330                 335

Leu Val Asn Cys Lys Phe Gly Gln Phe Pro Thr Leu Lys Leu Lys Ser
            340                 345                 350

Leu Lys Arg Leu Thr Phe Thr Ser Asn Lys Gly Gly Asn Ala Phe Ser
        355                 360                 365

Glu Val Asp Leu Pro Ser Leu Glu Phe Leu Asp Leu Ser Arg Asn Gly
    370                 375                 380

Leu Ser Phe Lys Gly Cys Cys Ser Gln Ser Asp Phe Gly Thr Thr Ser
385                 390                 395                 400

Leu Lys Tyr Leu Asp Leu Ser Phe Asn Gly Val Ile Thr Met Ser Ser
                405                 410                 415

Asn Phe Leu Gly Leu Glu Gln Leu Glu His Leu Asp Phe Gln His Ser
            420                 425                 430

Asn Leu Lys Gln Met Ser Glu Phe Ser Val Phe Leu Ser Leu Arg Asn
        435                 440                 445

Leu Ile Tyr Leu Asp Ile Ser His Thr His Thr Arg Val Ala Phe Asn
    450                 455                 460

Gly Ile Phe Asn Gly Leu Ser Ser Leu Glu Val Leu Lys Met Ala Gly
465                 470                 475                 480

Asn Ser Phe Gln Glu Asn Phe Leu Pro Asp Ile Phe Thr Glu Leu Arg
```

-continued

```
                485                 490                 495

Asn Leu Thr Phe Leu Asp Leu Ser Gln Cys Gln Leu Glu Gln Leu Ser
            500                 505                 510

Pro Thr Ala Phe Asn Ser Leu Ser Ser Leu Gln Val Leu Asn Met Ser
        515                 520                 525

His Asn Asn Phe Phe Ser Leu Asp Thr Phe Pro Tyr Lys Cys Leu Asn
    530                 535                 540

Ser Leu Gln Val Leu Asp Tyr Ser Leu Asn His Ile Met Thr Ser Lys
545                 550                 555                 560

Lys Gln Glu Leu Gln His Phe Pro Ser Ser Leu Ala Phe Leu Asn Leu
                565                 570                 575

Thr Gln Asn Asp Phe Ala Cys Thr Cys Glu His Gln Ser Phe Leu Gln
            580                 585                 590

Trp Ile Lys Asp Gln Arg Gln Leu Leu Val Glu Val Glu Arg Met Glu
        595                 600                 605

Cys Ala Thr Pro Ser Asp Lys Gln Gly Met Pro Val Leu Ser Leu Asn
    610                 615                 620

Ile Thr Cys Gln Met Asn Lys Thr Ile Ile Gly Val Ser Val Leu Ser
625                 630                 635                 640

Val Leu Val Val Ser Val Val Ala Val Leu Val Tyr Lys Phe Tyr Phe
                645                 650                 655

His Leu Met Leu Leu Ala Gly Cys Ile Lys Tyr Gly Arg Gly Glu Asn
            660                 665                 670

Ile Tyr Asp Ala Phe Val Ile Tyr Ser Ser Gln Asp Glu Asp Trp Val
        675                 680                 685

Arg Asn Glu Leu Val Lys Asn Leu Glu Glu Gly Val Pro Pro Phe Gln
    690                 695                 700

Leu Cys Leu His Tyr Arg Asp Phe Ile Pro Gly Val Ala Ile Ala Ala
705                 710                 715                 720

Asn Ile Ile His Glu Gly Phe His Lys Ser Arg Lys Val Ile Val Val
                725                 730                 735

Val Ser Gln His Phe Ile Gln Ser Arg Trp Cys Ile Phe Glu Tyr Glu
            740                 745                 750

Ile Ala Gln Thr Trp Gln Phe Leu Ser Ser Arg Ala Gly Ile Ile Phe
        755                 760                 765

Ile Val Leu Gln Lys Val Glu Lys Thr Leu Leu Arg Gln Gln Val Glu
    770                 775                 780

Leu Tyr Arg Leu Leu Ser Arg Asn Thr Tyr Leu Glu Trp Glu Asp Ser
785                 790                 795                 800

Val Leu Gly Arg His Ile Phe Trp Arg Arg Leu Arg Lys Ala Leu Leu
                805                 810                 815

Asp Gly Lys Ser Trp Asn Pro Glu Gly Thr Val Gly Thr Gly Cys Asn
            820                 825                 830

Trp Gln Glu Ala Thr Ser Ile
        835


<210> SEQ ID NO 55
<211> LENGTH: 36
<212> TYPE: DNA
<213> ORGANISM: Artificial Sequence
<220> FEATURE:
<223> OTHER INFORMATION: Chemically synthesized

<400> SEQUENCE: 55

gaccattgaa gaattccggt tctcttgctc tcctcg                                36
```

-continued

<210> SEQ ID NO 56
<211> LENGTH: 44
<212> TYPE: DNA
<213> ORGANISM: Artificial Sequence
<220> FEATURE:
<223> OTHER INFORMATION: Chemically synthesized

<400> SEQUENCE: 56
cgaggtagta gtctaagtat gttaaccgga attcttcaat ggtc 44

<210> SEQ ID NO 57
<211> LENGTH: 38
<212> TYPE: DNA
<213> ORGANISM: Artificial Sequence
<220> FEATURE:
<223> OTHER INFORMATION: Chemically synthesized

<400> SEQUENCE: 57
ggcaacattt agaattagtc aactgtaaat ttggacag 38

<210> SEQ ID NO 58
<211> LENGTH: 38
<212> TYPE: DNA
<213> ORGANISM: Artificial Sequence
<220> FEATURE:
<223> OTHER INFORMATION: Chemically synthesized

<400> SEQUENCE: 58
ctgtccaaat ttacagttga ctaattctaa atgttgcc 38

<210> SEQ ID NO 59
<211> LENGTH: 26
<212> TYPE: DNA
<213> ORGANISM: Artificial Sequence
<220> FEATURE:
<223> OTHER INFORMATION: Chemically synthesized

<400> SEQUENCE: 59
atttgtatag ttaacctgaa ctcatc 26

<210> SEQ ID NO 60
<211> LENGTH: 34
<212> TYPE: DNA
<213> ORGANISM: Artificial Sequence
<220> FEATURE:
<223> OTHER INFORMATION: Chemically synthesized

<400> SEQUENCE: 60
ggggcggccg cgggaagctt gaatccctgc atag 34

<210> SEQ ID NO 61
<211> LENGTH: 32
<212> TYPE: DNA
<213> ORGANISM: Artificial Sequence
<220> FEATURE:
<223> OTHER INFORMATION: Chemically synthesized

<400> SEQUENCE: 61
ggggatatct ttgcaaacac aacaaacttg ac 32

<210> SEQ ID NO 62
<211> LENGTH: 29
<212> TYPE: DNA
<213> ORGANISM: Artificial Sequence
<220> FEATURE:

-continued

<223> OTHER INFORMATION: Chemically synthesized

<400> SEQUENCE: 62
gggctcgagc ttgtacatat aacaggtag 29

<210> SEQ ID NO 63
<211> LENGTH: 48
<212> TYPE: DNA
<213> ORGANISM: Artificial Sequence
<220> FEATURE:
<223> OTHER INFORMATION: Chemically synthesized

<400> SEQUENCE: 63
gctttttcag aagttgatct accggtcctt gagtttctag atctcagt 48

<210> SEQ ID NO 64
<211> LENGTH: 48
<212> TYPE: DNA
<213> ORGANISM: Artificial Sequence
<220> FEATURE:
<223> OTHER INFORMATION: Chemically synthesized

<400> SEQUENCE: 64
actgagatct agaaactcaa ggaccggtag atcaacttct gaaaaagc 48

<210> SEQ ID NO 65
<211> LENGTH: 21
<212> TYPE: DNA
<213> ORGANISM: Artificial Sequence
<220> FEATURE:
<223> OTHER INFORMATION: Chemically synthesized

<400> SEQUENCE: 65
cattgatgag ttcaggttaa c 21

<210> SEQ ID NO 66
<211> LENGTH: 31
<212> TYPE: DNA
<213> ORGANISM: Artificial Sequence
<220> FEATURE:
<223> OTHER INFORMATION: Chemically synthesized

<400> SEQUENCE: 66
atgcaccggt agggccactt ttttaaaact g 31

<210> SEQ ID NO 67
<211> LENGTH: 31
<212> TYPE: DNA
<213> ORGANISM: Artificial Sequence
<220> FEATURE:
<223> OTHER INFORMATION: Chemically synthesized

<400> SEQUENCE: 67
atgcaccggt tctcagctat ctagatctta g 31

<210> SEQ ID NO 68
<211> LENGTH: 33
<212> TYPE: DNA
<213> ORGANISM: Artificial Sequence
<220> FEATURE:
<223> OTHER INFORMATION: Chemically synthesized

<400> SEQUENCE: 68
atgcgatatc tgaaagggtg ttgtctttga aag 33

-continued

<210> SEQ ID NO 69
<211> LENGTH: 106
<212> TYPE: DNA
<213> ORGANISM: Artificial Sequence
<220> FEATURE:
<223> OTHER INFORMATION: Chemically synthesized

<400> SEQUENCE: 69
ccgttaacat atacaaatga tttttcagat gatattgtta agttccattg cttggcgaat 60
gtttctgcaa tgtctctggc aggtgtgact attgaaaggg taaaag 106

<210> SEQ ID NO 70
<211> LENGTH: 28
<212> TYPE: DNA
<213> ORGANISM: Artificial Sequence
<220> FEATURE:
<223> OTHER INFORMATION: Chemically synthesized

<400> SEQUENCE: 70
ccaccggtag atcaacttct gaaaaagc 28

<210> SEQ ID NO 71
<211> LENGTH: 23
<212> TYPE: DNA
<213> ORGANISM: Artificial Sequence
<220> FEATURE:
<223> OTHER INFORMATION: Chemically synthesized

<400> SEQUENCE: 71
ccgttaacat acttagacta cta 23

<210> SEQ ID NO 72
<211> LENGTH: 120
<212> TYPE: DNA
<213> ORGANISM: Artificial Sequence
<220> FEATURE:
<223> OTHER INFORMATION: Chemically synthesized

<400> SEQUENCE: 72
gatatctgaa agggtgttgt ctttgaaaga attgccagcc atttttaatg tgttgagact 60
ggtcaagcca agaaatatac catcgaagtc aattttggtg ttagtatgag aaatgtcaag 120

<210> SEQ ID NO 73
<211> LENGTH: 36
<212> TYPE: DNA
<213> ORGANISM: Artificial Sequence
<220> FEATURE:
<223> OTHER INFORMATION: Chemically synthesized

<400> SEQUENCE: 73
ctctttttgc agagctctta agggagagac tgtgaa 36

<210> SEQ ID NO 74
<211> LENGTH: 36
<212> TYPE: DNA
<213> ORGANISM: Artificial Sequence
<220> FEATURE:
<223> OTHER INFORMATION: Chemically synthesized

<400> SEQUENCE: 74
ttcacagtct ctcccttaag agctctgcaa aaagag 36

<210> SEQ ID NO 75
<211> LENGTH: 22
<212> TYPE: DNA

-continued

<213> ORGANISM: Artificial Sequence
<220> FEATURE:
<223> OTHER INFORMATION: Chemically synthesized

<400> SEQUENCE: 75
ccggatcccc tcagtcttat gc 22

<210> SEQ ID NO 76
<211> LENGTH: 24
<212> TYPE: DNA
<213> ORGANISM: Artificial Sequence
<220> FEATURE:
<223> OTHER INFORMATION: Chemically synthesized

<400> SEQUENCE: 76
ccggatccaa tggatttgtg catg 24

<210> SEQ ID NO 77
<211> LENGTH: 29
<212> TYPE: DNA
<213> ORGANISM: Artificial Sequence
<220> FEATURE:
<223> OTHER INFORMATION: Chemically synthesized

<400> SEQUENCE: 77
ggcttaagag ctctgcaaaa agaatagtc 29

<210> SEQ ID NO 78
<211> LENGTH: 28
<212> TYPE: DNA
<213> ORGANISM: Artificial Sequence
<220> FEATURE:
<223> OTHER INFORMATION: Chemically synthesized

<400> SEQUENCE: 78
ggcttaaggg agagactgtg aatacatc 28

<210> SEQ ID NO 79
<211> LENGTH: 22
<212> TYPE: DNA
<213> ORGANISM: Artificial Sequence
<220> FEATURE:
<223> OTHER INFORMATION: Chemically synthesized

<400> SEQUENCE: 79
ccgctagcat tgacatcacg gc 22

<210> SEQ ID NO 80
<211> LENGTH: 87
<212> TYPE: PRT
<213> ORGANISM: Homo sapiens

<400> SEQUENCE: 80

```
Arg Leu Ala Tyr Leu Asp Tyr Tyr Leu Asp Asp Ile Ile Asp Leu Phe
1               5                   10                  15

Asn Cys Leu Thr Asn Val Ser Ser Phe Ser Leu Val Ser Val Thr Ile
            20                  25                  30

Glu Arg Val Lys Asp Phe Ser Tyr Asn Phe Gly Trp Gln His Leu Glu
        35                  40                  45

Leu Val Asn Cys Lys Phe Gly Gln Phe Pro Thr Leu Lys Leu Lys Ser
    50                  55                  60

Leu Lys Arg Leu Thr Phe Thr Ser Asn Lys Gly Gly Asn Ala Phe Ser
65                  70                  75                  80
```

-continued

Glu Val Asp Leu Pro Ser Leu
85

<210> SEQ ID NO 81
<211> LENGTH: 86
<212> TYPE: PRT
<213> ORGANISM: Mus musculus

<400> SEQUENCE: 81

Arg Leu Thr Tyr Thr Asn Asp Phe Ser Asp Asp Ile Val Lys Phe His
1 5 10 15

Cys Leu Ala Asn Val Ser Ala Met Ser Leu Ala Gly Val Ser Ile Lys
20 25 30

Tyr Leu Glu Asp Val Pro Lys His Phe Lys Trp Gln Ser Leu Ser Ile
35 40 45

Ile Arg Cys Gln Leu Lys Gln Phe Pro Thr Leu Asp Leu Pro Phe Leu
50 55 60

Lys Ser Leu Thr Leu Thr Met Asn Lys Gly Ser Ile Ser Phe Lys Lys
65 70 75 80

Val Ala Leu Pro Ser Leu
85

<210> SEQ ID NO 82
<211> LENGTH: 39
<212> TYPE: PRT
<213> ORGANISM: Homo sapiens

<400> SEQUENCE: 82

Gln Lys Gln Tyr Trp Val Cys Asn Ser Ser Asp Ala Ser Ile Ser Tyr
1 5 10 15

Thr Tyr Cys Asp Lys Met Gln Tyr Pro Ile Ser Ile Asn Val Asn Pro
20 25 30

Cys Ile Glu Leu Lys Gly Ser
35

<210> SEQ ID NO 83
<211> LENGTH: 39
<212> TYPE: PRT
<213> ORGANISM: Mus musculus

<400> SEQUENCE: 83

Glu Lys Gln Gln Trp Phe Cys Asn Ser Ser Asp Ala Ile Ile Ser Tyr
1 5 10 15

Ser Tyr Cys Asp His Leu Lys Phe Pro Ile Ser Ile Ser Ser Glu Pro
20 25 30

Cys Ile Arg Leu Arg Gly Thr
35

<210> SEQ ID NO 84
<211> LENGTH: 23
<212> TYPE: DNA
<213> ORGANISM: Artificial Sequence
<220> FEATURE:
<223> OTHER INFORMATION: Chemically synthesized

<400> SEQUENCE: 84
ggaagcttaa ccaccatgtt gcc 23

<210> SEQ ID NO 85
<211> LENGTH: 6
<212> TYPE: PRT

-continued

<213> ORGANISM: Homo sapiens

<400> SEQUENCE: 85

Gly Gly Tyr Ser Trp His
1 5

<210> SEQ ID NO 86
<211> LENGTH: 16
<212> TYPE: PRT
<213> ORGANISM: Homo sapiens

<400> SEQUENCE: 86

Tyr Ile His Tyr Ser Gly Tyr Thr Asp Phe Asn Pro Ser Leu Lys Thr
1 5 10 15

<210> SEQ ID NO 87
<211> LENGTH: 9
<212> TYPE: PRT
<213> ORGANISM: Homo sapiens

<400> SEQUENCE: 87

Lys Asp Pro Ser Asp Gly Phe Pro Tyr
1 5

<210> SEQ ID NO 88
<211> LENGTH: 11
<212> TYPE: PRT
<213> ORGANISM: Homo sapiens

<400> SEQUENCE: 88

Arg Ala Ser Gln Ser Ile Ser Asp His Leu His
1 5 10

<210> SEQ ID NO 89
<211> LENGTH: 7
<212> TYPE: PRT
<213> ORGANISM: Homo sapiens

<400> SEQUENCE: 89

Tyr Ala Ser His Ala Ile Ser
1 5

<210> SEQ ID NO 90
<211> LENGTH: 9
<212> TYPE: PRT
<213> ORGANISM: Homo sapiens

<400> SEQUENCE: 90

Gln Asn Gly His Ser Phe Pro Leu Thr
1 5

<210> SEQ ID NO 91
<211> LENGTH: 5
<212> TYPE: PRT
<213> ORGANISM: Homo sapiens

<400> SEQUENCE: 91

Asp Ser Tyr Ile His
1 5

<210> SEQ ID NO 92
<211> LENGTH: 17
<212> TYPE: PRT
<213> ORGANISM: Homo sapiens -continued

<400> SEQUENCE: 92

```
Trp Thr Asp Pro Glu Asn Val Asn Ser Ile Tyr Asp Pro Arg Phe Gln
1               5                   10                  15

Gly
```

<210> SEQ ID NO 93
<211> LENGTH: 11
<212> TYPE: PRT
<213> ORGANISM: Homo sapiens

<400> SEQUENCE: 93

```
Gly Tyr Asn Gly Val Tyr Tyr Ala Met Asp Tyr
1               5                   10
```

<210> SEQ ID NO 94
<211> LENGTH: 10
<212> TYPE: PRT
<213> ORGANISM: Homo sapiens

<400> SEQUENCE: 94

```
Ser Ala Ser Ser Ser Val Ile Tyr Met His
1               5                   10
```

<210> SEQ ID NO 95
<211> LENGTH: 7
<212> TYPE: PRT
<213> ORGANISM: Homo sapiens

<400> SEQUENCE: 95

```
Arg Thr Tyr Asn Leu Ala Ser
1               5
```

<210> SEQ ID NO 96
<211> LENGTH: 9
<212> TYPE: PRT
<213> ORGANISM: Homo sapiens

<400> SEQUENCE: 96

```
His Gln Trp Ser Ser Phe Pro Tyr Thr
1               5
```

<210> SEQ ID NO 97
<211> LENGTH: 7
<212> TYPE: PRT
<213> ORGANISM: Homo sapiens

<400> SEQUENCE: 97

```
Thr Tyr Asn Ile Gly Val Gly
1               5
```

<210> SEQ ID NO 98
<211> LENGTH: 16
<212> TYPE: PRT
<213> ORGANISM: Homo sapiens

<400> SEQUENCE: 98

```
His Ile Trp Trp Asn Asp Asn Ile Tyr Tyr Asn Thr Val Leu Lys Ser
1               5                   10                  15
```

<210> SEQ ID NO 99
<211> LENGTH: 11
<212> TYPE: PRT
<213> ORGANISM: Homo sapiens -continued

<400> SEQUENCE: 99

Met Ala Glu Gly Arg Tyr Asp Ala Met Asp Tyr
1 5 10

<210> SEQ ID NO 100
<211> LENGTH: 11
<212> TYPE: PRT
<213> ORGANISM: Homo sapiens

<400> SEQUENCE: 100

Arg Ala Ser Gln Asp Ile Thr Asn Tyr Leu Asn
1 5 10

<210> SEQ ID NO 101
<211> LENGTH: 7
<212> TYPE: PRT
<213> ORGANISM: Homo sapiens

<400> SEQUENCE: 101

Tyr Thr Ser Lys Leu His Ser
1 5

<210> SEQ ID NO 102
<211> LENGTH: 9
<212> TYPE: PRT
<213> ORGANISM: Homo sapiens

<400> SEQUENCE: 102

Gln Gln Gly Asn Thr Phe Pro Trp Thr
1 5